United States Patent
Cramer et al.

(10) Patent No.: US 7,330,793 B2
(45) Date of Patent: Feb. 12, 2008

(54) METHOD FOR SEARCHING HETEROGENEOUS COMPOUND DATABASES USING TOPOMERIC SHAPE DESCRIPTORS AND PHARMACOPHORIC FEATURES

(76) Inventors: Richard D. Cramer, 48 Camino de Milagro, Sante Fe, NM (US) 87506; Robert J. Jilek, 1204 Golden Harvest Dr., St. Peters, MO (US) 63376; Qian Liu, 13 Cool Meadows Dr., Ballwin, MO (US) 63011; Stephan Guessregen, 7 Trewyn Park, Holsworthy, Devon (GB) EX22 6LS; Bernd Wendt, Schulstr. 30, 86947 Weil (DE); Katherine M. Andrews, 48 Camino de Milagro, Sante Fe, NM (US) 87506

( * ) Notice: Subject to any disclaimer, the term of this patent is extended or adjusted under 35 U.S.C. 154(b) by 0 days.

(21) Appl. No.: 09/825,448

(22) Filed: Apr. 2, 2001

(65) Prior Publication Data
US 2003/0060982 A1 Mar. 27, 2003

(51) Int. Cl.
*G01N 33/48* (2006.01)
(52) U.S. Cl. .............. 702/19; 702/21; 702/22; 702/27; 702/30
(58) Field of Classification Search ............ 702/19, 702/27, 22, 30, 21; 703/11, 12
See application file for complete search history.

(56) References Cited

U.S. PATENT DOCUMENTS 5,418,944 A * 5/1995 DiPace et al. ............... 707/3
6,240,374 B1 * 5/2001 Cramer et al. ............ 435/7.1

FOREIGN PATENT DOCUMENTS

WO  WO 9944055 A1 * 9/1999

* cited by examiner

*Primary Examiner*—John Barlow
*Assistant Examiner*—Stephen J Cherry
(74) *Attorney, Agent, or Firm*—Laurence Weinberger

(57) ABSTRACT

Heterogeneous compound databases can be searched for compounds which are likely to have the same biological activity as a known (query) molecule. Query molecules and the molecules in the database are split into fragments according to common fragmentation rules. Fragments are aligned in a uniform conformation according to a topomeric alignment process and interaction energy fields, typically steric fields, between a probe and the fragment atoms are generated to capture the fragment shapes. Comparison of the fields for the query fragments with the fields for the database compound fragments yields a measure of shape similarity. Searches for similarly shaped substructures and cores can also be readily accomplished. Pharmacophoric style features can be defined for the topomerically aligned fragments but with user specified weighting of the importance of each. Differences in features are defined with the same dimensionality as shape so that both shape and features can be used to search.

14 Claims, 2 Drawing Sheets

METHOD FOR SEARCHING HETEROGENEOUS COMPOUND DATABASES USING TOPOMERIC SHAPE DESCRIPTORS AND PHARMACOPHORIC FEATURES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates generally to the field of pharmaceutical research and to the three dimensional searching of structures of chemical compounds to identify compounds which may share a biological activity with a known compound. In particular the invention concerns a method for searching databases of commercially available compounds which may or may not share any common synthetic linage.

2. Description of Related Art

The advent of high throughput screening of chemical compounds for biological activity has dramatically changed the paradigm of pharmaceutical research in recent years. Coupled with combinatorial synthesis, it is now possible to test millions of compounds on an efficient basis. However, the cost per hit of such searching remains extremely high given the enormous number of compounds which can be tested and the typically low "hit" rates which are achieved. As a result, greater emphasis has been placed on the testing of compound libraries which are believed to contain a higher percentage of potentially relevant molecules. The skills of computational chemists have been employed to design such compound libraries for testing.

Two type of libraries were considered possible: first, a library which explored the diversity of structures in chemical space across the range of compounds which could be synthesized without oversampling the same area of diversity space (redundant testing); and second, a library in which the compounds would be likely to have the same biological activity as a known molecule or drug. The major problem confronting computational chemists in the selection of compounds for such libraries was how to characterize the compounds in a manner which would permit the desired selections. Bioscientists have long known that the three dimensional shape of a compound which acts as a ligand to a larger biomolecule must be complimentary to the shape of the binding site of the larger biomolecule. In studying the relationships between the chemical structure of a molecule and its biological activity (structure activity relationships [SAR]) many techniques to characterize the three dimensional shape of molecules were devised. One of the most successful of the techniques for generating a quantitative structure activity relationship (QSAR) characterized the shape of molecules by defining an interaction energy field between a probe molecule and each part of the studied molecule in a three dimensional grid surrounding the molecule. The shape data thus generated for a series of molecules could be correlated with the biological activity of the molecules to produce the QSAR. This technique by Cramer and Wold (Comparative Molecular Field Analysis [CoMFA]) is described in detail in U.S. Pat. No. 5,025,388 and U.S. Pat. No. 5,307,287.

Use of the CoMFA approach required detailed considerations of two major factors: 1) the proper alignment of the test molecules; and 2) the conformation or conformations of the molecules which had to be taken into account. In addition, the technique worked only with molecules sharing the same biological activity. However, the technique clearly demonstrated the power of utilizing three dimensional shape descriptors in molecular analysis.

Over time many three dimensional shape descriptors and methods of library selection were attempted by computational chemists. U.S. Pat. No. 5,703,792 to Chapman describes one such approach. Two major problems confronted the field and cast doubt on the generality or accuracy of all the methods which had been devised. The first problem was that no one could show that the molecular structural descriptors which had been used were generally valid; that is, that the descriptors described molecules in a manner which correlated with biological activity across a range of biological systems. Any descriptor which would be used to select compounds for libraries would have to be valid irrespective of the biological activity which might be tested against the library. The second problem was that there was likewise no way to demonstrate that the methods of handling multiple conformations in the prior art methods were either accurate or applicable across all types of molecules.

The solution to these problems by Cramer, Patterson, Clark, and Ferguson are taught in U.S. Pat. No. 6,185,506. The validity of a molecular structural descriptor can be demonstrated across multiple biological activities by employing the Patterson plot methodology described in the patent. Both two and three dimensional descriptors can be evaluated by the methodology, and, in principal, there is no limitation on the dimensionality of the descriptors which can be evaluated. Using the validation technique, valid descriptors were identified which could be used with assurance to design libraries having desired properties. By this method the two dimensional prior art fingerprint Tanimoto descriptor was shown to be valid as well as a new three dimensional descriptor described below. The validation methodology also identified a neighborhood distance characteristic of the descriptors which could be used in the design of the libraries. In addition, the neighborhood distance led directly to methods for searching the libraries, and, once a molecule had shown activity in a screen, for expanding the search for other molecules having the same activity.

Further, a solution to the problem of identifying a generally appropriate molecular conformation or conformations to take into account was taught. An alignment rule for molecular parts (topomeric alignment) is demonstrated which generates a uniform orientation. The shape of the molecular part is characterized, as in CoMFA, by a field of interaction energies calculated between a probe and the atoms in the aligned molecular part at each point in a three dimensional grid surrounding the molecular part. The steric interaction energies are principally used although, in the appropriate circumstances, electrostatic interaction energies may be added. Although the alignment may be arbitrary and unlikely for any particular molecule, the field shape descriptor of the topomeric alignments was shown to be a valid molecular structural descriptor by means of the Patterson plot method.

Using descriptors having an associated neighborhood distance, molecules could be identified which shared shape characteristics in a way which was meaningfully related to their biological activity. The problems of efficient library design and selection of combinatorially accessible molecules could be further addressed. In U.S. patent application Ser. No. 08/903,217, presently allowed, the construction and searching of a virtual library is described. The virtual library contains validated molecular structural descriptions of each component part which could be used in a specified combinatorial synthesis. All possible product molecules which could be combinatorially derived from the component parts can be searched, without the necessity of generating the product structures during the search, for product molecules having desired properties by searching through only a combination of the descriptors of the component parts of the product molecules. In the preferred embodiment the Tanimoto and the three dimensional topomeric CoMFA descriptors are employed.

Due to the combinatorial nature of the number of product molecules whose characteristics can be determined, a relatively small number of structural variations (tens of thousands), cores, and synthetic schemes employing only two attachment points can yield a searchable library of billions of possible molecules according to the method of the patent. Indeed, the number of searchable molecules outnumbers the number of molecules ever reported by several orders of magnitude. By the techniques disclosed in the patent, this virtual library can be searched very fast to construct diverse libraries of molecules likely to share the same biological activity or to find molecules which share the same biological activity as a combinatorially derived query molecule. Further, query molecules which derive from unknown synthetic routes can be fragmented and the molecular descriptor characterization of the fragments used to search for similarly shaped fragments and potential molecules with likely similar biological activity defined in the virtual library. In practice the topomeric field molecular structural descriptor has proven to be very valuable in searching the virtual library. The powerful and fast searching capabilities of the virtual library method have yielded significant advances.

However, the molecules in the virtual library which can be searched by definition derive from a combinatorial assembly of a relatively few number of constituent parts and can be said to be homogeneous in that sense. By virtue of the exceedingly large size of the virtual library, 5 molecules may be identified which are not readily available. Also, although the possible product molecules which can be searched are the result of known combinatorial synthetic schemes, the actual synthesis may not be easily achieved. In the day to day world of pharmaceutical research, large assemblages of available molecules can be commercially obtained. These assemblages are not the result of any particular combinatorial synthesis but rather represent the assembly of a wide range of molecules from many different sources and syntheses, some known, some unknown. Therefore, these assemblages of molecules can be characterized as heterogeneous.

It would be useful if heterogeneous assemblages of available molecules could be searched for molecules which are likely to have a biological activity similar to a known compound before synthesis of new compounds is undertaken with the concomitant additional time and expense.

BRIEF SUMMARY OF THE INVENTION

Databases which contain the structures of a heterogenous assembly of available molecules can be searched for molecules having a biological activity similar to a known compound. Each molecule specified by the database is split into several fragments according to defined rules and the shape of those fragments is compared to the shape of the fragments generated from a query molecule using the topomeric field molecular structural descriptor. The molecules having the closest matching shapes to the query molecule are selected for further testing.

DETAILED DESCRIPTION OF THE INVENTION

Figure 1:
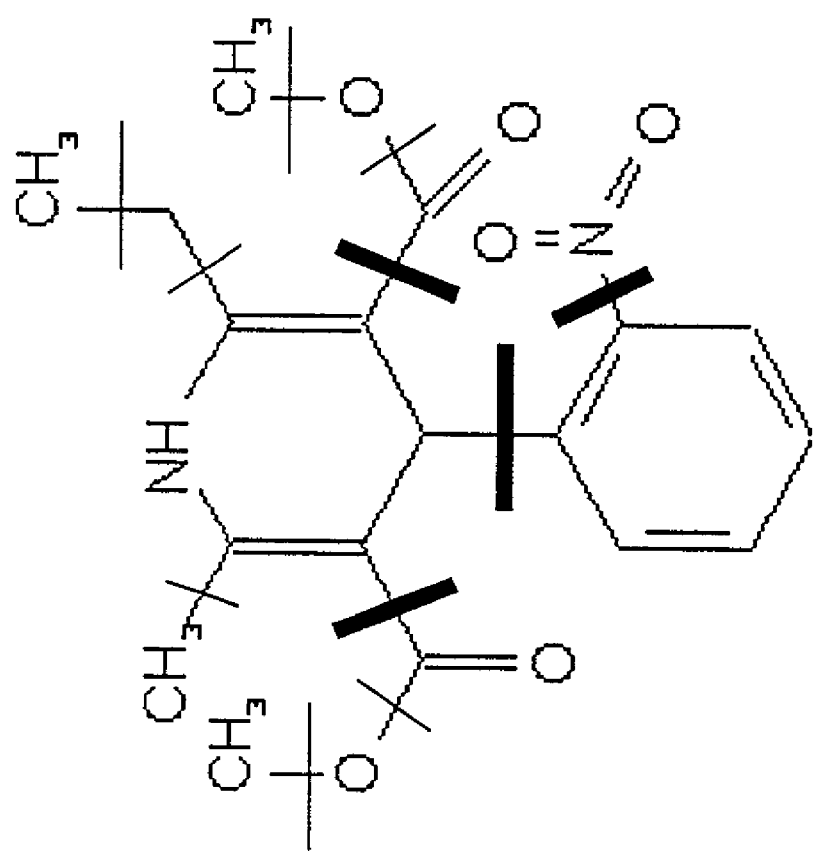
FIG. 1 shows a number of possible ways to fragment a molecule into two pieces in accordance with the fragmentation rule.

Computational Environment:

Generally, all calculations and analyses to perform the method of the disclosed invention are implemented in a modern computational chemistry environment using software designed to handle molecular structures and associated properties and operations. For purposes of this Application, such an environment is specifically referenced. In particular, the computational environment and capabilities of the SYBYL, UNITY, and CONCORD software programs developed and/or marketed by Tripos, Inc. (St. Louis, Mo.) are specifically utilized. The software code to implement the method of the disclosed invention is set out in the Appendices to this Application. Software with similar functionalities to SYBYL, UNITY, and CONCORD are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use Silicon Graphics, Inc. (SGI) "R12000" computers having 350-400 MHz processors and between 256 Mb and 512 Mb of memory with 8-10 Gb hard drive storage disks. In addition SGI "Origin" or "O2" or "O2100" computers can be used. Access to several gigabytes of storage and faster Silicon Graphics, Inc. processors is useful.

Incorporation of Patent Disclosures:

The disclosures of U.S. Pat. No. 6,185,506 and of U.S. patent application Ser. No. 08/903,217 are expressly and completely incorporated into this application as if fully set forth herein.

Topomeric Alignment:

As taught in the incorporated U.S. Patent and patent application, molecular fragments may be aligned following topologically-based rules to generate a single, consistent, unambiguous, aligned topomeric conformation. The procedure also takes full account of chiral atoms. All fragments which are to be compared in a search must be aligned with the same topomeric rules. In the present method such a topomeric alignment is used, the details of which are fully set out in the attached software code.

Calculation of Fields:

The basic CoMFA methodology provides for the calculation of both steric and electrostatic fields. It has been found up to the present point in time that using only the steric fields yields a better molecular structural descriptor than a combination of steric and electrostatic fields. There appear to be three factors responsible for this observation. First is the fact that steric interactions—classical bioisosterism—are certainly the best defined and probably the most important of the selective non-covalent interactions responsible for biological activity. Second, adding the electrostatic interaction energies may not add much more information since the differences in electrostatic fields are not independent of the differences in steric fields. Third, the addition of the electrostatic fields will halve the contribution of the steric field to the differences between one shape and another. This will dilute out the steric contribution and also dilute the neighborhood property. Clearly, reducing the importance of a primary descriptor is not a way to increase accuracy. However, it is certainly possible that in a given special situation the electrostatic contribution might contribute significantly to the overall "shape". Under these unique circumstances, it would be appropriate to also use the electrostatic interaction energies or other molecular characterizers, and such are considered within the scope of this disclosure. In particular, as will be discussed below, it has been found that the additional information typically associated with pharmacophore mapping can be utilized to further characterize the similarity between topomerically aligned molecular fragments.

The steric fields of the topomerically aligned molecular fragments are generated almost exactly as in a standard CoMFA analysis using an $sp^3$ carbon atom as the probe. In standard CoMFA, both the grid spacing and the size of the lattice space for which data points are calculated will depend on the size of the molecule and the resolution desired. Typically, a 2 Å grid spacing in employed both in CoMFA and in the heterogenous database searching method of the present disclosure. However the grid dimensions are varied in the present invention. For query molecules, the size of the grid is adjusted to encompass the smallest region that all of the query fragments will fit into. This significantly reduces the number of calculations that are necessary without reducing the ability of the descriptor to fully characterize the structures. This modification will be discussed in more detail below. The steric fields are set at a cutoff value (maximum value) as in standard CoMFA for lattice points whose total steric interaction with any side-chain atom(s) is greater than the cutoff value.

One difference from the usual CoMFA procedure is that atoms which are separated by one or more rotatable bonds are set to make reduced contributions to the overall steric field. An attenuation factor, preferably about 0.85, is applied to the steric field contributions which result from these atoms. For atoms at the end of a long molecule, the attenuation factor produces very small field contributions (ie: $[0.85]^N$) where N is the number of rotatable bonds. This attenuation factor is applied in recognition of the fact that the rotation of the atoms provides for a flexibility of the molecule which permits the parts of the molecule furthest away from the point of attachment to assume whatever orientation may be imposed by the unknown receptor. If such atoms were weighted equally, the contributions to the fields of the significant steric differences due to the more anchored atoms (whose disposition in the volume defined by the receptor site is most critical) would be overshadowed by the effects of these flexible atoms.

Topomer Similarity:

The notion of topomer similarity between a pair of molecules is defined as the "distance" represented by the difference between the molecular fields which serve to characterize the molecules' shapes. As an example, assume two molecules A and B which have each been placed in their topomeric alignment and the steric field values calculated for each point in the surrounding three dimensional grids. Let each grid point be denoted by its corresponding Cartesian X, Y, Z coordinate so that for each molecule the grid points are defined as $X_0, Y_0, Z_0 \ldots X_N, Y_N, Z_N$.

For each molecule A and B the field values, $V^A$ and $V^B$, at each point in the grid are denoted as:
$V^A_{X0}, V^A_{Y0}, V^A_{Z0} \ldots V^A_{XN}, V^A_{YN}, V^A_{ZN}$ and $V^B_{X0}, V^B_{Y0}, V^B_{Z0} \ldots V^B_{XN}, V^B_{YN}, V^B_{ZN}$.

The root sum square of distances between the fields is then defined as:

$$\sqrt{\begin{array}{l}(V^A_{X0}:V^B_{X0})^2 + (V^A_{Y0}:V^B_{Y0})^2 + (V^A_{Z0}:V^B_{Z0})^2 + \ldots + \\ (V^A_{XN}:V^B_{XN})^2 + (V^A_{YN}:V^B_{YN})^2 + (V^A_{ZN}:V^B_{ZN})^2\end{array}}$$

This distance is conveniently denoted as:

$\sqrt{(A:B)^2}$

For identical molecular structures, the distance equals 0. Therefore, the closer the value of the distance is to zero, the closer in shape two molecules will be. When searching among many possible structures, the minimum calculated value of the distance is sought.

Fragmentation:

The following critical question which frequently occurs in chemical research, and especially in biological research, can now be addressed. The problem, as it is usually presented, takes the form: given an arbitrary query molecule (generally one previously found to exhibit a desired activity), find biologically similar molecules, that is molecules of similar 3D shape and activity. Generally, such a query molecule will not have resulted from a combinatorial synthesis, and, in fact, no knowledge of a possible synthetic route to the molecule may be available. In searching the virtual library of application Ser. No. 08/903,217, the topomeric 3D shape data within the virtual libraries actually describe fragments (structural variations) of molecules. To find similarly shaped molecules within the virtual library, the query molecule must be fragmented and the shapes of its fragments compared with the shapes of corresponding fragments (structural variations) in the virtual library. The difficulty is that a query molecule can be fragmented in so very many ways. The solution adopted for virtual library searching was a way to emphasize those fragmentations that are most likely to conform to efficient synthetic routes from available starting materials, without requiring the searcher of the virtual library to have any knowledge of what synthetic routes it includes.

The solution employed a "fragmentation table", where each row constitutes a rule of the following sort: "for each occurrence of this particular structural feature combination (structural variation) in the query molecule, decompose the query molecule in a particular way specified in terms of this structural feature, and search only those combinatorial libraries that utilize specified reactions (sequences) and/or building blocks, mapping specified query fragments onto specified classes of building blocks". Each such query decomposition found generates a search of the virtual library, returning all those products whose sum of squares of differences in shape between corresponding product and query fragments is less than a user specified neighborhood distance threshold. Passing the query molecule (by means of a suitable computer program) against all the rows of this table generates all searches.

The situation is much more complicated when a search of a database of heterogeneous compounds is desired. Not only is it necessary to fragment the query molecule, but each molecule in the database has to be likewise fragmented and comparisons made between the query fragments and the fragments arising from each molecule. Typically, anywhere from 2 to 50 different fragments might be generated by fragmenting each molecule in the database. To compare 6 fragments from a query molecule to an average of 20 fragments from each of 50,000 molecules in a heterogeneous database would require 6×20×50,000=6,000,000 field comparisons. [Actually, as will be described below, because fragment pairs or triplets are involved, cross comparisons increase this number.] This is at least an order of magnitude greater than the typical 6 fragment query comparison to even 50,000 structural variations in the virtual library. In principal, a virtual library of every fragment occurring in all of the molecules in all examined heterogenous databases could be assembled, but the size of such a virtual library and the complexities of searching are not trivial.

The method adopted for the present invention does not precalculate and store the metric characteristics of each fragment of each heterogenous database molecule. Rather, as each molecule is fragmented, the topomeric alignment and associated field is generated on-the-fly for each fragment and compared to the topomerically aligned field of a query molecule fragment. While the full fragmentation table scheme employed with the virtual library of application Ser. No. 08/903,217 may be employed, experience with fragmentations has shown that for medicinal type molecules the following fragmentation rule (which is a subset of the more general fragmentation method) produces meaningful fragments:

"Break the molecule at acyclic bonds either singly or in pairs to generate sets of either 2 or 3 fragments respectively where each fragment must contain greater than a user specified number of heavy atoms."

Assuming a setting that every fragment must contain at least three heavy atoms, FIG. 1 shows an example of how the rule is applied in a typical molecule (either a query molecule or a database molecule) to generate fragments. To generate the fragments, the whole structure is evaluated for each new fragmentation position. The two-piece fragmentations which will be performed are indicted by the thick lines. The two-piece fragmentations that will not be performed (because one of the resulting fragments contains less than three heavy atoms) are indicated by the thin lines. In this example, if, instead of requiring three heavy atoms, the user required five heavy atoms, then only the fragmentation between the two rings would be performed.

Figure 2:
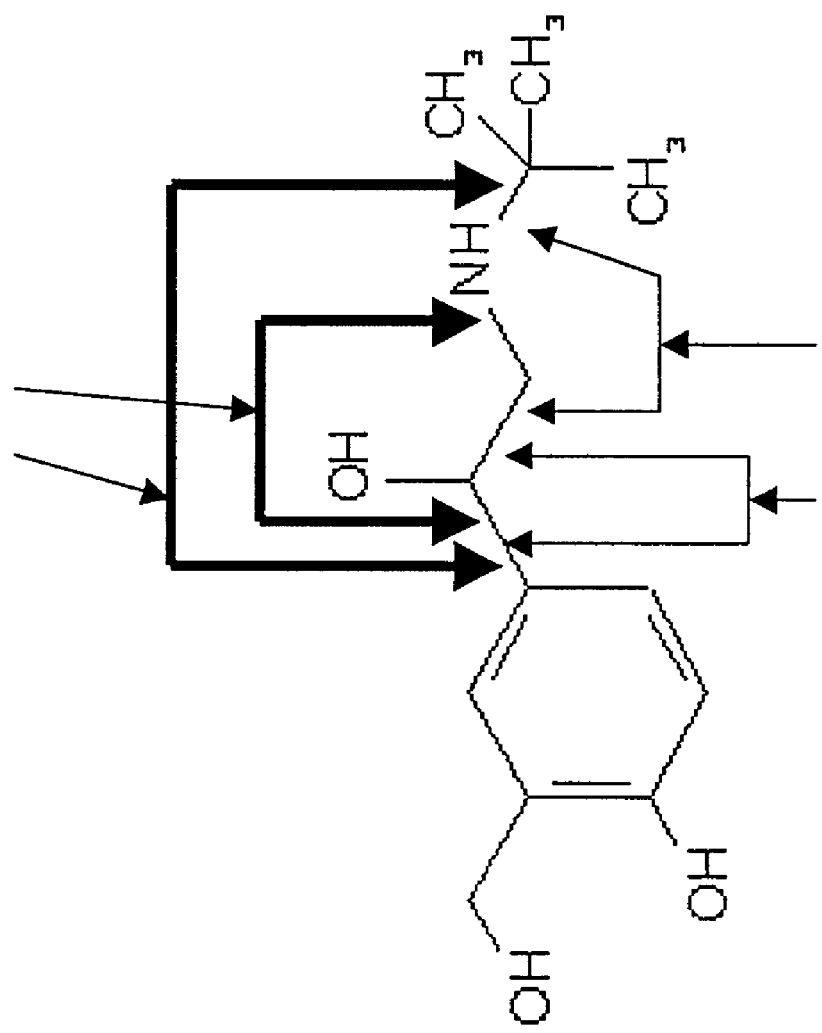
FIG. 2 shows a number of possible ways to fragment a molecule into three pieces in accordance with the fragmentation rule.

An example of a three piece fragmentation is shown in FIG. 2. Assuming again a setting that every fragment must contain at least three heavy atoms, the heavy lines indicate by arrows the two position in which the molecule would be fragmented into 3 fragments. The light lines indicate by arrows some of the three piece fragmentations that will not be performed because at least one of the fragments has fewer than three heavy atoms. If, instead of requiring three heavy atoms, the user required five heavy atoms, then no three-piece fragmentations would be performed.

At the present time, it has been found that generating three fragments is necessary when a two fragment scheme does not yield significant results. The three fragment scheme seems to find similar shapes that are sometimes missed in two fragment analysis. However, due to the higher computational overhead of three fragment searching, searches are first performed at the two fragment level. Four fragment searches may be necessary for some types of molecules, but at the time of filing the present disclosure, such situations have not been identified. Clearly the searching method of the present invention is not limited to the number of fragments which are generated but is generally applicable to as many fragments as the user wishes to consider.

Topomeric 3D Searching:

When analyzing molecules for shape similarity, it should be recognized that not all the elements of a molecule's shape may be required for proper interaction with a larger biomolecule. Perhaps in some instances, the entire shape is critical to the match. In other instances, only part of the molecule's shape may be critical to the match and other parts relatively unimportant. When comparing shapes of query molecules to those found in a heterogenous database, it is important to be able to compare not only the overall shape of the molecules, but also subparts. The method and software of the present invention permit many types of shape comparisons as will be discussed below.

Different heterogenous databases of compounds store compound structures in different formats such as SMILES, SLN, or an MDL format. Many software programs are available for interconverting the structures from one format to another. For the present application, the inventors use UNITY to convert compound information to SLN (Sybyl Line Notation) format. Compound information is then transferred to the CONCORD software program. CONCORD generates the three dimensional structure of the molecule. The starting point for topomeric searching of compounds listed in a heterogenous database are the CONCORD generated three dimensional structures of the database molecules and the query molecule. These structures are provided as input to the software programs set forth in the Appendices to the present disclosure.

The user specified fragmentation pattern (2 or 3 fragments and the number of included heavy atoms) is applied to the query molecule and the first database specified molecule. After each set of shape comparisons, the next database specified molecule is taken up in order. After the fragmentation patterns have been identified for each molecule (query or database), each fragment is aligned according to the topomeric rules.

In the preferred embodiment, the fragment is translated and placed into the grid so that the atom from which the "broken" acyclic bond extends into the fragment of interest is placed at the 0,0,0 coordinate. The "broken" bond (the attachment bond) is then directed along the X axis (standard topomer alignment) and the part of the molecule which is considered the fragment is aligned topomerically in the grided space. Alternatively, the atom in the fragment of interest which is connected to the acyclic bond which is "broken" is placed at the 0,0,0, position. This results in virtually insignificant differences in the topomer distances which are calculated.

Another feature of the present method is that a variable size grid region is used. Since some fragments are small and others large, the same volume of three dimensional grid space is not required to contain each fragment. Nothing is gained by placing a small fragment in a large grid space and only results in calculating an unnecessary number of extra grid location interactions. For the query molecule, the grid is adjusted to encompass the smallest region in which all the query fragments will fit. For database molecule fragments, the initial database molecule grid is one unit larger in all dimensions that the grid determined for the query fragments. The grid size is expanded by one unit in each dimension until the accumulated sum of the grid intersection points (starting with the query grid size and adding all the intersection points contained in each expanded grid) is greater than 10,000 or the grid has been expanded from its initial size by 11 units in each dimension. This procedure is followed since most computers, even those configured for molecular modeling, have a memory capacity which can be exceeded by allowing for unlimited grid size and number of intersection points. The grid size limitations are not required by the inherent method of the invention. Compression of the data from the thousands of data points in a large grid also aids in reducing the memory requirement for large grids. When a situation is encountered where the database molecular fragment extends outside of the maximum grid size, an "outside of the grid" factor is applied my multiplying the number of atoms outside the grid by the maximum interaction energy possible (typically 900) and adding that value as additional term in the root sum of squares similarity calculation. The use of dynamic grid sizing increases the throughput performance of the method considerably.

Whole Molecule Two Piece Comparisons:

As noted, for a two piece comparison both the query molecule and the database molecule are always split into just two pieces at each acyclic bond starting with the whole molecule each time. If there are 4 acyclic bonds and the heavy atom count matches the user selected value (default is typically=4), four two fragment pairs will be generated. As an example of the shape comparison, consider a query molecule which can only be broken at one acyclic bond to form fragments A and B. Consider also that a database molecule can only be broken at one acyclic bond into fragments C and D. Among the four fragments, there are two sets of comparisons possible: A:C & B:D, and A:D & B:C. A first comparison is made between: A:C and B:D. [In the actual calculation the squared differences in the field values between each grid location in each fragment are kept and the square root is only taken at the end of the comparison process.] Thus for the A:C & B:D comparison, a distance is determined as:

$$\sqrt{(A:C)^2 + (B:D)^2}$$

This value is retained for comparison. For the A:D & B:C comparison, a distance is determined as:

$$\sqrt{(A:D)^2 + (B:C)^2}$$

This value is compared to the value determined for the first A:C & B:D set and the lower value (greater similarity) retained. Thus, there are two comparison for each pair of molecules. It has been found that generally one will be significantly more similar than the other. The lower (more similar) value is retained and compared to the values obtained for the query against every other molecule in the database. Ultimately, the molecules in the database which are most similarly shaped to the query molecule will be determined by those with the smallest field difference.

As a further example consider a query molecule which can be broken at four acyclic bonds to form four two fragment pairs and a database molecule which can be broken at five acyclic bonds to form five two fragment pairs. this may be represented as:

| Query | Database |
|-------|----------|
| A | I |
| B | J |
| C | K |
| D | L |
| E | M |
| F | N |
| G | O |
| H | P |
|   | Q |
|   | R |

The first comparison will be A:I & B:J and A:J & B:I. A second comparison will be A:K & B:L and A:L & B:K. Similar comparisons will be obtained between each query fragment pair and each database molecule fragment pair. Of all the comparisons, the one having the smallest difference in field value will be kept for further comparison to the values obtained for all the molecules in the database. These comparison are whole molecule comparison because each fragment of the query molecule is compared to each fragment of every database molecule in sets of two (representing a complete molecule).

Whole Molecule Three Piece Comparisons:

If a three piece fragmentation scheme is employed the same shape comparison principles apply but are further complicated by the presence of the central fragment. In two piece fragmentation, each fragment has only one attachment bond which may be placed at the 0,0,0, grid coordinate. There is, therefore, only one topomeric alignment for the fragment. However, the central fragment in a three piece fragmentation will have two attachment bonds one each at the points were the two side fragments have been severed. There will, therefore, be two starting points for the topomeric alignment which will result in a different topomer shape of the aligned fragment. Each of these shapes must be included in the comparison.

As an example consider a query and a database molecule each which may be broken into three three piece fragmentations:

| Query | Database |
|-------|----------|
| A | J |
| B | K |
| B' | K' |
| C | L |
| D | M |
| E | N |
| E' | N' |
| F | O |
| G | P |
| H | Q |
| H' | Q' |
| I | R |

The primed fragments represent the second orientation of the central fragment of the three. Fields are calculated for all fragments as before. Considering just the first fragment set from both the query and database molecules the first set of distance comparisons are: A:J & B:K & B':K' & C:L and the distances is:

$$\sqrt{(A:J)^2 + (C:L)^2 + [(B:K)^2 + (B':K')^2]/2}$$

The last term takes the average contribution of the center piece. Similarly, the other possible comparisons are calculated as:

$$\sqrt{(A:L)^2+(C:J)^2+[(B:K)^2+(B':K')^2]/2}$$

From the two sets of comparisons, the one with the lower field difference (more similar) is retained for comparison. All the other comparisons between each three fragment set of the query and each three fragment set of the database molecule are calculated and the one with the lowest field difference is retained for comparison with those generated for all the other database molecules.

One further complication which arises with three piece fragmentation is that it is sometimes necessary to apply an attachment bond penalty to the calculated distance to reflect differences in the structure. Since there are two attachment bond points, the spatial relationship between those points will influence the shape of the whole molecule. However, considering just the fragments will not totally reflect the shape characteristics specified by the spatial relationship of the attachment points. This is an attempt to preserve the three dimensional structure of the whole molecule. A penalty value is thus added to the shape differences (increasing the apparent difference or similarity) to compensate. The penalty value is calculated as:

$$\sqrt{[(B:K)2+(B':K')^2]/2}$$

This penalty value is multiplied by an arbitrary factor depending on the user's belief in the significance of the structural difference. The penalty is initially set at 10 in the code but might be set as high as 100. For instance, as an example consider the ortho, meta, and para positional attachment bonds on a ring. The overall molecular shape will vary significantly if two side chains are in the ortho versus the para position with respect to each other. Accordingly, for the 1 atom difference of an ortho relationship, a penalty of 10 would be applied; for the 2 atom difference of a meta relationship, a 20 unit penalty would be applied; and for the 3 atom difference of a para relationship, a penalty of 30 would be applied. The point is that in determining the shape comparisons, a substituent can not just be moved around the ring and have it match without some penalty to reflect the difference in position.

For large molecules small changes in the number of atoms in the molecule is less likely to effect the overall shape than for small molecules. For effective shape comparisons, large structures need to be less sensitive to steric difference while small structures need to be more sensitive to steric differences. Experience has shown that there is a pivot point around 25 heavy atoms with structures considered large with more than 25 heavy atoms. Increasing the weighting of the steric contributions for small structures and decreasing it for larger structures has been found with experimental data sets to cut the number of false positives in half for small structures and allow more hits for large structures without eliminating many small structure hits.

Accordingly, for structures having more than 25 heavy atoms the steric field values calculated for each point in the grid may be decreased by as much as 33% (field values multiplied by 0.67). For structures having fewer than 25 heavy atoms the steric field values calculated for each point in the grid may be increased by as much as 100% (field values multiplied by 2.0). A non-linear multiple seems to work best.

In addition to using a variable grid size, another observation leads to a method of increasing the effectiveness and throughput of the searching methodology. It has been observed that for molecules which have a size difference of over +/−12 heavy atoms, there is little likelihood of finding molecules which match in shape. Consider a query with 20 heavy atoms and a database molecule with 33 heavy atoms. Since to start with there will be 13 atoms in the database molecule which will not be matched in the query, a large distance (dissimilarity) will already be found due to the missing atoms. The likelihood that all of the remaining atoms will lie in equivalent positions so that only the missing atoms will contribute to the difference in field values (and hence in similarity) is vanishingly small. Experimental runs on known data sets bears out this observation. Before any fragmentation is done, the difference in heavy atom size of the query and database compound is determined, and, if the difference is greater than 12 heavy atoms, the comparison is skipped.

Subset Searching:

As noted above, only part of the shape characteristic of many molecules may be responsible for the binding of those molecules to larger biomolecules. Accordingly, a search is desired which would find whether any part of the query molecule has the same shape as any part of the database molecule. This can be thought of as a partial fragment match. The method of this invention directly permits this type of search to be conducted. The query molecule is fragmented into two parts and the database molecule is fragmented into three parts in as many different ways as possible. For each possible three piece fragmentation you get:

| Query | Database |
|-------|----------|
| E     | A        |
| F     | B        |
|       | C        |

In order to determine whether any part of the database molecule matches any part of the query the following comparisons are done:

| | |
|---|---|
| E:A | E:B |
| F:B | F:C |
| F:A | F:B |
| E:B | E:C |

Since you are interested in locating any part of the database molecule which is closely similar in shape to all parts of the query molecule, the difference in heavy atom count exclusion which is applied to whole molecule searching is modified for subset matching. Instead of excluding the search if there is a +/−12 heavy atom difference, for subset searching the exclusion is not applied unless there is a +/−30 heavy atom difference.

Core Searching:

In some instances it is desirable to find another core of similar shape to a known core upon which a series of molecules may be built. For instance, suppose a patented series of compounds can be recognized as built upon a particular core. If that core can be replaced with a similarly shaped but chemically different core, it may be possible to construct an entirely new series of compounds active at the same site without infringing the patented series. To conduct this type of search the core and its two attachment bonds needs to be specified. How the searcher decides on the core structure is up to the searcher. The core is aligned in its two possible topomeric orientations and the fields calculated. The topomerically aligned field of only the central fragment of all possible three piece fragmentations of the database molecules are compared to the core fields as A:C & A':C:

| Query | Database |
|-------|----------|
| A     | B        |
| A'    | C        |
|       | D        |

Again, as before in the case of three fragment searching which involves a central fragment with two attachment positions, attachment penalties can be assigned to better characterize/distinguish the overall molecular shape based on where the attachment bonds are placed with respect to each other on the query core structure. For core searching, the penalty multiplier is typically set at 50. The molecules identified in the database which have central fragments generating the smallest values (greatest similarity) in the comparison to the specified core would be examined for possible use as cores.

Features:

As noted earlier, there may be some circumstances where the electrostatic field may be used in addition to the steric field to characterize the shape of a topomerically aligned fragment. A much more useful characterization has been implemented which extends ideas from pharmacophore modeling for use in searching heterogenous databases of compounds. It is well recognized that certain characteristic interactions of molecules in addition to shape play an important role in determining whether that molecule will bind to a larger biomolecule. Complimentarity of shape permits the molecules to approach each other closely enough for these interactions to take place. In pharmacophore modeling the presence and location of feature classes containing molecular characteristics thought important to the binding of the molecule is tracked as well as the distances and directions between the features. An absence of any given feature in a molecule or a different location is considered to significantly reduce the likelihood of that molecule's binding and, thus, typical pharmacophore modeling is an all or nothing proposition. Clearly, in the present methodology due to the topomeric alignment of fragments all distance and direction attributes of features present in the fragments are lost.

However, an alternative approach to incorporating the characteristic interactions in conjunction with the shape similarity matching described above has proven to generate an exceedingly powerful and accurate discovery methodology. The classic five feature classes are employed: positive charge, negative charge, hydrogen-bond-donating, hydrogen-bond-accepting, and aromatic. When present in either the query molecule or the database molecule, the features are assigned X,Y,Z point locations in the topomer alignment either centered on the relevant atom, or, in the case of aromatic rings, the centroid of the ring is specified. Generating the topomer conformation of a molecular fragment not only fixes the steric shape of that fragment, but is also fixes the Cartesian coordinates of each pharmacophoric feature contained within the fragment. The search strategy can be summarized as finding all the database molecule fragments which have features, similarly located in topomer space and similar in any other detailed feature property, that match each of the features in the topomerized fragments of the query structure.

In keeping with the distance definitions used for steric shape similarity, differences in features are defined with the same dimensionality as shape so that both shape and features can be used to characterize a fragment for searching. Feature by feature differences are also combined in a root sum square rather than a straight sum fashion. Thus, a second feature mismatch would not be as costly as the first one. To determine the feature "distance", each of the pharmacophoric features in the query structure is considered in turn, by identifying the closest feature of the same pharmacophoric class in the database molecule fragment. If there is no such feature or if the nearest such feature is more than 1.5 Å distant, the dissimilarity sum of squares is increased by a maximum of 100×100 units. (Units are chosen to be commensurate with the steric shape units of kcal/mole-Angstrom$^3$.) If there is a matching feature within 0.5 Å, the dissimilarity is set to zero. For a feature separation between 0.5 Å and 1.5 Å the dissimilarity penalty increment is obtained by linear interpolation between 0 and 100×100 unit values. Further, it is possible to scale/weight the feature contribution to increase or decrease its relative contribution with respect to the steric contribution to the observed similarity (distance).

Note that the use of the term "distance" with the feature searching methodology of the present invention is not meant to refer to an actual physical "distance" as considered in traditional pharmacophore techniques. For a two piece fragmentation the distance (similarity) between fragments is calculated as:

| Query | Database |
|-------|----------|
| A     | C        |
| B     | D        |

$$\sqrt{(A{:}C)_{FEATURES}^2 + (A{:}C)_{STERIC}^2 + (B{:}D)_{FEATURES}^2 + (B{:}D)_{STERIC}^2}$$

The cross terms for the A:D and B:C comparisons follow a similar definition as earlier. It has been observed that if the value of:

$$\sqrt{(A{:}C)_{FEATURES}^2 + (B{:}D)_{FEATURES}^2}$$

is too high, the distance will be large (little similarity) and the full calculation including the time consuming calculation of steric field can be skipped. This also increases the effectiveness and throughput of the method.

While the relative weight of each feature's contribution to the field can be varied, in the basic method, an attempt is made to match all features in a query with the nearest feature of the same class in the database molecule. This is similar to a pharmacophore type match, but there is no concern with matching interfeature distances in the topomeric conformation. Further, unlike standard pharmacophore searching, the user is able to assign adjustable penalties in the event that an exact match is not possible. For instance, a nearby spatial match of one type of feature might be more acceptable to the user than a nearby spatial match of another feature. The distance penalty for the spatially mismatched first feature could be set much lower than for a spatially mismatched of the second feature. The features method also permits handling of situations where a feature is present in a database molecule but not in the query molecule. In standard pharmacophore technique, this situation would lead to a total mismatch. However, in the present method the user can assign a distance (similarity) penalty for the absence of the match to the query, but need not totally ignore either the overall shape of the query or the contribution of the other features in judging the similarity of the structures.

Partial Feature Matching:

It is recognized that very frequently the binding of small molecules to receptors is highly dependant on the interaction between hydrogen-bond-donating and hydrogen-bond-accepting atoms. For partial feature matching, the search for charged groups and aromatic rings may be turned off. A large penalty (10,000 units) is applied for donors and acceptors which do not align. In addition, the number of donor or acceptor matches required can be varied. This capability is included since it is recognized that frequently only 2 or 3 groups are required to make a small molecule active. For partial feature matching, all the hydrogen-bond-donating and hydrogen-bond-accepting features are examined but only those generating the lowest 2 or 3 distances (including applicable penalties) across all (A:C, A:D, B:C, & B:D) the fragment comparisons for the compounds are used.

A further variation of the partial feature matching method considers the situation where the user determines that there is only one feature which is most important to match. If that feature is present and properly located, there is no penalty, the field differences are zero and the similarity is great. The flip side of single feature matching is that if the feature doesn't match a very large penalty is imposed to clearly yield a large difference (greater distance and low similarity).

Feature matching has been found to greatly increase the effectiveness of the heterogenous database searching since it compliments the shape specific searching. Use of both steric shape searching and feature searching of a topomerically aligned fragments has been found to be as good as or better than any equivalent 2D searching with fingerprints which has been, until now, the gold standard of searching technologies. In addition, the results of shape and feature similarity searching yields actual molecular structures which chemists recognize as being members of the same class of compounds. Also, unlike fragment searching, molecular structures are clearly identified which can serve as bases for continued development.

The method of the present invention for the first time permits the three dimensional searching of a heterogenous compound database for compounds that are likely to have the same biological activity as a query molecule. The results identify molecular structures having similar shape properties, and, when used with features, similar pharmacophoric properties. The identification of the structural fragments which contribute to the identified similarity provide an insight into the shape requirements of the receptor, and just as importantly, into likely additional molecular structures and corresponding shapes which will likely share the same activity. Thus, lead development is more straight forward from a knowledge of the relevant shape characteristics of the fragments provided by the method of this patent disclosure than from any two dimensional searching technique.

Output:

The most commonly used output reports the single best match between the query molecule and all molecules in the heterogenous database. The two or three piece fragment which was responsible for the match is also reported. A variation of the output, displays the fragment of the best hits and the query fragment that it matches. Once can also ask the system to list all hits with field differences less than some value; in other words a list of the most similar molecules.

The software code written in the C language contained in the Appendices implements all the capacities of the present invention. The CT_TOP.C code provides all the calculation functionalities. DBTOP.C contains the command line interface, the user inputs, code to read the input structures, calls to the CT_TOP.C routines, and output interface. CT_TOP.H lists all the required data structures used. The code needs to be compiled by a standard C compiler before being run as is well understood in the art. All together, all code necessary to fully disclose an enabling embodiment of the invention in the computational chemistry environment specified earlier is set forth in the Appendices.

From the proceeding description of the construction, generation, and searching of a heterogeneous database of molecules, it should be clear that there are many variations which may be employed and, having taught how to generate and search one specific embodiment, all equivalent embodiments are considered within the scope of this disclosure.

While the preceding written description is provided as an aid in understanding, it should be understood that the source code listings appended to this application constitute a complete disclosure of the best mode currently known to the inventors of the methods of heterogeneous database searching.

Thus, while this invention has been particularly described with reference to the drug lead identification art, it is clear that the validation of molecular structural descriptors and their use in selecting structurally diverse sets of chemical compounds can be applied anywhere a large number of compounds is encountered from which a representative subset is desired. Since the implications and advances in the art provided by the methods of this invention are still so new, the entire range of possible uses for the methods of this invention can not be fully described at the present time. However, such as yet identified uses are considered to fall under the teachings and claims of this invention if validated molecular structural descriptors are employed to characterize the diversity of molecules.

APPENDIX "A" - DBTOP.C

```c
#include <stdio.h>
#include <stdlib.h>
#include <malloc.h>
#include <ctype.h>
#include <time.h>
#include <memory.h>
#include "ct.h"
#include "ct_proto.h"
#include "import_proto.h"
#include "utl_mem.h"
#include "utl_scan.h"
#include "utl_set.h"
#include "comfa.h"
#include "parseopt.h"
#include "ct_top.h"

/* Option variables */
static char *hitlist;
static char *UnityDatabase;
static char *UnitySetName;
static char *QueryFileName;
static char *queryDetailFileName;
static double radius = 120.0;
static int min_atoms = -1;
static int AllowTerminalAtoms = -1;
static double reductionFactor = 0.85;
static double attachmentFactor = -1.0;
static double max_attachpen = 100.0; /* 2x attachmentFactor - about 2 angstroms */
static double featureFactor = 1.0;
static double extraFeaturePenalty = 0.1;
static int stericPivot = 30;
static int partialMatch = 0;
static int useFallback = 1;
static int do2piece = 1;
static int do3piece = 1;
static int doSubset = 0;  /* query 2 piece, with structure 3 piece */
static int minHevSubset = -1; /* -1 means to auto adjust, 4 hev atoms less than query */
static int minHev = -1;
static int maxHev = -1;
static int hevDiff = -2;
static int normalize = -1;
static int max_hits = 0;
static int useFeatureCharges = 1;
static char *str_featureWeights;
static char *OutputFileName;
static char *report_modes[] = { "tsv", "tsvd", "regid", "sln", "detail", "core", "matrix",(char *) 0 };
```

```c
static char *region_modes[] = { "normal", "big", "huge", (char *) 0 };
static char *feature_modes[] = { "unitypref", "unity", "topomer", (char *) 0 };
static FeatureSetName featureSet = UseTopomerFeatures;
static int reportWarnings = 1;
static int regionMode;
static double stepSize = 2.0;
static int debugLevel = 2;
static char *debugFileName;
static int res_alloc;
static double *parseFeatureWeights(char *sptr );
int token_string(char *str, char token, int maxtoks, int skipMult, char **tokens );
static int DoCoreSearching( struct CtConnectionTable *qct, FILE *infp, FILE *outfp );
static int TriposSponge(int cnt);
static double getLoad(char *line);

typedef enum
{
        ReportTSV,
        ReportTSVD,
        ReportRegid,
        ReportSln,
        ReportDetail,
        ReportCore,
        ReportMatrix,
        ReportBrief,
        ReportStats,
} ReportMode;

static ReportMode rmode;

/*
        WARNING: If you add or subtract options before -report adjust REPORT_OFFSET accordingly.

*/
#define FEATURE_SET_OFFSET 15
define REPORT_OFFSET 28 static struct ParseOptions Options[] = {
        { "hitlist", ParseOptString, &hitlist,
                "Name of a sln hitlist containing structures to search with 3D coordinates." },
        { "database", ParseOptString, &UnityDatabase,
                "Name of a Sybyl/3DB database\n\tWithout -database or -hitlist stdin is used." },
        { "use_subset", ParseOptString, &UnitySetName,
                "Name of selection set to use vs entire database." },
        { "query", ParseOptString, &QueryFileName,
                "Name     of     a     file     containing     the     query structure.\n-------------------------------------------------------\nField Options\n"},
```

```
{ "distance", ParseOptDouble, &radius,
    "maximum shape units distance to report as a hit, default is 120." },
{ "stericpivot", ParseOptInt, &stericPivot,
    "autoscale steric pivot point. Queries having fewer than N heavy atoms are more sensative to steric differences. \n\t\t0 is disabled. Default 30." },
{ "partialmatch", ParseOptInt, &partialMatch,
    "donor and acceptor partial match. The lowest N HBD/HBA feature penalties contribute to the distance. \n\t\t0 is disabled. Default is 0" },
{ "minatoms", ParseOptInt, &min_atoms,
    "minimum number of HEV atoms per fragment, default is 4. (a negative value sets the minimum number of 2piece splits" },
{ "terminal", ParseOptBoolean, &AllowTerminalAtoms,
    "Use +terminal to enable the counting of terminal atoms, default -terminal." },
{ "hevdiff", ParseOptInt, &hevDiff,
    "Maximum allowed heavy atom count difference to compare compounds, \n\t\tdefault 12 inclusive, 30 with +subset, -1 means disabled." },
{ "hev_min", ParseOptInt, &minHev,
    "Minimum number of heavy atoms required in structure to search. Default 10\n" },
{ "hev_max", ParseOptInt, &maxHev,
    "Maximum number of heavy atoms allowed in structure to search. Default 80\n" },
{ "attach", ParseOptDouble, &attachmentFactor,
    "attachment penalty factor for 3 piece comparisons, default 10.0, 50 for core mode" },
{ "max_attach", ParseOptDouble, &max_attachpen,
    "maximum attachment penalty for core searching -report core, default 100.0 " },
{ "feature", ParseOptDouble, &featureFactor,
    "Feature scaling factor, default 1.0" },
{ "usefeatureset", ParseOptEnum, feature_modes,
    "Default is topomer" },
{ "charge", ParseOptBoolean, &useFeatureCharges,
    "use -charge to disable charge group features, they have a high default penalty " },
{ "weight", ParseOptString, &str_featureWeights,
    "Comma seperated list of 5 feature weights, aromatic, pos charge groups, neg, HBA, HBD, \n\t\tdefault 20,200,200,100,100 " },
{ "extra", ParseOptDouble, &extraFeaturePenalty,
    "Extra feature penalty factor applied to feature weight, default 0.1 " },
{ "arom", ParseOptBoolean, &normalize,
    "Default is false for database, true otherwise -arom disables +arom enables " },
{ "agscale", ParseOptDouble, &reductionFactor,
    "Aggregate scaling factor for rotatable bonds, default 0.85." },
{ "2piece", ParseOptBoolean, &do2piece,
    "Use -2piece to disable 2 piece comparisons." },
{ "3piece", ParseOptBoolean, &do3piece,
    "use -3piece to disable 3 piece comparisons." },
{ "subset", ParseOptBoolean, &doSubset,
    "use +subset to enable subset searching. \n\t\tQuery is allowed to hit larger structure containing a portion of the 2 piece fragmentation." },
{ "stepsize", ParseOptDouble, &stepSize,
    "Step size of the grid points, default 2.0, lower values take longer" },
```

```
        { "fallback", ParseOptBoolean, &useFallback,
                "Use -fallback to disable using smaller minimum atoms when no splitting
occurs.\n--------------------------------------------------------------\nOutput Options\n" },
        { "besthits", ParseOptInt, &max_hits,
                "Will report the compounds with the N lowest shapeunit scores less than or equal to the
-shapeunits value." },
        { "output", ParseOptString, &OutputFileName,
                "Will report results to this filename, default is stdout." },
        { "report", ParseOptEnum, report_modes,
                "Reporting mode, default is TSV " },
        { "qdetail", ParseOptString, &queryDetailFileName,
                "write query fragments to this filename." },
        { "debugFile", ParseOptString, &debugFileName,
                "write debugging information to this file, CAUTION: creates extension amount of
information per compound" },
};

/* static variables */
static top_result **result_root;
static int result_idx;
static int cnt = 0;
static int nhit = 0;
static time_t tnow;

/* local functions */
static FILE *open_input_source(char *unitydb, char *setname, char *hitlist, int *r_ispipe );
static void saveResult(top_result *res, int max_hits, double *r_radius );
static int top_result_compare(const void *vnrec, const void *vtrec );
static void formatTSV(FILE *fp, struct CtConnectionTable *ct, double comfa_diff, int idx);
static int formatDetail(FILE *fp, top_result *res, int reportHitFrags );
static void formatTSVD(FILE *fp, top_result *res );
static void formatRegid(FILE *fp, struct CtConnectionTable *ct, int idx);
static void writeDetailHeader(FILE *fp, ReportMode rmode);
static void writeTSVDHeader(FILE *fp);
static int echo_hitlistLine(char *line);
static void setAttr(struct CtConnectionTable *ct, char *name, char *value );
static void writeQueryDetails(char *fname );

#if 0
#define CACHE_COUNTERS 1
endif int main(int argc, char *argv[] )
{
        FILE *outfp;
        FILE *in_fp;
        FILE *qfp;
```

```
        FILE *dfp = (FILE *) 0;
        int isPipe;
        int i;
        struct CtConnectionTable *ct;
        struct CtConnectionTable *qct;
        struct CtConnectionTable *core_qct;
        char *tptr;
        char *sln;
        char *regid;
        int t_frags, t_2compare, t_3compare, t_fcompare, t_filtered, t_feat;
        int nargs;
        double comfa_diff;
        int filtered;
        top_result *res;
        double *cord;
        int natoms;
        int noCordCnt = 0;
        int mixtures = 0;
        int nParts;
        int keepCts;
        top_result *rptr;
        double outsidePerc;
        int queryHevCount;
        int strHevCount;
        int realHevCount;
        int hevFiltered = 0;
        int strHevDiff;
        double *myFeatureWeights;
#ifdef CACHE_COUNTERS
        int e0, e1;
        long long c0, c1;
endif ifdef M_MXFAST
        mallopt(M_MXFAST,128);
#endif
#ifdef M_BLKSZ
        mallopt(M_BLKSZ,16*1024);
#endif
#ifdef M_FREEHD
        mallopt(M_FREEHD,1);
#endif
#ifdef M_MXCHK
        mallopt(M_MXCHK, 100000);
#endif
```

```
        nargs = UTL_PARSE_OPT( argc, argv, sizeof(Options) / sizeof(struct ParseOptions), Options
);
        if ( !nargs )
                return -1;

#if 0
        if (!LM_STANDALONE_INIT() )
        {
                fprintf(stderr,"License intialization failed.\n");
                return -1;
        }
        if ( !LM_STANDALONE_VALID_LICENSE("QSAR") )
        {
                fprintf(stderr,"A valid QSAR license is required.\n");
                return -1;
        }
endif rmode = ReportTSV;
        if ( Options[REPORT_OFFSET]._explicit )
        {
                tptr = *((char **) Options[REPORT_OFFSET].value);
                if ( !strcmp(tptr,"tsv") )
                        rmode = ReportTSV;
                else if ( !strcmp(tptr,"tsvd") )
                        rmode = ReportTSVD;
                else if ( !strcmp(tptr,"regid" ) )
                        rmode = ReportRegid;
                else if ( !strcmp(tptr,"detail" ) )
                        rmode = ReportDetail;
                else if ( !strcmp(tptr,"sln" ) )
                        rmode = ReportSln;
                else if ( !strcmp(tptr,"core" ) )
                        rmode = ReportCore;
                else if ( !strcmp(tptr,"matrix" ) )
                        rmode = ReportMatrix;
                else
                {
                        fprintf(stderr,"Not a valid reporting option:%s\n", tptr );
                        return -1;
                }
        }
        if ( Options[FEATURE_SET_OFFSET]._explicit )
        {
                tptr = *((char **) Options[FEATURE_SET_OFFSET].value);
                if ( !strcmp(tptr,"topomer" ) )
                        featureSet = UseTopomerFeatures;
                else if ( !strcmp(tptr,"unity" ) )
```

```
                        featureSet = UseUnityFeatures;
            else
                        featureSet = UsePreferredUnityFeatures;
            fprintf(stderr,"Using %s feature set %d\n", tptr, featureSet );
}
if ( hevDiff == -2 )
{
            if ( rmode == ReportCore )
                        hevDiff = -1;
            else if ( doSubset )
                        hevDiff = 30;
            else
                        hevDiff = 12;
}
if ( minHev == -1 )
{
            if ( rmode == ReportCore )
                        minHev = 1;
            else if ( doSubset )
                        minHev = 10;
            else
                        minHev = 10;
}
if ( maxHev == -1 )
{
            if ( rmode == ReportCore )
                        maxHev = 1000;
            else if ( doSubset )
                        maxHev = 80;
            else
                        maxHev = 80;
}
if ( attachmentFactor == -1 )
{
            if ( rmode == ReportCore )
                        attachmentFactor = 50.0;
            else
                        attachmentFactor = 10.0;
}
if ( min_atoms == -1 )
{
            if ( rmode == ReportCore )
                        min_atoms = 1;
            else
                        min_atoms = 4;
}
if ( AllowTerminalAtoms == -1 )
{
```

```
                if ( rmode = = ReportCore )
                        AllowTerminalAtoms = 1;
                else
                        AllowTerminalAtoms = 0;
        }
        if ( normalize = = -1 )                 /* User didn't specify, so auto select based upon input
type */
        {
                if ( UnityDatabase )
                        normalize = 0;
                else
                        normalize = 1;
        }
        if ( !UnityDatabase && !normalize )
                fprintf(stderr,"\nWARNING: Make sure structures in hitlist are in aromatic and
standardized form when using -arom\n\n" );
#if 0
        if ( Options[REGION_OFFSET]._explicit )
        {
                tptr = *((char **) Options[REGION_OFFSET].value);
                if ( !strcmp(tptr,"normal" ) )
                        regionMode = 0;
                else if ( !strcmp(tptr,"big" ) )
                        regionMode = 1;
                else if ( !strcmp(tptr,"huge" ) )
                        regionMode = 2;
                else
                {
                        fprintf(stderr,"not a valid region mode:%s\n", tptr );
                        return -1;
                }
        }
endif if ( stepSize < 1.5 || stepSize > 2.5 )
        {
                fprintf(stderr,"You must be kidding on this stepsize. Please keep between 1.5 and 2.5 .\n"
);
        }
if 0
        TOP_STER_REGION_MODE(regionMode);
#endif
if 0
        if ( rmode != ReportTSV )
        {
                fprintf(stderr,"other report options not supported, see -debugFile \n");
                fprintf(stderr,"What formatting options do you want? \n" );
                goto bailout;
```

```
        }
endif if ( !QueryFileName && rmode != ReportMatrix )
        {
                fprintf(stderr,"No query file specified.\n");
                return -1;
        } qfp = (FILE *) 0;
        if ( rmode != ReportMatrix )
        {
                qfp = fopen(QueryFileName, "r");
                if ( !qfp )
                {
                        fprintf(stderr,"Failed to open query file:%s\n", QueryFileName );
                        return -1;
                }
        } if ( debugFileName )
        {
                dfp = fopen(debugFileName,"w");
                if ( dfp )
                {
                        fprintf(dfp,"#SYBYL/3DB HITLIST\n#@CLASS STRLIST\n");
                        fprintf(dfp,"#@FIELD TS_SID      INT\n");
                        fprintf(dfp,"#@FIELD TS_QID      INT\n");
                }
        } if ( str_featureWeights )
                myFeatureWeights = parseFeatureWeights(str_featureWeights);
        else
                myFeatureWeights = (double *) 0;

in_fp = open_input_source(UnityDatabase, UnitySetName, hitlist, &isPipe );
        if ( !in_fp )
        {
                return -1;
        } if ( OutputFileName )
        {
                outfp = fopen(OutputFileName, "w");
                if ( !outfp )
                {
                        fprintf(stderr,"Failed to open %s for output\n", OutputFileName );
```

```
                goto bailout;
        }
}
else
        outfp = stdout;

keepCts = 0;
if ( rmode = = ReportDetail )
        keepCts = 1;
if ( rmode = = ReportDetail || rmode = = ReportSln )
{
        writeDetailHeader(outfp, rmode );
}
else if (rmode = = ReportTSVD )
        writeTSVDHeader(outfp);
else if (rmode = = ReportTSV)
        fprintf(outfp,"TOPSIM\n");

qct = (struct CtConnectionTable *) 0;
while ( qfp && !qct && UTL_SCAN_GETS(qfp, "\\", (char *) 0, &sln ) > 0 )
{
        if ( *sln = = '#' )
                continue;
        qct = DB_IMPORT_SLN(sln);
        if ( qct )
                queryHevCount = TOP_HEV_COUNT(qct);
} if ( qfp && !qct )
{
        fprintf(stderr,"No query contained in :%s\n", QueryFileName );
bailout:
        if ( isPipe )
                pclose(in_fp);
        return -1;
} if ( rmode = = ReportCore )
{
        core_qct = qct;
        qct = (struct CtConnectionTable *) 0;
}
        if ( TOP_QUERY_OPTIONS(qct, do2piece, do3piece, doSubset, min_atoms, stericPivot, partialMatch,
                AllowTerminalAtoms, useFallback, hevDiff, 0, reductionFactor, featureFactor,
```

```
                attachmentFactor, stepSize,
                        featureSet, useFeatureCharges, myFeatureWeights, extraFeaturePenalty, dfp,
debugLevel) && qct )
        {
                fprintf(stderr,"Failed to setup topomer searching for query.\n");
                fprintf(stderr,"Most likely no 3D coordinates or cannot split query.\n");
                goto bailout;
        }
        if ( rmode = = ReportCore )
        {
                DoCoreSearching(core_qct, in_fp, outfp );
                qct = core_qct;
                goto closeup;
        }
        if ( rmode = = ReportMatrix )
        {
                DoMatrixSearching(in_fp, outfp);
                goto closeup;
        } if ( qct && queryDetailFileName )
        {
                writeQueryDetails(queryDetailFileName);
        } ifdef CACHE_COUNTERS
        e0 = 1;
        e1 = 25;                /* 26 L2 data cache, 25 L1 data cache, see perfex */
        start_counters(e0, e1);
#endif
        while ( UTL_SCAN_GETS(in_fp, "\\", (char *) 0, &sln ) > 0 )
        {
                if ( *sln = = '#' )
                {
                        if ( rmode = = ReportDetail && echo_hitlistLine(sln) )
                                DB_CT_SLN_WRITE(outfp, sln );
                        continue;
                }
                cnt++;

ct = (struct CtConnectionTable *) 0;
                if ( hevDiff > = 0 )
                {
                        strHevCount = slnHevCount(sln);
                        strHevDiff = queryHevCount - strHevCount;
                        if ( strHevDiff < 0 )
                                strHevDiff *= -1;
                        if ( strHevDiff > hevDiff || strHevCount < minHev || strHevCount >
```

```
                    maxHev )
                                        hevFiltered++;
                        else
                                ct = DB_IMPORT_SLN(sln);
                }
                else
                        ct = DB_IMPORT_SLN(sln);

if ( !(cnt % 1000) )
                {
#ifdef CACHE_COUNTERS
                        read_counters(e0, &c0, e1, &c1 );
                        start_counters(e0, e1);
                        fprintf(stderr,"cache miss rate: %8.3lf\n", (double) ( ( (long double) c1 / (long
double) c0 ) ) * 10000.0 );
#endif
#ifdef TRIPOS_VERSION
                        TOP_GET_STATS(!(cnt % 10000), &t_frags, &t_2compare, &t_3compare,
&t_fcompare, &t_filtered, &t_feat, &outsidePerc);
#else
                        TOP_GET_STATS(0, &t_frags, &t_2compare, &t_3compare, &t_fcompare,
&t_filtered, &t_feat, &outsidePerc);
endif if 0
                        if ( outsidePerc > 10.0 )
                        {
                                fprintf(stderr,"Warning %8.4lf percent of the fields evaluated have atoms
outside the field, try using a larger field.\n",
                                        outsidePerc );
                        }
endif
                        time(&tnow);
                        fprintf(stderr,"hit  %3d of  %4d   filtered  %4d  (%d+%d+%d+%d,
No3D+Mix+Hev+Feat) out:%6.3lf Avg Frags: %7.2lf & Comparisons: %7.2lf %s",
                                nhit, cnt, noCordCnt + mixtures + hevFiltered + t_feat, noCordCnt,
mixtures, hevFiltered, t_feat,  outsidePerc,
                                (double) t_frags / (double) cnt,  (double) t_fcompare / (double) cnt,
                                ctime(&tnow) );
#if 0
                        fprintf(stderr,"completed: %d no3D: %d mixtures: %d frags: %d comparisons:
%d %d %d  %8.4lf %8.4lf %8.4lf %8.4lf\n",
                                cnt, noCordCnt, mixtures,
                                t_frags, t_2compare, t_3compare, t_fcompare,
                                (double) t_frags / (double) cnt,
                                (double) t_2compare / (double) cnt,
                                (double) t_3compare / (double) cnt,
                                (double) t_fcompare / (double) cnt );
```

```
endif
                    }
                    if ( !ct )
                            continue;
                    cord = (double *) 0;
                    DB_CT_GET_CT_ATTR(ct, CtCt3DCoordSet, &cord, &natoms );
                    if ( !cord )
                    {
                            DB_CT_DELETE_CT(ct);
                            if ( dfp )
                                    fprintf(dfp, "# compound %d missing cordinates\n", cnt );
                            noCordCnt++;
                            continue;
                    }
                    DB_CT_UTL_COUNT_FRAGS(ct, 0, (int *) 0, 0, (int *) 0, &nParts );
                    if ( nParts != 1 )
                    {
                            DB_CT_DELETE_CT(ct);
                            mixtures++;
                            continue;
                    } if ( normalize )
                    {
                            DB_CT_NORM_AROM(ct);
                            DB_CT_STANDARD(ct, (int *) 0);
                            UTL_ERROR_CLEAR();
                    } if ( max_hits > 0 )
                    {
                            res = TOP_COMPARE_WDETAIL(ct, radius, cnt,keepCts);
                            if ( res )
                            {
                                    nhit++;
                                    saveResult(res, max_hits, &radius );
                            }
                            else
                                    DB_CT_DELETE_CT(ct);
                    }
                    else if ( rmode == ReportDetail || rmode == ReportTSVD || rmode == ReportSln
)
                    {
                            res = TOP_COMPARE_WDETAIL(ct, radius, cnt, keepCts );
                            if ( res )
                            {
                                    nhit++;
                                    if ( rmode == ReportDetail )
```

```
                              formatDetail(outfp, res, 1 );
                      else if ( rmode == ReportSln )
                              formatDetail(outfp, res, 0 );
                      else
                              formatTSVD(outfp,res);
                      TOP_FREE_RESULT(res, 1);
                }
                DB_CT_DELETE_CT(ct);
          }
          else
          {
                comfa_diff = TOP_COMPARE( ct, radius, &filtered, cnt );
                if ( comfa_diff >= 0.0 && ( comfa_diff <= radius || radius < 0.0 ) )
                {
                      nhit++;
                      if ( rmode == ReportTSV)
                              formatTSV(outfp, ct, comfa_diff, cnt );
                      else    /* if ( rmode == ReportRegid ) */
                              formatRegid(outfp, ct, cnt );
                }
                DB_CT_DELETE_CT(ct);
          }
      }
#ifdef TRIPOS_VERSION
      TOP_GET_STATS(1,&t_frags,&t_2compare,&t_3compare,&t_fcompare,&t_filtered,&t_feat,
&outsidePerc);
#else
      TOP_GET_STATS(0,&t_frags,&t_2compare,&t_3compare,&t_fcompare,&t_filtered,&t_feat,
&outsidePerc);
#endif
      time(&tnow);
              fprintf(stderr,"hit   %3d  of   %4d   filtered   %4d   (%d+%d+%d+%d,
No3D+Mix+Hev+Feat) out:%6.3lf Avg Frags: %7.2lf & Comparisons: %7.2lf %s",
                      nhit, cnt, noCordCnt + mixtures + hevFiltered + t_feat, noCordCnt, mixtures,
hevFiltered, t_feat, outsidePerc,
                      (double) t_frags / (double) cnt, (double) t_fcompare / (double) cnt,
                      ctime(&tnow) );
      if ( max_hits > 0 )
      {
              if ( result_idx > 1 && result_idx != max_hits )
                      qsort( (void *) result_root, (size_t) result_idx, (size_t) sizeof(top_result *) ,
                              top_result_compare );
              for ( i = 0; i < max_hits && i < result_idx; i++ )
              {
                      res = result_root[i];
                      if ( !res )
                              continue;
                      if ( rmode == ReportTSV )
```

```
                        formatTSV(outfp, res->ct, res->comfa_diff, res->idx);
                else if ( rmode == ReportTSVD )
                        formatTSVD(outfp, res );
                else if ( rmode == ReportRegid )
                        formatRegid(outfp, res->ct, res->idx );
                else if ( rmode == ReportDetail )
                        formatDetail(outfp, res, 1 );
                else if ( rmode == ReportSln )
                        formatDetail(outfp, res, 0 );
            }
        } for ( i = 0; i < res_alloc; i++ )
        {
                rptr = result_root[i];
                if ( !rptr )
                        continue;
                if ( rptr->ct )
                        DB_CT_DELETE_CT(rptr->ct);
                TOP_FREE_RESULT(rptr, 1);
                result_root[i] = (top_result *) 0;
        }
closeup:
        if ( qct )
                DB_CT_DELETE_CT(qct);
        if ( isPipe )
                pclose(in_fp);
        else if ( in_fp != stdin )
                fclose(in_fp);
        if ( dfp )
                fclose(dfp);
        if (outfp != stdout )
                fclose(outfp);
        if ( rmode != ReportMatrix )
                dump_frag_stats();
        return 0;
} static FILE *open_input_source(char *unitydb, char *setname, char *hitlist, int *r_ispipe )
{
        char *command;
        int len;
        FILE *fp;

if ( unitydb )
        {
                len = strlen(unitydb) + 128;
```

```
                if ( setname )
                        len += strlen(setname);
                command = malloc(len);

if ( setname )
                        sprintf(command,"dbexport -database %s -use_set %s -query regid +coords
-visual '*'", unitydb, setname );
                else
                        sprintf(command,"dbexport -database %s -query regid +coords -visual '*'",
unitydb );

fp = popen(command,"r");
                if ( !fp )
                        fprintf(stderr,"Failed to start the command:\n%s\n", command );
                else
                        *r_ispipe = 1;
                free(command);
                return fp;
        }
        if ( hitlist && strcmp(hitlist,"-") )
        {
                fp = fopen(hitlist,"r");
                if ( !fp )
                        fprintf(stderr,"Failed to open the hitlist: %s\n", hitlist );
                *r_ispipe = 0;
                return fp;
        }
        *r_ispipe = 0;
        return stdin;
} static int top_result_compare(const void *vnrec, const void *vtrec )
{
        top_result **n = (top_result **) vnrec;
        top_result **t = (top_result **) vtrec;
        double cdiff;

cdiff = (*n)->comfa_diff - (*t)->comfa_diff;
        if ( cdiff > 0.0 )
                return 1;
        else if ( cdiff < 0.0 )
                return -1;
        return (*t)->idx - (*n)->idx;
}
```

```c
static void saveResult(top_result *res, int max_hits, double *r_radius )
{
        static int res_max;
        top_result *rptr;
        int i;
        static char *suffix[] = { "th", "st", "nd", "rd" };
        int sidx;

if ( !result_root )
        {
                res_max = max_hits;
                res_alloc = max_hits + 5 + max_hits / 10;   /* a little extra */
                result_root = (top_result **) calloc(res_alloc, sizeof(top_result *) );
        } if ( res )
        {
                result_root[result_idx] = res;
                result_idx++;
                if ( result_idx == res_alloc )
                {
                        qsort( (void *) result_root, (size_t) res_alloc, (size_t) sizeof(top_result *) ,
                                top_result_compare );
                        for ( i = res_max; i < res_alloc; i++ )
                        {
                                rptr = result_root[i];
                                if ( !rptr )
                                        continue;
                                if ( rptr->ct )
                                        DB_CT_DELETE_CT(rptr->ct);
                                TOP_FREE_RESULT(rptr, 1);
                                result_root[i] = (top_result *) 0;
                        } result_idx = res_max;   /* start finding a few more to add in */
                        rptr = result_root[res_max-1];
                        if ( *r_radius && *r_radius > 0.0 &&  rptr->comfa_diff < *r_radius )
                        {
                                sidx = 0;
                                if ( res_max < 4 )
                                        sidx = res_max;
                                fprintf(stderr," %d%s lowest shape distance: %8.2lf old: %8.2lf after: %d\n",
                                                res_max, suffix[ sidx ],
                                                rptr->comfa_diff, *r_radius, cnt );
                                *r_radius = rptr->comfa_diff;
                        }
                }
```

```
        }
} static void setAttr(struct CtConnectionTable *ct, char *name, char *value )
{
        char *tval;

tval = (char *) 0;

DB_CT_GET_CT_ATTR(ct, CtCtUserValue, &tval, name );
        if ( tval )
                DB_CT_UTL_MOD_SIMPLE_CT_ATTR(ct, CtCtUserValue, value, name );
        else
                DB_CT_SET_CT_ATTR(ct, CtCtUserValue, value, name );
        UTL_ERROR_CLEAR();
} static int formatDetail(FILE *fp, top_result *res, int reporthitFrags )
{
        char name[40];
        char value[40];
        int i;
        int noSub;
        struct CtConnectionTable *ct;

if ( !fp || !res || !res->ct )
                return -1;

ct = res->ct;

sprintf(value,"%d", (int) res->comfa_diff );
        setAttr(ct,"TOPSIM", value );

sprintf(value,"%d", (int) res->best2 );
        setAttr(ct,"TS_2P", value );

sprintf(value,"%d", (int) res->best3 );
        setAttr(ct, "TS_3P", value );

if ( doSubset )
        {
                sprintf(value,"%d", (int) res->bestSub );
                setAttr(ct, "TS_SUBSET", value );
        } if ( res->best3 < res->best2 )
```

```
            noSub = 3;
else
            noSub = 2;

if ( !reporthitFrags )
{
        for ( i = 0; i < 3; i++ )
        {
                sprintf(value,"%d", res->qids[i] + 1 );
                sprintf(name,"TS_QID%d", i+1 );
                setAttr(ct, name, value );

sprintf(value,"%d", res->strids[i] +1 );
                sprintf(name,"TS_SID%d", i+1 );
                setAttr(ct,name,value);
        }
        for ( i = 0; i < noSub; i++ )
        {
                sprintf(value,"%8.4lf", res->hexDiffs[i] );
                sprintf(name,"TS_S%d", i+1 );
                setAttr(ct,name,value);
        }
        for ( i = 0; i < noSub; i++ )
        {
                sprintf(value,"%8.4lf", res->featureDiffs[i] );
                sprintf(name,"TS_F%d", i+1 );
                setAttr(ct,name,value);
        }
}
if ( res->attachmentPenalty != 0.0 )
{
        sprintf(value,"%8.3lf", res->attachmentPenalty );
        setAttr(ct,"TS_ATTACH_PEN", value );
}
DB_CT_WRITE(fp, ct );

if ( reporthitFrags )
{
        for ( i = 0; i < noSub; i++ )
        {
                ct = res->strFrags[i];
                if ( !ct )
                        continue;
                sprintf(value,"%8.4lf", res->hexDiffs[i] );
                setAttr(ct, "TS_STERIC", value );

sprintf(value,"%8.4lf", res->featureDiffs[i] );
                setAttr(ct, "TS_FEATURE", value );
```

```c
                sprintf(value,"%d", res->qids[i] + 1);
                setAttr(ct, "TS_QID", value );

sprintf(value,"%d", res->strids[i] + 1 );
                setAttr(ct, "TS_SID", value );

sprintf(value,"%d", res->outside[i] );
                setAttr(ct, "TS_OUTR", value );

DB_CT_WRITE(fp, ct );
            }
        }
        return 0;
} static void formatTSV(FILE *fp, struct CtConnectionTable *ct, double comfa_diff, int idx)
{
        char *regid;

regid = (char *) 0;
        if ( ct )
        {
                DB_CT_GET_CT_ATTR(ct, CtCtRegId, ®id );
                if ( !regid )
                        DB_CT_GET_CT_ATTR(ct, CtCtName, &regid );
        }
        if ( regid )
                fprintf(fp, "%s\t%d\n", regid, (int) comfa_diff );
        else
                fprintf(fp, "Str%d\t%d\n", idx, (int) comfa_diff );
} static void formatRegid(FILE *fp, struct CtConnectionTable *ct, int idx)
{
        char *regid;

regid = (char *) 0;
        if ( ct )
                DB_CT_GET_CT_ATTR(ct, CtCtRegId, &regid );     /* Don't get name, only regid */
        if ( regid )
                fprintf(fp, "%s\n", regid);
        else
                fprintf(fp, "Str%d\n", idx);
} static void formatTSVD(FILE *fp, top_result *res )
{
        char *regid;
```

```c
        char tmpname[20];

regid = (char *) 0;
        if ( res->ct )
        {
                DB_CT_GET_CT_ATTR(res->ct, CtCtRegId, ®id );
                if ( !regid )
                        DB_CT_GET_CT_ATTR(res->ct, CtCtName, &regid );
        }
        if ( !regid )
        {
                sprintf(tmpname,"Str%d", res->idx );
                regid = tmpname;
        }
        if ( doSubset )
                fprintf( fp,
"%s\t%d\t%d\t%d\t%d\t%8.4lf\t%8.4lf\t%8.4lf\t%8.4lf\t%8.4lf\t%8.4lf\t%8.4lf\n",
                        regid,
                        (int) res->comfa_diff, (int) res->best2, (int) res->best3, (int) res->bestSub,
                        res->hexDiffs[0], res->hexDiffs[1], res->hexDiffs[2],
                        res->attachmentPenalty,
                        res->featureDiffs[0], res->featureDiffs[1], res->featureDiffs[2] );
        else
                fprintf( fp,
"%s\t%d\t%d\t%d\t%8.4lf\t%8.4lf\t%8.4lf\t%8.4lf\t%8.4lf\t%8.4lf\t%8.4lf\n",
                        regid,
                        (int) res->comfa_diff, (int) res->best2, (int) res->best3,
                        res->hexDiffs[0], res->hexDiffs[1], res->hexDiffs[2],
                        res->attachmentPenalty,
                        res->featureDiffs[0], res->featureDiffs[1], res->featureDiffs[2] );
} static void writeDetailHeader(FILE *fp, ReportMode rmode)
{ time(&tnow);

fprintf(fp,"#SYBYL/3DB HITLIST\n#\n");
        fprintf(fp,"# Created: %s", ctime(&tnow) );
        fprintf(fp,"#\n#@CLASS STRLIST\n#\n");

fprintf(fp,"#@FIELD TOPSIM\tINT\n");
        fprintf(fp,"#@FIELD TS_2P\tINT\n");
        fprintf(fp,"#@FIELD TS_3P\tINT\n");
        if ( doSubset )
                fprintf(fp,"#@FIELD TS_SUBSET\tINT\n");
        if ( rmode == ReportDetail )
        {
```

```c
            fprintf(fp,"#@FIELD TS_STERIC\tDOUBLE\n");
            fprintf(fp,"#@FIELD TS_FEATURE\tDOUBLE\n");
            fprintf(fp,"#@FIELD TS_QID\tINT\n");
            fprintf(fp,"#@FIELD TS_SID\tINT\n");
            fprintf(fp,"#@FIELD TS_OUTR\tINT\n");
        }
        else
        {
            fprintf(fp,"#@FIELD TS_S1\tDOUBLE\n");
            fprintf(fp,"#@FIELD TS_S2\tDOUBLE\n");
            fprintf(fp,"#@FIELD TS_S3\tDOUBLE\n");
            fprintf(fp,"#@FIELD TS_F1\tDOUBLE\n");
            fprintf(fp,"#@FIELD TS_F2\tDOUBLE\n");
            fprintf(fp,"#@FIELD TS_F3\tDOUBLE\n");
            fprintf(fp,"#@FIELD TS_QID1\tINT\n");
            fprintf(fp,"#@FIELD TS_SID1\tINT\n");
            fprintf(fp,"#@FIELD TS_QID2\tINT\n");
            fprintf(fp,"#@FIELD TS_SID2\tINT\n");
            fprintf(fp,"#@FIELD TS_QID3\tINT\n");
            fprintf(fp,"#@FIELD TS_SID3\tINT\n");
        }
        fprintf(fp,"#@FIELD TS_ATTACH_PEN\tDOUBLE\n");
} static void writeTSVDHeader(FILE *fp)
{
        if ( doSubset )

fprintf(fp,"TOPSIM\tTS_2P\tTS_3P\tTS_SUBSET\tTS_S1\tTS_S2\tTS_S3\tTS_ATTACH_PEN\tFS_F1\tFS_F2\tFS_F3\n" );
        else fprintf(fp,"TOPSIM\tTS_2P\tTS_3P\tTS_S1\tTS_S2\tTS_S3\tTS_ATTACH_PEN\tFS_F1\tFS_F2\tFS_F3\n" );
} static int echo_hitlistLine(char *line)
{
        char *tptr;
        static char *keep_fields[] = { "FIELD", "DATABASE", "QUERY", "CORE", (char *) 0 };
        int i;

if ( *line != '#' || *(line+1) != '@' )
                return 0;

tptr = line+2;
        if ( !*tptr )
                return 0;
```

```
        for ( i = 0; keep_fields[i]; i++ )
        {
                if ( !strncmp(tptr,keep_fields[i], strlen(keep_fields[i]) ) )
                        return 1;
        }
        return 0;
} static void writeQueryDetails(char *fname )
{
        time_t tnow;
        FILE *fp;

fp = fopen(fname,"w");
        if ( !fp )
        {
                fprintf(stderr,"Unable to write to query detail filename: %s\n", fname );
                return;
        } time(&tnow);

fprintf(fp,"#SYBYL/3DB HITLIST\n#\n");
        fprintf(fp,"# Created: %s", ctime(&tnow) );
        fprintf(fp,"#\n#@CLASS STRLIST\n#\n");

fprintf(fp,"#@FIELD TS_QID\tINT\n");

TOP_QUERY_DUMP(fp, "TS_QID");
        fclose(fp);

} static int slnHevCount(char *sln)
{
        char *tptr;
        int inbrace = 0;
        int hevCount = 0;

tptr = sln;

while (*tptr)
        {
                if ( *tptr == '[' )
                {
                        while (*tptr && *tptr != ']' )
                        {
```

```
                if ( *tptr == '"' )
                {
                        tptr++;
                        while (*tptr && *tptr != '"' )
                                tptr++;
                        if (*tptr)
                                tptr++;
                }
                else
                        tptr++;
            }
        }
        if ( isupper(*tptr) && *tptr != 'H' )
                hevCount++;
        if ( *tptr == '<' )
                return hevCount;
        tptr++;
    }
    return hevCount;
} static double *parseFeatureWeights(char *sptr )
{
    static double weights[6];
    char *tokens[7];
    int ntoks;
    int i;

ntoks = token_string(sptr, ',', 6, 0, tokens );

if ( ntoks != 5 )
    {
        fprintf(stderr,"Invalid argument to -weights,  please specify 5 weights for arom,neg,pos,HBA,HBD \n");
        exit(-1);
    }
    for ( i = 0; i < 5; i++ )
    {
        weights[i] = atof(tokens[i]);
        if ( weights[i] < 0.0 )
                weights[i] = 0.0;
    }
    return weights;
}

/* returns the number of tokens found .
```

The string str will be modified, tokens will be modified to the null character
*/
```
int token_string(char *str, char token, int maxtoks, int skipMult, char **tokens )
{
        char *tptr;
        int ntoks;
        int len, idx;
        int intok = 0;

for ( len = 0, tptr = str; *tptr; tptr++, len++ )
        {
                if ( *tptr == token )
                        *tptr = '\0';
        }
        ntoks = idx = 0;
        tptr = str;

if ( !skipMult )
        {
                tokens[0] = str;
                ntoks = 1;
        } while (ntoks < maxtoks && idx < len )
        {
                if ( skipMult )
                {
                        if ( *tptr )
                        {
                                if ( !intok )
                                {
                                        tokens[ntoks++] = tptr;
                                        intok = 1;
                                }
                        }
                        else
                                intok = 0;
                }
                else
                {
                        if ( *tptr == '\0' )
                                tokens[ntoks++] = tptr+1;
                }
                idx++;
                tptr++;
        }
        return ntoks;
}
```

```
static int DoCoreSearching( struct CtConnectionTable *qct, FILE *infp, FILE *outfp )
{
        int cnt = 0;
        int nhit = 0;
        double *cord;
        char *sln;
        struct CtConnectionTable *ct;
        top_result *res;
        int natoms;
        int nParts;
        int hasCore;
        int err;
        static FILE *corefp;
        static int reportCores = -1;
        char *regid;

if ( reportCores == -1 )
        {
                reportCores = 0;
                if ( (sln = getenv("DBTOP_CORES") ) )
                {
                        corefp = fopen(sln,"w");
                        if ( !corefp )
                                fprintf(stderr,"Failed to open %s to report the core regids\n", sln );
                        else
                        {
                                reportCores = 1;
                                fprintf(stderr,"Writing the regid for each structure with a core to %s\n", sln );
                        }
                }
        } time(&tnow);

fprintf(outfp,"#SYBYL/3DB HITLIST\n#\n");
        fprintf(outfp,"# Created: %s", ctime(&tnow) );
        fprintf(outfp,"#\n#@CLASS STRLIST\n#\n");

fprintf(outfp,"#@FIELD CORESIM\tINT\n");
        fprintf(outfp,"#@FIELD TS_UNIQ_ID\tINT\n");
        fprintf(outfp,"#@FIELD TS_HIT_ID\tINT\n");
        fprintf(outfp,"#@FIELD TS_ATTACH_PEN\tINT\n");
        fprintf(outfp,"#@FIELD TS_FEATURE\tINT\n");
        fprintf(outfp,"#@FIELD TS_STERIC\tINT\n");
        fprintf(outfp,"#@FIELD TS_QID\tINT\n");
```

```
err = TOP_CORE_QUERY(qct, outfp);
if ( err )
        return err;

while ( UTL_SCAN_GETS(infp, "\\", (char *) 0, &sln ) > 0 )
{
        if ( *sln == '#' )
                continue;
        cnt++;
        UTL_ERROR_CLEAR();
        ct = DB_IMPORT_SLN(sln);

if ( !(cnt % 1000) )
        {
                time(&tnow);
                fprintf(stderr,"core searching hit %3d of %4d  %s", nhit, cnt, ctime(&tnow) );
        }
        if ( !ct )
                continue;
        cord = (double *) 0;
        DB_CT_GET_CT_ATTR(ct, CtCt3DCoordSet, &cord, &natoms );
        if ( !cord )
        {
                DB_CT_DELETE_CT(ct);
                continue;
        }
        DB_CT_UTL_COUNT_FRAGS(ct, 0, (int *) 0, 0, (int *) 0, &nParts );
        if ( nParts != 1 )
        {
                DB_CT_DELETE_CT(ct);
                continue;
        } if ( normalize )
        {
                DB_CT_NORM_AROM(ct);
                DB_CT_STANDARD(ct, (int *) 0);
        }
        DB_CT_UTL_FIND_RINGS(ct);
        UTL_ERROR_CLEAR();
        regid = (char *) 0;
        DB_CT_GET_CT_ATTR(ct, CtCtRegId, ®id );
        if ( !regid )
                DB_CT_GET_CT_ATTR(ct, CtCtName, &regid );

res = TOP_CORE_SEARCH(ct, radius, max_attachpen, &hasCore );
        if ( corefp && hasCore )
        {
```

```c
                    regid = (char *) 0;
                    DB_CT_GET_CT_ATTR(ct, CtCtRegId, ®id );
                    if ( !regid )
                            DB_CT_GET_CT_ATTR(ct, CtCtName, &regid );
                }
                if ( res )
                {
                        DB_CT_WRITE(outfp, res->strFrags[0] );
                        DB_CT_WRITE(outfp, res->strFrags[1] );
                        fflush(outfp);
                        nhit++;
                }
                DB_CT_DELETE_CT(ct);
        }
        time(&tnow);
        fprintf(stderr,"core searching hit %3d of %4d  %s", nhit, cnt, ctime(&tnow) );
        return 0;
} static int DoMatrixSearching(FILE *infp, FILE *outfp )
{
        char **slns;
        int alloc_slns;
        int nused;
        char *sln;
        int *matrix;
        int i,j;
        int matrixSize;

nused = 0;
        alloc_slns = 501;
        slns = (char **) calloc(alloc_slns, sizeof(char *) );

while ( UTL_SCAN_GETS(infp, "\\", (char *) 0, &sln ) > 0 )
        {
                if ( *sln == '#' )
                        continue;
                if ( nused >= alloc_slns )
                {
                        alloc_slns *= 2;
                        slns = (char **) realloc((char *) slns, alloc_slns * sizeof(char *) );
                }
                slns[nused] = strdup(sln);
                nused++;
        }
        matrix = TOP_MATRIX_SEARCH(slns, nused);
        if ( !matrix )
                return -1;
```

```
            matrixSize = nused * nused;
            for (i = 0; i < matrixSize; i++ )
            {
                    fprintf(outfp,"%d\n", matrix[i]);
            }
    }
```

APPENDIX "B" - CT_TOP.H define TRIPOS_VERSION 1

```c
typedef enum
{
        UseUnityFeatures,
        UsePreferredUnityFeatures,
        UseTopomerFeatures
} FeatureSetName;

typedef struct top_result_def
{
        struct CtConnectionTable *ct;  /* is NOT FREED by TOP_FREE_RESULT, managed by caller */
        int idx;
        void *userdata; /* pointer to something else if needed */
        int filtered;
        double comfa_diff;
        double best2;   /* best 2 piece hit */
        double best3;   /* best 3 piece hit */
        double bestSub; /* best subset hit, when enabled */
        int hit3Piece; /* if true a 3 piece fragment was hit */
        struct CtConnectionTable *qFrags[3]; /* call TOP_FREE_RESULT to free memory, just pointers */
        struct CtConnectionTable *strFrags[3]; /* copies */
        double hexDiffs[3];
        double featureDiffs[3];
        double attachmentPenalty;  /* for 3 piece only */
        int qids[3];
        int strids[3];
        int outside[3];
} top_result;

/* Topomer heterogenius searching functions.
        1st call TOP_QUERY_OPTIONS with the query ct
        2nd call TOP_COMPARE_WDETAIL or TOP_COMPARE to do a topomer comparison
*/

/* only hits return a non nill pointer, use radius = -1.0 to return all results */
int TOP_QUERY_OPTIONS(struct CtConnectionTable *ct, int do2piece, int do3piece, int doSubset, int
minatoms, int autoScale, int partialMatch, int terminalFlag, int fallbackFlag, int hevDiff, int filterFlag,
double reductionFactor, double featureFactor, double attachmentFactor, double stepSize, FeatureSetName
featureSet, int useFeatureCharges, double *feat_weights, double extraPenalty, FILE *queryfp, int
debugLevel );
top_result *TOP_COMPARE_WDETAIL(struct CtConnectionTable *ct, double radius, int idx, int
keepCts );
double TOP_COMPARE(struct CtConnectionTable *ct, double radius, int *filtered, int idx );
```

/* TOP_COMPARE is faster, but no detail is returned, only the comfa_diff, negative upon failure results are returned even if below radius */ void TOP_FREE_RESULT(top_result *res, int freeRef);
void TOP_QUERY_DUMP(FILE *fp, char *id_fieldname );
int TOP_GET_STATS(int dumpRegions, int *r_tfrags, int *r_2compare, int *r_3compare, int *r_fcompare, int *r_filtered, int *r_feat, double *r_outsidePerc );
int TOP_HEV_COUNT(struct CtConnectionTable *ct);
top_result *TOP_CORE_SEARCH(struct CtConnectionTable *ct, double radius, double max_attachpen, int *r_hascore );
int TOP_CORE_QUERY( struct CtConnectionTable *ct, FILE *fp);
int *TOP_MATRIX_SEARCH(char **slns, int numSlns );

APPENDIX "C" - CT_TOP.C

```c
#include <stdio.h>
#include <stdlib.h>
#include <stdarg.h>
#include <ctype.h>
#include <string.h>
include <malloc.h> include "ct.h"
include "import_proto.h"
#include "ct_int.h"
#include "ct_proto.h"
#include "srch2_proto.h"

#include "utl_mem.h"
#include "utl_str.h"
#include "utl_error.h"
#include "set.h"

#include "utl_geom.h"
#include "utl_set.h"
#include "comfa.h"
#include "ct_top.h"

#ifndef TRUE
#define TRUE 1
endif define SPLIT_DEBUG 1
/*
#define DEBUG_VALID_B
#define HEV_STATS 1
#define CALC_BATCH_DIFF 1
#define USE_HEX 1
#define STD_REGION 1
#define NO_COMPRESSION 1
#define NUMBER_OF_COMPRESSION_FIELDS 5
#define NO_STRMAP 1
#define DEBUG_DETAIL 1
*/ define MAX_FEATURES 200 ifdef NUMBER_OF_COMPRESSION_FIELDS
define COMPRESSION_POINTS NUMBER_OF_COMPRESSION_FIELDS * 2
```

```
else
#define COMPRESSION_POINTS 0
endif define NO_REGIONS 11
static int max_regions;
static double qxmin = 999.0;
static double qymin = 999.0;
static double qzmin = 999.0;
static double qxmax = -999.0;
static double qymax = -999.0;
static double qzmax = -999.0;

static double aggreg_descale = 0.85;

struct bond_detail_rec {
        set_ptr to_atts;  /* if this is a topomerically labile bond,
                        points to set of atoms in fragment rooted at "to" */
        int best[3];      /*  "  " , ordered best three attachments to the "to" atom */
        int identical[2];  /*  "  " , TRUE if n'th and n-1'th sttachments are identical */
        int nat1vs2[2];   /*  "  " , difference, in # atoms, between n'th and n-1'th attachment */
        int lastnat[2];   /*  "  " , # ats in n-1'th attachment */
};

struct bond_top_rec {
        int from, to;    /* end atom IDs */
        struct bond_detail_rec *detail;  /* FALSE if bond is not topomerically labile */
} ;

struct top_graph {
        int maxatoms, maxbonds;     /* allocated maximum values */
        int natoms, nbonds;
        int *bstart;     /* pointers to first bond_top_rec for each atom */
        struct bond_top_rec *bstuff;
} ;

typedef struct aromset_def {
        int numAtoms;
        int *atoms;
} AromSet;

typedef struct frag_def {
        int baseAtom;
        int copyBaseAtom;  /* baseAtom is from the Original ct, copyBaseAtom references this ct, the fragment */
        int atomCnt;
```

```
        int hevCnt;
        int aromCnt;
        int id;
        int outside;
        int npoints;    /* number of points in this region, sizeof topField */
        int regionIdx;  /* which region to use, deterines size of *topField */
        int *atoms;
        struct CtConnectionTable *ct;
        double *cords;  /* a pointer into the ct's cordinates, don't free */
        double *topField;
#ifdef STD_REGION
        double *stdField;
        double *stdDiff;
#endif
#ifdef USE_HEX
        char *topHex;
        char *topInt;   /* parsed string of ints , well chars valued 0-15*/
        int topIntSize;
#endif
        double *AtWts;
        double *hexDiff;  /* sizeof number of fragments for comparing against current compound X */
        double *featureDiff;
        double *feature2PDiff;
        double *feature3PDiff;
        double *featureSubsetDiff;
        int *origMapping;    /* Maps this ct's atoms into the ct into Split */
        double *cent;   /* aromCnt * 4, x, y, z, and attrition factor is the 4th double */
        double outsidePenalty;
        double *qtf[NO_REGIONS];  /* query topomer fields */
} Frag;

typedef struct split2_def {
        int bondId;
        int frag1;
        int frag2;
        int *b1;
        int *b2;
#ifndef NO_STRMAP
        int *strMap;         /* size of number of 2 piece fragments in structure see alloc2Map */
        int *subsetMap;              /* size is the number of 3 piece fragmetns in the structure see
allocSubsetMap */
#endif
} split2;

typedef struct split3_def {
        int bond1;
        int bond2;
```

```
        int frag1;
        int frag2;
        int frag3;
        int frag4;
        int *b1;            /* atoms, change to a1,a2,a3 */
        int *b2;
        int *b3;
        int *b4;
#ifndef NO_STRMAP
        int *strMap;        /* size of number of 3 piece fragments in structure see alloc3Map */
#endif
} split3;

typedef struct split_def {
        split2 *s2;
        split3 *s3;
        Frag *frags;
        struct CtConnectionTable *ct;
        int s2cnt;
        int s3cnt;
        int numFrags;
        int atomCount;   /* number of atoms in the ct */
        int *atomMask;      /* Which atoms are Hev atoms, and optionally not terminal atoms */
        int bondCount;   /* Number of bonds in the ct */
        int *bondMask;      /* Bonds where splits occur */
        int *singleBonds;   /* single bonds not in rings, and not to primary atoms, H,Cl,Br */
        int numHev;         /* number of heavy atoms in the ct */
        int *featureMask; /* array the size of atomCount.  Mask representing if this atom is which
features. */
        int featureCnts[5];  /* total number of features, by type */
        int *aromMask;      /* for features, the atoms which hit one of the aromatic patterns */
        int numArom;
        AromSet *aromSets;   /* an array the size of numArom */
        int fragsBuilt;
        int connectedHBTotalCnt;
        int *connectedHBCnt; /* size of atomCount. # of connected atoms which are HBA & HBD and
atom is HBA or HBD */
        int *connectedHBAtoms; /* size of atomCount * 5 */
#ifndef NO_STRMAP
        int alloc2Map;
        int alloc3Map;
        int allocSubsetMap;
#endif
} Split;

typedef struct branch_info_def {
        int toAtom;
```

```
        int chainSize;
        double molWeight;
} branchInfo;

typedef enum
{
        FeatureNone = 0x0,
        FeatureArom = 0x1,
        FeaturePos  = 0x2,
        FeatureNeg  = 0x4,
        FeatureHBA  = 0x8,
        FeatureHBD  = 0x10
} FeatureType;

static FeatureType fMasks[4] = { FeaturePos, FeatureNeg, FeatureHBA, FeatureHBD };

typedef struct feature_pat_def
{
        FeatureType f_type;
        int weight;
        int atomicId;      /* if non-zero this atomic id must be present, Nitrogen and Oxygen are the only ones checked for */
        int ringIndicator; /* if non-zero indicator if must be in ring, 1 is must be ring, -1 must not be in ring */
        char *sln;
        struct CtConnectionTable *ct;
        void *pattern;
} FeaturePattern;

typedef struct {
  fpt lo[3],       /* corner with lowest values for each axis     */
      hi[3],       /*    "      "  hi-est  "    "   "    "        */
      stepsize[3]; /* increment between points                    */
  int nstep[3],    /* derived as 1 + (hi-lo + epsilon) / stepsize */
      n;           /* n = product of nstep[i]                     */
  int atom_type;   /* SYBYL atom type, for steric energy computation */
  fpt pt_charge;   /* elemental charge at point, for electrostatics */
  fpt *weight;     /* weight[n] is applied in all computations,e.g=1 */
  int avg_type;    /* box of 'scale', sphere, sphere x vdw, ...?  */
  fpt avg_scale;   /* scale whose meaning derived from avg_type   */
  int arb,         /*    arbitrary int for later use              */
      *parb;       /*    "      pointer "    "                    */
      } l_Box, *l_BoxPtr ;

typedef struct {
  char *filename ;  /* name of the region's file (if any)         */
  int n_boxes;      /* number of boxes which make up the region   */
  int n_points ;    /* number of points in this region altogether */
```

```
l_BoxPtr box_array;    /* box_array[n_regions], each one a Box    */
int n_refs       ;     /* number of CURRENT references to this memory */
long when_made;        /* creation stamp                          */
      } l_ComfaRegion, *l_RegionPtr ;

typedef struct {
        unsigned int crc;
        char *sln;
        int hitcnt;
} UniqSln;

static l_ComfaRegion *regions[NO_REGIONS];
static int regionUseCnts[NO_REGIONS];
static l_RegionPtr stdRegion;
static int minRegion;
static int minRegion2P;
static int minRegion3P;

static int tot_frags;
static int tot_uniq_frags;
static int compounds;
static int searchCnt;

static int t_2compare;
static int t_3compare;
static int t_fcompare;
static int t_filtered;
static int t_featFiltered;
static int t_outside;
static int t_fields;

static int *g_atomDist;
static struct CtConnectionTable *g_ct;

static double def_featureWeights[6] = { 20.0, 200.0, 200.0, 100.0, 100.0 };
static double featureWeights[6]     = { 20.0, 200.0, 200.0, 100.0, 100.0 };

/* Local prototypes */ struct top_graph *TOP_INIT_GRAPH( struct top_graph *g, struct CtConnectionTable *ct );
static void ashow( set_ptr aset );
static Split *FindBreakPoints(CtConnectionTable *ct, int minHev, int termflag, int createFrags );
static int *findDirectionalNeighbors(CtConnectionTable *ct, int atomIdx, int terminalAtomIdx, int
``` termIdx2 );
static double *computeVdwWeights(CtConnectionTable *ct, int atomIdx, int terminalAtomIdx, double reductionFactor, int **r_covered );
static int *createAtomMask(CtConnectionTable *ct, int termflag, int *r_hevCount);
static int validBreakPoint(CtConnectionTable *ct, int bondidx, int *atomMask, int minHev, int termflag, int rb1, int rb2 );
static int addSplit2(int bondId, int *b1, int *b2 );
static int addSplit3(int atomCnt, int bond1, int bond2, int *b1, int *b2, int *b3, int firstBase, int secondBase );
static void freeSplit(Split *s);
static void freeSplit2(split2 *s2, int cnt );
static void freeSplit3(split3 *s3, int cnt );
static void freeFrags(Frag *f, int cnt );
static void freeFragCts(Split *S);
static int freeStrMap(Split *S);
static int atomsOverlap(int atomcnt, int *b1, int *b2);
static int hevCount(int atomcnt, int *b, int *atomMask, int *r_numAtoms );
static int createFrag(int atomCnt, int *atoms, int *atomMask, int checkDup );
static Frag *createUniqFrags(int atomCnt, split2 *s2, int nums2, split3 *s3, int nums3, int *atomMask, int *r_numFrags );
static int getAtomIds(CtConnectionTable *ct, int a1, int *r_a2, int *r_a3 );
static double fieldHexDiff( char *cptr, char *cqtr, int nosq );
static double CompareAllFeatures(Split *query, Split *str, double radius );
static double CompareTwoCompounds(Split *query, Split *str, double radius, int *r_qidx, int *r_sidx, int *r_splitidx, int *r_three, int *r_subsetHit, double *best2, double *best3, double *bestSub, double *r_atp, int bailedout );
char *CT_FIELD2HEX( double *field, int size );
static char *hexStringToInts(char *cptr, int *r_size);
static double fieldIntDiff( char *cptr, char *cqtr, int s1, int s2 );
static double topFieldDiff(double *qry, double *str, int npoints );
static double topFieldCompressedDiff(double *qry, double *str, int npoints, double startPenalty );
static double fieldIntDiffSq( unsigned short *cptr, unsigned short *cqtr, int s1, int s2);
static double *computePathWeights(struct CtConnectionTable *ct, int baseAtom, int *atomDist, int *featureMask, int *ctMap );
static int getFromAtom(struct CtConnectionTable *ct, int *atomdist, double *molWeights, int atom, int toAtom, int baseAtom, double *cord );
static int debugHits( FILE *fp, Split *query, Split *str, int bestq, int bestStr, int bestIdx, int threeMatched );
static int topAlignCt(struct CtConnectionTable *ct, int baseAtom, int *featureMask, int *ctMapping );
static int traverseBranch( struct CtConnectionTable *ct, int atomId, int *atomdist, double *molweight, int rootToAtom, int *r_toatom, int *r_length, double *r_weight );
static int *findLargestBranch(struct CtConnectionTable *ct, int *atomdist, double *weights );
static CtBond *getBond(struct CtConnectionTable *ct, int id1, int id2 );
static int setTorsion(double *coo, int nAtoms, int a1, int a2, int a3, int a4, double value );
static int reflectAtoms( double *coo, int nAtoms, int npt, int *aplane );
static int setBaseTorsion(double *coo, int nAtoms, int a3, int a4, double value );
static int setRootTorsion(double *coo, int nAtoms, int a2, int a3, int a4, double value );
static int get_details( top_result *res, Split *query, Split *str, int bestq, int bestStr, int bestIdx, int threeMatched, int subsetHit, int keepCts );
static top_result *top_compare(struct CtConnectionTable *ct, double radius, int details, int idx, int keepCts );
static struct CtConnectionTable *makeFragCopy(struct CtConnectionTable *ct, int id, int hexdiff );
static void writeCopy(FILE *fp, struct CtConnectionTable *ct, int id, int hexdiff, char *fieldname );
static void setAttr(struct CtConnectionTable *ct, char *name, char *value );
static double computeAttachmentPenalty( Frag *qry, Frag *str, Frag *other_qry, Frag *other_str );
static FeaturePattern *InitFeaturePatterns(int *r_numPatterns);
static int SearchForFeatures(Split *S);
static int computeCentroid( double *cords, int *atoms, int numAtoms, double *r_x, double *r_y, double *r_z );
static void addCentroid(Frag *fptr, int natoms, double attrFact, double x, double y, double z );
static double compareFeatures(Split *qs, Frag *qry, Split *ss, Frag *str, int query2ndAttach, int str2ndAttach );
static double featureScaling(int *featureCnts, int *extraFeatureCnts, double *featureContributions, int nbest );
static int BuildTopomers(CtConnectionTable *ct, Split *S, Split *query);
static int BuildFrags(Split *S);
static int atomsOutside(double *coords, int natoms, l_RegionPtr regp, double *atwts, double *r_outpen );
static int makeTopRegions(double stepSize, int numFrags);
static l_RegionPtr getRegionToUse(double *coords, int natoms, int *r_idx, int *n_points );
static void getQueryExtents(double *coords, int atomCnt );
static int getCordExtents(double *coords, int natoms, double *r_minx, double *r_miny, double *r_minz, double *r_maxx, double *r_maxy, double *r_maxz );
static double *compressField(double *fptr, int npoints );
static int compareFields(double *orig, double *atombased, int npoints );
static void stripCharge(struct CtConnectionTable *ct, CtAtom *aptr, int atomidx);
static int dupCheckCore(struct CtConnectionTable *ct, int *r_uniqid, int *r_hitid );
struct CtConnectionTable *getLargestFrag(struct CtConnectionTable *ct );
static void CoverConnectedHB(Split *qs, struct CtConnectionTable *ct, double *HB);
static int double_compare(const void *vnrec, const void *vtrec );
static double MeasureClosest(Split *qs, Frag *q1, Split *str, Frag *f1, double *da, double *aa, int *r_nofeatures);
static void PartialMatchFeatures(Split *qs, int mode, Frag *q1, Frag *q2, Frag *q3, Frag *q4, Split *str, Frag *f1, Frag *f2, Frag *f3, Frag *f4, int matchCnt );
static int makeSplit3(CtConnectionTable *ct, int *atomMask, split2 *sall, int cnt, int minHev );
static int getFromChiralAtoms(struct CtConnectionTable *ct, int *atomdist, double *molw, int atom, int toAtom, int *r_fromAtom, int *r_toatom);
static int getFromRingCount(struct CtConnectionTable *ct, int *atomdist, int atom, int toAtom );
static double get_path_mw( set_ptr aset, struct CtConnectionTable *ct, double mw );

static split2 *g_split2;
static int g_splitcnt;
static int g_splitalloc;

static split3 *g_split3;

```
static int g_split3Cnt;
static int g_split3Alloc;

static Frag *g_fragHead;
static int g_fragCnt;
static int g_fragAlloc;

static char *regid;

/* Query options */
static struct CtConnectionTable *q_ct;
static double q_bailout;
static FeatureSetName q_featureSet;
static int q_useFeatureCharges;
static double q_attachPenFactor = 100.0;
static double q_featureFactor = 1.0;
static double q_extraFeatureFactor = 0.1;
static int q_minatoms;  /* minimum HEV atoms per fragment */
static int q_autoScale; /* automatic scaling of sensativity of neighbors based upon the query. */
static int q_partialMatch; /* partial match count for HBA and HBD */
static double autoScaleFactor;  /* steric auto scaling factor */
static int q_termFlag;  /* if TRUE term atoms are counted */
static int q_do2piece;  /* if TRUE do 2 piece comparisons */
static int q_do3piece;  /* if TRUE do 3 piece comparisons */
static int q_doSubset;  /* if TRUE do subset comparisions, 2 piece query with 3 piece structure. Hit larger compounds */
static int q_minSubsetSize = 15;
static int q_matrixMode;
static int q_coremode;
static int q_coremode_align;
static int q_fallback; /* if TRUE fallback on minatoms to 3 and count terminal atoms */
static int q_hevDiff;     /* maximum allowed hev atoms, inclusive */
static int q_filter;      /* if TRUE filtering is enabled */
static int q_regionMode;
static double q_stepSize = 2.0;
static double q_ReductionFactor = 0.85;  /* reduction factor */
static int q_debugLevel;
static FILE *q_debugfp;
static FILE *debug2;
static Split *qs; /* query split structure & topomers */ static int qmode;

if 0
int top_test_debug(char *fname)
{
        if ( debug_fp )
```

```c
            fclose(debug_fp);
        debug_fp = (FILE *) 0;
        if ( fname )
            debug_fp = fopen(fname,"w");
        return 0;
}
endif int TOP_QUERY_OPTIONS(struct CtConnectionTable *ct,
        int do2piece, int do3piece, int doSubset, int minatoms, int autoScaleSteric, int partialMatch,
        int terminalFlag, int fallbackFlag, int hevDiff, int filterFlag,
        double reductionFactor, double featureFactor, double attachmentFactor,
        double stepSize, FeatureSetName featureSet, int useFeatureCharges, double *feat_weights, double extraPenalty,
        FILE *debug_fp, int debugLevel )
{
        int i;
        double *cord;
        double *wptr;
        int numSplits;

if (ct && !DB_CT_GET_CT_ATTR( ct, CtCt3DCoordSet, &cord, &i))
        {
                UTL_ERROR_CLEAR();
                return -1;
        }
        UTL_ERROR_CLEAR();

if ( feat_weights )
                wptr = feat_weights;
        else
                wptr = def_featureWeights;

if ( useFeatureCharges )
                def_featureWeights[1] = def_featureWeights[2] = 0.0;
        else
                def_featureWeights[1] = def_featureWeights[2] = 200.0;

for ( i = 0; i < 5; i++ )
                featureWeights[i] = wptr[i];

qmode = 1;
        if ( ct )
        {
                DB_CT_NORM_AROM(ct);
                DB_CT_STANDARD(ct, (int *) 0);
```

```
        DB_CT_UTL_FIND_RINGS(ct);
} numSplits = 8;
if ( minatoms < -1 )
{
        fallbackFlag = numSplits = minatoms * -1;
        minatoms = ct->atomCount / 2;
}
q_featureSet = featureSet;
q_useFeatureCharges = useFeatureCharges;
q_extraFeatureFactor = extraPenalty;
q_minatoms = minatoms;
q_autoScale = autoScaleSteric;
if ( q_autoScale < 0 )
        q_autoScale = 0;
if ( q_autoScale && q_autoScale < 20 )
        q_autoScale = 20;
q_partialMatch = partialMatch;
q_termFlag = terminalFlag;
q_do2piece = do2piece;
q_do3piece = do3piece;
q_doSubset = doSubset;
q_fallback = fallbackFlag;
q_filter  = filterFlag;
q_debugfp = debug_fp;
q_debugLevel = debugLevel;
q_hevDiff = hevDiff;
q_ReductionFactor = reductionFactor;
q_featureFactor = featureFactor;
q_attachPenFactor = attachmentFactor * attachmentFactor; /* square what is passed in */
q_stepSize = stepSize;

if ( ct )
{
        fprintf(stderr,"Initializing query...\n");
        qs = FindBreakPoints(ct, minatoms, terminalFlag, TRUE );
        i = minatoms;
        if ( terminalFlag == 0 )
                i--;
        if ( q_fallback > 1 )
        {
                while ( ((!qs || qs->s2cnt < q_fallback ) && i >= 3)
                {
                        if ( qs )
                                freeSplit(qs);
                        qs = FindBreakPoints(ct, i, 1, TRUE );
                        q_minatoms = i;
```

```
#ifdef TRIPOS_VERSION
            if ( qs )
                    fprintf(stderr,"Minatoms: %d    number of fragments: %d
2piece:%d 3piece: %d\n",
                                    i, qs->numFrags, qs->s2cnt, qs->s3cnt );
#endif
            i--;
         }
      }
      else
      {
            if ( !qs || qs->numFrags == 0 )
                fallbackFlag = 1;
            while ( (!qs || qs->numFrags == 0) && i >= 3)
            {
                if ( qs )
                        freeSplit(qs);
                qs = FindBreakPoints(ct, i, 1, TRUE );
                i--;
            }
      }
#ifdef TRIPOS_VERSION
         if ( q_minatoms != minatoms )
                fprintf(stderr,"running the query with a minimum heavy atom count of %d vs
%d\n", q_minatoms, minatoms );
#endif
         if ( qs )
         {
            qs->ct = ct;
            SearchForFeatures(qs);
            BuildFrags(qs);
            BuildTopomers(ct, qs, (Split *) 0);
         }
         fprintf(stderr,"query initialized.\n");
         qmode = 0;
         if ( qs && qs->numFrags > 0 )
         {
                        /* 25 is just a guess as of right now, 1/19/01. Need to evaluate.
                        Small structures are hitting too many compounds. So we
need to make the steric and features more sensative
                        large structures are not hitting enough structures so make
less sensative.

example values: 12 hev atoms  25.0 / 12.0  ~ = 2.1
increases the steric contribution by a little bit more than twice as much.
                                                      50 hev atoms 25.0 / 50.0
= 0.5 would decrease the steric contribution by half. This may be too much
                                                      75 hev atoms 25.0 / 75.0
```

```
        = 0.33 would decrease the steric contribution by 1/3. again maybe too much.
            */
                if ( q_autoScale )
                {
                        autoScaleFactor = (double) q_autoScale / (double) qs->numHev ;  /*
based upon average drug like structure containing 25 heavy atoms */
                        if ( autoScaleFactor < 1.0 )
                                autoScaleFactor = (2.0 + autoScaleFactor) / 3.0;
                        fprintf(stderr,"Auto steric scaling factor : %8.2lf\n", autoScaleFactor );
                }
                else
                        autoScaleFactor = 1.0;
                return 0;  /* everything is just fine, found some fragments */
        }
        if ( qs )
        {
                freeSplit(qs);
                qs = (Split *) 0;
        }
    }
    qmode = 0;
    return -2;  /* failed */
} void TOP_QUERY_DUMP(FILE *fp, char *id_fieldname )
{
    int i;
    Frag *f;

if ( !fp || !id_fieldname || !qs )
            return;

if ( qs->ct )
            DB_CT_WRITE(fp, qs->ct);
    for ( i = 0; i < qs->numFrags; i++ )
    {
            f = qs->frags + i;
            if ( f->ct )
                    writeCopy(fp,f->ct, i, -1, id_fieldname );
    }
} top_result *TOP_COMPARE_WDETAIL( struct CtConnectionTable *ct, double radius, int idx, int keepCts )
{
    top_result *res;
    top_result *rescopy;
```

```c
        if ( radius <= 0.0 )
                radius = 99999.9;

res = top_compare(ct, radius, 1, idx, keepCts );
        if ( res && res->comfa_diff <= radius )
        {
                rescopy = (top_result *) malloc(sizeof(top_result) );
                memcpy((char *) rescopy, (char *) res, sizeof(top_result) );
                return rescopy;
        }
        else if ( res )
        {
                TOP_FREE_RESULT(res, 0 );
        }
        return (top_result *) 0;
}

/*
    Compare the ct structure with 3D coordinates with
    the ct specified to TOP_QUERY_OPTIONS,
    returns the topomeric difference or a negative value upon
    failure or being filtered out.
    returns the filtered status through the filtered pointer.

The input radius is passed in for filtering reasons
*/ double TOP_COMPARE(struct CtConnectionTable *ct, double radius, int *filtered, int idx )
{
        top_result *res;
        double comfa_diff;

UTL_ERROR_CLEAR();
        *filtered = 0;
        if ( radius <= 0.0 )
                radius = 99999.9;
        res = top_compare(ct, radius, 0, idx, 0 );
        if ( res )
        {
                comfa_diff = res->comfa_diff;
                TOP_FREE_RESULT(res,0);
                return comfa_diff;
        }
        return -1.0;
} static top_result *top_compare(struct CtConnectionTable *ct, double radius, int details, int idx, int keepCts )
```

```
{
        static top_result ts[1];
        int i;
        Split *s;
        double *cord;
        double comfa_diff, best2, best3;
        int qidx, sidx, splitidx, splitInThree, subsetHit;
        int bailedout;
        int strmin;
        static int env_minSubsetSize = -1;
#ifdef HEV_STATS
        static FILE *bfp;
        char *regid;
endif UTL_ERROR_CLEAR();
        if (!DB_CT_GET_CT_ATTR( ct, CtCt3DCoordSet, &cord, &i))
                return (top_result *) 0;
        DB_CT_UTL_FIND_RINGS(ct);

if ( q_fallback > 1 )
        {
                i = strmin = ct->atomCount / 2;
                s = FindBreakPoints(ct, i, q_termFlag, TRUE );
                if ( q_termFlag )
                        i--;
                while ( ( (!s || s->s2cnt < q_fallback ) && i )
                {
                        if ( s )
                                freeSplit(s);
                        strmin = i;
                        i--;
                        s = FindBreakPoints(ct, i, 1, TRUE );
                }
if 0
                fprintf(stderr,"structure min atoms:%d\n", strmin );
#endif
        }
        else
        {
                searchCnt++;
                s = FindBreakPoints(ct, q_minatoms, q_termFlag, TRUE );
                if ( !s )
                        return (top_result *) 0;
                i = q_minatoms;
                if ( q_termFlag )
                        i--;
```

```
            while ( s && s->numFrags == 0 && i && q_fallback )
            {
                    freeSplit(s);
                    s = FindBreakPoints(ct, i, 1, TRUE );
                    i--;
            }
    }
    if ( !s || !s->s2cnt )
    {
            if ( s )
                    freeSplit(s);
            return (top_result *) 0;
    } if ( env_minSubsetSize == -1 )
    {
            char *tptr;

tptr = getenv("DBTOP_MIN_HEV");
            if ( tptr )
            {
                    env_minSubsetSize = atoi(tptr);
                    if ( env_minSubsetSize < 0 )
                            env_minSubsetSize = 0;
            }
            else
                    env_minSubsetSize = 0;
    } q_minSubsetSize = env_minSubsetSize;   /* qs->numHev - # some number */
    q_bailout = radius * radius;
    memset((char *) ts, '\0', sizeof(top_result) );
    s->ct = ct;
    SearchForFeatures(s);
    if ( q_featureFactor > 0.0 )
            ts->comfa_diff = CompareAllFeatures(qs,s,radius );
    if ( ts->comfa_diff <= radius )
    {
            if ( q_featureFactor > 0.0 )
                    BuildTopomers(ct, s, qs);
            else
                    BuildTopomers(ct, s, (Split *) 0 );
            ts->comfa_diff = CompareTwoCompounds(qs, s, radius, &qidx, &sidx, &splitidx,
&splitInThree, &subsetHit,
                                        &(ts->best2),  &(ts->best3),  &(ts->bestSub),
&(ts->attachmentPenalty), bailedout );
    }
    else
```

```
        {
                t_featFiltered++;
                qidx = -1;      /* Indicate no indexing */
        }
        ts->ct = ct;    /* save a pointer to the ct being compared */
        ts->idx = idx;

#ifdef HEV_STATS
        regid = (char *) 0;
        DB_CT_GET_CT_ATTR(ct,CtCtRegId, ®id );
        if ( !regid )
                DB_CT_GET_CT_ATTR(ct,CtCtName, &regid );
        if ( !bfp )
                bfp = fopen("hev.stats", "w");
        fprintf(bfp,"%s %3d %3d %3d %3d %3d %3d %3d %3d %3d %3d\n", regid, s->numHev,
qs->numHev,
                qs->numHev - s->numHev,
                abs(s->numHev - qs->numHev),
                (int) ts->comfa_diff, (int) ts->best2, (int) ts->best3,
                s->numFrags, s->s2cnt, s->s3cnt );
        if ( !(idx % 100 ) )
                fflush(bfp);
endif if ( details && qidx >= 0 )
        {
                if ( get_details(ts, qs, s, qidx, sidx, splitidx, splitInThree, subsetHit, keepCts ) )
                {
                        ts->comfa_diff = q_bailout;
                        fprintf(stderr,"internal failure, please provide query, options, and structure
below.\n");
                        if ( s->ct )
                                DB_CT_WRITE(stderr, s->ct);
                }
        }
        freeSplit(s);

return ts;
} static double CompareAllFeatures(Split *query, Split *str, double radius )
{
        double best;
        static Split *qfeatInit;
        static int qFeatures[5];
                int sFeatures[5];
        static int tsearched;
```

```
double best2, best3, bestsub;
double d1, d2, d3, d4, d5, d6;
double dval[6];
int hevCnts[6];
double attPen[2];
int bestQ, bestStr;
int bestIdx;
int threeIsBetter = 0;
int SubIsBetter = 0;
int id1, id2, id3, id4;
int i,j,k, l;
int ids[3];
Frag *f, *sf;
Frag *q1, *q2, *q3, *q4;
Frag *fs1, *fs2, *fs3, *fs4;
Frag *fragPtrs[3];
Frag *qActive;
split2 *qs2, *ss2;
split3 *qs3, *ss3;
double *dptr;
double hexdiff;
int max3;
static Split *qInit;
double bailout;
static int t_quick;
int combo2, combo3;
int nskip2, nskip3;

memset((char *) sFeatures, '\0', sizeof(int) * 6 );
for ( i = 0; i < str->atomCount; i++ )
{
        if ( str->featureMask )
        {
                if ( str->featureMask[i] & FeaturePos )
                        sFeatures[1] += 1;
                if ( str->featureMask[i] & FeatureNeg )
                        sFeatures[2] += 1;
                if ( str->featureMask[i] & FeatureHBA )
                        sFeatures[3] += 1;
                if ( str->featureMask[i] & FeatureHBD )
                        sFeatures[4] += 1;
        }
}
sFeatures[0] = str->numArom;

if ( qfeatInit != query )
{
```

```c
        memset((char *) qFeatures, '\0', sizeof(int) * 6 );
        for ( i = 0; i < query->atomCount; i++ )
        {
                if ( query->featureMask )
                {
                        if ( query->featureMask[i] & FeaturePos )
                                qFeatures[1] += 1;
                        if ( query->featureMask[i] & FeatureNeg )
                                qFeatures[2] += 1;
                        if ( query->featureMask[i] & FeatureHBA )
                                qFeatures[3] += 1;
                        if ( query->featureMask[i] & FeatureHBD )
                                qFeatures[4] += 1;
                }
        }
        qFeatures[0] = query->numArom;
        qfeatInit = query;
        fprintf(stderr,"Query feature counts Arom: %d      Pos & Neg: %d & %d      HBA & HBD: %d & %d \n",
                qFeatures[0], qFeatures[1], qFeatures[2], qFeatures[3], qFeatures[4] );
}
if 0
        fprintf(stderr,"structure feature counts Arom: %d      Pos & Neg: %d & %d      HBA & HBD: %d & %d \n",
                sFeatures[0], sFeatures[1], sFeatures[2], sFeatures[3], sFeatures[4] );
endif tsearched++;
        if ( q_partialMatch == 0 )
        {
                for ( best = 0.0, i = 0; i < 5; i++ )
                {
#define SAFE_FEATURE_QUICK
#ifdef SAFE_FEATURE_QUICK
                        if ( qFeatures[i] && !sFeatures[i] )
                                best += featureWeights[i] * featureWeights[i] * (double) ( (qFeatures[i] - sFeatures[i]) );
#else
                        if ( qFeatures[i] > sFeatures[i] )
                                best += featureWeights[i] * featureWeights[i] * (double) ( (qFeatures[i] - sFeatures[i]) ) * q_ReductionFactor;
#endif
                }
                if ( best < 0.0 )
                        best = 0.0;
                best = sqrt(best);
                if ( best > radius )
                {
```

```
                        t_quick++;
                        return 9999.00;
                }
        }

BuildFrags(str);        /* Postpone building the frags after a quick feature filtering */ for ( i = 0, f = query->frags; i < query->numFrags; i++, f++ )
        {
                if ( q_partialMatch )
                {
                        if ( f->feature2PDiff )
                                free((char *) f->feature2PDiff);
                        if ( f->feature3PDiff )
                                free((char *) f->feature3PDiff);
                        if ( f->featureSubsetDiff )
                                free((char *) f->featureSubsetDiff);
                        f->feature2PDiff = (double *) calloc(str->numFrags,sizeof(double) );
                        f->feature3PDiff = (double *) calloc(str->numFrags,sizeof(double) );
                        f->featureSubsetDiff = (double *) calloc(str->numFrags,sizeof(double) );
                        for ( j = 0; j < str->numFrags; j++ )
                        {
                                f->feature2PDiff[j] = -1.0;
                                f->feature3PDiff[j] = -1.0;
                                f->featureSubsetDiff[j] = -1.0;
                        }
                        f->featureDiff = f->feature2PDiff;
                }
                else
                {
                        if ( f->featureDiff )
                                free((char *) f->featureDiff);
                        f->featureDiff = (double *) calloc(str->numFrags,sizeof(double) );
                        for ( j = 0; j < str->numFrags; j++ )
                        {
                                f->featureDiff[j] = -1.0;
                        }
                }
        } best = 9999.0 * 9999.0;
bailout = radius * radius;
best3 = best2 = bestsub = best;

combo2 = combo3 = nskip2 = nskip3 = 0;

/*
```

2 piece feature comparisons
*/
```
        if ( query->s2 && str->s2 && q_do2piece )
        {
            for ( i = 0, qs2 = query->s2; i < query->s2cnt ; i++, qs2++ )
            {
                q1 = query->frags + qs2->frag1;
                q2 = query->frags + qs2->frag2;
#ifndef NO_STRMAP
                if ( !qs2->strMap || str->s2cnt > query->alloc2Map )
                {
                    if ( qs2->strMap && query->alloc2Map )
                        free(qs2->strMap);
                    if ( str->s2cnt > 0 )
                        qs2->strMap = (int *) calloc(str->s2cnt, sizeof(int) );
                    else
                        qs2->strMap = (int *) 0;
                }
endif
                if ( qs2->frag1 == -1 || qs2->frag2 == -1)
                    continue;
                for ( j = 0, ss2 = str->s2; j < str->s2cnt; j++, ss2++ )
                {
#ifndef NO_STRMAP
                    qs2->strMap[j] = 0;
                    combo2++;
#endif
                    if ( ss2->frag1 == -1 || ss2->frag2 == -1)
                        continue;

fs1 = str->frags + ss2->frag1;
                    fs2 = str->frags + ss2->frag2;
                    id1 = fs1->id;
                    id2 = fs2->id;

if ( q_partialMatch )
                    {
                        PartialMatchFeatures(query, 2, q1, q2, (Frag *) 0, (Frag *) 0, str, fs1,
fs2, (Frag *) 0, (Frag *) 0, q_partialMatch );
                        PartialMatchFeatures(query, 2, q1, q2, (Frag *) 0, (Frag *) 0, str, fs2,
fs1, (Frag *) 0, (Frag *) 0, q_partialMatch );
                    }
                    else
                    {
                        if ( q1->featureDiff[id1] == -1.0 )
                            q1->featureDiff[id1] = compareFeatures( query, q1, str, fs1, -1,
```

```
-1 );
                    if ( q1->featureDiff[id2] == -1.0 )
                            q1->featureDiff[id2] = compareFeatures( query, q1, str, fs2, -1,
-1 );
                    if ( q2->featureDiff[id1] == -1.0 )
                            q2->featureDiff[id1] = compareFeatures( query, q2, str, fs1, -1,
-1 );
                    if ( q2->featureDiff[id2] == -1.0 )
                            q2->featureDiff[id2] = compareFeatures( query, q2, str, fs2, -1,
-1 );
                    } d1 = q1->featureDiff[id1] + q2->featureDiff[id2];
                    if ( d1 < best )
                    {
                            bestQ = i;
                            bestStr = j;
                            best = best2 = d1;
                            bestIdx = 0;
                    }
                    d2 = q1->featureDiff[id2] + q2->featureDiff[id1];
                    if ( d2 < best )
                    {
                            bestQ = i;
                            bestStr = j;
                            best = best2 = d2;
                            bestIdx = 1;
                    }
#ifndef NO_STRMAP
                    if ( d1 <= q_bailout || d2 < q_bailout )
                    {
                            qs2->strMap[j] = 1;
                            nskip2++;
                    }
endif
            }
        }
        if ( str->s2cnt > query->alloc2Map )
                query->alloc2Map = str->s2cnt;
    }

/*
3 piece feature comparisons
*/
    for ( i = 0, qs3 = query->s3; q_do3piece && qs3 && i < query->s3cnt; i++, qs3++ )
```

```
            {
                    q1 = query->frags + qs3->frag1;
                    q2 = query->frags + qs3->frag2;
                    q3 = query->frags + qs3->frag3;
                    q4 = query->frags + qs3->frag4;
#ifndef NO_STRMAP
                    if ( !qs3->strMap || str->s3cnt > query->alloc3Map )
                    {
                            if ( qs3->strMap && query->alloc3Map )
                                    free((char *) qs3->strMap);
                            if ( str->s3cnt > 0 )
                                    qs3->strMap = (int *) calloc(str->s3cnt, sizeof(int) );
                            else
                                    qs3->strMap = (int *) 0;
                    }
                    if ( qs3->frag1 == -1 || qs3->frag2 == -1 || qs3->frag3 == -1 )
                            continue;
endif
                    for ( j = 0, ss3 = str->s3; ss3 && j < str->s3cnt; j++, ss3++ )
                    {
#ifndef NO_STRMAP
                            qs3->strMap[j] = 0;
                            combo3++;
#endif
                            if ( ss3->frag1 == -1 || ss3->frag2 == -1 || ss3->frag3 == -1 )
                                    continue;
                            fs1 = str->frags + ss3->frag1;
                            fs2 = str->frags + ss3->frag2;
                            fs3 = str->frags + ss3->frag3;
                            fs4 = str->frags + ss3->frag4;
                            id1 = fs1->id;
                            id2 = fs2->id;
                            id3 = fs3->id;
                            id4 = fs4->id;

if ( q_partialMatch )
                            {
                                    PartialMatchFeatures(query, 3, q1, q2, q3, q4, str, fs1, fs2, fs3, fs4,
q_partialMatch );
                                    PartialMatchFeatures(query, 3, q1, q2, q3, q4, str, fs4, fs3, fs2, fs1,
q_partialMatch );
                            }
                            else
                            {
                                    if ( q1->featureDiff[id1] == -1.0 )
                                            q1->featureDiff[id1] = compareFeatures( query, q1, str, fs1, -1,
-1 );
```

```
                if ( q1->featureDiff[id4] == -1.0 )
                        q1->featureDiff[id4] = compareFeatures( query, q1, str, fs4, -1,
-1 );

if ( q4->featureDiff[id1] == -1.0 )
                        q4->featureDiff[id1] = compareFeatures( query, q4, str, fs1, -1,
-1 );

if ( q4->featureDiff[id4] == -1.0 )
                        q4->featureDiff[id4] = compareFeatures( query, q4, str, fs4, -1,
-1 );

if ( q2->featureDiff[id2] == -1.0 )
                        q2->featureDiff[id2] = compareFeatures( query, q2, str, fs2, -1,
-1 );

if ( q2->featureDiff[id3] == -1.0 )
                        q2->featureDiff[id3] = compareFeatures( query, q2, str, fs3, -1,
-1 );

if ( q3->featureDiff[id3] == -1.0 )
                        q3->featureDiff[id3] = compareFeatures( query, q3, str, fs3, -1,
-1 );

if ( q3->featureDiff[id2] == -1.0 )
                        q3->featureDiff[id2] = compareFeatures( query, q3, str, fs2, -1,
-1 );
        }
        attPen[0] = attPen[1] = 0.0;
        dval[0] = 0.0;
        dval[1] = 0.0;
        if ( q_attachPenFactor > 0.0 )
        {
                attPen[0] = ( computeAttachmentPenalty( q1, fs1, q4, fs4 ) +
computeAttachmentPenalty(q4, fs4, q1, fs1) );
                attPen[1] = ( computeAttachmentPenalty( q1, fs4, q4, fs1 ) +
computeAttachmentPenalty(q4, fs1, q1, fs4) );

dval[0] += attPen[0];
                dval[1] += attPen[1];
        }
        if ( q_featureFactor > 0.0 )
        {
                dval[0] += ( q1->featureDiff[id1] + q4->featureDiff[id4] ) / 2.0 +
q2->featureDiff[id2] + q3->featureDiff[id3];
                dval[1] += ( q1->featureDiff[id4] + q4->featureDiff[id1] ) / 2.0 +
q2->featureDiff[id3] + q3->featureDiff[id2];
```

```
        }
        max3 = 2;

for ( k = 0; k < max3; k++ )
        {
                if ( dval[k] < best )
                {
                        best = best3 = dval[k];
                        bestQ = i;
                        bestStr = j;
                        bestIdx = k;
                        threeIsBetter = 1;
                }
                else if ( dval[k] < best3 )
                        best3 = dval[k];
```
ifndef NO_STRMAP
```
                if ( dval[k] <= q_bailout && qs3->strMap[j] == 0 )
                {
                        qs3->strMap[j] = 1;
                        nskip3++;
                }
```
endif
```
            }
        }
    }
    if ( str->s3cnt > query->alloc3Map )
        query->alloc3Map = str->s3cnt;
```

/* subset feature comparisons

Compare the query 2 piece fragmentation with 3 piece structure fragmentation. Match A-B in query with A-B or B-C in structure, where
B is the center piece of the structure.

For comparing two piece with 3 piece. Frag 1 & 2 are a set, while fragment 3 and 4 are a set, in that the
attacment bond that is broken defines the connection between frag1 and frag2. Frag3 and frag4 are the second split. Frag1 and frag4 are
the center/core fragments. Aligned from the different starting attachment atom.

*/
```
        if ( query->s2 && str->s3 && q_doSubset )
```

```c
            {
                                /* loop over query 2 piece fragments, and compare with structure 3 piece
fragments. */
        for ( i = 0, qs2 = query->s2; i < query->s2cnt ; i++, qs2++ )
        {
                if ( qs2->frag1 == -1 || qs2->frag2 == -1)
                        continue;
                q1 = query->frags + qs2->frag1;
                q2 = query->frags + qs2->frag2;
#ifndef NO_STRMAP
                if ( !qs2->subsetMap || str->s3cnt > query->allocSubsetMap )
                {
                        if ( qs2->subsetMap && query->allocSubsetMap )
                                free(qs2->subsetMap);
                        if ( str->s3cnt > 0 )
                                qs2->subsetMap = (int *) calloc(str->s3cnt, sizeof(int) );
                        else
                                qs2->subsetMap = (int *) 0;

}
endif for ( j = 0, ss3 = str->s3; ss3 && j < str->s3cnt; j++, ss3++ )
                {
                        if ( ss3->frag1 == -1 || ss3->frag2 == -1 || ss3->frag3 == -1 )
                                continue;
#ifndef NO_STRMAP
                        qs2->subsetMap[j] = 0;
#endif
                        fs1 = str->frags + ss3->frag1;
                        fs2 = str->frags + ss3->frag2;
                        fs3 = str->frags + ss3->frag3;
                        fs4 = str->frags + ss3->frag4;
                        id1 = fs1->id;
                        id2 = fs2->id;
                        id3 = fs3->id;
                        id4 = fs4->id;

if ( q_partialMatch )
                        {
                                PartialMatchFeatures(query, 1, q1, q2, (Frag *) 0, (Frag *) 0, str, fs1,
fs2, (Frag *) 0, (Frag *) 0, q_partialMatch );
                                PartialMatchFeatures(query, 1, q1, q2, (Frag *) 0, (Frag *) 0, str, fs2,
fs1, (Frag *) 0, (Frag *) 0, q_partialMatch );
                                PartialMatchFeatures(query, 1, q1, q2, (Frag *) 0, (Frag *) 0, str, fs3,
fs4, (Frag *) 0, (Frag *) 0, q_partialMatch );
                                PartialMatchFeatures(query, 1, q1, q2, (Frag *) 0, (Frag *) 0, str, fs4,
```

```
                                fs3, (Frag *) 0, (Frag *) 0, q_partialMatch );
                                        }
                                        else
                                        {
                                                if ( q1->featureDiff[id1] == -1.0 )
                                                        q1->featureDiff[id1] = compareFeatures( query, q1, str, fs1, -1,
-1 );
                                                if ( q1->featureDiff[id2] == -1.0 )
                                                        q1->featureDiff[id2] = compareFeatures( query, q1, str, fs2, -1,
-1 );

if ( q2->featureDiff[id1] == -1.0 )
                                                        q2->featureDiff[id1] = compareFeatures( query, q2, str, fs1, -1,
-1 );
                                                if ( q2->featureDiff[id2] == -1.0 )
                                                        q2->featureDiff[id2] = compareFeatures( query, q2, str, fs2, -1,
-1 );

if ( q1->featureDiff[id3] == -1.0 )
                                                        q1->featureDiff[id3] = compareFeatures( query, q1, str, fs3, -1,
-1 );
                                                if ( q1->featureDiff[id4] == -1.0 )
                                                        q1->featureDiff[id4] = compareFeatures( query, q1, str, fs4, -1,
-1 );

if ( q2->featureDiff[id3] == -1.0 )
                                                        q2->featureDiff[id3] = compareFeatures( query, q2, str, fs3, -1,
-1 );
                                                if ( q2->featureDiff[id4] == -1.0 )
                                                        q2->featureDiff[id4] = compareFeatures( query, q2, str, fs4, -1,
-1 );
                                        } if ( q_featureFactor > 0.0 )
                                        {
                                                dval[0] =  q1->featureDiff[id1] + q2->featureDiff[id2];
                                                dval[1] =  q1->featureDiff[id2] + q2->featureDiff[id1];
                                                dval[2] =  q1->featureDiff[id3] + q2->featureDiff[id4];
                                                dval[3] =  q1->featureDiff[id4] + q2->featureDiff[id3];
                                        }
                                        else
                                                dval[0] = dval[1] = dval[2] = dval[3] = 0.0;

hevCnts[0] = hevCnts[1] = fs1->hevCnt + fs2->hevCnt;
                                        hevCnts[2] = hevCnts[3] = fs3->hevCnt + fs4->hevCnt;

max3 = 4;
```

```
                for ( k = 0; k < max3; k++ )
                {
                        if ( hevCnts[k] > q_minSubsetSize )
                        {
                                if ( dval[k] < best )
                                {
                                        best = bestsub = dval[k];
                                        bestQ = i;
                                        bestStr = j;
                                        bestIdx = k;
                                        SubIsBetter = 1;
                                }
                                else if ( dval[k] < bestsub )
                                {
                                        bestsub = dval[k];
                                }
                        } if ( dval[k] <= q_bailout && qs2->subsetMap[j] == 0 )
                        {
                                qs2->subsetMap[j] = 1;
                        }
                }
            }
        }
        if ( str->s3cnt > query->allocSubsetMap )
                query->allocSubsetMap = str->s3cnt;
    } /* end of subset */ if ( best < 0.0 )
            best = 0.0;
#if 0
    fprintf(stderr,"%d of %d 2p skipped %d of %d 3p skipped   best: %8.4lf \n",
                    combo2 - nskip2, combo2, combo3 - nskip3, combo3, sqrt(best) );
#endif
    return sqrt(best);
} void TOP_FREE_RESULT(top_result *res, int freeRef )
{
    int i;
    if ( !res )
            return;

for ( i = 0; i < 3; i++ )
    {
            if ( res->strFrags[i] )
```

```
                DB_CT_DELETE_CT(res->strFrags[i] );
        }
        if ( freeRef )
                free((char *) res );
} static char tempString[200];

struct top_graph *TOP_INIT_GRAPH( struct top_graph *g, struct CtConnectionTable *ct ) {
/*===================================================================================
========================== */
/* (re) initializes topomer graph info *g for structure *ct */ int b, nowats, nowbds, nowmax, ntoats, toats[20], ntoats2, na, nb, bct, inRing;
        struct top_graph *gnew;
        struct bond_top_rec *bptr;
        set_ptr    end_atoms=NIL,    nuls=NIL,    cnats=NIL,    nxcn=NIL,    a2chk=NIL,
TOP_CONN_ATOMS();
        CtBondTypeDef bType;

if(!DB_CT_GET_CT_ATTR( ct, CtCtAtomCount, &nowats ) || !DB_CT_GET_CT_ATTR( ct,
CtCtBondCount, &nowbds ) )
                goto error;

/* be sure rings were perceived */
        if (!DB_CT_UTL_FIND_RINGS( ct )) goto error;

/* (re)allocate all memory required by this structure, excepting sets of to_atts */
        if (g) {
/* free all dependent memory */
                for (b = 0; b < g->nbonds; b++) if (g->bstuff[b].detail) {
                        if (!UTL_SET_DESTROY( g->bstuff[b].detail->to_atts ) ) goto error;
                        if (!UTL_MEM_FREE( g->bstuff[b].detail ) ) goto error;
                        g->bstuff[b].detail = (struct bond_detail_rec *) 0;
                }
/* if this molecule is bigger, reallocate dependent data arrays */
                if (nowats > g->maxatoms) {
                        nowmax = (nowats > g->maxatoms * 2 ? nowats : g->maxatoms * 2 );
                        if (!( g->bstart = (int *) DB_CT_UTL_REALLOC (
                                ( char * ) g->bstart, sizeof(int) * nowmax ) ) ) goto error;
                        g->maxatoms = nowmax;
                }
/* note that bonds are 2x more because they are stored rooted from both ends */
                if (2 * nowbds > g->maxbonds ) {
                        nowmax = (2 * nowbds > g->maxbonds ? 2 * nowbds : g->maxbonds );
                        if (!( g->bstuff = (struct bond_top_rec *) DB_CT_UTL_REALLOC (
```

```
                    ( char * ) g->bstuff, sizeof(struct bond_top_rec) * nowmax ) ) ) goto error;
                g->maxbonds = nowmax;
        }
            gnew = g;
    }
    else {
        if (! (gnew = (struct top_graph *) UTL_MEM_ALLOC( sizeof( struct top_graph ) ) ))
goto error;
        if (! (gnew -> bstart = (int *) UTL_MEM_ALLOC( sizeof( int ) * 1000 ) )) goto error;
        gnew->maxatoms = 1000;
        if (! (gnew -> bstuff = (struct bond_top_rec *)
                UTL_MEM_ALLOC( sizeof(struct bond_top_rec) * 2000 ) )) goto error;
        gnew->maxbonds = 2000;
    }
    gnew->natoms = nowats;
    gnew->nbonds = nowbds;

if (!(a2chk = UTL_SET_CREATE( nowats + 1 ) )) goto error;
    if (!(nuls  = UTL_SET_CREATE( nowats + 1 ) )) goto error;
    if (!(cnats = UTL_SET_CREATE( nowats + 1 ) )) goto error;
    if (!(nxcn  = UTL_SET_CREATE( nowats + 1 ) )) goto error;
    if (!(end_atoms = UTL_SET_CREATE( nowats + 1 ) )) goto error;

/* fill in tree information */
    bptr = gnew->bstuff;
    bct = 0;
    for (na = 1; na <= nowats; na++ ) {
        if (!(DB_CT_GET_ANY_ATOM_ATTR( ct, na, CtAtomBondCount, &ntoats ) )) goto
error;
        if (ntoats > 20) {
            fprintf( stderr, "More than 20 bonds to atom %d.\n", na );
            goto error;
        }
        if (!(DB_CT_GET_ANY_ATOM_ATTR( ct, na, CtAtomBondToAtoms, &toats ) )) goto
error;
        gnew->bstart[na - 1] = bct;
        for (nb = 0; nb < ntoats; nb++, bct++, bptr++ ) {
            bptr->from = na;
            bptr->to = toats[ nb ] ;
/* is this a topomerically labile bond? */
            if (!(b = DB_CT_UTL_GET_BONDID( ct, na, bptr->to ) )) goto error;
            if (!DB_CT_GET_BOND_ATTR( ct, b, CtBondIsInRing, &inRing)
                || !DB_CT_GET_BOND_ATTR( ct, b, CtBondType, &bType )
                || !DB_CT_GET_ANY_ATOM_ATTR( ct, toats[ nb ],
CtAtomBondCount, &ntoats2 ) ) goto error;
            if (!inRing && bType == CtBondTypeSingle && ntoats > 1 && ntoats2 >
1 ) {
/*
```

```
                    if(!(bptr->to_atts = TOP_CONN_ATOMS( ct, bptr->to, bptr->from,
                            nuls, cnats, nxcn, end_atoms ) )) goto error;
*/
                    if(!(TOP_MARK_BEST( ct, bptr->to, bptr->from, TRUE, bptr, NIL,
NIL, NIL,
                            a2chk, nuls, cnats, nxcn, end_atoms ) )) goto error;
                }
                else bptr->detail = (struct bond_detail_rec *) 0;
            }
        }
        if(end_atoms) UTL_SET_DESTROY(end_atoms);
        if(nuls) UTL_SET_DESTROY(nuls);
        if(nxcn) UTL_SET_DESTROY(nxcn);
        if(cnats) UTL_SET_DESTROY(cnats);
/*      if(a2chk) UTL_SET_DESTROY(a2chk);    jilek (to do) was cnats */
        return gnew ;
error:
        return (struct top_graph *) 0;
} set_ptr TOP_CONN_ATOMS(
/                                                                              *
=============================================================
========================= */
/* returns the set of all atoms in *ct which are attached to atom1,
        except that any path ending in atom2 is truncated.
        The returned set is created here (to be freed by user when finished)
        For efficiency in reprocessing the same structure,
                four working sets are supplied by caller */ struct CtConnectionTable *ct,
        int atom1,
        int atom2,
        set_ptr nuls, set_ptr cnats, set_ptr nxcn, set_ptr end_atoms )
{
        int natot, ntoats, toats[20], natt, nats, elem, nuats;
        set_ptr a2chk=NIL;

if (!DB_CT_GET_CT_ATTR( ct, CtCtAtomCount, &natot )) goto error;
        UTL_SET_CLEAR(end_atoms);
        UTL_SET_INSERT( end_atoms, atom2 );

if (!(a2chk = UTL_SET_CREATE( natot + 1 ) )) goto error;
/* root at first set of attached atoms */
        if (!(DB_CT_GET_ANY_ATOM_ATTR( ct, atom1, CtAtomBondCount, &ntoats) )) goto error;
        if (ntoats > 20) goto toomanyattms;
        if(!(DB_CT_GET_ANY_ATOM_ATTR( ct, atom1, CtAtomBondToAtoms, &toats ) )) goto error;
        for (natt=0; natt<ntoats; natt++) UTL_SET_INSERT( a2chk, toats[ natt ] );
```

```
        if (UTL_SET_EMPTY( a2chk )) return( FALSE );

UTL_SET_DIFF_INPLACE( a2chk, end_atoms, a2chk );
        nats = UTL_SET_CARDINALITY( a2chk );
        UTL_SET_COPY_INPLACE( cnats, a2chk );
/* breadth first search */
        while (TRUE) {
        UTL_SET_CLEAR( nxcn );
        elem = -1;
        while ( (elem = UTL_SET_NEXT( cnats, elem)) >= 0 ) {
                UTL_SET_CLEAR( nu1s );
            if (!(DB_CT_GET_ANY_ATOM_ATTR( ct, elem, CtAtomBondCount, &ntoats ) )) goto error;
            if (ntoats > 20) goto toomanyattms;
            if (!(DB_CT_GET_ANY_ATOM_ATTR( ct, elem, CtAtomBondToAtoms, &toats ) )) goto error;
            for (natt=0; natt<ntoats; natt++) UTL_SET_INSERT( nu1s, toats[ natt ] );
                UTL_SET_DELETE( nu1s, atom1 );
                UTL_SET_DIFF_INPLACE( nu1s, end_atoms, nu1s );
                UTL_SET_OR_INPLACE( nxcn, nu1s, nxcn );
                UTL_SET_DIFF_INPLACE( nxcn, a2chk, nxcn );
        }
        UTL_SET_OR_INPLACE( a2chk, nxcn, a2chk );
        nuats = UTL_SET_CARDINALITY( a2chk );
        if (nuats <= nats) break;
        nats = nuats;
        UTL_SET_COPY_INPLACE( cnats, nxcn );
        }
        return a2chk;
error:
        return (set_ptr) NIL;

toomanyattms:
    fprintf( stderr, "More than twenty atoms attached to some atom in this structure.\n" );
    goto error;
} int TOP_MARK_BEST(
/*                                                                              *
================================================================================
=============================== */
/* adds information for prioritizing attachments to an atom */
        struct CtConnectionTable *ct,
        int a1,                          /* the root atom */
        int a2,                          /* the base of the root -- skip it */
        int full_data,                   /* provide information relating to near symmetries? + attached
sets */
        struct bond_top_rec *bptr,       /* output here if full_data=TRUE */
        int *only_atoms,                 /* output here if full_data=FALSE */
        double *coo_in,                          /* atomic coords (retrieved from ct if not provided */
```

```
        set_ptr attach3set,          /* if provided, a super root atom(s)
                       for entire group (highest priority path is shortest to here) */
        set_ptr a2chk, set_ptr nu1s, set_ptr cnats, set_ptr nxcn, set_ptr end_atoms )
{
define MAX_NP 8 struct pathrec {
      int root, nrings, chosen, nats, done, a3id;
      double mw;
      set_ptr path, nxt1s;
    } ;

struct pathrec p[MAX_NP];

int retval, toroot, ntoats, toats[20], natt, a, np, growing, nats, natot, ncycles, pnow, ringclosed,
debug=FALSE;
    int nuats, elem, new_rings, pdone, p2do, best, decision, naout, lastnats = 0, lastdecision, arec2,
a4;
    double *coo, t1, t2, diff, pot1, pot2, podiff, get_path_mw();

np = 0;
    if (!(coo = coo_in)) {
            if (!DB_CT_GET_CT_ATTR( ct, CtCt3DCoordSet, &coo, &natot )) goto error;
    } else if (!DB_CT_GET_CT_ATTR( ct, CtCtAtomCount, &natot )) goto error;

if (full_data) if (!( bptr->detail = (struct bond_detail_rec* )
           UTL_MEM_CALLOC( sizeof( struct bond_detail_rec ), 1 ) )) goto error;

toroot = attach3set || !a2;
    UTL_SET_CLEAR( end_atoms );
    if (a2) UTL_SET_INSERT( end_atoms, a2 );
    arec2 = a2;

UTL_SET_CLEAR( a2chk );
    if (!(DB_CT_GET_ANY_ATOM_ATTR( ct, a1, CtAtomBondCount, &ntoats) )) goto error;
    if (ntoats > 20) goto toomanyattms;
    if (!(DB_CT_GET_ANY_ATOM_ATTR( ct, a1, CtAtomBondToAtoms, &toats ) )) goto error;
    for (natt=0; natt<ntoats; natt++) UTL_SET_INSERT( a2chk, toats[ natt ] );
      if (a2) UTL_SET_DELETE( a2chk, a2 );

/* initialize path records */
    a = -1;
    np = 0;
    while (np < MAX_NP && (a = UTL_SET_NEXT( a2chk, a)) >= 0 ) {
      if (!(p[np].path = UTL_SET_CREATE( natot + 1 ) )) goto error;
      if (!(p[np].nxt1s = UTL_SET_CREATE( natot + 1 ) )) goto error;
      p[np].root = a;
      p[np].nrings = p[np].done = p[np].a3id = 0;
```

```
            UTL_SET_INSERT( p[np].path, a );
            np++;
         }
   /* grow the paths */
      growing = TRUE;
      nats = 0;
      ncycles = 0;
      while (growing ) {
         nuats = 0;
         ringclosed = FALSE;
         for (pnow = 0; pnow < np; pnow++ ) if (!p[pnow].done) {
            UTL_SET_COPY_INPLACE( cnats, p[pnow].path );
            UTL_SET_CLEAR( nxcn );
            elem = -1;
   /* accumnulate this generation of attached atoms into nxcn */
            while ( (elem = UTL_SET_NEXT( cnats, elem)) >= 0 ) {
               UTL_SET_CLEAR( nuls );
                  if(!(DB_CT_GET_ANY_ATOM_ATTR( ct, elem, CtAtomBondCount, &ntoats) )) goto error;
               if (ntoats > 20) goto toomanyattms;
               if (!(DB_CT_GET_ANY_ATOM_ATTR( ct, elem, CtAtomBondToAtoms, &toats ) )) goto
error;
               for (natt=0; natt<ntoats; natt++) UTL_SET_INSERT( nuls, toats[ natt ] );
               UTL_SET_DELETE( nuls, a1 );
               UTL_SET_DIFF_INPLACE( nuls, end_atoms, nuls );

UTL_SET_OR_INPLACE( nxcn, nuls, nxcn );
               UTL_SET_DIFF_INPLACE( nxcn, p[pnow].path, nxcn );
            }
            UTL_SET_COPY_INPLACE( p[pnow].nxtls, nxcn );
         }
   /* mark if reached root */
         for (pnow = 0; pnow < np; pnow++) {
   /* remove duplicate atoms caused by new ring closure */
            for (pdone = 0; pdone < np; pdone++ ) if (pdone != pnow) {
               UTL_SET_AND_INPLACE( p[pnow].path, p[pdone].nxtls, a2chk );
               if ((new_rings = UTL_SET_CARDINALITY( a2chk ))) {
   /* we have ring closure(s) */
                  ringclosed = TRUE;
                  UTL_SET_OR_INPLACE( end_atoms, a2chk, end_atoms );
                  UTL_SET_DIFF_INPLACE( p[pdone].nxtls, a2chk, p[pdone].nxtls );
               }
            }
   /* stop growing a path that has reached anything in attach3set */
            if (toroot) {
               elem = -1;
               while ((elem = UTL_SET_NEXT( attach3set, elem)) >= 0 ) {
                  if (UTL_SET_MEMBER( p[pnow].path, elem ) ) {
```

```
                    p[pnow].done = TRUE;
                    break;
                }
            }
        }
    }
/* add all OK new atoms to all paths */
    for (pnow = 0; pnow < np; pnow++) {
        UTL_SET_OR_INPLACE( p[pnow].path, p[pnow].nxt1s, p[pnow].path );
        UTL_SET_CLEAR( p[pnow].nxt1s );
    }
/* done growing paths if no more atoms added to any path .. */
    for (pdone = 0, nuats = 0; pdone < np; pdone++ )
            nuats += UTL_SET_CARDINALITY( p[pdone].path );
    if (nuats<=nats && !ringclosed) growing = FALSE;
    nats = nuats;
/* .. or after 100 atom layers out regardless */
    ncycles++;
    if (ncycles >= 100) growing = FALSE;
}
/* debugging */
    if (debug) for (pdone = 0; pdone < np; pdone++) {
        sprintf( tempString, "Path %d (from %d): ",
            pdone+1, p[pdone].root );
        fprintf( stdout, tempString );
        ashow( p[pdone].path );
    } if (full_data) {
        if (!( bptr->detail->to_atts = UTL_SET_CREATE( natot + 1 ) )) goto error;
        UTL_SET_INSERT( bptr->detail->to_atts, a1 );
    }

/* compute the path properties */
    for (pdone = 0; pdone < np; pdone++) { p[pdone].chosen = toroot;
        if (toroot) {
            p[pdone].chosen = FALSE;
            elem = -1;
            while ((elem = UTL_SET_NEXT( attach3set, elem)) >= 0 ) {
                if (UTL_SET_MEMBER( p[pdone].path, elem ) ) {
/* recording atom ID for later use */
                    p[pdone].chosen = TRUE;
                    p[pdone].a3id = elem;
                    arec2 = p[pdone].root;
                    break;
                }
```

```
                }
        }
        p[pdone].nats = UTL_SET_CARDINALITY( p[pdone].path );
        p[pdone].nrings = p[pdone].nrings ? 1 : 0;
        p[pdone].mw = 0.0;
        p[pdone].done = 0;
            if (full_data) UTL_SET_OR_INPLACE( bptr->detail->to_atts,  p[pdone].path,
bptr->detail->to_atts );
    }

/* return all root atoms, ordered best to worst */
for (p2do = 0; p2do < np; p2do++ ) {
/* start with first unchosen atom */
    for (pdone = 0; pdone < np; pdone++) if (!p[pdone].done) {
        best = pdone;
        break;
    }
/* look for something better */
    for (pdone = 0; pdone < np; pdone++) if (!p[pdone].done && pdone != best) {
        decision = FALSE;
        if (p[best].chosen != p[pdone].chosen) {
                decision = TRUE;
                if (!p[best].chosen && p[pdone].chosen) best = pdone;
        }
        if (!decision) {
          if (p[pdone].nats != p[best].nats ) {
                decision = TRUE;
                if (p[pdone].nats > p[best].nats) best = pdone;
          }
        }
        if (!decision) {
            p[pdone].mw = get_path_mw( p[pdone].path, ct, p[pdone].mw );
            p[best].mw = get_path_mw( p[best].path, ct, p[best].mw );
            if (p[pdone].mw - p[best].mw > 0.01 * p[best].mw ||
                p[pdone].mw - p[best].mw < -0.01 * p[best].mw ) {
              decision = TRUE;
              if (p[pdone].mw - p[best].mw > 0.01 * p[best].mw) best = pdone;
            }
        }
/* checking relative geometries of attachments via "improper" torsion */

/* the phenyl ether problem -- if candidates are 180 degrees apart and we are on the
root side of the torsion, pick the atom to the "right", not the "left", of the main chain */ if (!decision && toroot && p[pdone].a3id ) {
/* are we 180 apart? */
                a4 = p[pdone].a3id;
                pot1 = UTL_GEOM_TAU( coo+(a4-1)*3, coo+(a1-1)*3, coo+(arec2-1)*3,
```

```
            coo+(p[best].root-1)*3 );
                pot2  =  UTL_GEOM_TAU(  coo+(a4-1)*3,  coo+(a1-1)*3,  coo+(arec2-1)*3,
coo+(p[pdone].root-1)*3 );
                podiff = pot1 - pot2;
                while (podiff < 0.0) podiff += 360.0;
                while (pot2 < 0.0) pot2 += 360.0;
                if (podiff < 190.0 && podiff > 170.0 ) {
                        decision = TRUE;
                        if (pot2 < 180.0) best = pdone;
                }
         }
         if (!decision) {
/* if not already set, according to the previous special case, then */
/* if torsions differ by 360 degrees then we have trans, prefer the +180 */
                t1 = UTL_GEOM_TAU ( coo+(p[pdone].root-1)*3, coo+(a1-1)*3, coo+(arec2-1)*3,
coo+(p[best].root-1)*3 );
                t2 = UTL_GEOM_TAU ( coo+(p[best].root-1)*3, coo+(a1-1)*3, coo+(arec2-1)*3,
coo+(p[pdone].root-1)*3 );
                diff = t1 - t2;
                if (diff > 355.0) best = pdone;
                else if (diff > -355.0) {
                    while (t1 < 0.0) t1 += 360.0;
                    if (t1 > 170.0 && t1 <= 350.0) best = pdone;
                }
         }
     }
/* output all information about this atom */
   if (p2do < 3) {
     if (full_data) {
        if (p2do) {
                bptr->detail->identical[ p2do - 1 ] = lastdecision ? 1 : 0 ;
                bptr->detail-> nat1vs2[ p2do - 1 ] = lastnats - p[best].nats;
                bptr->detail-> lastnat[ p2do - 1 ] = p[best].nats;
        }
        bptr->detail->best[ p2do ] = p[best].root;
     } else only_atoms[ p2do ] = p[best].root;
   } lastnats = p[best].nats;
   lastdecision = decision;
   p[best].done = TRUE;
}
   retval = TRUE;
error:
        retval = TRUE;
   for (pnow = 0; pnow < np; pnow++ ) {
      if (p[pnow].path) UTL_SET_DESTROY(p[pnow].path);
      if (p[pnow].nxt1s) UTL_SET_DESTROY(p[pnow].nxt1s);
```

```
    }
    return( retval );
toomanyattms:
    fprintf( stderr, "Too many attachments to an atom (>20)\n" );
    goto error;
} if 0
/*================================================================
============================== */
/* adds information for prioritizing attachments to an atom */
static int topMarkBest(
        Frag *fragP,
        struct CtConnectionTable *ct,
        int *atoms,           /* sizeof ct->atomCount, true false for each atom to use */
        int a1,               /* the root atom */
        int a2,               /* the base of the root -- skip it */
        int full_data,        /* provide information relating to near symmetries? + attached
sets */
{
#if 0
        struct bond_top_rec *bptr,  /* output here if full_data=TRUE */
        int *only_atoms,            /* output here if full_data=FALSE */
        double *coo_in,                  /* atomic coords (retrieved from ct if not provided */
        set_ptr attach3set,          /* if provided, a super root atom(s)
                    for entire group (highest priority path is shortest to here) */
        set_ptr a2chk, set_ptr nu1s, set_ptr cnats, set_ptr nxcn, set_ptr end_atoms )
endif define MAX_NP 8
        struct pathrec {
            int root, nrings, chosen, nats, done, a3id;
            double mw;
            set_ptr path, nxt1s;
        };

struct pathrec p[MAX_NP];

int retval, toroot, ntoats, toats[20], natt, a, np, growing, nats, natot, ncycles, pnow, ringclosed,
debug=FALSE;
        int nuats, elem, new_rings, pdone, p2do, best, decision, naout, lastnats = 0, lastdecision, arec2,
a4;
        double *coo, t1, t2, diff, pot1, pot2, podiff, get_path_mw();
        set_ptr a2chk;

np = 0;
```

```
        if (!DB_CT_GET_CT_ATTR( ct, CtCt3DCoordSet, &coo, &natot )) goto error;
        natot = ct->atomCount;

#if 0
        toroot = attach3set || !a2;
        UTL_SET_CLEAR( end_atoms );
        if (a2) UTL_SET_INSERT( end_atoms, a2 );
        arec2 = a2;
endif a2chk = UTL_SET_CREATE(natot + 1);

UTL_SET_CLEAR( a2chk );
        if (!(DB_CT_GET_ANY_ATOM_ATTR( ct, a1, CtAtomBondCount, &ntoats) )) goto error;
        if (ntoats > 20) goto toomanyattms;
        if (!(DB_CT_GET_ANY_ATOM_ATTR( ct, a1, CtAtomBondToAtoms, &toats ) )) goto error;
        for (natt=0; natt<ntoats; natt++) UTL_SET_INSERT( a2chk, toats[ natt ] );
#if 0
        if (a2) UTL_SET_DELETE( a2chk, a2 );
endif /* initialize path records */
        a = -1;
        np = 0;
        while (np < MAX_NP && (a = UTL_SET_NEXT( a2chk, a)) >= 0 ) {
          if (!(p[np].path = UTL_SET_CREATE( natot + 1 ) )) goto error;
          if (!(p[np].nxtls = UTL_SET_CREATE( natot + 1 ) )) goto error;
          p[np].root = a;
          p[np].nrings = p[np].done = p[np].a3id = 0;
          UTL_SET_INSERT( p[np].path, a );
          np++;
        }

/* grow the paths */
        growing = TRUE;
        nats = 0;
        ncycles = 0;
        while (growing ) {
          nuats = 0;
          ringclosed = FALSE;
          for (pnow = 0; pnow < np; pnow++ ) if (!p[pnow].done) {
            UTL_SET_COPY_INPLACE( cnats, p[pnow].path );
            UTL_SET_CLEAR( nxcn );
            elem = -1;
/* accumnulate this generation of attached atoms into nxcn */
            while ( (elem = UTL_SET_NEXT( cnats, elem)) >= 0 ) {
              UTL_SET_CLEAR( nuls );
              if (!(DB_CT_GET_ANY_ATOM_ATTR( ct, elem, CtAtomBondCount, &ntoats) )) goto error;
```

```
        if (ntoats > 20) goto toomanyattms;
        if (!(DB_CT_GET_ANY_ATOM_ATTR( ct, elem, CtAtomBondToAtoms, &toats ) )) goto
error;
        for (natt=0; natt<ntoats; natt++) UTL_SET_INSERT( nu1s, toats[ natt ] );
        UTL_SET_DELETE( nu1s, a1 );
        UTL_SET_DIFF_INPLACE( nu1s, end_atoms, nu1s );

UTL_SET_OR_INPLACE( nxcn, nu1s, nxcn );
        UTL_SET_DIFF_INPLACE( nxcn, p[pnow].path, nxcn );
    }
    UTL_SET_COPY_INPLACE( p[pnow].nxt1s, nxcn );
}
/* mark if reached root */
    for (pnow = 0; pnow < np; pnow++) {
/* remove duplicate atoms caused by new ring closure */
        for (pdone = 0; pdone < np; pdone++ ) if (pdone != pnow) {
            UTL_SET_AND_INPLACE( p[pnow].path, p[pdone].nxt1s, a2chk );
            if ((new_rings = UTL_SET_CARDINALITY( a2chk ))) {
/* we have ring closure(s) */
                ringclosed = TRUE;
                UTL_SET_OR_INPLACE( end_atoms, a2chk, end_atoms );
                UTL_SET_DIFF_INPLACE( p[pdone].nxt1s, a2chk, p[pdone].nxt1s );
            }
        }
/* stop growing a path that has reached anything in attach3set */
        if (toroot) {
            elem = -1;
            while ((elem = UTL_SET_NEXT( attach3set, elem)) >= 0 ) {
                if (UTL_SET_MEMBER( p[pnow].path, elem ) ) {
                    p[pnow].done = TRUE;
                    break;
                }
            }
        }
    }
/* add all OK new atoms to all paths */
    for (pnow = 0; pnow < np; pnow++) {
        UTL_SET_OR_INPLACE( p[pnow].path, p[pnow].nxt1s, p[pnow].path );
        UTL_SET_CLEAR( p[pnow].nxt1s );
    }
/* done growing paths if no more atoms added to any path .. */
    for (pdone = 0, nuats = 0; pdone < np; pdone++ )
        nuats += UTL_SET_CARDINALITY( p[pdone].path );
    if (nuats<=nats && !ringclosed) growing = FALSE;
    nats = nuats;
/* .. or after 100 atom layers out regardless */
    ncycles++;
    if (ncycles >= 100) growing = FALSE;
```

```
        }
/* debugging */
    if (debug) for (pdone = 0; pdone < np; pdone++) {
        sprintf( tempString, "Path %d (from %d): ",
                pdone+1, p[pdone].root );
        fprintf( stdout, tempString );
        ashow( p[pdone].path );
    } if (full_data) {
        if (!( bptr->detail->to_atts = UTL_SET_CREATE( natot + 1 ) )) goto error;
        UTL_SET_INSERT( bptr->detail->to_atts, a1 );
    }

/* compute the path properties */
    for (pdone = 0; pdone < np; pdone++) { p[pdone].chosen = toroot;
        if (toroot) {
                p[pdone].chosen = FALSE;
                elem = -1;
                while ((elem = UTL_SET_NEXT( attach3set, elem)) >= 0 ) {
                    if (UTL_SET_MEMBER( p[pdone].path, elem ) ) {
/* recording atom ID for later use */
                        p[pdone].chosen = TRUE;
                        p[pdone].a3id = elem;
                        arec2 = p[pdone].root;
                        break;
                    }
                }
        }
        p[pdone].nats = UTL_SET_CARDINALITY( p[pdone].path );
        p[pdone].nrings = p[pdone].nrings ? 1 : 0;
        p[pdone].mw = 0.0;
        p[pdone].done = 0;
        if (full_data) UTL_SET_OR_INPLACE( bptr->detail->to_atts, p[pdone].path,
bptr->detail->to_atts );
    }

/* return all root atoms, ordered best to worst */
    for (p2do = 0; p2do < np; p2do++ ) {
/* start with first unchosen atom */
        for (pdone = 0; pdone < np; pdone++) if (!p[pdone].done) {
            best = pdone;
            break;
        }
/* look for something better */
        for (pdone = 0; pdone < np; pdone++) if (!p[pdone].done && pdone != best) {
```

```
        decision = FALSE;
        if (p[best].chosen != p[pdone].chosen) {
                decision = TRUE;
                if (!p[best].chosen && p[pdone].chosen) best = pdone;
        }
    if (!decision) {
      if (p[pdone].nats != p[best].nats ) {
                decision = TRUE;
                if (p[pdone].nats > p[best].nats) best = pdone;
      }
    }
    if (!decision) {
      p[pdone].mw = get_path_mw( p[pdone].path, ct, p[pdone].mw );
      p[best].mw = get_path_mw( p[best].path, ct, p[best].mw );
      if (p[pdone].mw - p[best].mw > 0.01 * p[best].mw ||
          p[pdone].mw - p[best].mw < -0.01 * p[best].mw ) {
                decision = TRUE;
                if (p[pdone].mw - p[best].mw > 0.01 * p[best].mw) best = pdone;
      }
    }
/* checking relative geometries of attachments via "improper" torsion */

/* the phenyl ether problem -- if candidates are 180 degrees apart and we are on the
root side of the torsion, pick the atom to the "right", not the "left", of the main chain */ if (!decision && toroot && p[pdone].a3id ) {
/* are we 180 apart? */
                a4 = p[pdone].a3id;
                pot1   =   UTL_GEOM_TAU(   coo+(a4-1)*3,   coo+(a1-1)*3,   coo+(arec2-1)*3,
coo+(p[best].root-1)*3 );
                pot2   =   UTL_GEOM_TAU(   coo+(a4-1)*3,   coo+(a1-1)*3,   coo+(arec2-1)*3,
coo+(p[pdone].root-1)*3 );
                podiff = pot1 - pot2;
                while (podiff < 0.0) podiff += 360.0;
                while (pot2 < 0.0) pot2 += 360.0;
                if (podiff < 190.0 && podiff > 170.0 ) {
                        decision = TRUE;
                        if (pot2 < 180.0) best = pdone;
                }
        }
        if (!decision) {
/* if not already set, according to the previous special case, then */
/* if torsions differ by 360 degrees then we have trans, prefer the +180 */
                t1 = UTL_GEOM_TAU ( coo+(p[pdone].root-1)*3, coo+(a1-1)*3, coo+(arec2-1)*3,
coo+(p[best].root-1)*3 );
                t2 = UTL_GEOM_TAU ( coo+(p[best].root-1)*3, coo+(a1-1)*3, coo+(arec2-1)*3,
coo+(p[pdone].root-1)*3 );
                diff = t1 - t2;
```

```
                    if (diff > 355.0) best = pdone;
                    else if (diff > -355.0) {
                        while (t1 < 0.0) t1 += 360.0;
                        if (t1 > 170.0 && t1 <= 350.0) best = pdone;
                    }
                }
            }
        /* output all information about this atom */
        if (p2do < 3) {
            if (full_data) {
                if (p2do) {
                    bptr->detail->identical[ p2do - 1 ] = lastdecision ? 1 : 0 ;
                    bptr->detail-> nat1vs2[ p2do - 1 ] = lastnats - p[best].nats;
                    bptr->detail-> lastnat[ p2do - 1 ] = p[best].nats;
                }
                bptr->detail->best[ p2do ] = p[best].root;
            } else only_atoms[ p2do ] = p[best].root;
        } lastnats = p[best].nats;
        lastdecision = decision;
        p[best].done = TRUE;
    }
    retval = TRUE;
error:
        retval = TRUE;
    for (pnow = 0; pnow < np; pnow++ ) {
        if (p[pnow].path) UTL_SET_DESTROY(p[pnow].path);
        if (p[pnow].nxt1s) UTL_SET_DESTROY(p[pnow].nxt1s);
    }
    return( retval );
toomanyattms:
    fprintf( stderr, "Too many attachments to an atom (>20)\n" );
    goto error;
}
endif static double get_path_mw( set_ptr aset, struct CtConnectionTable *ct, double mw )
/* returns the total atomic weight of all atoms in aset */
{
    int elem = -1;
    double aw, ans = 0.0;

if (mw) return( mw );
    elem = -1;
    while ( ( (elem = UTL_SET_NEXT( aset, elem)) >= 0 ) {
        if (!(DB_CT_GET_ANY_ATOM_ATTR( ct, elem, CtAtomAtomicWeight, &aw ) )) return( 0.0
);
```

```
        ans += aw;
    }
    return( ans );
} static void ashow( set_ptr aset )
/* for interactive debugging, shows a set's membership in terms of atom ID */
{
    char buff[1000], *b;
    int elem;

*buff = '\0';
    b = buff;
    elem = -1;
    while ( (elem = UTL_SET_NEXT( aset, elem)) >= 0 ) {
        sprintf( b, " %d", elem );
        b = buff + strlen( buff );
    }
    sprintf( b, "\n" );
    fprintf( stdout, buff );
}

/* CoMFA region descriptor -- here it's a hidden data type */ double *TOP_STER_EVAL_RB_ATTEN(
/*======================================================================== *
 ========================================= */
/* computes and returns a CoMFA steric field, to be freed by caller when done */ struct CtConnectionTable *ct,
        l_RegionPtr regp,
        int root,        /* atom ID of fragment root */
        double *acoord,  /* atomic coordinate array. If NIL, coordinates are retrieved from ct
*/
        set_ptr a2use,   /* optionally, if not NIL, field results only from this set of atoms */
        double *ext_vdw_wt ) /* optionally, if not NIL, these are additional user-supplied wts for field
calculation */

{
        int natot, nat, ix, iy, iz;
        double *steric=NIL, *AtWts=NIL, *TOP_FIELD_RB_WTS(), *ftemp, *coord, *vAwt=NIL,
*vBwt=NIL, *va, *vb, *st;
        double radnow, epsnow, diff, dis2, dis6, dis12, x, y, z, atm_steric, sum_steric,
TOP_GET_ATOM_VDW_RADIUS();

#define MIN_SQ_DISTANCE 1.0e-4
define RADIUS_C3   1.7
```

```c
#define EPSILON_C3  .107
#define STERIC_MAX       30.0

/* get coordinates, # atoms, RB attenuation for each atom */
    if ((ftemp = acoord )) {
        if (!DB_CT_GET_CT_ATTR( ct, CtCtAtomCount, &natot )) goto error;
    } else if (!DB_CT_GET_CT_ATTR( ct, CtCt3DCoordSet, &ftemp, &natot )) goto error;
    if (!(AtWts = TOP_FIELD_RB_WTS( ct, root, a2use ) )) goto cleanup;

/* compute VDW terms for each atom (not for each atom type as in SYBYL) */
    if (!(vAwt = (double *) UTL_MEM_ALLOC( sizeof(double) * natot ))) goto cleanup;
    if (!(vBwt = (double *) UTL_MEM_ALLOC( sizeof(double) * natot ))) goto cleanup;
    if (regp->box_array[0].atom_type != 1 || regp->n_boxes != 1)
        fprintf( stderr, "WARNING: The C.3 probe atom type in a single box is alway used in the steric field calculation.\n" );
    for (nat=1; nat <= natot; nat++) if (!a2use || UTL_SET_MEMBER( a2use, nat )) {
        radnow = TOP_GET_ATOM_VDW_RADIUS( ct, nat, &epsnow );
        radnow += RADIUS_C3;
        epsnow = sqrt( epsnow * EPSILON_C3 );
        vAwt[ nat-1 ] = epsnow * 2.0 * pow( radnow, 6.0 )  * AtWts[ nat-1 ];
        vBwt[ nat-1 ] = epsnow *       pow( radnow, 12.0 ) * AtWts[ nat-1 ];
        if (ext_vdw_wt) {
           vAwt[ nat-1 ] *= ext_vdw_wt[ nat-1 ];
           vBwt[ nat-1 ] *= ext_vdw_wt[ nat-1 ];
        }
    }

/* empty output array */
    if (!(steric = (double *) UTL_MEM_CALLOC( regp->n_points, sizeof( double )) )) goto cleanup;
    st = steric;

/* cycling over output array elements */
    for (iz=0, z=regp->box_array[0].lo[2]; iz < regp->box_array[0].nstep[2]; iz++, z += regp->box_array[0].stepsize[2])
      for (iy=0, y=regp->box_array[0].lo[1]; iy < regp->box_array[0].nstep[1]; iy++, y += regp->box_array[0].stepsize[1])
        for (ix=0, x=regp->box_array[0].lo[0]; ix < regp->box_array[0].nstep[0]; ix++, x += regp->box_array[0].stepsize[0])
        {
/* cycling over ligand atoms */
          for ( nat = 0, coord = ftemp, sum_steric = 0, va = vAwt, vb = vBwt; nat < natot; nat++, va++, vb++)
             if (!a2use || UTL_SET_MEMBER( a2use, nat )) {
                dis2 =  x - *coord++ ; dis2 *= dis2;
             diff =  y - *coord++ ; diff *= diff; dis2 += diff;
             diff =  z - *coord++ ; diff *= diff; dis2 += diff;
                if ( dis2 < MIN_SQ_DISTANCE ) atm_steric = STERIC_MAX * AtWts[ nat ];
```

```
            else {
                dis6 = dis2 * dis2 * dis2;
                dis12= dis6 * dis6 ;
                atm_steric = (*vb)/dis12 - (*va)/dis6;
                atm_steric = atm_steric > ( STERIC_MAX * AtWts[ nat ] ) ? STERIC_MAX *
AtWts[ nat ] : atm_steric;
            }
            sum_steric += atm_steric;
        }
        else coord += 3;

*st = sum_steric > STERIC_MAX ? STERIC_MAX : sum_steric;
        st++;
    }
cleanup:
    if (AtWts) UTL_MEM_FREE( AtWts );
    if (vAwt) UTL_MEM_FREE( vAwt );
    if (vBwt) UTL_MEM_FREE( vBwt );
error:
    return( steric );
} static l_RegionPtr getRegionToUse(double *coords, int natoms, int *r_idx, int *r_npoints )
{
    l_ComfaRegion *r;
    static double minx, maxx, miny, maxy, minz, maxz;
    int i;
    double x,y,z;
    double cminx, cminy, cminz, cmaxx, cmaxy, cmaxz;
    double edgeFact = 0.05;

cminx = cminy = cminz = 99999.0;
    cmaxx = cmaxy = cmaxz = -99999.0;

for ( i = 0; i < natoms; i++ )
    {
        x = *coords;
        y = *(coords+1);
        z = *(coords+2);

if ( x < cminx )
            cminx = x;
        if ( x > cmaxx )
            cmaxx = x;

if ( y < cminy )
            cminy = y;
```

```
                if ( y > cmaxy )
                        cmaxy = y;

if ( z < cminz )
                        cminz = z;
                if ( z > cmaxz )
                        cmaxz = z;

coords += 3;
        } for ( i = minRegion; i < max_regions; i++ )
        {
                r = regions[i];

minx = r->box_array[0].lo[0] + edgeFact;
                miny = r->box_array[0].lo[1] + edgeFact;
                minz = r->box_array[0].lo[2] + edgeFact;

maxx    =    minx   +   (   (double)   r->box_array[0].nstep[0]   -1.0   )   *
r->box_array[0].stepsize[0] - (edgeFact*2.0);
                maxy    =    miny   +   (   (double)   r->box_array[0].nstep[1]   -1.0   )   *
r->box_array[0].stepsize[1] - (edgeFact*2.0);
                maxz    =    minz   +   (   (double)   r->box_array[0].nstep[2]   -1.0   )   *
r->box_array[0].stepsize[2] - (edgeFact*2.0);

#if 0
                if ( r->box_array[0].lo[0] == 0.0 )
                        minx = -0.1;
endif if ( cminx >= minx && cmaxx <= maxx && cminy >= miny && cmaxy <= maxy
&& cminz >= minz && cmaxz <= maxz )
                {
                        *r_idx = i;
                        *r_npoints = r->n_points;
                        regionUseCnts[i] += 1;
                        return r;
                }
        } i = max_regions - 1;
        *r_idx = i;
        regionUseCnts[i] += 1;
        r = regions[i];
        *r_npoints = r->n_points;

return r;
```

}

```c
static int getCordExtents(double *coords, int natoms, double *r_minx, double *r_miny, double *r_minz,
double *r_maxx, double *r_maxy, double *r_maxz )
{
        double minx, maxx, miny, maxy, minz, maxz;
        double x,y,z;
        int i;

minx = maxx = *coords;
        miny = maxy = *(coords+1);
        minz = maxz = *(coords+2);
        coords += 3;

for ( i = 1; i < natoms; i++ )
        {
                x = *coords;
                y = *(coords+1);
                z = *(coords+2);
                coords += 3;

if ( x < minx )
                        minx = x;
                else if ( x > maxx )
                        maxx = x;

if ( y < miny )
                        miny = y;
                else if ( y > maxy )
                        maxy = y;

if ( z < minz )
                        minz = z;
                else if ( z > maxz )
                        maxz = z;
        }
        *r_minx = minx;
        *r_maxx = maxx;

*r_miny = miny;
        *r_maxy = maxy;

*r_minz = minz;
        *r_maxz = maxz;

return 0;
}
```

```c
static int atomsOutside(double *coords, int natoms, l_RegionPtr regp, double *atwts, double *r_outpen
)
{
        static l_RegionPtr lastreg;
        static double minx, maxx, miny, maxy, minz, maxz;
        int i;
        int outside;
        double x,y,z;
        double dist;
        double edgeFact = 0.0;
        double incrfact;
        double outsidePen = 0.0;

if ( regp != lastreg )
        {
                minx = regp->box_array[0].lo[0] + edgeFact;
                miny = regp->box_array[0].lo[1] + edgeFact;
                minz = regp->box_array[0].lo[2] + edgeFact;

maxx  =  minx  +  (double)  ( regp->box_array[0].nstep[0]  -1  )  *
regp->box_array[0].stepsize[0] - (edgeFact*2.0);
                maxy  =  miny  +  (double)  ( regp->box_array[0].nstep[1]  -1  )  *
regp->box_array[0].stepsize[1] - (edgeFact*2.0);
                maxz  =  minz  +  (double)  ( regp->box_array[0].nstep[2]  -1  )  *
regp->box_array[0].stepsize[2] - (edgeFact*2.0);

/* When calculating atoms outside the region, count the atoms close to the edge
                        as well.
                */ lastreg = regp;
if 0
                fprintf(stderr,"%6.2lf %6.2lf  %6.2lf %6.2lf %6.2lf %6.2lf \n",
                        minx, maxx, miny, maxy, minz, maxz );
#endif
        } outsidePen = 0.0;
        for ( i = outside = 0; i < natoms; i++ )
        {
                x = *coords;
                y = *(coords+1);
                z = *(coords+2);

if ( x < minx || x > maxx || y < miny || y > maxy || z < minz || z > maxz )
                {
                        outside++;
```

```
                /* calculate a crude distance anyway */
        dist = 0.0;
        if ( x < minx )
                dist += x*x - minx*minx;
        else if ( x > maxx )
                dist += x*x - maxx*maxx;

if ( y < miny )
                dist += y*y - miny*miny;
        else if ( y > maxy )
                dist += y*y - maxy*maxy;

if ( z < minz )
                dist += z*z - minz*minz;
        else if ( z > maxz )
                dist += z*z - maxz*maxz;

dist = fabs(dist); /* just in case */ if ( dist >= 1.0 )
                incrfact = STERIC_MAX * atwts[i];
        else
                incrfact = STERIC_MAX * atwts[i] * dist;
        outsidePen += incrfact*incrfact;
#if 0
                fprintf(stderr,"outside %d atom:%d %6.2lf %6.2lf %6.2lf points: %d %6.2lf
%6.2lf %6.2lf %6.2lf %6.2lf %6.2lf \n",
                        outside, i, x, y, z, regp->n_points, minx, miny, minz, maxx, maxy,
maxz );
#endif
            }
            coords += 3;
        }
        *r_outpen = outsidePen;
#if 0
        fprintf(stderr,"i_extent: x %d %d y %d %d z %d %d\n",
                (int) cminx, (int) cmaxx, (int) cminy, (int) cmaxy, (int) cminz, (int) cmaxz );
        fprintf(stderr,"extent: x %6.1lf %6.1lf %6.1lf %6.1lf %6.1lf %6.1lf \n",
                cminx, cmaxx, cminy, cmaxy, cminz, cmaxz );
#endif
        if ( outside )
                t_outside++; /* t_outside count's how many compounds have at least one atom outside
the field */
        t_fields++;
        return outside;
} double *TOP_STER_EVAL_ALL_RB_ATTEN(
```

/*==========================================================================*/
/* computes and returns a CoMFA steric field, to be freed by caller when done */ struct CtConnectionTable *ct,
    l_RegionPtr regp,
    int root,    /* atom ID of fragment root */
    double *acoord,    /* atomic coordinate array. If NIL, coordinates are retrieved from ct */
    double *AtWts )  /* optionally, if not NIL, these are additional user-supplied wts for field calculation */
{
ifndef NO_COMPRESSION
    static int max_alloc;
    static double *st_steric;
endif
    int natot, nat, ix, iy, iz;
    double *steric=NIL, *TOP_FIELD_RB_WTS(), *ftemp, *coord, *vAwt=NIL, *vBwt=NIL, *va, *vb, *st;
    double radnow, epsnow, diff, dis2, dis6, dis12, x, y, z, atm_steric, sum_steric, TOP_GET_ATOM_VDW_RADIUS();
    double xd, yd, zd;
    double maxw;
    double stepz, stepy, stepx;
    int nstepz, nstepy, nstepx;
    double lowz, lowy, lowx;
if 0
    int startEmpty, endEmpty;
endif
    int npoints;
    int freeWeights = 0;
    int outsideCnt = 0;
if 0
    static double mindis = 99999.0;
    static double maxdis = -99999.0;
    static double maxdists[50];
    static int distIdx = -1;
    double abs_steric;
endif define MIN_SQ_DISTANCE 1.0e-4
define RADIUS_C3   1.7
define EPSILON_C3  .107
define STERIC_MAX     30.0 if 0
    if ( distIdx == -1 )

```c
        {
                for ( nat = 0; nat < 50; nat++ )
                        maxdists[nat] = STERIC_MAX * -1.0;
                distIdx = 0;
        }
endif /* get coordinates, # atoms, RB attenuation for each atom */
        if ((ftemp = acoord )) {
                if (!DB_CT_GET_CT_ATTR( ct, CtCtAtomCount, &natot )) goto error;
        } else if (!DB_CT_GET_CT_ATTR( ct, CtCt3DCoordSet, &ftemp, &natot )) goto error;

#if 0
        AtWts = computeVdwWeights(ct, root - 1, -1, q_ReductionFactor, (int **) 0 );
#endif
        if ( !AtWts )
        {
                AtWts = (double *) malloc( natot * sizeof(double) );
                for ( nat = 0; nat < natot; nat++ )
                        AtWts[nat] = 1.0;
                freeWeights = 1;
        }
if 0
        if (!(AtWts = TOP_FIELD_RB_WTS( ct, root, (set_ptr) 0 ) )) goto cleanup;
        for ( nat = 0; q_debugfp && ext_vdw_wt && nat < ct->atomCount; nat++ )
        {
                fprintf(q_debugfp ,"#    weights  %d  %8.3lf  %8.3lf\n", nat+1, AtWts[nat],
ext_vdw_wt[nat] );
        }
endif /* compute VDW terms for each atom (not for each atom type as in SYBYL) */
        if (!(vAwt = (double *) UTL_MEM_ALLOC( sizeof(double) * natot ))) goto cleanup;
        if (!(vBwt = (double *) UTL_MEM_ALLOC( sizeof(double) * natot ))) goto cleanup;
        if (regp->box_array[0].atom_type != 1 || regp->n_boxes != 1)
                fprintf( stderr, "WARNING: The C.3 probe atom type in a single box is alway used in
the steric field calculation.\n" );
        for (nat=1; nat <= natot; nat++)
        {
                radnow = TOP_GET_ATOM_VDW_RADIUS( ct, nat, &epsnow );
                radnow += RADIUS_C3;
                epsnow = sqrt( epsnow * EPSILON_C3 );
                vAwt[ nat-1 ] = epsnow * 2.0 * pow( radnow, 6.0 ) * AtWts[ nat-1 ];
                vBwt[ nat-1 ] = epsnow *       pow( radnow, 12.0 ) * AtWts[ nat-1 ];
#if 0
                if (ext_vdw_wt) {
```

```
                vAwt[ nat-1 ] *= ext_vdw_wt[ nat-1 ];
                vBwt[ nat-1 ] *= ext_vdw_wt[ nat-1 ];
            }
endif
        }

/* empty output array */
        /* Don't initialize with calloc, we set each field, waist of time, it really is.
           A 38% speedup was performed by calling malloc vs calloc
        */ nstepz = regp->box_array[0].nstep[2];
        nstepy = regp->box_array[0].nstep[1];
        nstepx = regp->box_array[0].nstep[0];

stepz = regp->box_array[0].stepsize[2];
        stepy = regp->box_array[0].stepsize[1];
        stepx = regp->box_array[0].stepsize[0];

npoints = nstepz * nstepy * nstepx;

lowz = regp->box_array[0].lo[2];
        lowy = regp->box_array[0].lo[1];
        lowx = regp->box_array[0].lo[0];

#ifndef NO_COMPRESSION
        if ( npoints > max_alloc )
        {
            if ( !max_alloc )
                max_alloc = 4000;
            while ( npoints > max_alloc )
                max_alloc *= 2;

if ( st_steric )
                free((char *) st_steric );
            st_steric = (double *) malloc(sizeof(double) * max_alloc );
        }
        steric = st_steric;;
#else
        steric = (double *) malloc( npoints * sizeof( double ) );
endif st = steric;

/* cycling over output array elements */
        for (iz=0, z=lowz; iz < nstepz; iz++, z += stepz )
            for (iy=0, y=lowy; iy < nstepy; iy++, y += stepy )
```

```
              for (ix=0, x=lowx; ix < nstepx; ix++, x += stepx )
              {
/* cycling over ligand atoms */
              for ( nat = 0, coord = ftemp, sum_steric = 0.0, va = vAwt, vb = vBwt;
                    nat < natot && sum_steric < STERIC_MAX;
                    nat++, va++, vb++)
              {
#if 0
                    dis2 =  x - *coord++ ; dis2 *= dis2;
              diff = y - *coord++ ; diff *= diff; dis2 += diff;
              diff = z - *coord++ ; diff *= diff; dis2 += diff;
#endif
                    xd = x - *coord++;
                    yd = y - *coord++;
                    zd = z - *coord++;
                    dis2 = xd*xd + yd*yd + zd*zd;
#if 0
                    if ( dis2 > 49.0 )
                          continue;
endif
                    if ( dis2 >= MIN_SQ_DISTANCE )
                    {
                       dis6 = dis2 * dis2 * dis2;
                       dis12= dis6 * dis6 ;
                       atm_steric = (*vb)/dis12 - (*va)/dis6;
#if 0
                              abs_steric = fabs(atm_steric);
                              if ( AtWts[nat] == 1.0 && dis2 > 0.0 )
                              {
                                    if ( dis2 < mindis && abs_steric < 0.001 )
                                    {
                                          fprintf(stderr,"%10.8lf dis:%7.3lf\n", atm_steric, dis2
);
                                          mindis = dis2;
                                    }
                                    distIdx = (int) dis2;
                                    if ( distIdx < 49 && abs_steric > maxdists[distIdx] )
                                    {
                                          fprintf(stderr,"idx %d: %10.8lf dis:%10.5lf abs:%8.4lf
max\n", distIdx, atm_steric, dis2, abs_steric);
                                          maxdists[distIdx] = abs_steric;
                                    }
                              }
endif
                       maxw = STERIC_MAX * AtWts[ nat ];
                       if ( atm_steric > maxw )
                             atm_steric = maxw;
```

```
                }
                else
                {
                        atm_steric = STERIC_MAX * AtWts[ nat ];
                }
                sum_steric += atm_steric;
        }
        *st = sum_steric > STERIC_MAX ? STERIC_MAX : sum_steric;
        st++;
    } if 0
    for ( st = steric, iz = startEmpty = 0; iz < npoints && *st < 0.01 ; iz++, st++ )
    {
            startEmpty++;
    }
    for ( st = steric + (npoints -1), iz = npoints, endEmpty = 0; iz && *st < 0.01; iz--, st-- )
    {
            endEmpty++;
    }
    fprintf(stderr,"%d %d of %d  %6.2lf \n",
            startEmpty, endEmpty, npoints, ((double) (startEmpty+endEmpty)*100.0)/(double) npoints );
#endif
cleanup:
        if (AtWts && freeWeights) free ( (char*) AtWts );
        if (vAwt) UTL_MEM_FREE( vAwt );
        if (vBwt) UTL_MEM_FREE( vBwt );
error:
        return( steric );
} double *TOP_STER_ATOM_EVAL_ALL_RB_ATTEN(
/*===========================================================================
========================== */
/* computes and returns a CoMFA steric field, to be freed by caller when done,
   this version only computes the fields around each atom, outer loop is the ct's atoms */ struct CtConnectionTable *ct,
        l_RegionPtr regp,
        int root,           /* atom ID of fragment root */
        double *acoord,     /* atomic coordinate array. If NIL, coordinates are retrieved from ct
*/
        double *AtWts )  /* optionally, if not NIL, these are additional user-supplied wts for field calculation */
{
ifndef NO_COMPRESSION
```

```
                static int max_alloc;
                static double *st_steric;
endif
        int natot, nat, ix, iy, iz;
        double *steric=NIL, *TOP_FIELD_RB_WTS(), *ftemp, *coord, *vAwt=NIL, *vBwt=NIL,
*st;
        double va, vb;
        double radnow, epsnow, diff, dis2, dis6, dis12, x, y, z, atm_steric, sum_steric,
TOP_GET_ATOM_VDW_RADIUS();
        double xd, yd, zd;
        double maxw;
        double stepz, stepy, stepx;
        int nstepz, nstepy, nstepx;
        double lowz, lowy, lowx;
        double curr_lowz, curr_lowy, curr_lowx;
        int curr_nstepsz, curr_nstepsy, curr_nstepsx;
        int curr_ix, curr_iy, curr_iz;
        double curr_x, curr_y, curr_z;
        int max_steps;  /* assumes stepz, stepy, and stepx are the same step size */
        int max_xSteps, max_ySteps, max_zSteps;
#if 0
        int startEmpty, endEmpty;
endif
        int npoints;
        int freeWeights = 0;
        int outsideCnt = 0;
if 0
        static double mindis = 99999.0;
        static double maxdis = -99999.0;
        static double maxdists[50];
        static int distIdx = -1;
        double abs_steric;
endif define MIN_SQ_DISTANCE 1.0e-4
define RADIUS_C3    1.7
#define EPSILON_C3   .107
define STERIC_MAX        30.0 if 0
        if ( distIdx == -1 )
        {
                for ( nat = 0; nat < 50; nat++ )
                        maxdists[nat] = STERIC_MAX * -1.0;
                distIdx = 0;
        }
endif
```

```
/* get coordinates, # atoms, RB attenuation for each atom */
        if ((ftemp = acoord )) {
                if (!DB_CT_GET_CT_ATTR( ct, CtCtAtomCount, &natot )) goto error;
        } else if (!DB_CT_GET_CT_ATTR( ct, CtCt3DCoordSet, &ftemp, &natot )) goto error;

#if 0
        AtWts = computeVdwWeights(ct, root - 1, -1, q_ReductionFactor, (int **) 0 );
#endif
        if ( !AtWts )
        {
                AtWts = (double *) malloc( natot * sizeof(double) );
                for ( nat = 0; nat < natot; nat++ )
                        AtWts[nat] = 1.0;
                freeWeights = 1;
        }
if 0
        if (!(AtWts = TOP_FIELD_RB_WTS( ct, root, (set_ptr) 0 ) )) goto cleanup;
        for ( nat = 0; q_debugfp && ext_vdw_wt && nat < ct->atomCount; nat++ )
        {
                fprintf(q_debugfp ,"#    weights   %d   %8.3lf   %8.3lf\n", nat+1, AtWts[nat],
ext_vdw_wt[nat] );
        }
endif /* compute VDW terms for each atom (not for each atom type as in SYBYL) */
        if (!(vAwt = (double *) UTL_MEM_ALLOC( sizeof(double) * natot ))) goto cleanup;
        if (!(vBwt = (double *) UTL_MEM_ALLOC( sizeof(double) * natot ))) goto cleanup;
        if (regp->box_array[0].atom_type != 1 || regp->n_boxes != 1)
                fprintf( stderr, "WARNING: The C.3 probe atom type in a single box is alway used in
the steric field calculation.\n" );
        for (nat=1; nat <= natot; nat++)
        {
                radnow = TOP_GET_ATOM_VDW_RADIUS( ct, nat, &epsnow );
                radnow += RADIUS_C3;
                epsnow = sqrt( epsnow * EPSILON_C3 );
                vAwt[ nat-1 ] = epsnow * 2.0 * pow( radnow, 6.0 )  * AtWts[ nat-1 ];
                vBwt[ nat-1 ] = epsnow *       pow( radnow, 12.0 ) * AtWts[ nat-1 ];
#if 0
                if (ext_vdw_wt) {
                   vAwt[ nat-1 ] *= ext_vdw_wt[ nat-1 ];
                   vBwt[ nat-1 ] *= ext_vdw_wt[ nat-1 ];
                }
endif
        }

/* empty output array */
                /* Don't initialize with calloc, we set each field, waist of time, it really is.
```

A 38% speedup was performed by calling malloc vs calloc
*/

```
        nstepz = regp->box_array[0].nstep[2];
        nstepy = regp->box_array[0].nstep[1];
        nstepx = regp->box_array[0].nstep[0];

stepz = regp->box_array[0].stepsize[2];
        stepy = regp->box_array[0].stepsize[1];
        stepx = regp->box_array[0].stepsize[0];

npoints = nstepz * nstepy * nstepx;

lowz = regp->box_array[0].lo[2];
        lowy = regp->box_array[0].lo[1];
        lowx = regp->box_array[0].lo[0];

max_steps = (int) (4.0 / stepx);
        if ( max_steps <= 0 || ((double) max_steps * stepx ) < 4.0 )
                max_steps += 1;

max_xSteps = max_ySteps = max_zSteps = max_steps * 2;

if ( max_xSteps > nstepx )
                max_xSteps = nstepx;
        if ( max_ySteps > nstepy )
                max_ySteps = nstepy;
        if ( max_zSteps > nstepz )
                max_zSteps = nstepz;
#if 0
        fprintf(stderr,"max steps: %d %d %d %d\n", max_steps, max_xSteps, max_ySteps, max_zSteps
);
endif ifndef NO_COMPRESSION
        if ( npoints > max_alloc )
        {
                if ( !max_alloc )
                        max_alloc = 4000;
                while ( npoints > max_alloc )
                        max_alloc *= 2;

if ( st_steric )
                        free((char *) st_steric );
                st_steric = (double *) malloc(sizeof(double) * max_alloc );
        }
        steric = st_steric;;
```

```
            memset((char *) st_steric, '\0', sizeof(double) * npoints );
#else
            steric = (double *) calloc( npoints,sizeof( double ) );
endif st = steric;

for ( nat = 0, coord = ftemp;
                    nat < natot;
                    nat++ )
        {
            va = *(vAwt + nat);
            vb = *(vBwt + nat);
            curr_x = *coord;
            curr_y = *(coord+1);
            curr_z = *(coord+2);
            coord += 3;

iz = (int) ( fabs(curr_z - lowz + 0.5) / stepz);
            iy = (int) ( fabs(curr_y - lowy + 0.5) / stepy);
            ix = (int) ( fabs(curr_x - lowx + 0.5) / stepx);

curr_iz = iz - max_steps;
            curr_iy = iy - max_steps;
            curr_ix = ix - max_steps;

curr_nstepsz = iz + max_steps + 1;
            curr_nstepsy = iy + max_steps + 1;
            curr_nstepsx = ix + max_steps + 1;

/* check boundary conditions, where the atom is near the outside of the region
*/
            if ( curr_iz < 0 )
                curr_iz = 0;
            if ( curr_iy < 0 )
                curr_iy = 0;
            if ( curr_ix < 0 )
                curr_ix = 0;

/* Compute the fringe if outside the range */
            if ( curr_iz >= nstepz )
                curr_iz = nstepz - 1;
            if ( curr_iy >= nstepy )
                curr_iy = nstepy - 1;
            if ( curr_ix >= nstepx )
```

```
                curr_ix = nstepx - 1;

if ( curr_nstepsz > nstepz )
            curr_nstepsz = nstepz;

if ( curr_nstepsy > nstepy )
            curr_nstepsy = nstepy;

if ( curr_nstepsx > nstepx )
            curr_nstepsx = nstepx;

curr_lowz = lowz + (double) curr_iz * stepz;
    curr_lowy = lowy + (double) curr_iy * stepy;
    curr_lowx = lowx + (double) curr_ix * stepx;

maxw = STERIC_MAX * AtWts[ nat ];

#if 0
fprintf(stderr,"xyz %6.1lf %6.1lf %6.1lf low: %6.1lf %6.1lf %6.1lf steps: %d %d %d clow: %6.1lf
%6.1lf %6.1lf idx: %d %d %d ridx: %d %d %d csteps:%d %d %d\n",
                    curr_x, curr_y, curr_z,
                    lowx, lowy, lowz,
                    nstepx, nstepy, nstepz,
                    curr_lowx, curr_lowy, curr_lowz,
                    curr_ix, curr_iy, curr_iz,
                    ix, iy, iz,
                    curr_nstepsx, curr_nstepsy, curr_nstepsz );
endif /* cycling over output array elements */
            for ( iz=curr_iz, z=curr_lowz; iz < curr_nstepsz; iz++, z += stepz )
            {
                    zd = z - curr_z;
                    zd = zd*zd;
                    for (iy=curr_iy, y=curr_lowy; iy < curr_nstepsy; iy++, y += stepy )
                    {
                            yd = y - curr_y;
                            yd = yd*yd;
#if 0
                            if ( (zd+yd) > 49.0 )
                                    continue;
endif
                            st = st_steric + ( (iz * nstepy * nstepx ) + (iy * nstepx ) + curr_ix);
#if 0
                            fprintf(stderr,"base %d from %d %d %d (matrix: %d %d %d)\n",
                                    (iz * nstepy * nstepx ) + (iy * nstepx) + curr_ix,
                                    curr_ix, iy, iz, nstepx, nstepy, nstepz );
```

```
                                if ( !(iy%3) )
                                        sleep(1);
#endif
                                for (ix=curr_ix, x=curr_lowx; ix < curr_nstepsx; ix++, x += stepx
)
                                {
                                        sum_steric = *st;
                                        xd = x - curr_x;
                                        dis2 = xd*xd + yd + zd;

#if 0
                                        if ( dis2 > 49.0 )
                                                continue;
endif if ( dis2 >= MIN_SQ_DISTANCE )
                                        {
                                                dis6 = dis2 * dis2 * dis2;
                                                dis12= dis6 * dis6 ;
                                                atm_steric = vb/dis12 - va/dis6;
                                                if ( atm_steric > maxw )
                                                        atm_steric = maxw;
                                        }
                                        else
                                        {
                                                atm_steric = maxw;
                                        }
                                        sum_steric += atm_steric;
                                        *st = sum_steric > STERIC_MAX ? STERIC_MAX : sum_steric;
                                        st++;
                                }
                        }
                }
        }
if 0
        for ( st = steric, iz = startEmpty = 0; iz < npoints && *st < 0.01 ; iz++, st++ )
        {
                startEmpty++;
        }
        for ( st = steric + (npoints -1), iz = npoints, endEmpty = 0; iz && *st < 0.01; iz--, st-- )
        {
                endEmpty++;
        }
        fprintf(stderr,"%d %d of %d  %6.2lf \n",
                startEmpty, endEmpty, npoints, ((double) (startEmpty+endEmpty)*100.0)/(double)
npoints );
#endif
```

```
cleanup:
        if (AtWts && freeWeights) free ( (char*) AtWts );
        if (vAwt) UTL_MEM_FREE( vAwt );
        if (vBwt) UTL_MEM_FREE( vBwt );
error:
        return( steric );
} int TOP_STER_REGION_MODE(int regionMode )
{
        if ( regionMode < 0 )
                regionMode = 0;
        else if ( regionMode > 2 )
                regionMode = 2;

q_regionMode = regionMode;
} static int makeTopRegions(double stepSize, int numFrags)
{
        int i;
        l_ComfaRegion *r;
        l_Box *b;
        int nsteps;
        static double lastStepSize;
        static int printed;
        int intStep;
        int baseSteps = 5;
        int steps[3];
        double fullMult;
        int maxtrixSize;
        int totalPoints;
        int bigseen = 0;
        double baseX, baseY, baseZ;
        int done;

if ( lastStepSize == stepSize )
                return 0;
        lastStepSize = stepSize;
        baseX = -0.1;
        baseY = -6.0;
        baseZ = -4.0;
        totalPoints = 0;

if ( qxmin != 999.0 && qmode )
        {
                baseX = (double) ( (int) (qxmin - 1.0) );
                baseY = (double) ( (int) (qymin - 1.0) );
```

```
                baseZ = (double) ( (int) (qzmin - 1.0) );

baseSteps = 0;
                steps[0] = (int) ((qxmax - baseX + 1.50) / stepSize) + 1;
                steps[1] = (int) ((qymax - baseY + 1.50) / stepSize) + 1;
                steps[2] = (int) ((qzmax - baseZ + 1.50) / stepSize) + 1;
#ifdef TRIPOS_VERSION
                fprintf(stderr,"%6.2lf %6.2lf %6.2lf, %6.2lf %6.2lf %6.2lf %d %d %d\n",
                        qxmin, qymin, qzmin, qxmax, qymax, qzmax, steps[0], steps[1], steps[2]
);
endif }
        else
        {
                steps[0] = steps[1] = steps[2] = 5;
        }
        maxtrixSize = steps[0] * steps[1] * steps[2];

max_regions = NO_REGIONS;
/*
        We have to limit the number of regions generated to conserve memory.

If the initial region size to fit the query in is huge, then let's not
        create too many regions around it.
*/ for ( i = bigseen = done = 0; !done && i < max_regions; i++ )
        {
                if ( regions[i] )
                        free((char *) regions[i] );
                r = (l_RegionPtr) UTL_MEM_CALLOC(1,sizeof(l_ComfaRegion));
                r->n_boxes = 1;
                regions[i] = r;
                if ( r->box_array )
                        free((char *) r->box_array );
                b = r->box_array = (l_BoxPtr) UTL_MEM_CALLOC(1,sizeof(l_Box) );
                b[0].atom_type = 1;
                b[0].stepsize[0] = b[0].stepsize[1] = b[0].stepsize[2] = stepSize;

b[0].lo[0] = baseX;
                b[0].lo[1] = baseY;
                b[0].lo[2] = baseZ;
                b[0].nstep[0] = steps[0];
                b[0].nstep[1] = steps[1];
                b[0].nstep[2] = steps[2];

#ifdef TRIPOS_VERSION
```

```
            if ( !printed )
            {
                    fprintf(stderr,"%d: steps: %d,%d,%d stepsize: %6.2lf base: %6.2lf %6.2lf %6.2lf\n",
                            i, steps[0], steps[1], steps[2], stepSize, b[0].lo[0], b[0].lo[1], b[0].lo[2]
            );
            }
endif r->n_points = steps[0] * steps[1] * steps[2];
            totalPoints += r->n_points;

done = 0;
            if ( i >= 3 && steps[0] > 12 && steps[1] > 12 && steps[2] > 12 )
                    done = i+1;

if ( r->n_points > 3000 || totalPoints > 6000 )
            {
                    if ( bigseen == 0 && r->n_points < 5000 && totalPoints < 10000 )
                    {
                            baseX -= stepSize;
                            baseY -= stepSize;
                            baseZ -= stepSize;
                            steps[0] += 2;
                            steps[1] += 2;
                            steps[2] += 2;
                            bigseen = 1;
                    }
                    else
                    {
                            done = i+1;
                    }
            }
            else
            {
                    if ( i < 4 )
                    {
                            steps[0] += 1;
                            steps[1] += 1;
                            steps[2] += 1;
                            if ( i % 2 )
                            {
                                    baseZ -= stepSize;
                                    baseX -= stepSize;
                            }
                            else
                                    baseY -= stepSize;
```

```
                }
        else
        {
                if ( steps[0] < 13 )
                {
                        steps[0] += 1;
                        if ( !((i+4) % 4) )
                                baseX -= stepSize;
                }
                if ( steps[1] < 13 )
                {
                        steps[1] += 1;
                        if ( (i+2) % 3 )
                                baseY -= stepSize;
                }
                if ( steps[2] < 13 )
                {
                        steps[2] += 1;
                        if ( i % 2 )
                                baseZ -= stepSize;
                }
            }
        }
    }
    if ( done && done < NO_REGIONS )
            max_regions = done;
    printed = 1;
    return 1;
} l_RegionPtr TOP_MAKE_STD_REGION()
/*========================================================================
========================= */
/* creates a run-time description of the standard CoMFA region used for topomers
        source of region description is $DSERV_TB/rsh.rgn */
{
    l_RegionPtr R;

if (!(R = (l_RegionPtr) UTL_MEM_CALLOC(1,sizeof(l_ComfaRegion)))) goto error;
    R->n_boxes = 1;
    if (!(R->box_array = (l_BoxPtr) UTL_MEM_CALLOC(1,sizeof(l_Box)))) goto error;

if ( q_regionMode == 0 )
    {
            R->n_points = 1000;
            R->box_array[0].lo[0] = -4.0;
            R->box_array[0].lo[1] = -12.0;
```

```
            R->box_array[0].lo[2] = -8.0;
            R->box_array[0].hi[0] = 14.0;
            R->box_array[0].hi[1] = 6.0;
            R->box_array[0].hi[2] = 10.0;
            R->box_array[0].stepsize[0] = 2.0;
            R->box_array[0].stepsize[1] = 2.0;
            R->box_array[0].stepsize[2] = 2.0;
            R->box_array[0].nstep[0] = 10;
            R->box_array[0].nstep[1] = 10;
            R->box_array[0].nstep[2] = 10;
            R->box_array[0].atom_type = 1;   /* c.3 atom */
      }
      else if ( q_regionMode == 1 )  /* bigger */
      {
            R->n_points = 13*13*13;
            R->box_array[0].lo[0] = -4.0;
            R->box_array[0].lo[1] = -16.0;
            R->box_array[0].lo[2] = -10.0;
            R->box_array[0].hi[0] = 18.0;
            R->box_array[0].hi[1] = 8.0;
            R->box_array[0].hi[2] = 14.0;
            R->box_array[0].stepsize[0] = 2.0;
            R->box_array[0].stepsize[1] = 2.0;
            R->box_array[0].stepsize[2] = 2.0;
            R->box_array[0].nstep[0] = 13;
            R->box_array[0].nstep[1] = 13;
            R->box_array[0].nstep[2] = 13;
            R->box_array[0].atom_type = 1;   /* c.3 atom */
      }
      else /* Huge, just huge */
      {
            R->n_points = 25*25*20;              /* 12,500 points */
            R->box_array[0].lo[0] = -12.0;
            R->box_array[0].lo[1] = -30.0;
            R->box_array[0].lo[2] = -20.0;
            R->box_array[0].hi[0] = 36.0;
            R->box_array[0].hi[1] = 18.0;
            R->box_array[0].hi[2] = 18.0;
            R->box_array[0].stepsize[0] = 2.0;
            R->box_array[0].stepsize[1] = 2.0;
            R->box_array[0].stepsize[2] = 2.0;
            R->box_array[0].nstep[0] = 25;
            R->box_array[0].nstep[1] = 25;
            R->box_array[0].nstep[2] = 20;
            R->box_array[0].atom_type = 1;   /* c.3 atom */
      }
      return R;
error:
```

```
        return (l_RegionPtr) 0;
} double *TOP_FIELD_RB_WTS( struct CtConnectionTable *ct, int rootid,
/                                                                                *
================================================================
========================= */
        set_ptr a2use    /* optionally, if not NIL, need to process only this set of atoms */
             )
/* constructs and returns weighting-by-rotatable-bond array for each atom */
{
/* pseudo code for FIELD_RB_WTS()

while saw new atoms
    uncover atoms that stopped last shell growth
    grow next "rotational shell"
    while adding to shell
      for each atom in shell
        get neighbors not seen
        for each neighbor
          if bond is rotatable (acyclic, > 1 attached atom, not =,am,#)
            cover all other atoms attached to atom for this shell
          add it to shell
*/
  double  *ansr = NIL, *vals = NIL, factor, nowfact = 1.0;
  int     nats, b, aggcount, atid, aggid, loop, size, inRing, natt, ntoats, toats[20];
  set_ptr    aggats = NIL, allats = NIL, nu1s = NIL, endatms = NIL, end_cands = NIL;
  CtBondTypeDef bType;

/* be sure rings were perceived */
  if (!DB_CT_UTL_FIND_RINGS( ct )) goto cleanup;

if (!DB_CT_GET_CT_ATTR( ct, CtCtAtomCount, &nats )) goto cleanup;

/* output data allocations */
  if (!( vals = (double*) UTL_MEM_ALLOC( sizeof(double)*nats))) goto cleanup;

factor = aggreg_descale;
  if (!(allats = UTL_SET_CREATE( nats + 1 ) )) goto cleanup;
  if (!(aggats = UTL_SET_CREATE( nats + 1 ) )) goto cleanup;
  if (!(nu1s = UTL_SET_CREATE( nats + 1 ) )) goto cleanup;
  if (!(endatms = UTL_SET_CREATE( nats + 1 ) )) goto cleanup;
  if (!(end_cands = UTL_SET_CREATE( nats + 1 ) )) goto cleanup;
  UTL_SET_INSERT( aggats, rootid );
  UTL_SET_INSERT( allats, rootid );
  aggcount = loop = 1;
  while (TRUE) {
    while (TRUE) {
```

```
        aggid = -1;
        while ((aggid = UTL_SET_NEXT( allats, aggid )) >= 0 ) {
/* put (acceptable) atoms attached to aggid into nuls */
            UTL_SET_CLEAR( nuls );
                if(!(DB_CT_GET_ANY_ATOM_ATTR( ct, aggid, CtAtomBondCount, &ntoats ))) goto
error;
                if (ntoats > 20) goto toomanyattms;
                if(!(DB_CT_GET_ANY_ATOM_ATTR( ct, aggid, CtAtomBondToAtoms, &toats ))) goto
error;
                    for (natt=0; natt < ntoats; natt++) if(!a2use || UTL_SET_MEMBER(a2use, toats[natt]))
                        UTL_SET_INSERT( nuls, toats[ natt ] );
/* remove atoms already processed from nuls */
            UTL_SET_DIFF_INPLACE( nuls, allats, nuls );
            UTL_SET_DIFF_INPLACE( nuls, endatms, nuls );
/* identifying any atoms that terminate this aggregate */
            atid = -1;
            while ((atid = UTL_SET_NEXT( nuls, atid )) >= 0 ) {
/* skipping monovalent atoms */
                if(!(DB_CT_GET_ANY_ATOM_ATTR( ct, atid, CtAtomBondCount, &ntoats ))) goto
error;
                if (ntoats > 1) {
                    if (!(b = DB_CT_UTL_GET_BONDID( ct, atid, aggid ) )) goto error;
                    if (!DB_CT_GET_BOND_ATTR( ct, b, CtBondIsInRing, &inRing)
                        || !DB_CT_GET_BOND_ATTR( ct, b, CtBondType, &bType ) ) goto
error;
                    if (!inRing && bType == CtBondTypeSingle ) {
/* have an end-of-aggregate atom, mark as end atoms all other attached atoms */
                        UTL_SET_CLEAR( end_cands );
                        if (!(DB_CT_GET_ANY_ATOM_ATTR( ct, atid, CtAtomBondCount, &ntoats
) )) goto error;
                        if (ntoats > 20) goto toomanyattms;
                        if(!(DB_CT_GET_ANY_ATOM_ATTR( ct, atid, CtAtomBondToAtoms, &toats ))) goto
error;
                        for (natt=0; natt < ntoats; natt++) if(!a2use || UTL_SET_MEMBER(a2use, toats[natt]))

UTL_SET_INSERT( end_cands, toats[ natt ] );
                        UTL_SET_DELETE( end_cands, aggid );
                        UTL_SET_OR_INPLACE( endatms, end_cands, endatms );
                    }
                }
            }
            UTL_SET_OR_INPLACE( aggats, nuls, aggats );
        }
        if (UTL_SET_CARDINALITY( aggats ) <= aggcount ) break;
        aggcount = UTL_SET_CARDINALITY( aggats );
        UTL_SET_OR_INPLACE( allats, aggats, allats );
    }
/* debugging stuff .. */
```

```
/*
    sprintf( tempString, "Aggregate %d (weight = %f ):", loop, nowfact );
    UBS_OUTPUT_MESSAGE( stdout, tempString );
    ashow( aggats, molp );
    ashow( aggats, molp );
*/
/* if no atoms added, we are done! */
    if (UTL_SET_EMPTY( aggats )) break;
/* record scaling factor for atoms in this aggregate */
    atid = -1;
    while ((atid = UTL_SET_NEXT( aggats, atid )) >= 0 ) {
            vals[ atid-1 ] = nowfact;
    }
    UTL_SET_OR_INPLACE( allats, aggats, allats );
    UTL_SET_CLEAR( aggats );
    UTL_SET_CLEAR( endatms );
    aggcount = 0;
    nowfact *= factor;
    loop++;
  }
  ansr = vals;

cleanup:
error:
  if (aggats) UTL_SET_DESTROY( aggats );
  if (allats) UTL_SET_DESTROY( allats );
  if (endatms) UTL_SET_DESTROY( endatms );
  if (end_cands) UTL_SET_DESTROY( end_cands );
  if (nuls) UTL_SET_DESTROY( nuls );
  return( ansr );

toomanyattms:
  fprintf( stderr, "More than twenty atoms attached to some atom in this structure.\n" );
  goto error;
} static char *fhex_field = NIL;
static int field_length = 0;

char *CT_FIELD2HEX( double *field, int size )
/*==================================================================
======================================== */
/* maps field to a hex string coarsely representing the field -
        caller must NOT free this string! */
{
  char *f;
  int i, j, fd;
```

```c
static double cutoff[16] = {9999.,  0.,  2.,  4.,  6.,  8., 10., 12.,
        14., 16., 18., 20., 22., 24., 26., 30. };

if ( size != field_length) {
    if (fhex_field) UTL_MEM_FREE( fhex_field );
    if (!(fhex_field = UTL_MEM_ALLOC( sizeof( char) * (size+1) ) )) return NIL;
    field_length = size;
}
for (f = fhex_field, j = 0; j < size; j++, f++ ) {
    for ( i = 1, fd = FALSE; i < 16; i++ ) if (field[ j ] <= cutoff[ i ]) {
        fd = TRUE;
        break;
    }
    if (!fd) {
        fprintf( stderr, "Illegal steric field value set to missing.\n" );
        i = 0;
    }
    sprintf( f, "%.1x", i );
}
*f = '\0';
return fhex_field;
} double TOP_GET_ATOM_VDW_RADIUS( struct CtConnectionTable *ct, int nat, double *epsnow )
/*
==================================================================================
=================================================== */
/* hard coded to assign classical TAFF VDW properties */
{
    int sybat;
    char *sybname;
    static double a_eps[34] = {
            0.000, 0.107, 0.107, 0.107, 0.107,
            0.095, 0.095, 0.095, 0.116, 0.116,       /* 5 - 9 */
            0.095, 0.314, 0.095, 0.042, 0.434,
            0.314, 0.109, 0.623, 0.314, 0.095,       /* 15 - 19 */
            0.000, 0.400, 0.400, 0.600, 0.400,
            0.100, 0.000, 0.042, 0.095, 0.314,
            0.314, 0.095, 0.116, 0.107 };

static double rval[34] = {
            0.000, 1.700, 1.700, 1.700, 1.700,
            1.550, 1.550, 1.550, 1.520, 1.520,       /* 5 -9 */
            1.800, 1.550, 1.800, 1.500, 1.850,
            1.750, 1.470, 1.980, 1.800, 1.550,       /* 15 - 19 */
            0.000, 1.200, 1.200, 1.200, 1.200,
            1.341, 0.000, 2.100, 1.550, 1.800,
            1.800, 1.550, 1.520, 1.700 };
```

```
    if (!(DB_EX_ELEM_TO_SYB_ATOM_TYPE( ct, nat, &sybname, &sybat ))) {
        fprintf( stderr, "Warning: Atom type not found for atom ID %d.\n", nat );
        *epsnow = 0.0;
        return 0.0;
    }
    if ( sybat < 0 || sybat > 33 )
    {
        *epsnow = 0.0;
        return 0.0;
    }
    *epsnow = a_eps[sybat];
    return rval[sybat];

#if 0
    switch (sybat) {
case 1: /* c.3 */
case 2: /* c.2 */
case 3: /* c.ar */
case 4: /* c.1 */
case 33: /* c+ */
            *epsnow = .107; return( 1.7 );
case 5: /* n.3 */
case 6: /* n.2 */
case 7: /* n.1 */
case 11: /* n.ar */
case 19: /* n.lp3 */
case 28: /* n.am */
case 31: /* N+ */
            *epsnow = .095; return( 1.55 );
case 8: /* o.3 */
case 9: /* o.2 */
case 32: /* o.ar */
            *epsnow = .116; return( 1.52 );
case 10: /* s.3 */
case 12: /* p.3 */
case 18: /* s.2 */
case 29: /* S.O */
case 30: /* s.o2 */
            *epsnow = .314; return( 1.8 );
case 13: /* H */
            *epsnow = .042; return( 1.5 );
case 14: /* Br */
            *epsnow = .434; return( 1.85 );
case 15: /* Cl */
            *epsnow = .314; return( 1.75 );
```

```
case 16: /* F */
         *epsnow = .109; return( 1.47 );
case 17: /* I */
         *epsnow = .623;    return( 1.98 );
case 21: /* Na */
case 22: /* K */
case 24: /* Li */
         *epsnow = 0.4; return( 1.2 );
case 23: /* Ca */
         *epsnow = 0.6; return( 1.2 );
case 25: /* Al */
         *epsnow = 0.1; return( 1.341 );
case 27: /* Si */
         *epsnow = 0.042; return( 2.1 );
default:
         fprintf( stderr, "WARNING: Assigning no steric field from atom type; %s\n", sybname
);
         *epsnow = 0.0; return( 0.0 );
    }
endif
} int TOP_REFLECT_COO( double *coo, set_ptr atms, int npt, int *aplane )
/*===========================================================================
============================================ */
/* reflects atms through the plane defined by the atoms whose IDs are in aplane, by modifying values
in coo */
{ double cent[3], eval[3], evec[3][3], mat[3][3], x, xsq, xy, xz,
           y, ysq, yz, z, zsq, *cx, *cy, *cz, l, m, n, d, *xyz, h;
    int na, nrot, elem;

/* Now perform the sums to determine the parameters of the plane   */
/* equation.                                                       */
    x = xsq = y = ysq = z = zsq = xy = xz = yz = 0.0;
    for (na = 0; na < npt; na++ ) {
        cx = coo + 3 * ( aplane[ na ] - 1 );
        x   += *cx;
        xsq += (*cx) * (*cx);
        cy = cx + 1;
        y   += *cy;
        ysq += (*cy) * (*cy);
        cz = cy + 1;
        z   += *cz;
        zsq += (*cz) * (*cz);
        xy  += (*cx) * (*cy);
```

```
          xz += (*cx) * (*cz);
          yz += (*cy) * (*cz);
     }
     cent[0] = x / (double) npt;
     cent[1] = y / (double) npt;
     cent[2] = z / (double) npt;

mat[0][0] = xsq - x * cent[0];
     mat[0][1] = xy  - x * cent[1];
     mat[0][2] = xz  - x * cent[2];
     mat[1][0] = xy  - y * cent[0];
     mat[1][1] = ysq - y * cent[1];
     mat[1][2] = yz  - y * cent[2];
     mat[2][0] = xz  - z * cent[0];
     mat[2][1] = yz  - z * cent[1];
     mat[2][2] = zsq - z * cent[2];

/* calculate the plane */
     if (!UTL_GEOM_SYMM_EIGENSYS ((double *)mat, 3, eval, (double *) evec, &nrot))  goto error;

l = evec[0][0];
     m = evec[1][0];
     n = evec[2][0];
     d = (l * cent[0] + m * cent[1] + n * cent[2]);

/* perform reflection on the input coordinate sets */
     elem = -1;
     while ( (elem = UTL_SET_NEXT( atms, elem)) >= 0 ) {
          xyz = coo + (elem - 1) * 3;
          h = l * xyz[0] + m * xyz[1] + n * xyz[2] - d;
          xyz[0] -= 2.0 * l * h;
          xyz[1] -= 2.0 * m * h;
          xyz[2] -= 2.0 * n * h;
     } return TRUE;
error:
     return FALSE;
} static int reflectAtoms( double *coo, int nAtoms, int npt, int *aplane )
/*================================================================================================== */
/* reflects atms through the plane defined by the atoms whose indexes (base 0 )are in aplane, by modifying values in coo */
{
```

```
double cent[3], eval[3], evec[3][3], mat[3][3], x, xsq, xy, xz,
       y, ysq, yz, z, zsq, *cx, *cy, *cz, l, m, n, d, *xyz, h;
int na, nrot, elem;
       int *dn;

if( npt >= 3 )
               dn = findDirectionalNeighbors(g_ct, aplane[1], aplane[0], aplane[2] );
       else
               return FALSE;

/* Now perform the sums to determine the parameters of the plane   */
/* equation.                                                        */
    x = xsq = y = ysq = z = zsq = xy = xz = yz = 0.0;
    for (na = 0; na < npt; na++ ) {
        cx = coo + 3 * ( aplane[ na ] );
        x   += *cx;
        xsq += (*cx) * (*cx);
        cy = cx + 1;
        y   += *cy;
        ysq += (*cy) * (*cy);
        cz = cy + 1;
        z   += *cz;
        zsq += (*cz) * (*cz);
        xy  += (*cx) * (*cy);
        xz  += (*cx) * (*cz);
        yz  += (*cy) * (*cz);
    }
    cent[0] = x / (double) npt;
    cent[1] = y / (double) npt;
    cent[2] = z / (double) npt;

mat[0][0] = xsq - x * cent[0];
    mat[0][1] = xy  - x * cent[1];
    mat[0][2] = xz  - x * cent[2];
    mat[1][0] = xy  - y * cent[0];
    mat[1][1] = ysq - y * cent[1];
    mat[1][2] = yz  - y * cent[2];
    mat[2][0] = xz  - z * cent[0];
    mat[2][1] = yz  - z * cent[1];
    mat[2][2] = zsq - z * cent[2];

/* calculate the plane */
    if (!UTL_GEOM_SYMM_EIGENSYS ((double *)mat, 3, eval, (double *) evec, &nrot)) goto error;

l = evec[0][0];
    m = evec[1][0];
    n = evec[2][0];
    d = (l * cent[0] + m * cent[1] + n * cent[2]);
```

```c
/* perform reflection on the input coordinate sets */
elem = -1;
for ( elem = 0; elem < nAtoms; elem++ )
{
    if ( dn[elem] <= 0 )
            continue;
    xyz = coo + (elem * 3);
    h = l * xyz[0]  +  m * xyz[1]  +  n * xyz[2] - d;
    xyz[0] -= 2.0 * l * h;
    xyz[1] -= 2.0 * m * h;
    xyz[2] -= 2.0 * n * h;
} if ( dn ) free((char *) dn );
  return TRUE;
error:
    if ( dn ) free((char *) dn );
  return FALSE;
} static int setTorsion(double *coo, int nAtoms, int a1, int a2, int a3, int a4, double value )
/* rotates atoms to the value for the torsional angle defined by a1,a2,a3,a4, by modifying values in coo
*/
{
  double angle, delta, matrix[3][3];
  int elem;
        int *dn;

dn = findDirectionalNeighbors(g_ct, a3, a2, -1 );
  angle = UTL_GEOM_TAU( coo+(a1*3), coo+(a2*3), coo+(a3*3), coo+(a4*3) );
  if (UTL_ERROR_IS_SET()) UTL_ERROR_CLEAR();
  if (angle < 0.0) angle += 360.0;

while (value < 0.0)
    value += 360.0;

while (value > 360.0)
    value -= 360.0;

delta = angle - value;
  UTL_GEOM_MFORM( coo+(a2*3), coo+(a3*3), delta, matrix );
  for ( elem = 0; elem < nAtoms; elem++ )
  {
        if ( dn[elem] > 0 )
            UTL_GEOM_ROTATE( coo+(a3*3), matrix, coo+(elem*3) );
  }
        free((char *) dn );
  return 1;
```

}

```
static int setRootTorsion(double *coo, int nAtoms, int a2, int a3, int a4, double value )
/* rotates atoms to the value for the torsional angle defined by a1,a2,a3,a4, by modifying values in coo
*/
{
  double angle, delta, matrix[3][3];
  double cord1[3];
        double cord2[3];
  int elem;

cord1[0] = -1.802;
  cord1[1] = 1.666;
  cord1[2] = 0.0;

if ( q_coremode_align )
                cord2[0] = -2.004;
        else
                cord2[0] = -0.504;

cord2[1] = 1.424;
  cord2[2] = 0.0;

angle = UTL_GEOM_TAU( cord2, coo+(a2*3), coo+(a3*3), coo+(a4*3) );
  if (UTL_ERROR_IS_SET()) UTL_ERROR_CLEAR();
  if (angle < 0.0) angle += 360.0;

while (value < 0.0)
    value += 360.0;

while (value > 360.0)
    value -= 360.0;

delta = angle - value;
#ifdef DEBUG_DETAIL
        if ( q_debugfp )
                fprintf(q_debugfp, "# root value: %8.3lf %6.0lf %8.3lf\n", angle, value, delta );
#endif
  UTL_GEOM_MFORM( coo+(a2*3), coo+(a3*3), delta, matrix );
  elem = -1;
  for ( elem = 0; elem < nAtoms; elem++ )
    UTL_GEOM_ROTATE( coo+(a3*3), matrix, coo+(elem*3) );
  return 1;
} static int setBaseTorsion(double *coo, int nAtoms, int a3, int a4, double value )
/* rotates atoms to the value for the torsional angle defined by a1,a2,a3,a4, by modifying values in coo
*/
```

```
{
  double angle, delta, matrix[3][3];
  double cord1[3];
      double cord2[3];
  int elem;

cord1[0] = -1.802;
  cord1[1] = 1.666;
  cord1[2] = 0.0;
  cord2[0] = -0.504;
  cord2[1] = 1.424;
  cord2[2] = 0.0;

angle = UTL_GEOM_TAU( cord1, cord2, coo+(a3*3), coo+(a4*3) );
  if (UTL_ERROR_IS_SET()) UTL_ERROR_CLEAR();
  if (angle < 0.0) angle += 360.0;

while (value < 0.0)
    value += 360.0;

while (value > 360.0)
    value -= 360.0;

delta = angle - value;
  UTL_GEOM_MFORM( cord2, coo+(a3*3), delta, matrix );
  elem = -1;
  for ( elem = 0; elem < nAtoms; elem++ )
    UTL_GEOM_ROTATE( coo+(a3*3), matrix, coo+(elem*3) );
  return 1;
} int TOP_SET_TORSION( double *coo, set_ptr atms, int a1, int a2, int a3, int a4, double value )
/*===========================================================================
================================= */
/* rotates atms to the value for the torsional angle defined by a1,a2,a3,a4, by modifying values in coo
*/
{ double angle, delta, matrix[3][3];
  int elem;

angle = UTL_GEOM_TAU( coo+(a1-1)*3, coo+(a2-1)*3, coo+(a3-1)*3, coo+(a4-1)*3 );
  if (UTL_ERROR_IS_SET()) goto error;
  if (angle < 0.0) angle += 360.0;

while (value < 0.0)
    value += 360.0;
```

```
      while (value > 360.0)
        value -= 360.0;

delta = angle - value;
      UTL_GEOM_MFORM( coo+(a2-1)*3, coo+(a3-1)*3, delta, matrix );
      elem = -1;
      while ((elem = UTL_SET_NEXT( atms, elem)) > 0)
        UTL_GEOM_ROTATE( coo+(a3-1)*3, matrix, coo+(elem-1)*3 );

return( TRUE );

error:
      return( FALSE );
    } int TOP_ALIGN_MOL( double *coo, int natms, int a1, int a2, int a3 )
    /*
    =========================================================================
    ==================================== */
    /* rotates and translates all coordinates so that a1 is at origin, a2 lies along x axis, and a3 lies in the xy plane */
    {
      double    matrix[3][3], tv[3], u[3], *c;
      int i, nc;

if (!UTL_GEOM_ALIGN( coo+(a1-1)*3, coo+(a2-1)*3, coo+(a1-1)*3, coo+(a3-1)*3, matrix)) goto error;
      if ( q_coremode_align )
              c = coo+(a2-1)*3;
          else
              c = coo+(a1-1)*3;
      for (i = 0; i < 3; i++, c++) {
        u[i] = *c ;
        tv[i] = -u[i];
      } for (nc = 0, c = coo; nc < natms; nc++ ) {
          UTL_GEOM_ROTATE( u, matrix, c);
          for (i = 0; i < 3; i++, c++) *c += tv[ i ];
      }
      return TRUE;
    error:
      return FALSE;
    }
    /* New code Sept, 2000 */

/*
```

FindBreakPoints - takes in a ct and returns an array the size of the number of bonds in the ct. Each cell indicates true or false if this is a break point bond break points: are single bonds with at least N heavy atoms on each side of the attachment, not in a ring, and optionally they can be terminal atoms int minHev - optional argument which forces at least N hev atoms for this to be a breakpoint bond.

int termflag - if true the heavy atoms can be terminal heavy atoms, for example Fl, Br, Cl Author: Rob Jilek   Sept, 2000

*/

```
static Split *FindBreakPoints(CtConnectionTable *ct, int minHev, int termflag, int createFrags )
{
        int *bdata;
        int *singleBonds;
        int *bptr;
        CtBond *bondp;
        int idx;
        int *rb1, *rb2;
        int *atomMask;
        int hevCnt;
        int hevDiff;
        Split *S;

int bcnt;
        CtBondTypeDef bondType;
        CtSimpleBondTypeDef simpleTypes;

#ifdef DEBUG_VALID_B
        fprintf(stdout,"new breakpoints  minHev: %d  Allow term: %s\n",
                minHev, (termflag) ? "Yes" : "No" );
endif S = (Split *) 0;

if ( !ct || !ct->bondCount )
                return S;
        atomMask = createAtomMask(ct, termflag, &hevCnt);

if ( !q_coremode && qs && q_hevDiff >= 0 )
        {
```

```c
            hevDiff = abs(hevCnt - qs->numHev);
            if ( hevDiff > q_hevDiff )
            {
                    if ( createFrags )
                            t_filtered++;
                    free((char *) atomMask );
                    return S;
            }
    }
    if ( hevCnt < (minHev*2) )
    {
            free((char *) atomMask );
            return S;
    }
    bdata = (int *) calloc(ct->bondCount, sizeof(int) );
    singleBonds = (int *) calloc(ct->bondCount, sizeof(int) );
    S = (Split *) calloc(1, sizeof(Split) );

for ( idx = 0, bondp = ct->bonds;
                    idx < ct->bondCount;
                    idx++, bondp++ )
    {
            if ( ! ( bondp->simpleBondType == CtSimpleBondTypeSingle ||
                            bondp->simpleBondType == CtSimpleBondTypeNotSimple ) )
                    continue;       /* must be single, check NotSimple next. */ if ( bondp->simpleBondType == CtSimpleBondTypeNotSimple )
            {
                    bondType = DB_CT_GET_BOND_TYPE(ct, STD_ID(idx), &bcnt,
&simpleTypes );
                    if ( bondType != CtBondTypeSingle )
                            continue;
            }
            if ( AB_IN_RING(bondp) )
                    continue;
            singleBonds[idx] = 1;

if ( minHev > 0 && !validBreakPoint(ct, idx, atomMask, minHev, termflag, &rb1, &rb2
))
                    continue;
            if ( createFrags )
                    addSplit2(idx, rb1, rb2 );
            else
            {
                    free((char *) rb1 );
                    free((char *) rb2 );
                    S->s2cnt++;
            }
```

```
            bdata[idx] = 1;              /* found a good one */
    } if ( createFrags && ( q_do3piece || q_doSubset ) && hevCnt > = (minHev*3) )
            makeSplit3(ct, atomMask, g_split2, g_splitcnt, minHev );

if ( createFrags )
            S-> frags = createUniqFrags(ct-> atomCount, g_split2, g_splitcnt, g_split3, g_split3Cnt,
atomMask,
                    &(S-> numFrags) );
    S-> numHev = hevCnt;

#ifdef DEBUG_VALID_BXX
    fprintf(stdout,"bonds (base 0): ");
    for ( idx = 0;
                idx < ct-> bondCount;
                idx+ + )
    {
            if ( bdata[idx] )
                    fprintf(stdout,"%d ", idx );
    }
    fprintf(stdout,"\n");
endif if ( createFrags )
    {
            S-> s2 = g_split2;
            S-> s3 = g_split3;
            S-> s2cnt = g_splitcnt;
            S-> s3cnt = g_split3Cnt;
    }

S-> bondCount = ct-> bondCount;
    S-> atomCount = ct-> atomCount;
    S-> bondMask = bdata;
    S-> atomMask = atomMask;
    S-> singleBonds = singleBonds;
    S-> aromSets = (AromSet *) 0;

g_split2 = (split2 *) 0;
    g_split3 = (split3 *) 0;
    g_splitcnt = g_splitalloc = g_split3Cnt = g_split3Alloc = 0;

return S;
}
```

```
static void freeSplit(Split *s)
{
        int i;
        AromSet *aset;

if ( !s )
                return;
        freeSplit2(s->s2, s->s2cnt);
        freeSplit3(s->s3, s->s3cnt);
        freeFrags(s->frags, s->numFrags);
        if ( s->bondMask )
                free((char *) s->bondMask );
        if ( s->atomMask )
                free((char *) s->atomMask );
        if ( s->singleBonds )
                free((char *) s->singleBonds );

if ( s->featureMask )
                free((char *) s->featureMask );
        if ( s->aromMask )
                free((char *) s->aromMask);
        if ( s->aromSets )
        {
                for ( i = 0, aset = s->aromSets; i < s->numArom; i++, aset++ )
                        free((char *) aset->atoms);
                free((char *) s->aromSets );
        }
        free((char *) s);
} static void freeSplit2(split2 *s2, int cnt )
{
        split2 *sptr;
        int i;

if ( !s2 )
                return;

for ( i = 0, sptr = s2; i < cnt; sptr++, i++ )
        {
                free((char *) sptr->b1);
                free((char *) sptr->b2);
        }
        free((char *) s2);
} static void freeSplit3(split3 *s3, int cnt )
{
```

```
        split3 *sptr;
        int i;

if ( !s3 )
                return;

for ( i = 0, sptr = s3; i < cnt; sptr++, i++ )
        {
                free((char *) sptr->b1);
                free((char *) sptr->b2);
                free((char *) sptr->b3);
                if ( sptr->b4 )
                        free((char *) sptr->b4 );
        }
        free((char *) s3);
} static void freeFrags(Frag *f, int cnt )
{
        Frag *fptr;
        int i,j;

for ( i = 0, fptr = f; i < cnt; i++, fptr++ )
        {
#ifdef USE_HEX
                if ( fptr->topHex )
                        free(fptr->topHex );
                if ( fptr->topInt)
                        free((char *) fptr->topInt );
#endif
ifdef STD_REGION
                if ( fptr->stdField)
                        free((char *) fptr->stdField );
#endif
                if ( fptr->hexDiff )
                        free((char *) fptr->hexDiff );
                if ( fptr->featureDiff )
                        free((char *) fptr->featureDiff);
                if ( fptr->ct )
                        DB_CT_DELETE_CT(fptr->ct);
                else if ( fptr->cords )
                        free((char *) fptr->cords);   /* if the ct exists, then coords is a pointer into the ct's coordinates */
                if ( fptr->origMapping )
                        free((char *) fptr->origMapping );
                if ( fptr->cent )
                        free((char *) fptr->cent);
                if ( fptr->AtWts )
```

```c
                free((char *) fptr->AtWts );
                for ( j = 0; j < max_regions; j++ )
                {
                        if ( fptr->qtf[j] && fptr->qtf[j] != fptr->topField )
                                free((char *) fptr->qtf[j] );
                }
                if ( fptr->topField )
                        free((char *) fptr->topField );
        }
        free((char *) f );
} static void freeFragCts(Split *S)
{
        Frag *fptr;
        int i,j;
        double *coords;

for ( i = 0, fptr = S->frags; i < S->numFrags; i++, fptr++ )
        {
                if ( fptr->ct && fptr->cords )
                {
                        coords = (double *) malloc(fptr->ct->atomCount * sizeof(double) * 3 );
                        memcpy((char *) coords, fptr->cords, sizeof(double) * fptr->ct->atomCount * 3);

fptr->cords = coords;

DB_CT_DELETE_CT(fptr->ct);
                        fptr->ct = (struct CtConnectionTable *) 0;
                }
        }
}
static int freeStrMap(Split *S)
{
        split2 *s2;
        split3 *s3;
        int i;

#ifdef NO_STRMAP
        return -1;
#else
        if ( !S )
                return 0;
        for ( i = 0, s2 = S->s2; i < S->s2cnt; i++, s2++ )
        {
                if ( s2->strMap )
                {
                        free((char *) s2->strMap );
```

```
                    s2->strMap = (int *) 0;
            }
    }
    S->alloc2Map = 0;

for ( i = 0, s3 = S->s3; i < S->s3cnt; i++, s3++ )
    {
            if ( s3->strMap )
            {
                    free((char *) s3->strMap );
                    s3->strMap = (int *) 0;
            }
    }
    S->alloc3Map = 0;
#endif
} static int addSplit2(int bondId, int *b1, int *b2 )
{
    split2 *s;

if ( g_splitcnt >= g_splitalloc )
    {
            if ( g_split2 && g_splitalloc )
            {
                    g_split2 = (split2 *) realloc((char *) g_split2, g_splitalloc * 2 * sizeof(split2) );
                    g_splitalloc *= 2;
            }
            else
            {
                    g_splitalloc = 3;
                    g_split2 = (split2 *) calloc(sizeof(split2), g_splitalloc );
            }
    }
    s = g_split2 + g_splitcnt;
    s->bondId = bondId;
    s->b1 = b1;
    s->b2 = b2;
#ifndef NO_STRMAP
    s->strMap = (int *) 0;
#endif
    g_splitcnt++;
} static int printBondArray(int atomCnt, int *b)
{
    int i;
```

```c
        for ( i = 0; i < atomCnt; i++ )
        {
                fprintf(stdout,"%2d ", b[i] );
        }
        fprintf(stdout,"\n");
} static int addSplit3(int atomCnt, int bond1, int bond2, int *b1, int *b2, int *b3, int firstBase, int secondBase )
{
        split3 *s;

if ( g_split3Cnt >= g_split3Alloc)
        {
                if ( g_split3 && g_split3Alloc )
                {
                        g_split3 = (split3 *) realloc((char *) g_split3, g_split3Alloc * 2 * sizeof(split3) );
                        g_split3Alloc *= 2;
                }
                else
                {
                        g_split3Alloc = 2;
                        g_split3 = (split3 *) calloc(sizeof(split3), g_split3Alloc );
                }
        }
        s = g_split3 + g_split3Cnt;
        s->bond1 = bond1;
        s->bond2 = bond2;
#ifndef NO_STRMAP
        s->strMap = (int *) 0;
#endif
        s->b1 = (int *) malloc(sizeof(int) * atomCnt );
        s->b2 = (int *) malloc(sizeof(int) * atomCnt );
        s->b3 = (int *) malloc(sizeof(int) * atomCnt );
        memcpy((char *) s->b1, (char *) b1, sizeof(int) * atomCnt );
        memcpy((char *) s->b2, (char *) b2, sizeof(int) * atomCnt );
        memcpy((char *) s->b3, (char *) b3, sizeof(int) * atomCnt );

s->b4 = (int *) malloc(sizeof(int) * atomCnt );
        memcpy((char *) s->b4, (char *) b1, sizeof(int) * atomCnt );
        if ( firstBase >= 0 && secondBase >= 0 )
        {
                s->b4[firstBase] = 1;
                s->b4[secondBase] = -1;  /* this is the base for query */
        } g_split3Cnt++;
```

}

```c
/* returns a true value if the atom arrays overlap and the anchor is contained
        within b1. It returns the index + 1 (base 1) indexed into b1
*/
static int atomsOverlap(int atomcnt, int *b1, int *b2)
{
        int i;
        int overlap = 0;

for ( i = 0; i < atomcnt; i++ )
        {
                if ( b1[i] == 1 && b2[i] )
                        return i+1;
        }
        return 0;
} static Frag *createUniqFrags(int atomCnt, split2 *s2, int nums2, split3 *s3, int nums3, int *atomMask,
int *r_numFrags )
{
        int i;
        split2 *s2ptr;
        split3 *s3ptr;
        Frag *fragHead;
        int no2p;

g_fragHead = (Frag *) 0;
        g_fragCnt = g_fragAlloc = 0;

if ( q_coremode == 0 )
                g_fragAlloc = (nums2*2) + (nums3*2);
        else
                g_fragAlloc = nums3*2;

if ( g_fragAlloc > 0 )
                g_fragHead = (Frag *) calloc(sizeof(Frag), g_fragAlloc );

no2p = 0;
        if ( !q_coremode || qmode )
        {
                for ( i = 0, s2ptr = s2; i < nums2; i++, s2ptr++ )
                {
                        s2ptr->frag1 = createFrag(atomCnt, s2ptr->b1, atomMask, 0 );
                        s2ptr->frag2 = createFrag(atomCnt, s2ptr->b2, atomMask, 0 );
                }
        }
```

```c
        no2p = g_fragCnt;
        if ( q_coremode == 0 )
        {
                for ( i = 0, s3ptr = s3; i < nums3; i++, s3ptr++ )
                {
                        s3ptr->frag1 = createFrag(atomCnt, s3ptr->b1, atomMask, 0 );
                        s3ptr->frag2 = createFrag(atomCnt, s3ptr->b2, atomMask, 1 );
                        s3ptr->frag3 = createFrag(atomCnt, s3ptr->b3, atomMask, 1 );
                        s3ptr->frag4 = createFrag(atomCnt, s3ptr->b4, atomMask, 0 );
                }
        }
        else
        {
                for ( i = 0, s3ptr = s3; i < nums3; i++, s3ptr++ )
                {
                        s3ptr->frag1 = createFrag(atomCnt, s3ptr->b1, atomMask, 0 );  /* b1 and b4
are the center pieces */
                        s3ptr->frag2 = createFrag(atomCnt, s3ptr->b4, atomMask, 0 );
                }
        }
        if ( q_debugfp )
                fprintf(q_debugfp, "# There are %d uniq 2D fragments and %d 3D\n", no2p, g_fragCnt
- no2p );

tot_frags += nums2 * 2 + nums3 * 3;
        tot_uniq_frags += g_fragCnt;
        compounds++;

fragHead = g_fragHead;
        *r_numFrags = g_fragCnt;

g_fragHead = (Frag *) 0;
        g_fragCnt = g_fragAlloc = 0;

return fragHead;
} int dump_frag_stats(void)
{
        fprintf(stderr,"AVG uniq frags: %8.3lf AVG frags: %8.3lf # structures for which fragments were
built : %d\n",
                (double) ((double) tot_uniq_frags / (double) compounds),
                (double) ((double) tot_frags / (double) compounds),
                compounds);
} static int masksMatch(int cnt, int *m1, int *m2 )
```

```
{
        int rc;

rc = !memcmp((char *) m1, (char *) m2, sizeof(int) * cnt );
        return rc;
} static int createFrag(int atomCnt, int *atoms, int *atomMask, int checkDup )
{
        int i, j, found;
        Frag *curr;
        int numAtoms, hevAtoms;
        int baseAtom;

hevAtoms = hevCount(atomCnt, atoms, atomMask, &numAtoms );
        for ( i = 0, baseAtom = -1; i < atomCnt; i++ )
        {
                if ( atoms[i] == -1 )
                {
                        baseAtom = i;
                        break;
                }
        }
        if ( baseAtom == -1 )
        {
                fprintf(stderr,"base atom not found\n" );
                for ( i = 0; i < atomCnt; i++ )
                        fprintf(stderr,"%d ", atoms[i] );
                fprintf(stderr,"\n");
                return -1;
        } if ( checkDup )
        {
                for ( j = 0, curr = g_fragHead; j < g_fragCnt; j++, curr++ )
                {
                        if ( curr->baseAtom == baseAtom && curr->atomCnt == numAtoms &&
                                curr->hevCnt == hevAtoms && masksMatch(atomCnt, curr->atoms, atoms) )
                        {
                                return curr->id;
                        }
                }
        }
        if ( g_fragCnt >= g_fragAlloc )
        {
#if 0
                fprintf(stderr,"%d %d\n", g_fragCnt, g_fragAlloc );
```

```c
                    fflush(stderr);
endif
            if ( g_fragHead && g_fragAlloc )
            {
                    g_fragAlloc *= 2;
                    g_fragHead = (Frag *) realloc((char *) g_fragHead, g_fragAlloc * sizeof(Frag)
);
            }
            else
            {
                    g_fragAlloc = 20;
                    g_fragHead = (Frag *) calloc(sizeof(Frag), g_fragAlloc );
            }
    }
    curr = g_fragHead + g_fragCnt;
    memset((char *) curr, '\0', sizeof(Frag) );

curr->baseAtom = baseAtom;
    curr->atomCnt = numAtoms;
    curr->hevCnt = hevAtoms;
    curr->atoms = atoms;
    curr->id = g_fragCnt;
    curr->aromCnt = -1;          /* Indicate not computed */ g_fragCnt++;

return curr->id;
} static int hevCount(int atomcnt, int *b, int *atomMask, int *r_numAtoms )
{
    int hevCnt;
    int numAtoms;
    int i;

for ( i = hevCnt = numAtoms = 0; i < atomcnt; i++ )
    {
            if ( b[i] )
            {
                    numAtoms++;
                    if ( atomMask[i] )
                            hevCnt++;
            }
    }
    *r_numAtoms = numAtoms;
    return hevCnt;
}
```

```c
static int makeSplit3(CtConnectionTable *ct, int *atomMask, split2 *sall, int cnt, int minHev )
{
    int i, j, k;
    split2 *s1, *s2;
    CtBond *b1, *b2;
    int *inBoth;
    int *subset1;
    int *subset2;
    int *subset3;
    int *remaining;
    int overlap1, overlap2;
    int numAtoms;
    int numHev;
    int firstBase, secondBase;

for ( i = 0; i < cnt; i++ )
    {
        s1 = sall + i;
        b1 = ct->bonds + s1->bondId;
        for ( j = i+1; j < cnt; j++ )
        {
            s2 = sall + j;
            b2 = ct->bonds + s2->bondId;
            firstBase = secondBase = -1;

overlap1 = atomsOverlap(ct->atomCount, s1->b1, s2->b1);
            overlap2 = atomsOverlap(ct->atomCount, s1->b2, s2->b1);
            if ( !overlap1 || !overlap2 )
            {
                overlap1 = atomsOverlap(ct->atomCount, s1->b1, s2->b2);
                overlap2 = atomsOverlap(ct->atomCount, s1->b2, s2->b2);
                if ( !overlap1 || !overlap2 )
                {
                    continue;
                }
                inBoth = s2->b2;
                subset3 = s2->b1;
            }
            else
            {
                inBoth = s2->b1;
                subset3 = s2->b2;
            }
            if ( inBoth[overlap1 - 1] < inBoth[overlap2 -1] )
            {
                subset2 = s1->b2;
                remaining = s1->b1;
            }
```

```
                    else
                    {
                            subset2 = s1->b1;
                            remaining = s1->b2;
                    }
                    subset1 = (int *) calloc(sizeof(int), ct->atomCount );
#ifdef SPLIT_DEBUG
                            if ( q_debugfp )
                                    fprintf(q_debugfp,"# ");
#endif
                    for ( k = 0; k < ct->atomCount; k++ )
                    {
                            if ( remaining[k] && inBoth[k] )
                            {
                                    subset1[k] = remaining[k];
                                    if ( inBoth[k] == -1 )
                                            secondBase = k;
                                    if ( remaining[k] == -1 )
                                            firstBase = k;
                            }
#ifdef SPLIT_DEBUG
                            if ( q_debugfp )
                                    fprintf(q_debugfp,"%d ", subset1[k] );
#endif
                    }
#ifdef SPLIT_DEBUG
                    if ( q_debugfp )
                    {
                            fprintf(q_debugfp,"\n");
                            for ( k = 0; k < ct->atomCount; k++ )
                            {
                                    if (inBoth[k] == -1 )
                                            fprintf(q_debugfp, "# inBoth: %d\n", k );
                            }
                    }
endif
                    numHev = hevCount(ct->atomCount, subset1, atomMask, &numAtoms);
                    numHev -= 2;  /* subtract out the attachment atoms */
                    if ( numHev < minHev )
                    {
                            free((char *) subset1);
                            continue;
                    }
if 0
                    fprintf(stdout, "3 piece set\n");
                    printBondArray(ct->atomCount, s1->b1);
                    printBondArray(ct->atomCount, s1->b2);
                    printBondArray(ct->atomCount, s2->b1);
```

```
                printBondArray(ct->atomCount, s2->b2);
                printBondArray(ct->atomCount, subset1);
                printBondArray(ct->atomCount, subset2);
                printBondArray(ct->atomCount, subset3);
                fprintf(stdout,"---------------------------------------------------------------\n");
#endif
                addSplit3(ct->atomCount, s1->bondId, s2->bondId, subset1, subset2, subset3,
firstBase, secondBase );
                free((char *) subset1 );
            }
        }
        return g_split3Cnt;
} static int *findDirectionalNeighbors(CtConnectionTable *ct, int atomIdx, int terminalAtomIdx, int termIdx2 )
/*
        think of the arguments as: ct, to, from
        or
        from the atom (atomIdx) find atoms down the paths except for the terminal atoms
        For example:   C is the atom your interested in,
and you want to  find the atoms going down the paths connected to atoms 3 and 4, so you block 1 and
2 as terminal.
```

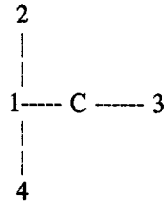

```
*/
{
        CtAtom *A;
        CtAtomBondData *bond;
        int *covered;
        int added;
        int level;
        int toAtom;
        int i, j;

if ( atomIdx < 0 || atomIdx >= ct->atomCount )
                return (int *) 0;
        if ( terminalAtomIdx >= ct->atomCount )
                return (int *) 0;
        if ( termIdx2 >= ct->atomCount )
                return (int *) 0;
```

```
        A = ct->atoms + atomIdx;           /* index is zero based */ covered = (int *) calloc(ct->atomCount, sizeof(int) );
        covered[atomIdx] = 1;
        if ( terminalAtomIdx >= 0 )
                covered[terminalAtomIdx] = -1;  /* -1 means do not cross this atom, it is the
anchor/terminal atom */
        if ( termIdx2 >= 0 )
                covered[termIdx2] = -1;    /* -1 means do not cross this atom, it is the
anchor/terminal atom */ added = 1;
        for ( level = 1; added && level <= ct->atomCount; level++ )
        {
                for ( i = added = 0; i < ct->atomCount; i++ )
                {
                        if ( covered[i] == level )
                        {
                                A = ct->atoms + i;
                                for ( j = 0, bond = A->bond; j < A->bondCount; j++, bond++
)
                                {
                                        toAtom = bond->toAtom;
                                        if ( covered[ toAtom ] )
                                                continue;
                                        covered[toAtom] = level + 1;
                                        added++;
                                }
                        }
                }
        }
        return covered;
} static double *computeVdwWeights(CtConnectionTable *ct, int atomIdx, int terminalAtomIdx, double
reductionFactor, int **r_covered )
/*
        see findDirectionalNeighbors for description.  Same thing, only modified for weights
*/
{
        CtAtom *A;
        CtAtomBondData *bond;
        CtBond *bptr;
        int *covered;
        int added;
        int level;
        int toAtom;
        int i, j;
```

```
Split *S;
int *bsplit;
int bondIdx;
double *v_weight;
double *r_weight;  /* reference weight, so anchor atoms are included in next aggregate */ v_weight = (double *) calloc(ct->atomCount, sizeof(double) );
for ( i = 0; i < ct->atomCount; i++ )
        v_weight[i] = 1.0;
if ( r_covered )
        *r_covered = (int *) 0;

if ( atomIdx < 0 || atomIdx >= ct->atomCount || reductionFactor == 1.0 )
        return v_weight;
if ( terminalAtomIdx >= ct->atomCount )
        return v_weight;
S = FindBreakPoints(ct, 2, 1, 0 );

if ( !S || S->s2cnt == 0 )
{
        if ( S )
                freeSplit(S);
        return v_weight;
}
bsplit = S->bondMask;
r_weight = (double *) calloc(ct->atomCount, sizeof(double) );
for ( i = 0; i < ct->atomCount; i++ )
        r_weight[i] = 1.0;

A = ct->atoms + atomIdx;          /* index is zero based */ covered = (int *) calloc(ct->atomCount, sizeof(int) );
covered[atomIdx] = 1;
if ( terminalAtomIdx >= 0 )
        covered[terminalAtomIdx] = -1;  /* -1 means do not cross this atom, it is the anchor/terminal atom */ added = 1;
for ( level = 1; added && level <= ct->atomCount; level++ )
{
        for ( i = added = 0; i < ct->atomCount; i++ )
        {
                if ( covered[i] == level )
                {
                        A = ct->atoms + i;
                        for ( j = 0, bond = A->bond; j < A->bondCount; j++, bond++ )
                        {
```

```
                        toAtom = bond->toAtom;
                        if ( covered[ toAtom ] )
                                continue;
                        bondIdx = bond->ptr - ct->bonds;
                        if ( bsplit[bondIdx] )
                                r_weight[toAtom] = r_weight[i] * reductionFactor;
                        else
                                r_weight[toAtom] = r_weight[i];
                        v_weight[toAtom] = r_weight[i];

covered[toAtom] = level + 1;
                        added++;
                    }
                }
            }
        }
        free((char *) r_weight );
        freeSplit(S);
        if ( r_covered )
                *r_covered = covered;
        else
                free((char *) covered);
        for ( i = 0; i < ct->atomCount; i++ )
        {
                if ( v_weight[i] < 0.6 )  /* minimum atom weight */
                        v_weight[i] = 0.6;
        }
        return v_weight;
} int TOP_HEV_COUNT(struct CtConnectionTable *ct)
{
        CtAtom *atomp;
        int i;
        int hevCount;

for ( i = hevCount = 0, atomp = ct->atoms; i < ct->atomCount; i++, atomp++ )
        {
                if ( atomp->class != CtAtomElement )
                        continue;
                if ( atomp->id.atomicNumber != HYDROGEN )
                        hevCount++;
        }
        return hevCount;
} static int *createAtomMask(CtConnectionTable *ct, int termflag, int *r_hevCount)
{
```

```
    int *atomMask;
    CtAtom *atomp;
    int i;
    int hevCount;

atomMask = (int *) calloc(ct->atomCount, sizeof(int) );

for ( i = hevCount = 0, atomp = ct->atoms; i < ct->atomCount; i++, atomp++ )
    {
            if ( atomp->class != CtAtomElement )
                    continue;
            if ( atomp->id.atomicNumber == HYDROGEN )
                    continue;
            hevCount++;  /* count hev if terminal or not */
            if ( !termflag && atomp->bondCount == 1 )
                    continue;                /* don't count the terminal atoms */ atomMask[i] = 1;
    }
    *r_hevCount = hevCount;
    return (atomMask);
}

/*
        for a bond in a ct determine if by splitting this bond the two remaining pieces,
contain at least N minimum number of heavy atoms (variable minHev). The terminal flag if
set to true count's terminal atoms, otherwise when false terminal atoms are not
counted even if they are heavy atoms.

Two arrays are returned the size of ct->atomCount, a three way indicator is set for
each atom in each set.

0: atom is not in set
        1: atom is in set:
        -1: atom is the anchor atom in the set.
*/ static int validBreakPoint(CtConnectionTable *ct, int bondidx, int *atomMask, int minHev, int termflag,
        int rb1, int rb2 )
{
        CtBond *bondp;
        CtAtom *atomp;
        int *d1, *d2;
        int d1hevcnt, d2hevcnt;
        int termPassed;
        int i;
```

```
#ifdef DEBUG_VALID_B
        int d1cnt, d2cnt;
endif bondp = ct->bonds + bondidx;

atomp = ct->atoms + bondp->atoms[0];
        if ( atomp->class != CtAtomElement || atomp->id.atomicNumber == HYDROGEN )
                return 0;

atomp = ct->atoms + bondp->atoms[1];
        if ( atomp->class != CtAtomElement || atomp->id.atomicNumber == HYDROGEN )
                return 0;

d1 = findDirectionalNeighbors(ct, bondp->atoms[0], bondp->atoms[1], -1 );
        d2 = findDirectionalNeighbors(ct, bondp->atoms[1], bondp->atoms[0], -1 );

#ifdef DEBUG_VALID_B
        d1cnt = d2cnt = 0;
        fprintf(stdout,"atom set: %d %d\n", bondp->atoms[0] + 1, bondp->atoms[1] + 1 );
        for ( i = 0; i < ct->atomCount; i++ )
        {
                if ( d1[i] > 0 )
                        fprintf(stdout,"%d ", i+1 );
        }
        fprintf(stdout,"\n");
        for ( i = 0; i < ct->atomCount; i++ )
        {
                if ( d2[i] > 0 )
                        fprintf(stdout,"%d ", i+1 );
        }
        fprintf(stdout,"\n");
endif for ( i = d1hevcnt = d2hevcnt = 0; i < ct->atomCount; i++ )
        {
#ifdef DEBUG_VALID_B
                if ( d1[i] > 0 )
                        d1cnt++;
                if ( d2[i] > 0 )
                        d2cnt++;
#endif
                if ( atomMask[i] )
                {
                        if ( d1[i] > 0 )
                                d1hevcnt++;
                        if ( d2[i] > 0 )
```

```c
                    d2hevcnt++;
            }
    } ifdef DEBUG_VALID_B
    fprintf(stdout,"%d of %d and %d of %d \n",
            d1hevcnt, d1cnt, d2hevcnt, d2cnt );
endif if ( d1hevcnt < minHev || d2hevcnt < minHev )
    {
            *rb1 = (int *) 0;
            *rb2 = (int *) 0;
            free(d1);
            free(d2);
            return 0;
    }
    *rb1 = d1;
    *rb2 = d2;
    return 1;
} static int BuildFrags(Split *S)
{
    int i, j;
    Frag *curr;
    int *atoms;
    int cnt;
    int atomCount;
    int *aptr;
    int atomsBaseIdx = -1;
    int copyBaseIdx;
    int *ordering;
    int natms;
    double *coo;
    struct CtConnectionTable *ct;

if ( !S || !S->ct )
    {
            fprintf(stderr,"Build frags has no ct to copy from \n");
            return -1;
    }
    if ( S->fragsBuilt )
            return 0;
    S->fragsBuilt = 1;
    ct = S->ct;

atomCount = ct->atomCount;
```

```
atoms = (int *) malloc( atomCount * sizeof(int) );

for ( i = 0, curr = S->frags; i < S->numFrags; i++, curr++ )
{
        if ( curr->ct )
        {
                continue;       /* already built */
        }
        memset((char *) atoms, '\0', sizeof(int) * atomCount );
        atomsBaseIdx = -1;
        for ( j = cnt = 0, aptr = curr->atoms; j < atomCount; j++, aptr++ )
        {
                if ( *aptr )
                {
                        if ( *aptr == -1 )
                                atomsBaseIdx = j;
                        atoms[cnt] = j + 1;
                        cnt++;
                }
        }
        curr->ct = DB_CT_UTL_COPY_CT(ct, cnt, atoms, &ordering, CtCopyKeepAllAttrs );
        if ( !curr->ct )
                continue;
        copyBaseIdx = -1;
        for ( j = 0; j < cnt; j++ )
        {
                if ( ordering[j] == atomsBaseIdx )
                        copyBaseIdx = j;
        }
        curr->copyBaseAtom = copyBaseIdx;
        if ( copyBaseIdx == -1 )
                continue;
        curr->origMapping = (int *) malloc(sizeof(int) * cnt );
        memcpy((char *) curr->origMapping, (char *) ordering, sizeof(int) * cnt );

DB_CT_UTL_FIND_RINGS(curr->ct);
        UTL_ERROR_CLEAR();
        DB_CT_GET_CT_ATTR( curr->ct, CtCt3DCoordSet, &coo, &natms);
        curr->cords = coo;
        topAlignCt(curr->ct, curr->copyBaseAtom, S->featureMask, curr->origMapping );
        /* align compound occording to topomer rules -- all trans */
        if ( qmode )
                getQueryExtents(curr->cords, curr->atomCnt);
}
if ( atoms )
        free((char *) atoms );
return 0;
```

```
} static void getQueryExtents(double *coords, int atomCnt )
{
        int i;
        double x,y,z;

for ( i = 0; i < atomCnt; i++ )
        {
                x = *coords;
                y = *(coords+1);
                z = *(coords+2);
                coords += 3;
                if ( x < qxmin )
                        qxmin = x;
                if ( x > qxmax )
                        qxmax = x;

if ( y < qymin )
                        qymin = y;
                if ( y > qymax )
                        qymax = y;

if ( z < qzmin )
                        qzmin = z;
                if ( z > qzmax )
                        qzmax = z;
        }
} static int BuildTopomers(CtConnectionTable *ct, Split *S, Split *query)
{
        int i, j;
        Frag *curr;
        int cnt;
        int atomCount;
        int *aptr;
        int a1;
        int genHex;
        double outside;
        static l_RegionPtr r;
        double *cf;
        double *cf2;
        char *hexStr;
        int *fragMask;
        split2 *qs2;
        split3 *qs3;
        split2 *s2;
```

```
        split3 *s3;
        int topskip;

if ( !S || !ct )
                return -1;
        if ( !stdRegion )
                stdRegion = TOP_MAKE_STD_REGION();
        UTL_ERROR_CLEAR();

if ( !q_matrixMode )
                makeTopRegions(q_stepSize, S->numFrags);
        else
        {
                regions[0] = stdRegion;
                max_regions = 1;
        }

S->ct = ct;
        BuildFrags(S);

genHex = 0;
#ifdef USE_HEX
        genHex = 1;
endif if ( q_debugfp )
                genHex = 1;
        fragMask = (int *) 0;
#ifndef NO_STRMAP
        if ( query )
        {
                fragMask = (int *) calloc(S->numFrags, sizeof(int) );

/* Find which fragments to actually build the topomer fields for, only those which the features
                        don't disqualify this fragment combination
                */
                if ( query->s2 && S->s2 && q_do2piece && query->alloc2Map )
                {
                        for ( i = 0, qs2 = query->s2;
                                i < query->s2cnt && qs2->strMap;
                                i++, qs2++ )
                        {
                                for ( j = 0; j < S->s2cnt; j++ )
                                {
                                        if ( qs2->strMap[j] )
                                        {
```

```
                    s2 = S->s2 + j;
                    fragMask[ s2->frag1 ] = 1;
                    fragMask[ s2->frag2 ] = 1;
                }
            }
        }
    }
    if ( query->s3 && S->s3 && q_do3piece && query->alloc3Map )
    {
        for ( i = 0, qs3 = query->s3; qs3->strMap && i < query->s3cnt; i++,
qs3++ )
        {
            for ( j = 0; j < S->s3cnt; j++ )
            {
                if ( qs3->strMap[j] )
                {
                    s3 = S->s3 + j;
                    fragMask[ s3->frag1 ] = 1;
                    fragMask[ s3->frag2 ] = 1;
                    fragMask[ s3->frag3 ] = 1;
                    fragMask[ s3->frag4 ] = 1;
                }
            }
        }
    }
    if ( query->s2 && S->s3 && q_doSubset && query->allocSubsetMap )
    {
        for ( i = 0, qs2 = query->s2; qs2->subsetMap && i < query->s2cnt; i++,
qs2++ )
        {
            for ( j = 0; j < S->s3cnt; j++ )
            {
                if ( qs2->subsetMap[j] )
                {
                    s3 = S->s3 + j;
                    fragMask[ s3->frag1 ] = 1;
                    fragMask[ s3->frag2 ] = 1;
                    fragMask[ s3->frag3 ] = 1;
                    fragMask[ s3->frag4 ] = 1;
                }
            }
        }
    }
endif for ( i = topskip = 0, curr = S->frags; i < S->numFrags; i++, curr++ )
    {
```

```
                if ( !curr->ct || curr->copyBaseAtom == -1 || !curr->cords )
                        continue;
#if 0
                if ( q_coremode && !qmode && i%2 )
                        continue;
endif
#ifndef NO_STRMAP
                if ( fragMask && fragMask[i] == 0 )
                {
                        topskip++;
                        continue;
                }
endif if ( q_debugfp )
                {
                        writeCopy(q_debugfp, curr->ct, i, -1, (searchCnt > 0 ) ? "TS_SID" : "TS_QID");
                        if ( debug2 )
                                writeCopy(debug2, curr->ct, i, -1, (searchCnt > 0 ) ? "TS_SID" : "TS_QID" );
                } a1 = curr->copyBaseAtom;
ifdef DEBUG_DETAIL
                if ( q_debugfp )
                {
                        fprintf(q_debugfp,"# frag: %d base: %d  atomCnt:%d\n",
                                i+1, a1+1, ct->atomCount);
                }
endif
                curr->AtWts = computeVdwWeights(ct, a1, -1, q_ReductionFactor, (int **) 0 );

if ( curr->id >= S->s2cnt )
                        minRegion = minRegion3P;
                else
                        minRegion = minRegion2P;
                if ( !qmode )
                {
                        r = getRegionToUse(curr->cords, curr->atomCnt, &(curr->regionIdx), &(curr->npoints) );
                        curr->outside = atomsOutside(curr->cords, curr->atomCnt, r, curr->AtWts, &(curr->outsidePenalty) );
                        curr->topField = TOP_STER_ATOM_EVAL_ALL_RB_ATTEN(curr->ct, r, a1+1,
                                curr->cords, curr->AtWts );
#ifndef NO_COMPRESSION
                        cf = compressField(curr->topField, r->n_points );
```

```
                              curr->topField = cf;
endif ifdef STD_REGION
                              curr->stdField = TOP_STER_EVAL_ALL_RB_ATTEN(curr->ct, stdRegion,
a1+1,
                                    curr->cords, curr->AtWts );
#endif
                        }
                  else
                  {
                        r = getRegionToUse(curr->cords, curr->atomCnt, &(curr->regionIdx),
&(curr->npoints) );

if ( curr->id >= S->s2cnt && curr->regionIdx > minRegion3P )
                        {
                              minRegion3P = curr->regionIdx;
                        }
                        if ( curr->regionIdx > minRegion2P )
                              minRegion2P = curr->regionIdx;
                        else
                              curr->regionIdx = minRegion2P;

for ( j = 0; j < max_regions; j++ )
                        {
                              r = regions[j];
#if 0
                              curr->qtf[j]    = TOP_STER_EVAL_ALL_RB_ATTEN(curr->ct,
regions[j], a1+1,
                                    curr->cords, curr->AtWts );
                              compareFields(curr->qtf[j], cf, r->n_points );
                              cf2 = compressField(cf, r->n_points );
                              free((char *) cf2 );
#endif
                              curr->qtf[j] = TOP_STER_ATOM_EVAL_ALL_RB_ATTEN(curr->ct,
regions[j], a1+1,
                                    curr->cords, curr->AtWts );
#ifndef NO_COMPRESSION
                              cf = compressField(curr->qtf[j], r->n_points );
                              curr->qtf[j] = cf;
#endif
                        }
                        if ( !((i+1) % 10 ) )
                              fprintf(stderr,"Built Query fragments: %d of %d\n", i+1, S->numFrags
);
#ifdef STD_REGION
                              curr->stdField = TOP_STER_EVAL_ALL_RB_ATTEN(curr->ct, stdRegion,
a1+1,
                                    curr->cords, curr->AtWts );
```

```
endif
                }
        }
        if ( q_debugfp && !qmode && curr->topField )
        {
                /* curr->topHex */
                cf = TOP_STER_EVAL_ALL_RB_ATTEN(curr->ct, stdRegion, al+1,
                        curr->cords, curr->AtWts );
                hexStr = strdup(CT_FIELD2HEX(cf, stdRegion->n_points));
                fprintf(q_debugfp, "# %s\n", hexStr );
#ifdef NO_COMPRESSION
                free((char *) cf);              /* don't free the field with compression enabled
*/
#endif
                free((char *) hexStr );
        }
    }
    if ( fragMask )
        free((char *) fragMask );

#if 0
    if ( topskip )
        fprintf(stderr,"skipped building %d of %d topomers\n", topskip, S->numFrags );
endif return 0;
} static CtBond *getBond(struct CtConnectionTable *ct, int id1, int id2 )
{
        int i;
        CtAtomBondData *abd;
        CtAtom *a;

a = ct->atoms + id1;
        for ( i = 0, abd = a->bond; i < a->bondCount; i++, abd++ )
        {
                if ( abd->toAtom == id2 )
                        return abd->ptr;
        }
        return (CtBond *) 0;
}

/*
Align the ct fragment according to topomer alignment rules,
adjust all torsions to a trans position for all single bonds with
non-terminal atoms and do reflection if needed for all prochiral atoms
Rob Jilek:  Nov. 2000
*/
```

```c
static int topAlignCt(struct CtConnectionTable *ct, int baseAtom, int *featureMask, int *ctMapping )
{
        int *atoms;
        int *atomDist;
        int *singleBonds;
        int *toAtoms;
        int *secChoice;
        double *molWeights;
        int i,j;
        int idx;
        int status;
        int distance;
        CtAtom *atomp;
        CtAtomBondData *bi;
        CtBond *bondp;
        CtBondTypeDef bondType;
        CtSimpleBondTypeDef simpleTypes;
        int bcnt;
        int priority[4];
        struct cipSupportDef *support;
        int a0, a1, a2, a3;
        int rbondsJoined;
        double *cord;
        double torsion;
        int dorefle;
        int mode;
        int hcnt, fcnt, clcnt, brcnt;
        int planeAtoms[3];
        char *atomMessage[] = { "na", "important", "chiral" };
        double *tors;

if (!DB_CT_GET_CT_ATTR( ct, CtCt3DCoordSet, &cord, &i))
                return -1;

g_ct = ct;

singleBonds = (int *) calloc(sizeof(int), ct->bondCount );
        atoms = (int *) calloc(sizeof(int), ct->atomCount );
        tors = (double *) calloc(sizeof(double), ct->atomCount );

for ( idx = 0, bondp = ct->bonds;
                        idx < ct->bondCount;
                        idx++, bondp++ )
                {
#define TOP_ALIGN_DOUBLE
#ifdef TOP_ALIGN_DOUBLE
                if ( bondp->simpleBondType == CtSimpleBondTypeNotSimple )
```

```
                {
                        bondType  =  DB_CT_GET_BOND_TYPE(ct,  STD_ID(idx),  &bcnt,
&simpleTypes );
                        if ( !( bondType == CtBondTypeSingle || bondType == CtBondTypeDouble
))
                                continue;
                }
                else
                {
                        if  (  !  (  bondp->simpleBondType    ==   CtSimpleBondTypeSingle   ||
bondp->simpleBondType == CtSimpleBondTypeDouble ) )
                                continue;       /* must be single or double */
                } else
                if ( ! ( bondp->simpleBondType == CtSimpleBondTypeSingle ||
                        bondp->simpleBondType == CtSimpleBondTypeNotSimple ) )
                        continue;       /* must be single, check NotSimple next. */ if ( bondp->simpleBondType == CtSimpleBondTypeNotSimple )
                {
                        bondType  =  DB_CT_GET_BOND_TYPE(ct,  STD_ID(idx),  &bcnt,
&simpleTypes );
                        if ( bondType != CtBondTypeSingle )
                                continue;
                }
endif
                if ( AB_IN_RING(bondp) )
                        continue;
#if 0
                /* Jan, 16th 2000 - align the hydrogens and other terminal atoms
                /* if either atom attached to this bond is terminal, then ignore this bond
*/
                atomp = ct->atoms + bondp->atoms[0];
                if ( atomp->bondCount == 1 )
                        continue;
                atomp = ct->atoms + bondp->atoms[1];
                if ( atomp->bondCount == 1 )
                        continue;
endif
                                                            /* We have a bond and the atoms we wish
to adjust the torsions on */
                singleBonds[idx] = 1;
                atoms[ bondp->atoms[0] ] = 1;
                atoms[ bondp->atoms[1] ] = 1;
        }

/* now add in the prochiral atoms */
```

```
support = DB_CT_CHIRAL_CIP_SETUP();

for ( i = 1; i <= ct->atomCount; i++ )
{
        status = DB_CT_UTL_IS_CHIRAL_TYPE(ct, i, 1, 1, &hcnt, &fcnt, &clcnt, &brcnt );
        if ( status == 0 )
                continue;
        if ( status == -1 )
        {
                UTL_ERROR_CLEAR();
                continue;
        }
        status = DB_CT_CHIRAL_GET_RS_PRIORITY(ct, i, priority, support );
        if ( status == 0 )
                continue;
        atoms[i-1] = 2;              /* mark it differently that this is a prochiral atom */
}
DB_CT_CHIRAL_CIP_FREE(support);

atomDist = findDirectionalNeighbors(ct, baseAtom, -1, -1 );
molWeights = computePathWeights(ct, baseAtom, atomDist, featureMask, ctMapping );
toAtoms = findLargestBranch(ct, atomDist, molWeights );
g_atomDist = atomDist;

a1 = baseAtom;
a2 = toAtoms[a1];
a3 = toAtoms[a2];
if ( a3 == -1 )
        TOP_ALIGN_MOL(cord, ct->atomCount, a1+1, a2+1, a2+1); /* function want's base 1 atom ids */
else
        TOP_ALIGN_MOL(cord, ct->atomCount, a1+1, a2+1, a3+1); /* function want's base 1 atom ids */ rbondsJoined = 0;
bondp = getBond(ct, a2, a3);
if ( bondp && AB_IN_RING(bondp) )
        rbondsJoined++;

torsion = 180.0;
if ( rbondsJoined == 1 )
        torsion = 90.0;

/* where a1 is baseAtom, a2 is toAtoms[a1], etc */
if ( a3 != -1 )
        setRootTorsion(cord, ct->atomCount, a1, a2, a3, torsion );
```

```
#ifdef DEBUG_DETAIL
        if ( q_debugfp )
        {
                fprintf(q_debugfp, "# root: fixed %d %d %d %6.0lf\n", a1, a2, a3, torsion );
                for ( i = 0; i < ct->atomCount; i++ )
                {
                        fprintf(q_debugfp, "# toAtom  %d -> %d  (%d %d) \n",
                                i, toAtoms[i], atomDist[i], ( toAtoms[i] >= 0 ) ? atomDist[ toAtoms[i] ] : -1 );
                }
        }
endif /* now adjust the torsion in atom distance order */ for ( distance = 2; distance <= ct->atomCount; distance++ )
        {
                for ( i = 0; i < ct->atomCount; i++ )
                {
                        if ( atoms[i] == 0 || i == baseAtom )
                                continue;           /* not interested in this atom */
                        if ( atomDist[i] != distance )
                                continue;           /* we are not doing this distance from the base atom now */
                        if ( atoms[i] == 2 && !getFromRingCount(ct, atomDist, i, toAtoms[i] ) ) /* a chiral atom */
                        {
                                                    /* we can NOT convert if either main chain bonds are in a ring */
                                a0 = baseAtom;
                                a2 = i;
                                getFromChiralAtoms(ct, atomDist, molWeights, i, toAtoms[i], &a1, &a3 );
#ifdef DEBUG_DETAIL
                                if ( q_debugfp )
                                        fprintf(q_debugfp,"# reflect torsion atoms: %d %d %d %d \n",
                                                a0, a1, a2, a3 );
#endif
                                if ( a0 != -1 && a1 != -1 && a2 != -1 && a3 != -1 && a0 != a1)
                                {
                                        torsion = UTL_GEOM_TAU( cord+(a0*3), cord+(a1*3), cord+(a2*3), cord+(a3*3) );
                                        UTL_ERROR_CLEAR();
                                        if ( torsion < 0.0 )
                                                torsion += 360.0;
                                        mode = (atomDist[i] -1) % 2;
#ifdef DEBUG_DETAIL
```

```c
            if ( q_debugfp )
                fprintf(q_debugfp,"# reflect torsion: %d %d %d %d %6.0lf mode:%d\n",
                        a0, a1, a2, a3, torsion, mode );
#endif
#ifdef ALTERNATE_CHIRAL
            if ( mode == 1 && torsion > 180.0 || mode == 0 && torsion < 180.0 )
#endif
            {
                planeAtoms[0] = a1;
                planeAtoms[1] = i;
                planeAtoms[2] = toAtoms[i];
                reflectAtoms(cord, ct->atomCount, 3, planeAtoms );
                tors[i] = torsion * 100.0;
#ifdef DEBUG_DETAIL
                if ( q_debugfp )
                    fprintf(q_debugfp,"# reflected: %d %d %d \n",
                            planeAtoms[0], planeAtoms[1], planeAtoms[2] );
#endif
#ifdef ALTERNATE_CHIRAL
            }
endif
        }
    }
    a1 = i;
    atomp = ct->atoms + i;
    for ( j = 0, bi = atomp->bond; j < atomp->bondCount; j++, bi++ )
    {
        if ( atomDist[ bi->toAtom ] != (distance+1) )
            continue;
        idx = bi->ptr - ct->bonds;
#ifdef DEBUG_DETAIL
        if ( q_debugfp )
            fprintf(q_debugfp, "# atominfo %d %d (%d %d) = %d\n",
                    a1 + 1, bi->toAtom + 1,
                    bi->ptr->refIdx, idx,
                    singleBonds[idx] );
#endif
        if ( singleBonds[ idx ] == 0 ) /* make sure rotatable bond */
            continue;
        a2 = bi->toAtom;
        a0 = getFromAtom(ct, atomDist, molWeights, i, a2, baseAtom, cord );

/* a2 = toAtoms[i]; */
        a3 = toAtoms[a2];
        if ( a0 == -1 || a1 == -1 || a2 == -1 || a3 == -1 )
```

```
                {
                        if ( q_debugfp )
                                fprintf(q_debugfp, "# not aligned one or more of the atom
ids is -1:  %d %d %d %d\n", a0, a1, a2, a3 );
                        continue;
                }

/* count the number of ring bonds joined */
                        rbondsJoined = 0;
                        bondp = getBond(ct, a0, a1);
                        if ( bondp && AB_IN_RING(bondp) )
                                rbondsJoined++;

bondp = getBond(ct, a2, a3);
                        if ( bondp && AB_IN_RING(bondp) )
                                rbondsJoined++;

torsion = 180.0;
                        if ( rbondsJoined == 1 )
                                torsion = 90.0;
                        else if ( rbondsJoined == 2 )
                                torsion = 60.0;
                        setTorsion(cord, ct->atomCount, a0, a1, a2, a3, torsion );
                        tors[a1] = torsion;
#ifdef DEBUG_DETAIL
                        if ( q_debugfp )
                                fprintf(q_debugfp,"# torsion: %d %d %d %d %6.0lf\n", a0, a1,
a2, a3, torsion );
#endif
                }
            }
        }
#ifdef DEBUG_DETAIL
        if ( q_debugfp )
        {
                for ( i = 0; i < ct->atomCount; i++ )
                {
                        fprintf(q_debugfp,"# %2d: %2d %2d %8.2lf %7.2lf %s \n",
                                i+1, atomDist[i], toAtoms[i], molWeights[i], tors[i],
                                atomMessage[ atoms[i] ]);
                }
        }
endif
        free((char *) atomDist);
        free((char *) molWeights);
        free((char *) toAtoms );
        free((char *) singleBonds);
        free((char *) atoms );
```

```c
        free((char *) tors );

return 0;
} static int getFromAtom(struct CtConnectionTable *ct, int *atomdist, double *molWeights, int atom, int
toAtom, int baseAtom, double *cord )
{
        int i;
        int bestb[4];
        int nlowest;
        int nbest;
        double bestw;
        CtAtom *A;
        CtAtom *aptr;
        CtAtomBondData *abd;
        double tors[4];
        double tlow;

A = ct->atoms + atom;

if ( atomdist[atom] == 1 )
                return -1;

/* otherwise it isn't the base atom */
        bestw = -1.0;
        bestb[0] = bestb[1] = bestb[2] = bestb[3] = -1;
        nbest = 0;

for ( i = nbest = 0, abd = A->bond; i < A->bondCount; i++, abd++ )
        {
                if ( atomdist[ abd->toAtom ] == ( atomdist[ atom ] - 1) )
                {
                        if ( molWeights[ abd->toAtom ] > bestw )
                        {
                                nbest = 0;
                                bestw = molWeights[ abd->toAtom ];
                                bestb[nbest] = abd->toAtom;
                                nbest++;
                        }
                        else if ( molWeights[ abd->toAtom ] == bestw && nbest < 4 )
                        {
                                bestb[nbest] = abd->toAtom;
                                nbest++;
                        }
```

```
            }
        }
        if ( nbest > 1 )
        {
                /* must break the tie */
                for ( i = nlowest = 0, tlow = 400.0; i < nbest; i++ )
                {
                        tors[i]   =   UTL_GEOM_TAU(cord+(baseAtom*3),   cord+(atom*3),
cord+(toAtom*3), cord+(bestb[i]*3) );
                        while (tors[i] < 0.0 )
                                tors[i] += 360.0;
                        while (tors[i] > 360.0 )
                                tors[i] -= 360.0;
                        UTL_ERROR_CLEAR();
#if 0
                        if ( tors[i] < 90.0 )
                                return bestb[i];
#endif
                        if ( tors[i] < tlow )
                        {
                                nlowest = i;
                                tlow = tors[i];
                        }
                }
                return bestb[nlowest];
        }
        else if ( nbest == 1 )
                return bestb[0];
        return -1;
} static int getFromRingCount(struct CtConnectionTable *ct, int *atomdist, int atom, int toAtom )
{
        int i;
        int rcnt;
        CtAtom *A;
        CtAtom *aptr;
        CtAtomBondData *abd;

A = ct->atoms + atom;

if ( atomdist[atom] == 1 )
                return 0;

/* otherwise it isn't the base atom */ for ( i = rcnt = 0, abd = A->bond; i < A->bondCount; i++, abd++ )
        {
```

```c
                if ( atomdist[ abd->toAtom ] = = ( atomdist[ atom ] - 1) )
                {
                        if ( AB_IN_RING(abd->ptr) )
                                rcnt++;
                }
                else if ( abd->toAtom = = toAtom && AB_IN_RING(abd->ptr) )
                        rcnt++;
        }
#ifdef DEBUG_DETAIL
        if ( q_debugfp )
                fprintf(q_debugfp,"# atom:%d  rcnt:%d\n", atom, rcnt );
#endif
        return rcnt;
} static int getFromChiralAtoms(struct CtConnectionTable *ct, int *atomdist, double *molw, int atom, int toAtom,
        int *r_fromAtom, int *r_toatom)
{
        int i;
        int ids[2];
        int weight[2];
        int idx = 0;
        int rcnt;
        CtAtom *A;
        CtAtom *aptr;
        CtAtomBondData *abd;
        int t_toAtom, t_length;
        double theWeight;

A = ct->atoms + atom;
        *r_fromAtom = *r_toatom = -1;

#ifdef DEBUG_DETAIL
        if ( q_debugfp )
                        fprintf(q_debugfp, "# chiral atom: %d bondcount: %d  toAtom:%d \n",
                                atom, A->bondCount, toAtom );
#endif
        for ( i = rcnt = idx = 0, abd = A->bond; i < A->bondCount; i++, abd++ )
        {
#ifdef DEBUG_DETAIL
                if ( q_debugfp )
                        fprintf(q_debugfp, "# atom: %d  dist:%d   toatom:%d  dist:%d \n",
                                atom, atomdist[atom], abd->toAtom, atomdist[ abd->toAtom ] );
#endif
                if ( abd->toAtom = = toAtom || idx >= 2 )
                        continue;
```

```
                        if ( atomdist[ abd->toAtom ] <= ( atomdist[ atom ] - 1) )
                        {
                                *r_fromAtom = abd->toAtom;
                                continue;
                        }
                        ids[idx] = abd->toAtom;
                        t_toAtom = t_length = -1;
                        theWeight = -1.0;
                        traverseBranch(ct, abd->toAtom, atomdist, molw, abd->toAtom, &t_toAtom, &t_length,
&theWeight );
                        weight[idx] = theWeight;
                        idx++;
                }
                if ( idx == 2 )
                {
                        if ( weight[0] >= weight[1] )
                                *r_toatom = ids[0];
                        else
                                *r_toatom = ids[1];
                }
                else if ( idx == 1 )
                        *r_toatom = ids[0];
} static int getToAtoms( struct CtConnectionTable *ct, int *atomDist, double *molWeights, int idx, int
*ratom1, int *ratom2 )
{
        int i;
        int targetDistance;
        CtAtomBondData *abd;
        CtAtom *A;
        double bestw;
        int besta;

A = ct->atoms + idx;
        targetDistance = atomDist[idx] + 1;
        bestw = -1.0;
        besta = -1;

*ratom1 = *ratom2 = -1;

for ( i = 0, abd = A->bond; i < A->bondCount; i++, abd++ )
        {
                if ( atomDist[ abd->toAtom ] == targetDistance )
                {
                        if ( molWeights[abd->toAtom ] > bestw )
                        {
                                bestw = molWeights[abd->toAtom];
```

```
                                besta = abd->toAtom;
                        }
                }
        }
        if ( besta == -1 )
                return -1;
        *ratom1 = besta;

A = ct->atoms + besta;
        targetDistance = atomDist[besta] + 1;
        bestw = -1.0;
        besta = -1;

for ( i = 0, abd = A->bond; i < A->bondCount; i++, abd++ )
        {
                if ( atomDist[ abd->toAtom ] == targetDistance )
                {
                        if ( molWeights[abd->toAtom ] > bestw )
                        {
                                bestw = molWeights[abd->toAtom];
                                besta = abd->toAtom;
                        }
                }
        }
        if ( besta == -1 )
                return -1;
        *ratom2 = besta;

return 0;
} static double *computePathWeights(struct CtConnectionTable *ct, int baseAtom, int *atomDist, int *featureMask, int *ctMap )
{
        int i,j,k;
        CtAtom *A;
        CtAtom *aptr;
        CtAtomBondData *abd;
        double *weights;
        int distance;
        int nextDistance;
        CtAtomBondData *found;
        double aweight;
        double *raw_weights;
        int toAtom;
        double adjval;
        static double maxadj = -1.0;
        static double feature_align = 1.0;
```

```
FeatureType qfeature, strFeature;

weights = (double *) calloc(sizeof(double), ct->atomCount );
raw_weights = (double *) calloc(sizeof(double), ct->atomCount );

for ( i = 0, aptr = ct->atoms; i < ct->atomCount; i++, aptr++ )
{
        aweight = 0.0;
        DB_CT_GET_ATOMP_ATOMIC_WEIGHT(aptr, &aweight);
        raw_weights[i] = aweight;
}
if ( maxadj == -1.0 )
{
        char *tptr;
        tptr = getenv("DBTOP_FEATURE_ALIGN_MAXADJ");
        if ( tptr )
        {
                maxadj = atof(tptr);
                fprintf(stderr,"Maximum feature adjustment for alignment: %8.2lf. Set from
environment variable: DBTOP_FEATURE_ALIGN_MAXADJ\n", maxadj );
        }
        else
                maxadj = 50.0;

tptr = getenv("DBTOP_FEATURE_ALIGN_SCALE");
        if ( tptr )
        {
                feature_align = atof(tptr);
                fprintf(stderr,"Feature alignment scaling factor: %8.2lf . Set from environment
variable: DBTOP_FEATURE_ALIGN_SCALE\n", feature_align );
        }
        else
                feature_align = 0.5;

if ( maxadj < 0.0 )
                maxadj = 0.0;

if ( feature_align < 0.0 )
                feature_align = 0.0;
} if ( q_featureFactor > 0.0 && maxadj > 0.0 && feature_align > 0.0 )
{
        for ( i = 0; i < ct->atomCount; i++ )
        {
                if ( featureMask[ ctMap[i] ] == FeatureNone )
                        continue;              /* no single atom feature at this atom */
                for ( k = 0, adjval = 0.0, strFeature = featureMask[ ctMap[i] ]; k < 4; k++
```

```
)
            {
                    if ( strFeature & fMasks[k] )
                            adjval  +=   q_featureFactor  *  featureWeights[k+1]  *
feature_align;
            }
            if ( adjval > maxadj )
                    adjval = maxadj;
            raw_weights[i] += adjval;
        }
    } for ( i = 0, A = ct->atoms; i < ct->atomCount; i++, A++ )
    {
        if ( i == baseAtom )
            continue;
        aptr = A;
        distance = atomDist[i];
        nextDistance = distance - 1;
        toAtom = i;
        while ( distance )
        {
            weights[i] += raw_weights[toAtom];

for ( found = (CtAtomBondData *) 0, j = 0, abd = aptr->bond; !found &&
j < aptr->bondCount; j++, abd++ )
            {
                if ( atomDist[ abd->toAtom ] == nextDistance )
                    found = abd;
            }
            if ( found )
            {
                aptr = ct->atoms + found->toAtom;
                toAtom = found->toAtom;
                nextDistance--;
                distance--;
            }
            else
                distance = 0;
        }
    }
    free((char *) raw_weights );
    return weights;
} static int traverseBranch( struct CtConnectionTable *ct, int atomId, int *atomdist, double *molweight,
int rootToAtom, int *r_toatom, int *r_length, double *r_weight )
{
```

```
        CtAtom *a;
        CtAtomBondData *abd;
        int j;

a = ct->atoms + atomId;
        if ( atomdist[ atomId ] > *r_length ||
                ( atomdist[ atomId ] == *r_length && molweight[atomId] > *r_weight ) )
        {
                *r_toatom = rootToAtom;
                *r_length = atomdist[atomId];
                *r_weight = molweight[atomId];
        }
        for ( j = 0, abd = a->bond; j < a->bondCount; j++, abd++ )
        {
                if ( atomdist[ abd->toAtom ] == ( atomdist[atomId] + 1 ) )
                {
#ifdef DEBUG_DETAIL
                        if ( debug2 )
                                fprintf(debug2,"# --> %d to %d  dist:%d %d  root:%d\n",
                                        atomId, abd->toAtom, atomdist[abd->toAtom],
atomdist[atomId], rootToAtom );
#endif
                        traverseBranch(ct, abd->toAtom, atomdist, molweight, rootToAtom, r_toatom,
r_length, r_weight );
                }
        }

}
/*
return an array containing the toAtom for each atom which points to the
largest chain bases on size and then weight.
*/ static int *findLargestBranch(struct CtConnectionTable *ct, int *atomdist, double *weights )
{
        int *bi;
        int i,j;
        int toAtom;
        int length;
        double theWeight;
        CtAtomBondData *abd;
        CtAtom *atom;

bi = (int *) calloc(sizeof(int), ct->atomCount );

for ( i = 0; i < ct->atomCount; i++ )
```

```c
        {
                atom = ct->atoms + i;
                toAtom = length = -1;
                theWeight = -1.0;
                for ( j = 0, abd = atom->bond; j < atom->bondCount; j++, abd++ )
                {
                        if ( atomdist[ abd->toAtom ] == ( atomdist[i] + 1 ) )
                        {
#ifdef DEBUG_DETAIL
                                if ( debug2 )
                                        fprintf(debug2,"# %d to %d  dist:%d %d\n",
                                                i, abd->toAtom, atomdist[abd->toAtom], atomdist[i] );
#endif
                                traverseBranch(ct, abd->toAtom, atomdist, weights, abd->toAtom,
&toAtom, &length, &theWeight );
                        }
                }
                bi[i] = toAtom;
        }
        return bi;
} static double CompareTwoCompounds(Split *query, Split *str, double radius, int *r_qidx, int *r_sidx,
int *r_splitidx, int *r_three, int *r_subsethit, double *r_best2, double *r_best3, double *r_bestsub,
double *r_att_pen, int bailedout )
{
        double best;
        double best2, best3, bestsub;
        double d1, d2, d3, d4, d5, d6;
        double dval[6];
        double cdval[6];
        double attPen[2];
        int hevCnts[6];
        int bestQ, bestStr;
        int bestIdx;
        int threeIsBetter = 0;
        int SubIsBetter = 0;
        int id1, id2, id3, id4;
        int i,j,k, l;
        int ids[3];
        Frag *f, *sf;
        Frag *q1, *q2, *q3, *q4;
        Frag *fs1, *fs2, *fs3, *fs4;
        Frag *fragPtrs[3];
        Frag *qActive;
        split2 *qs2, *ss2;
        split3 *qs3, *ss3;
```

```
        double *dptr;
        double hexdiff;
        double fieldDiff;
        double outPen;
        double bailout;
        double *cf[6];
        int max3;
        static Split *qInit;

*r_att_pen = 0.0;
        *r_qidx = bestQ = -1;
        if ( query->numFrags == 0 || str->numFrags == 0 )
                return 9999.0;

bailout = radius*radius;

regid = (char *) 0;
        DB_CT_GET_CT_ATTR(str->ct,CtCtRegId, ®id );
        if ( !regid )
                DB_CT_GET_CT_ATTR(str->ct,CtCtName, &regid );

#ifdef USE_HEX
        if ( qInit != query )
        {
                for ( i = 0, f = query->frags; i < query->numFrags; i++, f++ )
                {
                        if ( f->topHex )
                                f->topInt = hexStringToInts(f->topHex, &(f->topIntSize) );
                }
                qInit = query;
        }
endif for ( i = 0, f = query->frags; i < query->numFrags; i++, f++ )
        {
                if ( f->hexDiff )
                        free((char *) f->hexDiff );
#ifdef STD_REGION
                if ( f->stdDiff )
                        free((char *) f->stdDiff );
#endif
                f->hexDiff =   (double *) calloc(str->numFrags,sizeof(double) );
#ifdef STD_REGION
                f->stdDiff =   (double *) calloc(str->numFrags,sizeof(double) );
#endif
                for ( j = 0; j < str->numFrags; j++ )
                {
```

```c
                        f->hexDiff[j] = -1.0;
#ifdef STD_REGION
                        f->stdDiff[j] = -1.0;
#endif

}
        } ifdef USE_HEX
        for ( i = 0, f = str->frags; i < str->numFrags; i++, f++ )
        {
            if ( f->topHex )
                f->topInt = hexStringToInts(f->topHex, &(f->topIntSize) );
        }
endif ifdef CALC_BATCH_DIFF
        for ( i = 0, f = query->frags; i < query->numFrags; i++, f++ )
        {
            for ( j = 0, sf = str->frags; j < str->numFrags; j++, sf++ )
            {
#ifdef USE_HEX
                f->hexDiff[j] =    fieldIntDiff  (f->topInt,  sf->topInt,  f->topIntSize,
sf->topIntSize );
#else
                f->hexDiff[j] = topFieldDiff(f->topField, sf->topField, str->npoints );
#endif
                if ( f->featureDiff )
                    f->featureDiff[j] = compareFeatures(query, f, str, sf, -1, -1 );
#if 0
                fieldDiff = topFieldDiff(f->topField, sf->topField, str->npoints );
                fprintf(stderr,"hex vs raw:  hex:%7.4lf  field:%7.4lf  diff:%7.4lf \n",
                    f->hexDiff[j], fieldDiff, fieldDiff - f->hexDiff[j] );
#endif
if 0
                hexdiff = fieldHexDiff(f->topHex, sf->topHex, 0 );
                hexdiff *= hexdiff;
                if ( fabs( hexdiff - f->hexDiff[j] ) > 0.0001 )
                    fprintf(stderr,"field diff: %8.6lf %8.6lf  %8.5lf \n",
                            hexdiff, f->hexDiff[j],
                            hexdiff - f->hexDiff[j] );
#endif
            }
        }
endif if 0
        fprintf(stderr,"s2 cnts:%d %d\n", query->s2cnt, str->s2cnt );
```

```
            fflush(stderr);
endif
        best = best2 = best3 = bestsub = 9999.0 * 9999.0;

/*

2 piece steric field comparison

*/ if ( query->s2 && str->s2 && q_do2piece )
        {
            for ( i = 0, qs2 = query->s2; i < query->s2cnt; i++, qs2++ )
            {
                if ( qs2->frag1 == -1 || qs2->frag2 == -1)
                        continue;
                q1 = query->frags + qs2->frag1;
                q2 = query->frags + qs2->frag2;
                if ( q_partialMatch )
                {
                        q1->featureDiff = q1->feature2PDiff;
                        q2->featureDiff = q2->feature2PDiff;
                }
                for ( j = 0, ss2 = str->s2; j < str->s2cnt; j++, ss2++ )
                {
                        if ( ss2->frag1 == -1 || ss2->frag2 == -1)
                                continue;
#ifndef NO_STRMAP
                        if ( qs2->strMap && qs2->strMap[j] == 0 )
                                continue;          /* feature throws this one out */
#endif
                        id1 = (str->frags + ss2->frag1)->id;
                        id2 = (str->frags + ss2->frag2)->id;

fs1 = str->frags + ss2->frag1;
                        fs2 = str->frags + ss2->frag2;
                        t_2compare++;
#if 0
                        fprintf(stderr,"ids %d: %d %d\n", j, id1, id2 );
                        fflush(stderr);
endif outPen = fs1->outsidePenalty + fs2->outsidePenalty;
                        if ( outPen )
                        {
                                if ( outPen > bailout )
                                {
                                        continue;
```

```
        }
      } ifdef NO_COMPRESSION
               q1->hexDiff[id1]  =  topFieldDiff(q1->qtf[fs1->regionIdx], fs1->topField,
fs1->npoints );
               q1->hexDiff[id2]  =  topFieldDiff(q1->qtf[fs2->regionIdx], fs2->topField,
fs2->npoints );
               q2->hexDiff[id1]  =  topFieldDiff(q2->qtf[fs1->regionIdx], fs1->topField,
fs1->npoints );
               q2->hexDiff[id2]  =  topFieldDiff(q2->qtf[fs2->regionIdx], fs2->topField,
fs2->npoints );
#else
               if ( q_featureFactor > 0.0 && q1->featureDiff && q2->featureDiff )
               {
                       q1->hexDiff[id1]=topFieldCompressedDiff(q1->qtf[fs1->regionIdx],
fs1->topField, fs1->npoints, q1->featureDiff[id1] );
                       q1->hexDiff[id2]=topFieldCompressedDiff(q1->qtf[fs2->regionIdx],
fs2->topField, fs2->npoints, q1->featureDiff[id2] );
                       q2->hexDiff[id1]=topFieldCompressedDiff(q2->qtf[fs1->regionIdx],
fs1->topField, fs1->npoints, q2->featureDiff[id1] );
                       q2->hexDiff[id2]=topFieldCompressedDiff(q2->qtf[fs2->regionIdx],
fs2->topField, fs2->npoints, q2->featureDiff[id2] );
               }
               else
               {
                       q1->hexDiff[id1]=topFieldCompressedDiff(q1->qtf[fs1->regionIdx],
fs1->topField, fs1->npoints, 0.0 );
                       q1->hexDiff[id2]=topFieldCompressedDiff(q1->qtf[fs2->regionIdx],
fs2->topField, fs2->npoints, 0.0 );
                       q2->hexDiff[id1]=topFieldCompressedDiff(q2->qtf[fs1->regionIdx],
fs1->topField, fs1->npoints, 0.0 );
                       q2->hexDiff[id2]=topFieldCompressedDiff(q2->qtf[fs2->regionIdx],
fs2->topField, fs2->npoints, 0.0 );
               }
endif ifdef NO_COMPRESSION
ifdef COMPRESS_COMPARE
               cf[0] = compressField(q1->qtf[fs1->regionIdx], fs1->npoints );
               cf[4] = compressField(fs1->topField, fs1->npoints );
               cdval[0] = topFieldCompressedDiff( cf[0], cf[4], fs1->npoints );
               fprintf(stderr,"Compressed varies by %7.2lf  %6.2lf %6.2lf \n",
                       fabs(q1->hexDiff[id1] - cdval[0]), q1->hexDiff[id1], cdval[0] );

cf[1] = compressField(q1->qtf[fs2->regionIdx], fs2->npoints );
               cf[5] = compressField(fs2->topField, fs2->npoints );
               cdval[1] = topFieldCompressedDiff( cf[1], cf[5], fs2->npoints );
```

```
            fprintf(stderr,"Compressed varies by %7.2lf  %6.2lf %6.2lf \n",
                    fabs(q1->hexDiff[id2] - cdval[1]), q1->hexDiff[id2], cdval[1] );

free((char *) cf[4] );
            cf[2] = compressField(q2->qtf[fs1->regionIdx], fs1->npoints );
            cf[4] = compressField(fs1->topField, fs1->npoints );
            cdval[2] = topFieldCompressedDiff( cf[2], cf[4], fs1->npoints );
            fprintf(stderr,"Compressed varies by %7.2lf  %6.2lf %6.2lf \n",
                    fabs(q2->hexDiff[id1] - cdval[2]), q2->hexDiff[id1], cdval[2] );

free((char *) cf[5] );
            cf[3] = compressField(q2->qtf[fs2->regionIdx], fs2->npoints );
            cf[5] = compressField(fs2->topField, fs2->npoints );
            cdval[3] = topFieldCompressedDiff( cf[3], cf[5], fs2->npoints );

fprintf(stderr,"Compressed varies by %7.2lf  %6.2lf %6.2lf \n",
                    fabs(q2->hexDiff[id2] - cdval[3]), q2->hexDiff[id2], cdval[3] );

free((char *) cf[0] );
            free((char *) cf[1] );
            free((char *) cf[2] );
            free((char *) cf[3] );
            free((char *) cf[5] );
            free((char *) cf[4] );
#endif
endif ifdef STD_REGION q1->stdDiff[id1] = topFieldDiff(q1->stdField, fs1->stdField,
stdRegion->n_points );
            q1->stdDiff[id2] = topFieldDiff(q1->stdField, fs2->stdField,
stdRegion->n_points );
            q2->stdDiff[id1] = topFieldDiff(q2->stdField, fs1->stdField,
stdRegion->n_points );
            q2->stdDiff[id2] = topFieldDiff(q2->stdField, fs2->stdField,
stdRegion->n_points );

if ( q_debugfp && (
                ( q1->hexDiff[id1] - q1->stdDiff[id1] ) > 9.0 ||
                ( q1->hexDiff[id2] - q1->stdDiff[id2] ) > 9.0 ||
                ( q2->hexDiff[id1] - q2->stdDiff[id1] ) > 9.0 ||
                ( q2->hexDiff[id2] - q2->stdDiff[id2] ) > 9.0 ) )
            {
                fprintf(q_debugfp,"region diffs: %d.%d  %6.2lf %6.2lf %6.2lf %6.2lf
(idx: %d %d) \n",
                    i+1,j+1,
                    q1->hexDiff[id1] - q1->stdDiff[id1],
```

```
                         q1->hexDiff[id2] - q1->stdDiff[id2],
                         q2->hexDiff[id1] - q2->stdDiff[id1],
                         q2->hexDiff[id2] - q2->stdDiff[id2],
                                 fs1->regionIdx, fs2->regionIdx );
                 }
endif if ( q_featureFactor > 0.0 )
                 {
                         d1 = q1->hexDiff[id1] + q2->hexDiff[id2] + q1->featureDiff[id1]
    + q2->featureDiff[id2] + outPen;
                         d2 = q1->hexDiff[id2] + q2->hexDiff[id1] + q1->featureDiff[id2]
    + q2->featureDiff[id1] + outPen;
                 }
                 else
                 {
                         d1 = q1->hexDiff[id1] + q2->hexDiff[id2] + outPen;
                         d2 = q1->hexDiff[id2] + q2->hexDiff[id1] + outPen;
                 } if ( d1 < best )
                 {
                         bestQ = i;
                         bestStr = j;
                         best = best2 = d1;
                         bestIdx = 0;
                 } if ( d2 < best )
                 {
                         bestQ = i;
                         bestStr = j;
                         best = best2 = d2;
                         bestIdx = 1;
                 }
             }
         }
     }
if 0
         fprintf(stderr,"s3 cnts:%d %d\n", query->s3cnt, str->s3cnt );
         fflush(stderr);
endif

/*

3 piece steric field comparison
```

```
*/
        for ( i = 0, qs3 = query->s3; q_do3piece && qs3 && i < query->s3cnt; i++, qs3++ )
        {
                if ( qs3->frag1 == -1 || qs3->frag2 == -1 || qs3->frag3 == -1 )
                        continue;
                q1 = query->frags + qs3->frag1;
                q2 = query->frags + qs3->frag2;
                q3 = query->frags + qs3->frag3;
                q4 = query->frags + qs3->frag4;
                if ( q_partialMatch )
                {
                        q1->featureDiff = q1->feature3PDiff;
                        q2->featureDiff = q2->feature3PDiff;
                        q3->featureDiff = q3->feature3PDiff;
                        q4->featureDiff = q4->feature3PDiff;
                }
                for ( j = 0, ss3 = str->s3; ss3 && j < str->s3cnt; j++, ss3++ )
                {
                        if ( ss3->frag1 == -1 || ss3->frag2 == -1 || ss3->frag3 == -1 )
                                continue;
#ifndef NO_STRMAP
                        if ( qs3->strMap && qs3->strMap[j] == 0 )
                                continue;           /* can't hit this 3 piece combination because features throws it out */
#endif
                        fs1 = str->frags + ss3->frag1;
                        fs2 = str->frags + ss3->frag2;
                        fs3 = str->frags + ss3->frag3;
                        fs4 = str->frags + ss3->frag4;
                        id1 = fs1->id;
                        id2 = fs2->id;
                        id3 = fs3->id;
                        id4 = fs4->id;

t_3compare++;

#ifdef NO_COMPRESSION
#ifdef USE_HEX
                        if ( q1->hexDiff[id1] == -1.0 )
                                q1->hexDiff[id1]  =  fieldIntDiff(q1->topInt,  fs1->topInt, q1->topIntSize, fs1->topIntSize);

if ( q1->hexDiff[id4] == -1.0 )
                                q1->hexDiff[id4]  =  fieldIntDiff(q1->topInt,  fs4->topInt, q1->topIntSize, fs4->topIntSize);

if ( q4->hexDiff[id1] == -1.0 )
```

```
                    q4->hexDiff[id1]  =  fieldIntDiff(q4->topInt,  fs1->topInt,
q4->topIntSize, fs1->topIntSize);

if ( q4->hexDiff[id4] == -1.0 )
                    q4->hexDiff[id4]  =  fieldIntDiff(q4->topInt,  fs4->topInt,
q4->topIntSize, fs4->topIntSize);

if ( q2->hexDiff[id2] == -1.0 )
                    q2->hexDiff[id2]  =  fieldIntDiff(q2->topInt,  fs2->topInt,
q2->topIntSize, fs2->topIntSize);

if ( q2->hexDiff[id3] == -1.0 )
                    q2->hexDiff[id3]  =  fieldIntDiff(q2->topInt,  fs3->topInt,
q2->topIntSize, fs3->topIntSize);

if ( q3->hexDiff[id3] == -1 )
                    q3->hexDiff[id3]  =  fieldIntDiff(q3->topInt,  fs3->topInt,
q3->topIntSize, fs3->topIntSize);

if ( q3->hexDiff[id2] == -1 )
                    q3->hexDiff[id2]  =  fieldIntDiff(q3->topInt,  fs2->topInt,
q3->topIntSize, fs2->topIntSize);
#else
            if ( q1->hexDiff[id1] == -1.0 )
                    q1->hexDiff[id1]  =  topFieldDiff(q1->qtf[fs1->regionIdx]  ,
fs1->topField, fs1->npoints );

if ( q1->hexDiff[id4] == -1.0 )
                    q1->hexDiff[id4]  =  topFieldDiff(q1->qtf[fs4->regionIdx],
fs4->topField, fs4->npoints );

if ( q4->hexDiff[id1] == -1.0 )
                    q4->hexDiff[id1]  =  topFieldDiff(q4->qtf[fs1->regionIdx],
fs1->topField, fs1->npoints );

if ( q4->hexDiff[id4] == -1.0 )
                    q4->hexDiff[id4]  =  topFieldDiff(q4->qtf[fs4->regionIdx],
fs4->topField, fs4->npoints );

if ( q2->hexDiff[id2] == -1.0 )
                    q2->hexDiff[id2]  =  topFieldDiff(q2->qtf[fs2->regionIdx],
fs2->topField, fs2->npoints );

if ( q2->hexDiff[id3] == -1.0 )
                    q2->hexDiff[id3]  =  topFieldDiff(q2->qtf[fs3->regionIdx],
fs3->topField, fs3->npoints );

if ( q3->hexDiff[id3] == -1 )
```

```
                    q3->hexDiff[id3]  =  topFieldDiff(q3->qtf[fs3->regionIdx],
fs3->topField, fs3->npoints );

if ( q3->hexDiff[id2] == -1 )
                    q3->hexDiff[id2]  =  topFieldDiff(q3->qtf[fs2->regionIdx],
fs2->topField, fs2->npoints );

outPen  =  ( (fs1->outsidePenalty  +  fs2->outsidePenalty) / 2.0  )  +
fs2->outsidePenalty + fs3->outsidePenalty;
endif
endif ifndef NO_COMPRESSION
        if ( q1->hexDiff[id1] == -1.0 )
                    q1->hexDiff[id1] = topFieldCompressedDiff(q1->qtf[fs1->regionIdx]
, fs1->topField, fs1->npoints, 0.0 );

if ( q1->hexDiff[id4] == -1.0 )
                    q1->hexDiff[id4]=topFieldCompressedDiff(q1->qtf[fs4->regionIdx],
fs4->topField, fs4->npoints, 0.0 );

if ( q4->hexDiff[id1] == -1.0 )
                    q4->hexDiff[id1]=topFieldCompressedDiff(q4->qtf[fs1->regionIdx],
fs1->topField, fs1->npoints, 0.0 );

if ( q4->hexDiff[id4] == -1.0 )
                    q4->hexDiff[id4]=topFieldCompressedDiff(q4->qtf[fs4->regionIdx],
fs4->topField, fs4->npoints, 0.0 );

if ( q2->hexDiff[id2] == -1.0 )
                    q2->hexDiff[id2]=topFieldCompressedDiff(q2->qtf[fs2->regionIdx],
fs2->topField, fs2->npoints,
                        q2->featureDiff ? q2->featureDiff[id2] : 0.0 );

if ( q2->hexDiff[id3] == -1.0 )
                    q2->hexDiff[id3]=topFieldCompressedDiff(q2->qtf[fs3->regionIdx],
fs3->topField, fs3->npoints,
                        q2->featureDiff ? q2->featureDiff[id3] : 0.0 );

if ( q3->hexDiff[id3] == -1 )
                    q3->hexDiff[id3]=topFieldCompressedDiff(q3->qtf[fs3->regionIdx],
fs3->topField, fs3->npoints,
                        q3->featureDiff ? q3->featureDiff[id3] : 0.0 );

if ( q3->hexDiff[id2] == -1 )
                    q3->hexDiff[id2]=topFieldCompressedDiff(q3->qtf[fs2->regionIdx],
fs2->topField, fs2->npoints,
                        q3->featureDiff ? q3->featureDiff[id2] : 0.0 );
```

```
                    outPen = ( (fs1->outsidePenalty + fs2->outsidePenalty) / 2.0 ) +
fs2->outsidePenalty + fs3->outsidePenalty;
endif ifdef STD_REGION_3P
                    q1->stdDiff[id1]  =  topFieldDiff(q1->stdField,  fs1->stdField,
stdRegion->n_points );
                    q4->stdDiff[id1]  =  topFieldDiff(q4->stdField,  fs1->stdField,
stdRegion->n_points );
                    q1->stdDiff[id4]  =  topFieldDiff(q1->stdField,  fs4->stdField,
stdRegion->n_points );
                    q4->stdDiff[id4]  =  topFieldDiff(q4->stdField,  fs4->stdField,
stdRegion->n_points );
                    q2->stdDiff[id2]  =  topFieldDiff(q2->stdField,  fs2->stdField,
stdRegion->n_points );
                    q2->stdDiff[id3]  =  topFieldDiff(q2->stdField,  fs3->stdField,
stdRegion->n_points );
                    q3->stdDiff[id3]  =  topFieldDiff(q3->stdField,  fs3->stdField,
stdRegion->n_points );
                    q3->stdDiff[id2]  =  topFieldDiff(q3->stdField,  fs2->stdField,
stdRegion->n_points );

fprintf(stderr,"# region diffs %6.2lf %6.2lf %6.2lf %6.2lf %6.2lf %6.2lf %6.2lf
%6.2lf (idx: %d %d %d %d) out:%6.2lf\n",
                            q1->hexDiff[id1] - q1->stdDiff[id1],
                            q1->hexDiff[id4] - q1->stdDiff[id4],
                            q4->hexDiff[id1] - q4->stdDiff[id1],
                            q4->hexDiff[id4] - q4->stdDiff[id4],
                            q2->hexDiff[id2] - q2->stdDiff[id2],
                            q2->hexDiff[id3] - q2->stdDiff[id3],
                            q3->hexDiff[id3] - q3->stdDiff[id3],
                            q3->hexDiff[id2] - q3->stdDiff[id2],
                            fs1->regionIdx,  fs4->regionIdx,  fs2->regionIdx,
fs3->regionIdx, outPen );
endif attPen[0] = attPen[1] = 0.0;
            dval[0] = ( q1->hexDiff[id1] + q4->hexDiff[id4] ) / 2.0 + q2->hexDiff[id2]
+ q3->hexDiff[id3];
            dval[1] = ( q1->hexDiff[id4] + q4->hexDiff[id1] ) / 2.0 + q2->hexDiff[id3]
+ q3->hexDiff[id2];
            if ( outPen > 0.0 )
            {
                    dval[0] += outPen;
                    dval[1] += outPen;
            }
            if ( q_attachPenFactor > 0.0 )
```

```
            {
                attPen[0] = ( computeAttachmentPenalty( q1, fs1, q4, fs4 ) +
computeAttachmentPenalty(q4, fs4, q1, fs1) );
                attPen[1] = ( computeAttachmentPenalty( q1, fs4, q4, fs1 ) +
computeAttachmentPenalty(q4, fs1, q1, fs4) );

dval[0] += attPen[0];
                dval[1] += attPen[1];
            }
            if ( q_featureFactor > 0.0 )
            {
                dval[0] += ( q1->featureDiff[id1] + q4->featureDiff[id4] ) / 2.0 +
q2->featureDiff[id2] + q3->featureDiff[id3];
                dval[1] += ( q1->featureDiff[id4] + q4->featureDiff[id1] ) / 2.0 +
q2->featureDiff[id3] + q3->featureDiff[id2];
            }
            max3 = 2;

if ( dval[0] < 0.0 )
            {
#if 0
                if ( q_debugfp )
                    fprintf(q_debugfp, "3 below zero #0 %8.4lf %8.4lf  %8.4lf
%8.4lf (%d %d %d %d) \n",
                        q1->featureDiff[id1]  ,  q4->featureDiff[id4]  ,
q2->featureDiff[id2] , q3->featureDiff[id3],
                        id1, id4, id2, id3 );
#endif
                dval[0] = 0.0;
            }
            if ( dval[1] < 0.0 )
            {
#if 0
                if ( q_debugfp )
                    fprintf(q_debugfp, "3 below zero #1 %8.4lf %8.4lf  %8.4lf
%8.4lf (%d %d %d %d)\n",
                        q1->featureDiff[id4]  ,  q4->featureDiff[id1]  ,
q2->featureDiff[id3] , q3->featureDiff[id2],
                        id4, id1, id3, id2 );
#endif
                dval[1] = 0.0;
            } for ( k = 0; k < max3; k++ )
            {
                if ( dval[k] < best )
                {
```

```
                    best = best3 = dval[k];
                    bestQ = i;
                    bestStr = j;
                    bestIdx = k;
                    threeIsBetter = 1;
                    *r_att_pen = attPen[k] > 0.0 ? sqrt(attPen[k]) : 0.0;
                }
                else if ( dval[k] < best3 )
                    best3 = dval[k];
            }
        }
    }

/*
subset steric field comparison
*/ if ( query->s2 && str->s3 && q_doSubset )
    {
                    /* loop over query 2 piece fragments, and compare with the structure's
3 piece fragments. */
        for ( i = 0, qs2 = query->s2; i < query->s2cnt ; i++, qs2++ )
        {
            if ( qs2->frag1 == -1 || qs2->frag2 == -1)
                continue;
            q1 = query->frags + qs2->frag1;
            q2 = query->frags + qs2->frag2;
            if ( q_partialMatch )
            {
                q1->featureDiff = q1->featureSubsetDiff;
                q2->featureDiff = q2->featureSubsetDiff;
            }
            for ( j = 0, ss3 = str->s3; ss3 && j < str->s3cnt; j++, ss3++ )
            {
                if ( ss3->frag1 == -1 || ss3->frag2 == -1 || ss3->frag3 == -1 )
                    continue;
                if ( qs2->subsetMap && qs2->subsetMap[j] == 0 )
                    continue;              /* feature throws this one out */
                fs1 = str->frags + ss3->frag1;
                fs2 = str->frags + ss3->frag2;
                fs3 = str->frags + ss3->frag3;
                fs4 = str->frags + ss3->frag4;
                id1 = fs1->id;
                id2 = fs2->id;
                id3 = fs3->id;
```

```
                id4 = fs4->id;
#if 1
            if ( q1->hexDiff[id1] == -1.0 )
                    q1->hexDiff[id1]=topFieldCompressedDiff(q1->qtf[fs1->regionIdx],
fs1->topField, fs1->npoints, 0.0 );
            if ( q1->hexDiff[id2] == -1.0 )
                    q1->hexDiff[id2]=topFieldCompressedDiff(q1->qtf[fs2->regionIdx],
fs2->topField, fs2->npoints, 0.0 );

if ( q2->hexDiff[id1] == -1.0 )
                    q2->hexDiff[id1]=topFieldCompressedDiff(q2->qtf[fs1->regionIdx],
fs1->topField, fs1->npoints, 0.0 );
            if ( q2->hexDiff[id2] == -1.0 )
                    q2->hexDiff[id2]=topFieldCompressedDiff(q2->qtf[fs2->regionIdx],
fs2->topField, fs2->npoints, 0.0 );

if ( q1->hexDiff[id3] == -1.0 )
                    q1->hexDiff[id3]=topFieldCompressedDiff(q1->qtf[fs3->regionIdx],
fs3->topField, fs3->npoints, 0.0 );
            if ( q1->hexDiff[id4] == -1.0 )
                    q1->hexDiff[id4]=topFieldCompressedDiff(q1->qtf[fs4->regionIdx],
fs4->topField, fs4->npoints, 0.0 );

if ( q2->hexDiff[id3] == -1.0 )
                    q2->hexDiff[id3]=topFieldCompressedDiff(q2->qtf[fs3->regionIdx],
fs3->topField, fs3->npoints, 0.0 );
            if ( q2->hexDiff[id4] == -1.0 )
                    q2->hexDiff[id4]=topFieldCompressedDiff(q2->qtf[fs4->regionIdx],
fs4->topField, fs4->npoints, 0.0 );
#else
                    q1->hexDiff[id1]    =    topFieldCompressedDiff(q1->qtf[fs1->regionIdx],
fs1->topField, fs1->npoints, 0.0 );
                    q1->hexDiff[id2]    =    topFieldCompressedDiff(q1->qtf[fs2->regionIdx],
fs2->topField, fs2->npoints, 0.0 );
                    q2->hexDiff[id1]    =    topFieldCompressedDiff(q2->qtf[fs1->regionIdx],
fs1->topField, fs1->npoints, 0.0 );
                    q2->hexDiff[id2]    =    topFieldCompressedDiff(q2->qtf[fs2->regionIdx],
fs2->topField, fs2->npoints, 0.0 );
                    q1->hexDiff[id3]    =    topFieldCompressedDiff(q1->qtf[fs3->regionIdx],
fs3->topField, fs3->npoints, 0.0 );
                    q1->hexDiff[id4]    =    topFieldCompressedDiff(q1->qtf[fs4->regionIdx],
fs4->topField, fs4->npoints, 0.0 );
                    q2->hexDiff[id3]    =    topFieldCompressedDiff(q2->qtf[fs3->regionIdx],
fs3->topField, fs3->npoints, 0.0 );
                    q2->hexDiff[id4]    =    topFieldCompressedDiff(q2->qtf[fs4->regionIdx],
fs4->topField, fs4->npoints, 0.0 );
```

```
endif if ( q_featureFactor > 0.0 )
                {
                        dval[0] = q1->featureDiff[id1] + q2->featureDiff[id2];
                        dval[1] = q1->featureDiff[id2] + q2->featureDiff[id1];
                        dval[2] = q1->featureDiff[id3] + q2->featureDiff[id4];
                        dval[3] = q1->featureDiff[id4] + q2->featureDiff[id3];
                }
                else
                        dval[0] = dval[1] = dval[2] = dval[3] = 0.0;

dval[0] += q1->hexDiff[id1] + q2->hexDiff[id2];
                dval[1] += q1->hexDiff[id2] + q2->hexDiff[id1];
                dval[2] += q1->hexDiff[id3] + q2->hexDiff[id4];
                dval[3] += q1->hexDiff[id4] + q2->hexDiff[id3];
#if 0
                fprintf(stderr,"%d %d with %d %d Feature; %8.2lf %8.2lf Steric: %8.2lf %8.2lf \n",
                        q1->id,q2->id, id1, id2, q1->featureDiff[id1],
q2->featureDiff[id2], q1->hexDiff[id1], q2->hexDiff[id2] );

fprintf(stderr,"%d %d with %d %d Feauture: %8.2lf %8.2lf Steric: %8.2lf %8.2lf\n",
                        q1->id,q2->id, id2, id1, q1->featureDiff[id2],
q2->featureDiff[id1], q1->hexDiff[id2], q2->hexDiff[id1]);

fprintf(stderr,"%d %d with %d %d Feature: %8.2lf %8.2lf Steric: %8.2lf %8.2lf\n",
                        q1->id,q2->id, id3, id4, q1->featureDiff[id3],
q2->featureDiff[id4], q1->hexDiff[id3], q2->hexDiff[id4] );

fprintf(stderr,"%d %d with %d %d Feature: %8.2lf %8.2lf Steric: %8.2lf %8.2lf\n",
                        q1->id,q2->id, id4, id3, q1->featureDiff[id4],
q2->featureDiff[id3], q1->hexDiff[id4], q2->hexDiff[id3] );
endif hevCnts[0] = hevCnts[1] = fs1->hevCnt + fs2->hevCnt;
                hevCnts[2] = hevCnts[3] = fs3->hevCnt + fs4->hevCnt;
#if 0
                fprintf(stderr,"dvals: %8.2lf %8.2lf %8.2lf %8.2lf \n", dval[0], dval[1],
dval[2], dval[3] );
                fprintf(stderr,"hevCnts: %d %d min:%d\n", hevCnts[0], hevCnts[1],
q_minSubsetSize );
#endif
```

```
                max3 = 4;

for ( k = 0; k < max3; k++ )
                {
                        if ( hevCnts[k] >= q_minSubsetSize )
                        {
                                if ( dval[k] < best )
                                {
                                        best = bestsub = dval[k];
                                        bestQ = i;
                                        bestStr = j;
                                        bestIdx = k;
                                        SubIsBetter = 1;
                                }
                                else if ( dval[k] < bestsub )
                                        bestsub = dval[k];

if ( dval[k] < q_bailout && qs2->subsetMap[j] == 0 )
                                {
                                        qs2->subsetMap[j] = 1;
                                }
                        }
                }
            }
        }
    } /* end of subset */ ifdef DEBUG_DETAIL
if ( debug2 )
{
/* dump array of difference matrix values */
        if ( regid )
                fprintf(debug2,"%s\n", regid );
        for ( i = 0; i < query->numFrags; i++ )
        {
                fs1 = query->frags + i;
                dptr = fs1->hexDiff;
                for ( j = 0; j < str->numFrags; j++ )
                {
                        fprintf(debug2,"%7.2lf ", *(dptr+j) );
                }
                fprintf(debug2,"\n");
        }
        fprintf(debug2,"\n");
        for ( i = 0; i < query->numFrags; i++ )
        {
                fs1 = query->frags + i;
                for ( j = 0; j < str->numFrags; j++ )
```

```
            {
                    fs2 = str->frags + j;
                    fprintf(debug2,"%3d,%3d ", fs1->atomCnt, fs2->atomCnt );
            }
            fprintf(debug2,"\n");
    }
    fprintf(debug2,"\n");
    fprintf(debug2,"Query split 2\n");
    for ( i = 0; i < query->s2cnt; i++ )
    {
            qs2 = query->s2 + i;
            fprintf(debug2,"%d %d\n", qs2->frag1, qs2->frag2 );
    }
    fprintf(debug2,"\nStr split 2\n");
    for ( i = 0; i < str->s2cnt; i++ )
    {
            qs2 = str->s2 + i;
            fprintf(debug2,"%d %d\n", qs2->frag1, qs2->frag2 );
    }
    fprintf(debug2,"\nQuery split 3\n");
    for ( i = 0; i < query->s3cnt; i++ )
    {
            qs3 = query->s3 + i;
            fprintf(debug2,"%d %d %d\n", qs3->frag1, qs3->frag2, qs3->frag3 );
    }
    fprintf(debug2,"\nStr split 3\n");
    for ( i = 0; i < str->s3cnt; i++ )
    {
            qs3 = str->s3 + i;
            fprintf(debug2,"%d %d %d\n", qs3->frag1, qs3->frag2, qs3->frag3 );
    }
    fprintf(debug2,"-----------------------------------\n");
}
endif if 0
    fprintf(stderr,"done with this one\n");
    fflush(stderr);
endif
    if ( q_debugfp )
            fprintf(q_debugfp, "q %d str: %d idx %d 3is %d subis %d best2 %8.4lf best3 %8.4lf bestsub %8.4lf \n",
                    bestQ, bestStr, bestIdx, threeIsBetter, SubIsBetter, best2, best3, bestsub );
    *r_qidx = bestQ;
    *r_sidx = bestStr;
    *r_splitidx = bestIdx;
    *r_three = threeIsBetter;
```

```
        *r_subsethit = SubIsBetter;
        if ( best2 < 0.0 )
                best2 = 0.0;
        *r_best2 = sqrt(best2);
        if ( best3 < 0.0 )
                best3 = 0.0;
        *r_best3 = sqrt(best3);
        *r_bestsub = sqrt(bestsub);
        if ( best < 0.0 )
                best = 0.0;
        return sqrt(best);
} static int get_details( top_result *res, Split *query, Split *str,
int bestq, int bestStr, int bestIdx, int threeMatched, int subsetHit, int keepCts )
{
        split2 *qs2, *s2;
        split3 *qs3, *s3;
        int ids[3];
        Frag *f;
        Frag *sf;

if ( subsetHit )
        {
                threeMatched = 0;
                if ( bestq < 0 || bestq >= query->s2cnt )
                        return -1;
                if ( bestStr < 0 || bestStr >= str->s3cnt )
                        return -1;

qs2 = query->s2 + bestq;
                s3 = str->s3 + bestStr;
                switch ( bestIdx )
                {
#if 0
                        dval[0] +=  q1->hexDiff[id1] + q2->hexDiff[id2];
                        dval[1] +=  q1->hexDiff[id2] + q2->hexDiff[id1];
                        dval[2] +=  q1->hexDiff[id3] + q2->hexDiff[id4];
                        dval[3] +=  q1->hexDiff[id4] + q2->hexDiff[id3];
#endif
                        case 0:
                                ids[0] = s3->frag1;
                                ids[1] = s3->frag2;
                                break;

case 1:
                                ids[0] = s3->frag2;
                                ids[1] = s3->frag1;
```

```
                    break;

case 2:
                    ids[0] = s3->frag3;
                    ids[1] = s3->frag4;
                    break;

case 3:
                    ids[0] = s3->frag4;
                    ids[1] = s3->frag3;
                    break;

default:
                    return -1;
}
f = query->frags + qs2->frag1;
sf = str->frags + ids[0];
res->qids[0] = f->id;
res->outside[0] = sf->outside;
if ( f->ct && sf->ct )
{
        res->qFrags[0] = f->ct;
        res->hexDiffs[0] = sqrt( f->hexDiff [ ids[0] ] );
        if ( q_partialMatch )
                    f->featureDiff = f->featureSubsetDiff;
        if ( f->featureDiff )
                    res->featureDiffs[0] = sqrt( f->featureDiff [ ids[0] ] );
        else
                    res->featureDiffs[0] = 0.0;
}
else
{
        res->hexDiffs[0] = 1.0;
        res->featureDiffs[0] = 1.0;
}
if ( sf->ct && keepCts )
        res->strFrags[0]= makeFragCopy(sf->ct, ids[0], -1 );
f = query->frags + qs2->frag2;
sf = str->frags + ids[1];
res->qids[1] = f->id;
res->outside[1] = sf->outside;
if ( f->ct && sf->ct )
{
        res->qFrags[1] = f->ct;
        res->hexDiffs[1] = sqrt( f->hexDiff [ ids[1] ] );
        if ( q_partialMatch )
                    f->featureDiff = f->featureSubsetDiff;
        if ( f->featureDiff )
```

```c
                    res->featureDiffs[1] = sqrt( f->featureDiff[ ids[1] ] );
            else
                    res->featureDiffs[1] = 0.0;
    }
    else
    {
            res->hexDiffs[1] = 1.0;
            res->featureDiffs[1] = 1.0;
    }
    if ( sf->ct && keepCts )
            res->strFrags[1]= makeFragCopy(sf->ct, ids[1], -1 );
    res->qids[2] = -1;
    res->strids[0] = ids[0];
    res->strids[1] = ids[1];
    res->strids[2] = -1;
}
else if ( threeMatched )
{
    qs3 = query->s3 + bestq;
    s3 = str->s3 + bestStr;

switch(bestIdx)
    {
            case 0:
            case 2:
                    ids[0] = s3->frag1;
                    ids[1] = s3->frag2;
                    ids[2] = s3->frag3;
                    break;

case 1:
            case 3:
                    ids[0] = s3->frag4;
                    ids[1] = s3->frag3;
                    ids[2] = s3->frag2;
                    break;
#if 0
            case 2:
                    ids[0] = s3->frag2;
                    ids[1] = s3->frag1;
                    ids[2] = s3->frag3;
                    break;
            case 3:
                    ids[0] = s3->frag2;
                    ids[1] = s3->frag3;
                    ids[2] = s3->frag1;
                    break;
            case 4:
```

```
                        ids[0] = s3->frag3;
                        ids[1] = s3->frag2;
                        ids[2] = s3->frag1;
                        break;
                case 5:
                        ids[0] = s3->frag3;
                        ids[1] = s3->frag1;
                        ids[2] = s3->frag2;
                        break;
endif default:
                        return -1;
        } res->hexDiffs[0] = res->hexDiffs[1] = res->hexDiffs[2] = 0.0;
        f = query->frags + qs3->frag1;  /* always use the first query fragment for the center piece,
                        report the corresponding best hit (avg anyway) fragment from the structure fragment */
        res->qids[0] = f->id;
        if ( f->ct )
        {
                res->qFrags[0] = f->ct;
                res->hexDiffs[0] = sqrt( f->hexDiff [ ids[0] ] );
                if ( q_partialMatch )
                        f->featureDiff = f->feature3PDiff;
                if ( f->featureDiff )
                        res->featureDiffs[0] = sqrt( f->featureDiff [ ids[0] ] );
                else
                        res->featureDiffs[0] = 0.0;
        }
        f = str->frags + ids[0];
        if ( f->ct && keepCts )
                res->strFrags[0]= makeFragCopy(f->ct, ids[0], -1 );
        res->outside[0] = f->outside;

f = query->frags + qs3->frag2;
        res->qids[1] = f->id;
        if ( f->ct )
        {
                res->qFrags[1] = f->ct;
                res->hexDiffs[1]= sqrt( f->hexDiff [ ids[1] ] );
                if ( q_partialMatch )
                        f->featureDiff = f->feature3PDiff;
                if ( f->featureDiff )
                        res->featureDiffs[1]= sqrt( f->featureDiff [ ids[1] ] );
                else
```

```
                    res->featureDiffs[0] = 0.0;
            }
            f = str->frags + ids[1];
            if ( f->ct && keepCts )
                    res->strFrags[1]= makeFragCopy(f->ct, ids[1], -1 );
            res->outside[1] = f->outside;

f = query->frags + qs3->frag3;
            res->qids[2] = f->id;
            if ( f->ct )
            {
                    res->qFrags[2] = f->ct;
                    res->hexDiffs[2]= sqrt( f->hexDiff [ ids[2] ] );
                    if ( q_partialMatch )
                            f->featureDiff = f->feature3PDiff;
                    if ( f->featureDiff )
                            res->featureDiffs[2] = sqrt( f->featureDiff [ ids[2] ] );
                    else
                            res->featureDiffs[2] = 0.0;
            } f = str->frags + ids[2];
            if ( f->ct && keepCts )
                    res->strFrags[2]= makeFragCopy(f->ct, ids[2], -1 );
            res->outside[2] = f->outside;

res->strids[0] = ids[0];
            res->strids[1] = ids[1];
            res->strids[2] = ids[2];
    }
    else    /* A 2 piece hit */
    {
            qs2 = query->s2 + bestq;
            s2 = str->s2 + bestStr;

if ( bestIdx == 0 )
            {
                    ids[0] = s2->frag1;
                    ids[1] = s2->frag2;
            }
            else
            {
                    ids[0] = s2->frag2;
                    ids[1] = s2->frag1;
            } f = query->frags + qs2->frag1;
            sf = str->frags + ids[0];
```

```
                res->qids[0] = f->id;
                res->outside[0] = sf->outside;
                if ( f->ct && sf->ct )
                {
                        res->qFrags[0] = f->ct;
                        res->hexDiffs[0] = sqrt( f->hexDiff [ ids[0] ] );
                        if ( q_partialMatch )
                                f->featureDiff = f->feature2PDiff;
                        if ( f->featureDiff )
                                res->featureDiffs[0] = sqrt( f->featureDiff [ ids[0] ] );
                        else
                                res->featureDiffs[0] = 0.0;
                }
                if ( sf->ct && keepCts )
                        res->strFrags[0]= makeFragCopy(sf->ct, ids[0], -1 );
                f = query->frags + qs2->frag2;
                sf = str->frags + ids[1];
                res->qids[1] = f->id;
                res->outside[1] = sf->outside;
                if ( f->ct && sf->ct )
                {
                        res->qFrags[1] = f->ct;
                        res->hexDiffs[1] = sqrt( f->hexDiff [ ids[1] ] );
                        if ( q_partialMatch )
                                f->featureDiff = f->feature2PDiff;
                        if ( f->featureDiff )
                                res->featureDiffs[1] = sqrt( f->featureDiff [ ids[1] ] );
                        else
                                res->featureDiffs[1] = 0.0;
                }
                if ( sf->ct && keepCts )
                        res->strFrags[1]= makeFragCopy(sf->ct, ids[1], -1 );
                res->qids[2] = -1;
                res->strids[0] = ids[0];
                res->strids[1] = ids[1];
                res->strids[2] = -1;

}
        return 0;
} if 0 static int debugHits( FILE *fp, Split *query, Split *str, int bestq, int bestStr, int bestIdx, int threeMatched
)
{
        split2 *qs2, *s2;
        split3 *qs3, *s3;
```

```
int ids[3];
Frag *f;
Frag *sf;

if ( threeMatched )
{
        qs3 = query->s3 + bestq;
        s3 = str->s3 + bestStr;

switch(bestIdx)
        {
                case 0:
                case 2:
                        ids[0] = s3->frag1;
                        ids[1] = s3->frag2;
                        ids[2] = s3->frag3;
                        break;

case 1:
                case 3:
                        ids[0] = s3->frag4;
                        ids[1] = s3->frag3;
                        ids[2] = s3->frag2;
                        break;
#if 0
                case 2:
                        ids[0] = s3->frag2;
                        ids[1] = s3->frag1;
                        ids[2] = s3->frag3;
                        break;
                case 3:
                        ids[0] = s3->frag2;
                        ids[1] = s3->frag3;
                        ids[2] = s3->frag1;
                        break;
                case 4:
                        ids[0] = s3->frag3;
                        ids[1] = s3->frag2;
                        ids[2] = s3->frag1;
                        break;
                case 5:
                        ids[0] = s3->frag3;
                        ids[1] = s3->frag1;
                        ids[2] = s3->frag2;
                        break;
endif
                default:
```

```
                    return -1;
            }
            f = query->frags + qs3->frag1;

if ( f->ct )
            {
                    fprintf(fp,"# diff %8.4lf \n", sqrt( f->hexDiff [ ids[0] ] ) );
                    if ( bestIdx <= 1 )
                            writeCopy(fp, f->ct, qs3->frag1, (int) sqrt( f->hexDiff[ ids[0] ]),
"TS_QID" );
                    else
                            writeCopy(fp, f->ct, qs3->frag4, (int) sqrt( f->hexDiff[ ids[0] ]),
"TS_QID" );
                    f = str->frags + ids[0];
                    if ( f->ct )
                            writeCopy(fp,f->ct, ids[0], -1, "TS_SID");
            }
            f = query->frags + qs3->frag2;
            if ( f->ct )
            {
                    fprintf(fp,"# diff %8.4lf \n", sqrt( f->hexDiff [ ids[1] ] ) );
                    writeCopy(fp, f->ct, qs3->frag2, (int) sqrt( f->hexDiff[ids[1]] ), "TS_QID"
);
                    f = str->frags + ids[1];
                    if ( f->ct )
                            writeCopy(fp,f->ct, ids[1], -1, "TS_SID");
            }
            f = query->frags + qs3->frag3;
            if ( f->ct )
            {
                    fprintf(fp,"# diff %8.4lf \n", sqrt( f->hexDiff [ ids[2] ] ) );
                    writeCopy(fp, f->ct, qs3->frag3, (int) sqrt( f->hexDiff[ ids[2] ] ), "TS_QID");
                    f = str->frags + ids[2];
                    if ( f->ct )
                            writeCopy(fp,f->ct, ids[2], -1, "TS_SID");
            }
    }
    else
    {
            qs2 = query->s2 + bestq;
            s2 = str->s2 + bestStr;

if ( bestIdx == 0 )
            {
                    ids[0] = s2->frag1;
                    ids[1] = s2->frag2;
            }
            else
```

```
        {
                ids[0] = s2->frag2;
                ids[1] = s2->frag1;
        }
        f = query->frags + qs2->frag1;
        sf = str->frags + ids[0];
        if ( f->ct && sf->ct )
        {
                fprintf(fp,"# diff %8.4lf \n", sqrt( f->hexDiff [ ids[0] ] ) );
                writeCopy(fp, f->ct, qs2->frag1, (int) sqrt( f->hexDiff[ ids[0] ] ), "TS_QID"
);
                writeCopy(fp, sf->ct, ids[0], -1, "TS_SID" );
        }
        f = query->frags + qs2->frag2;
        sf = str->frags + ids[1];
        if ( f->ct && sf->ct )
        {
                fprintf(fp,"# diff %8.4lf \n", sqrt( f->hexDiff [ ids[1] ] ) );
                writeCopy(fp, f->ct, qs2->frag2, (int) sqrt( f->hexDiff[ ids[1] ] ), "TS_QID"
);
                writeCopy(fp, sf->ct, ids[1], -1,"TS_SID" );
        }
    }
    return 0;
}
endif static struct CtConnectionTable *makeFragCopy(struct CtConnectionTable *ct, int id, int hexdiff )
{
        char regName[80];
        char *regid;
        struct CtConnectionTable *copyct;

copyct = DB_CT_UTL_DUP_CT(ct, CtCopyKeepAllAttrs );
        if ( !copyct )
                return copyct;
        regid = (char *) 0;
        DB_CT_GET_CT_ATTR(ct, CtCtRegId, ®id );
        if ( hexdiff != -1 )
                sprintf(regName,"%s_%d_%d", (regid) ? regid : "str", id+1, hexdiff);
        else
                sprintf(regName,"%s_%d", (regid) ? regid : "str", id+1 );
        DB_CT_SET_CT_NAME_OR_REGID(copyct, CtCtRegId, regName );

return copyct;
} static void setAttr(struct CtConnectionTable *ct, char *name, char *value )
```

```
{
        char *tval;

tval = (char *) 0;

DB_CT_GET_CT_ATTR(ct, CtCtUserValue, &tval, name );
        if ( tval )
                DB_CT_UTL_MOD_SIMPLE_CT_ATTR(ct, CtCtUserValue, value, name );
        else
                DB_CT_SET_CT_ATTR(ct, CtCtUserValue, value, name );
        UTL_ERROR_CLEAR();
} static void writeCopy(FILE *fp, struct CtConnectionTable *ct, int id, int hexdiff, char *fieldname )
{
        struct CtConnectionTable *copyct;
        char value[80];

copyct = makeFragCopy(ct, id, hexdiff );
        if ( !copyct )
                return;
        if ( fieldname )
        {
                sprintf(value,"%d", id+1 );
                setAttr(copyct, fieldname, value );
        }
        DB_CT_WRITE(fp, copyct );
        DB_CT_DELETE_CT(copyct);
} static int getAtomIds(CtConnectionTable *ct, int a1, int *r_a2, int *r_a3 )
{
        CtAtom *A;
        CtAtom *a3;
        int i;
        CtAtomBondData *b;

A = ct->atoms + a1;
        *r_a2 = A->bond->toAtom;
        *r_a3 = -1;

A = ct->atoms + *r_a2;
        for ( i = 0, b = A->bond; i < A->bondCount; i++, b++ )
        {
                if ( b->toAtom != a1 )
                {
                        a3 = ct->atoms + b->toAtom;
```

```c
                    if ( *r_a3 == -1 || a3->id.atomicNumber != HYDROGEN )
                            *r_a3 = b->toAtom;
                    if ( a3->id.atomicNumber != HYDROGEN )
                            return 0;
            }
    }
    return -1;
}
/*******************************************************************
 modified from:
 * int SYB_MGEN_CONN_CFA_DIFF( identifier, nargs, args, writer )        *
 *      Dick Cramer, Nov. 20, 1996
 *
 * Computes difference between two CoMFA fields, represented as text
 * strings encoded by the expression generator %cfa_hex()
   C function CT_FIELD2HEX()
 *                                                                      *
 *********************************************************************/ static double fieldHexDiff( char *cptr, char *cqtr, int nosq )
{ define pow2(a) ( (a) * (a) )
        static double boundary[16];
                static double Dist[16][16];
                static double DnSq[16][16];
                static int InitDist;
                double xount;
        int i, j, nch, ptr, qtr;
        char  tempString[25];

if ( !cptr || !cqtr )
                        return 999999.0;

if ( (nch = strlen(cptr)) != strlen(cqtr) )
                        return 999999.0;

/* initialization on 1st call */
        if (!InitDist)
        {
                boundary[0] = 9999.;
                boundary[1] = -0.1 ;
                for (i=2;i< 15;i++)
                        boundary[i] = 2*i-3;
                boundary[15] = 30.0;

for (i=0;i<16;i++)
                {
```

```
                    for (j=0;j<16;j++)
                    {
                            DnSq[i][j] = (double) fabs( boundary[i] - boundary[j] );
                            Dist[i][j] = pow2( boundary[i] - boundary[j]);
                    }
            }
            InitDist = 1;
    }
    for (xount=0.0, i=0; i<nch; i += 2, cptr += 2, cqtr += 2)
    {
            sscanf( cptr, "%2x", &ptr );
            sscanf( cqtr, "%2x", &qtr );
            xount += nosq ?
                DnSq[ ptr & 0x0F    ][ qtr & 0x0F   ]
                + DnSq[ (ptr & 0xF0) >> 4][ (qtr & 0xF0) >> 4]
                        :
                Dist[ ptr & 0x0F    ][ qtr & 0x0F   ]
                + Dist[ (ptr & 0xF0) >> 4][ (qtr & 0xF0) >> 4] ;
    }
    return (nosq && xount > 0.0 ) ? xount : sqrt( xount );
} static char *hexStringToInts(char *cptr, int *r_size)
{
    int len, i;
    char *arr;
    int idx;

*r_size = 0;
    if ( !cptr )
            return (char *) 0;
    len = strlen(cptr);
    arr = malloc(len);

for ( i = idx = 0; i < len; i++, cptr++, idx++ )
    {
            if ( *cptr <= '9' )
                    arr[idx] = *cptr - '0';
            else
                    arr[idx] = *cptr - 'a' + 10;
    }
    *r_size = len;
    return arr;
} static double *compressField(double *topfield, int npoints )
{
```

```
        static double minv = -0.40;
        static double maxv = 0.40;
        static int nreported;
        static int max_alloc;
        static double *tbuff;
        static int ncomp;
        static int tpoints;
        static int newPoints;
        int cnt;
        double *tptr;
        double *cfield;
        int dsize;
        int i;
        double *fptr;
        int needpoints;
#ifdef NUMBER_OF_COMPRESSION_FIELDS
        double totals[NUMBER_OF_COMPRESSION_FIELDS];
        int cnts[NUMBER_OF_COMPRESSION_FIELDS];
        int gridsize;
        int grid;

gridsize = npoints / NUMBER_OF_COMPRESSION_FIELDS;
        for ( i = 0; i < NUMBER_OF_COMPRESSION_FIELDS; i++ )
        {
                totals[i] = 0.0;
                cnts[i] = 0;
        }
endif needpoints = npoints + COMPRESSION_POINTS;
        if ( needpoints > max_alloc )
        {
                if ( tbuff )
                        free( (char *) tbuff);
                if ( max_alloc == 0 )
                        max_alloc = 2000;
                while ( max_alloc < needpoints )
                        max_alloc *= 2;
                tbuff = (double *) malloc(sizeof(double) * max_alloc );
        } for ( i = cnt = dsize = COMPRESSION_POINTS, tptr = tbuff + COMPRESSION_POINTS,
fptr = topfield; i < npoints; i++, fptr++ )
        {
                if ( ( *fptr < maxv && *fptr > minv ) &&
                        (cnt > 0 || ((i+1) < npoints && *(fptr+1) < maxv && *(fptr+1)
> minv ) ) )
                        cnt++;
```

```c
            else
            {
                if ( cnt )
                {
                    *tptr++ = (double) (cnt + 100);
                    *tptr++ = *fptr;
                    dsize += 2;
                    cnt = 0;
                }
                else
                {
                    *tptr++ = *fptr;
                    dsize++;
                }
#ifdef NUMBER_OF_COMPRESSION_FIELDS
                if ( *fptr > 1.0 )
                {
                    grid = i / gridsize;
                    if ( grid >= NUMBER_OF_COMPRESSION_FIELDS )
                        grid = NUMBER_OF_COMPRESSION_FIELDS - 1;
                    cnts[grid] += 1;
                    totals[grid] += *fptr * *fptr;
                }
endif
            }
        }
        if ( cnt )
        {
            *tptr++ = (double) (cnt + 100);
            dsize++;
        }
#ifdef NUMBER_OF_COMPRESSION_FIELDS
        for ( i = 0; i < NUMBER_OF_COMPRESSION_FIELDS; i++ )
        {
            tbuff[i] = 0.0;
            if ( cnts[i] > 0 )
                tbuff[i] = totals[i] / (double) cnts[i];
            tbuff[ i + NUMBER_OF_COMPRESSION_FIELDS] = cnts[i];
        }
endif cfield = (double *) malloc(sizeof(double) * dsize );
        memcpy((char *) cfield, tbuff, sizeof(double) * dsize );

#if 0
        if ( nreported < 3 )
        {
            ncomp++;
```

```
            tpoints += npoints;
            newPoints += dsize;

if ( ncomp == 1000 )
            {
                    fprintf(stderr,"compression average for last %d frags: %6.2lf %d / %d\n",
                        ncomp,
                        (double) (newPoints * 100) / (double) tpoints,
                        newPoints, tpoints );
                    tpoints = newPoints = ncomp = 0;
                    nreported++;
            }
    }
endif if 0
        fprintf(stderr,"compressed perc: %5.1lf  new size: %d   old size:%d\n",
            (double) (dsize*100)/(npoints), dsize, npoints );
#endif
if 0
        fprintf(stderr,"un-compressed\n");
        for ( i = 0, fptr = topfield; i < npoints; i++, fptr++ )
            fprintf(stderr,"%6.2lf%s", *fptr, ((i+1) % 20) ? " " : "\n" );
        fprintf(stderr,"\ncompressed:\n");
        for ( i = 0, fptr = cfield; i < dsize; i++, fptr++ )
            fprintf(stderr,"%6.2lf%s", *fptr, ((i+1) % 20) ? " " : "\n" );
        fprintf(stderr,"\n");
endif
        return cfield;
} static double topFieldCompressedDiff(double *start_qry, double *start_str, int npoints, double startPenalty
)
{
        int i, j, k, minval;
        double dval, qval, sval, filtval;
        int qrySkip, strSkip;
        int qpoints, spoints;
        double *qry, *str;
#ifdef NUMBER_OF_COMPRESSION_FIELDS
        int distCnt1[NUMBER_OF_COMPRESSION_FIELDS];
        int distCnt2[NUMBER_OF_COMPRESSION_FIELDS];
        int dist;
        double avgval;
        double avg1[NUMBER_OF_COMPRESSION_FIELDS];
        double avg2[NUMBER_OF_COMPRESSION_FIELDS];
#endif
```

```
        if ( !start_qry || !start_str || !npoints )
                return 9999.0*9999.0;
        t_fcompare++;

#ifdef NUMBER_OF_COMPRESSION_FIELDS
        filtval = startPenalty;

for ( i = 0; i < NUMBER_OF_COMPRESSION_FIELDS; i++ )
        {
                avg1[i] = start_qry[i];
                distCnt1[i] = start_qry[i+NUMBER_OF_COMPRESSION_FIELDS];

avg2[i] = start_str[i];
                distCnt2[i] = start_str[i+NUMBER_OF_COMPRESSION_FIELDS];

#if 0
                fprintf(stderr,"%d: cnts: %d vs %d  avg:%9.3lf %9.3lf\n",
                        i, distCnt1[i], distCnt2[i], avg1[i], avg2[i] );
#endif
        } for ( i = 0; i < NUMBER_OF_COMPRESSION_FIELDS && filtval < q_bailout; i++ )
        {
                dist = abs(distCnt1[i] - distCnt2[i] );
                if ( distCnt1[i] > distCnt2[i] )
                {
                        dist = distCnt1[i] - distCnt2[i];
                        avgval = avg1[i];
                }
                else
                {
                        dist = distCnt2[i] - distCnt1[i];
                        avgval = avg2[i];
                }
                filtval += avgval * (double) dist;
        } if ( filtval > q_bailout )
                return filtval;
endif i = 0;
        sval = 0.0;
        strSkip = qrySkip = 0;
        qpoints = spoints = 0;

qry = start_qry + COMPRESSION_POINTS;
        str = start_str + COMPRESSION_POINTS;
```

```
while ( qpoints < npoints && spoints < npoints && sval < q_bailout )
{
        if ( qrySkip < 0 )
                qrySkip = 0;
        if ( strSkip < 0 )
                strSkip = 0;

if ( qrySkip == 0 && *qry > 100.0 )
        {
                qrySkip = (int) (*qry - 100.0);
        } if ( strSkip == 0 && *str > 100.0 )
        {
                strSkip = (int) (*str - 100.0);
        }
```

```
/* Example:
compressed: Query
117.00   3.18    3.21 104.00  30.00   30.00   30.00 103.00   30.00   30.00   30.00    1.17 103.00  26.87
 30.00  30.00   5.30 117.00  29.64    4.78
 30.00  30.00   0.20 101.00   5.30  30.00   30.00   30.00   30.00  13.90 101.00   30.00   30.00  30.00
 30.00   4.77 102.00   3.72  30.00  30.00
 30.00   1.05 117.00  29.64   5.86  30.00   30.00    0.19 101.00    5.33  30.00   30.00   30.00  30.00
 13.89 101.00  30.00  30.00  30.00  30.00
  4.54 102.00   3.61  30.00  27.54 120.00    0.19    3.70    3.84 104.00   30.00   30.00   30.00 103.00
 1.13  15.09   3.12   0.25
compressed: Str
122.00   1.76    0.67 105.00  30.00   30.00    1.47 104.00    1.75    0.68 125.00    3.64  21.47  30.00
  9.03 103.00  30.00  30.00  30.00  26.83
103.00   3.65   21.46  30.00   9.12 119.00    0.31    8.11 103.00    3.64   19.21   30.00   30.00 103.00
 30.00  30.00  30.00  30.00   0.28 102.00
  3.65  19.31  30.00  30.00 119.00    1.44   24.84    2.35 104.00   30.00   30.00   30.00 103.00  15.28
 30.00  30.00  30.00   1.40 103.00   7.38
 30.00   0.21 119.00   1.64   3.18 105.00   30.00   30.00 105.00   30.00   30.00
*/
```

```
        if ( strSkip == 0 && qrySkip == 0 )
        {
                while (spoints < npoints && qpoints < npoints && *str < 100.0 && *qry < 100.0 )
                {
                        dval = (*str - *qry) * autoScaleFactor;
                        dval *= dval;
                        sval += dval;

str++;
```

```
                    qry++;
                    qpoints++;
                    spoints++;
            }
    }
    else
    {
#if 0
            fprintf(stderr,"start: %d %d %d %d %d  %8.2lf strIdx:%d qryIdx:%d\n",
                    strSkip, qrySkip, spoints, qpoints, npoints, sval,
                    (int) (str - start_str), (int) (qry - start_qry) );
#endif
            if ( strSkip > qrySkip )
            {
                    if ( qrySkip > 0 )
                    {
                            qpoints += qrySkip;
                            spoints += qrySkip;
                            strSkip -= qrySkip;
                            qrySkip = 0;
                            qry++;
                    }
                    while (strSkip && qpoints < npoints && *qry < 100.0 )
                    {
                            dval = *qry * autoScaleFactor;
                            dval *= dval;
                            sval += dval;

strSkip--;
                            qpoints++;
                            spoints++;
                            qry++;
                    }
                    if ( strSkip == 0 )
                            str++;
            }
            else if ( qrySkip > strSkip )
            {
                    if ( strSkip > 0 )
                    {
                            qpoints += strSkip;
                            spoints += strSkip;
                            qrySkip -= strSkip;
                            strSkip = 0;
                            str++;
                    }
                    while ( qrySkip && spoints < npoints && *str < 100.0 )
                    {
```

```
                    dval = *str * autoScaleFactor;
                    dval *= dval;
                    sval += dval;

qrySkip--;
                    qpoints++;
                    spoints++;
                    str++;
                }
                if ( qrySkip == 0 )
                    qry++;
            }
            else
            {
                    /* they are the same, what luck */
                    qpoints += qrySkip;
                    spoints += strSkip;
                    qrySkip = 0;
                    strSkip = 0;
                    str++;
                    qry++;
            }
        }
    }
    /* Only one of the while loops can process */
    while ( qpoints < npoints )
    {
        if ( *qry < 100.0 )
        {
            dval = *qry * autoScaleFactor;
            dval *= dval;
            sval += dval;
            qpoints++;
        }
        else
        {
            qrySkip = (int) (*qry - 100.0);
            qpoints += qrySkip;
        }
        qry++;
    }
    while ( spoints < npoints )
    {
        if ( *str < 100.0 )
        {
            dval = *str * autoScaleFactor;
            dval *= dval;
            sval += dval;
```

```
                    spoints++;
            }
            else
            {
                    strSkip = (int) (*str - 100.0 );
                    spoints += strSkip;
            }
            str++;
    }
if 0
    if ( filtval > sval )
    {
            fprintf(stderr," filt higher than actual: %8.4lf actual: %8.4lf\n", filtval, sval );
    }
    if ( sval > q_bailout )
    {
            fprintf(stderr,"ACTUAL more than bailout: %8.3lf filtval: %8.3lf bail:%8.3lf \n", sval,
filtval, q_bailout );
    }
    if ( filtval > q_bailout )
            fprintf(stderr,"compressed field bailout %8.4lf actual:%8.4lf bailout: %8.4lf %s\n",
                    filtval, sval, q_bailout,
                    (sval > q_bailout ) ? "WORKED" : "FAILED" );
#endif
    return sval;
} static double topFieldDiff(double *qry, double *str, int npoints )
{
    double dval;
    double sval;
    int i;

if ( !qry || !str || !npoints )
            return 9999.0*9999.0;

for ( i = 0, sval = 0.0; i < npoints; i++ )
    {
            dval = *qry++ - *str++;
            dval *= dval;

sval += dval;
    }
    t_fcompare++;
    return sval;
}
```

```
static double fieldIntDiff( char *cptr, char *cqtr, int s1, int s2)
{
        static double Dist[16][16];
        static int InitDist;
        double xount;
        int i;

if ( s1 != s2 || !cptr || !cqtr )
                return 999999.0;

/* initialization on 1st call */
        if (!InitDist)
        {
                int j;
                double dval;
        double boundary[16];

boundary[0] = 9999.;
                boundary[1] = -0.1 ;
                for (i=2;i< 15;i++)
                        boundary[i] = 2*i-3;
                boundary[15] = 30.0;

for (i=0;i<16;i++)
                {
                        for (j=0;j<16;j++)
                        {
                                dval = boundary[i] - boundary[j];
                                Dist[i][j] = dval * dval;
                        }
                }
                InitDist = 1;
        }
        for (xount=0.0, i=0; i < s1 ; i++, cptr++, cqtr++ )
        {
                xount += Dist[*cptr][*cqtr];
        }
        t_fcompare++;
        return xount;
} if 0
static double 2nd_fieldIntDiff( unsigned short *cptr, unsigned short *cqtr, int s1, int s2)
{ define pow2(a) ( (a) * (a) )
        static double boundary[16];
```

```
              static double Dist[16][16];
              static double DnSq[16][16];
              static int InitDist;
              double xount;
              double dval;
    int i, j, nch, ptr, qtr;
    char  tempString[25];

if ( s1 != s2 || !cptr || !cqtr )
                       return 999999.0;

/* initialization on 1st call */
         if (!InitDist)
         {
                  boundary[0] = 9999.;
                  boundary[1] = -0.1 ;
                  for (i=2;i< 15;i++)
                           boundary[i] = 2*i-3;
                  boundary[15] = 30.0;

for (i=0;i<16;i++)
                  {
                           for (j=0;j<16;j++)
                           {
                                    dval = boundary[i] - boundary[j];
                                    DnSq[i][j] = (double) fabs( dval );
                                    Dist[i][j] = dval * dval;
                           }
                  }
                  InitDist = 1;
         }
         for (xount=0.0, i=0; i < s1 ; i++, cptr++, cqtr++ )
         {
                  ptr = (int) *cptr;
                  qtr = (int) *cqtr;
                  xount += Dist[ ptr & 0x0F    ][ qtr & 0x0F    ]
                           + Dist[ (ptr & 0xF0) >> 4][ (qtr & 0xF0) >> 4];
         }
         t_fcompare++;
         return xount;
} static double fieldIntDiffSq( unsigned short *cptr, unsigned short *cqtr, int s1, int s2)
{
         double rval;

if ( s1 != s2 || !cptr || !cqtr )
```

```c
                return 999999.0;
        rval = fieldIntDiff( cptr, cqtr, s1, s2 );
        if ( rval <= 0.0 )
                return 0.0;
        return sqrt( rval );
}
endif int TOP_GET_STATS(int dumpRegions, int *r_tfrags, int *r_2compare, int *r_3compare, int *r_fcompare, int *r_filtered, int *r_feat, double *r_outsidePerc )
{
        double perc;
        double tregions;
        int i;
        *r_tfrags = tot_uniq_frags;
        *r_2compare = t_2compare;
        *r_3compare = t_3compare;
        *r_fcompare = t_fcompare;
        *r_filtered = t_filtered;
        *r_feat = t_featFiltered;

if ( t_fields )
        {
                perc = ( (double) t_outside * 100.0 ) / (double) t_fields;
                *r_outsidePerc = perc;
        }
        else
                *r_outsidePerc = 0.0;

if ( dumpRegions )
        {
                for ( i = tregions = 0; i < max_regions; i++ )
                {
                        tregions += regionUseCnts[i];
                }
                if ( tregions )
                {
                        fprintf(stderr,"Region stats:\n");
                        for ( i = 0; i < max_regions; i++ )
                                fprintf(stderr," %5.2lf ", ( (double) regionUseCnts[i] * 100.0 ) / (double) tregions );
                        fprintf(stderr,"\n\n");
                }
        }
} static double computeAttachmentPenalty( Frag *qry, Frag *str, Frag *other_qry, Frag *other_str )
```

```
{
        double *qry_cords;
        double *str_cords;
        double dx, dy, dz;
        double pen;

if ( !qry->cords || !str->cords )
                return 0.0;
        pen = 0.0;

#if 0
        /*
                The query cords and structure cords copyBaseAtom point to the origin, so
                we don't need to compare them, we need to compare the other base atom, where
                it is now.
                Don't need to do this set, it's always zero, the is the atom which is at the origin.
        */
        qry_cords = qry->cords + (qry->copyBaseAtom*3);
        str_cords = str->cords + (str->copyBaseAtom*3);

dx = *qry_cords - *str_cords;
        dy = *(qry_cords+1) - *(str_cords+1);
        dz = *(qry_cords+2) - *(str_cords+2);

pen = (dx*dx + dy*dy + dz*dz) * q_attachPenFactor;
#ifdef DEBUG_DETAIL
        if ( q_debugfp )
                fprintf(q_debugfp, "# attach qry: %d str:%d %6.2lf %6.2lf %6.2lf %8.3lf (atoms:%d %d) (bases:%d %d %d %d)\n",
                        qry->id+1, str->id+1, dx, dy, dz, pen,
                        qry->ct->atomCount, str->ct->atomCount,
                        qry->copyBaseAtom,    str->copyBaseAtom,    other_qry->copyBaseAtom, other_str->copyBaseAtom );
#endif
endif qry_cords = qry->cords + (other_qry->copyBaseAtom*3);
        str_cords = str->cords + (other_str->copyBaseAtom*3);

dx = *qry_cords - *str_cords;
        dy = *(qry_cords+1) - *(str_cords+1);
        dz = *(qry_cords+2) - *(str_cords+2);

pen += (dx*dx + dy*dy + dz*dz) * q_attachPenFactor;
        return pen;
}
```

```c
static int double_compare(const void *vnrec, const void *vtrec )
{
        double *n = (double *) vnrec;
        double *t = (double *) vtrec;

return (int) *n - *t;
} static void PartialMatchFeatures(Split *qs, int mode, Frag *q1, Frag *q2, Frag *q3, Frag *q4, Split *str,
Frag *f1, Frag *f2, Frag *f3, Frag *f4, int matchCnt )
{
        double *aa, *da;
        double *either;
        int *both;
        double splitDiff;
        int i, cnt;
        int atomCount;
        int fcnt1, fcnt2, fcnt3, fcnt4;
        int noFrags;
        static Split *last_split;

if ( !qs || !qs->ct || !q1 || !q2 || !str || !f1 || !f2 || matchCnt == 0 || !qs->featureMask)
                return;
        if ( last_split != qs )
                qs->connectedHBCnt = (int *) 0;
        last_split = qs;

atomCount = qs->ct->atomCount;
        aa = (double *) calloc(sizeof(double), atomCount );
        da = (double *) calloc(sizeof(double), atomCount );
        either = (double *) calloc(sizeof(double),atomCount );
        both = (int *) calloc(sizeof(int),atomCount );

for ( i = 0; i < atomCount; i++ )
        {
                either[i] = da[i] = aa[i] = -1.0;
        } if ( mode == 2 )
        {
                q1->featureDiff = q1->feature2PDiff;
                q2->featureDiff = q2->feature2PDiff;
                if ( q3 )
                        q3->featureDiff = q3->feature2PDiff;
                if ( q4 )
                        q4->featureDiff = q3->feature2PDiff;
```

```
}
else if ( mode == 3 )
{
        q1->featureDiff = q1->feature3PDiff;
        q2->featureDiff = q2->feature3PDiff;
        if ( q3 )
                q3->featureDiff = q3->feature3PDiff;
        if ( q4 )
                q4->featureDiff = q4->feature3PDiff;
}
else
{
        q1->featureDiff = q1->featureSubsetDiff;
        q2->featureDiff = q2->featureSubsetDiff;
        if ( q3 )
                q3->featureDiff = q3->featureSubsetDiff;
        if ( q4 )
                q4->featureDiff = q4->featureSubsetDiff;
} fcnt1 = fcnt2 = fcnt3 = fcnt4 = 0;
q1->featureDiff[f1->id] = MeasureClosest(qs, q1, str, f1, da, aa, &fcnt1 );
q2->featureDiff[f2->id] = MeasureClosest(qs, q2, str, f2, da, aa, &fcnt2 );
if ( q3 && f3 )
        q3->featureDiff[f3->id] = MeasureClosest(qs, q3, str, f3, da, aa, &fcnt3 );
if ( q4 && f4 )
        q4->featureDiff[f4->id] = MeasureClosest(qs, q4, str, f4, da, aa, &fcnt4 );

noFrags = 0;
if ( fcnt1 )
        noFrags++;
if ( fcnt2 )
        noFrags++;
if ( fcnt3 )
        noFrags++;
if ( fcnt4 )
        noFrags++;

for ( i = cnt = 0; i < atomCount; i++ )
{
        if ( da[i] != -1.0 && ( either[i] == -1.0 || da[i] < either[i] ) )
                either[i] = da[i], cnt++;
        if ( aa[i] != -1.0 && ( either[i] == -1.0 || aa[i] < either[i] ) )
                either[i] = aa[i], cnt++;
        if ( da[i] != -1.0 && aa[i] != -1.0 )
                both[i] = 1;
}
```

```c
#if 0
        fprintf(stderr,"%d %d %d %d   frags:%d  frag_cnt:%d\n", fcnt1, fcnt2, fcnt3, fcnt4, noFrags, cnt );
#endif
        CoverConnectedHB(qs, qs->ct, either );

for ( i = cnt = 0, splitDiff = 0.0; i < atomCount; i++ )
        {
                if ( either[i] != -1.0 )
                {
                        if ( both[i] == 0 )
                                aa[cnt] = either[i];
                        else
                                aa[cnt] = ( aa[i] + da[i] ) / 2.0;
                        splitDiff += aa[cnt];
                        cnt++;
                }
        } if ( cnt > matchCnt )
                qsort( (void *) aa, (size_t) cnt , (size_t) sizeof(double),
                        double_compare );

for ( i = 0, splitDiff = 0.0; i < matchCnt && i < cnt; i++ )
                splitDiff += aa[i];

#if 0
        for ( i = 0; i < cnt; i++ )
                fprintf(stderr,"%8.2lf ", aa[i] );
        if ( cnt )
                fprintf(stderr,"\n");
endif splitDiff *= q_featureFactor;
        if ( cnt == 1 )
                splitDiff *= 2.0; /* If there is only one donor or acceptor, increase the weighting
automatically. Always a good thing. */
        if ( noFrags > 1 )
        {
                splitDiff /= (double) noFrags;
        } q1->featureDiff[f1->id] = q2->featureDiff[f2->id] = 0.0;
        if ( q3 )
                q3->featureDiff[f3->id] = 0.0;
        if ( q4 )
                q4->featureDiff[f4->id] = 0.0;
```

```
            if ( fcnt1 )
                    q1->featureDiff[f1->id] += splitDiff;
            if ( fcnt2 )
                    q2->featureDiff[f2->id] += splitDiff;
            if ( fcnt3 )
                    q3->featureDiff[f3->id] += splitDiff;
            if ( fcnt4 )
                    q4->featureDiff[f4->id] += splitDiff;

free((char *) aa);
            free((char *) da);
            free((char *) either);
            free((char *) both );
            return;
} static void CoverConnectedHB(Split *qs, struct CtConnectionTable *ct, double *HB )
{
            CtAtom *A;
            CtAtomBondData *bond;
            int queryMask;
            int aHB;
            int i, j, k, idx, cnt, coverCnt;
            int *Worse;

aHB = FeatureHBA | FeatureHBD;
            if ( !qs->connectedHBCnt )
            {
                    qs->connectedHBCnt = (int *) calloc(sizeof(int), ct->atomCount );
                    qs->connectedHBAtoms = (int *) calloc(sizeof(int), ct->atomCount * 5 );
                    qs->connectedHBTotalCnt = 0;

for ( i = 0, A = ct->atoms; i < ct->atomCount; i++, A++ )
                    {
                            queryMask = qs->featureMask [ i ];
                            if ( queryMask & aHB )
                            {
                                    for ( cnt = j = 0, bond = A->bond; j < A->bondCount && j < 5;
j++, bond++ )
                                    {
                                            queryMask = qs->featureMask [ bond->toAtom ];
                                            if ( queryMask & aHB )
                                            {
                                                    idx = i*5 + cnt;
                                                    qs->connectedHBCnt[i] += 1;
                                                    qs->connectedHBAtoms[idx] = bond->toAtom;
                                                    qs->connectedHBTotalCnt++;
```

```
                                    cnt++;
                                }
                            }
                        }
                    }
            }
            if ( qs->connectedHBTotalCnt == 0 )
                    return;
            Worse = (int *) calloc(sizeof(int), ct->atomCount );

for ( j = 1; j < 5; j++ )
            {
                    for ( i = 0; i < ct->atomCount; i++ )
                    {
                            if ( qs->connectedHBCnt[i] != j )
                                    continue;
                            for ( k = 0; k < qs->connectedHBCnt[i]; k++ )
                            {
                                    idx = i*5 + k;
                                    if ( HB[i] > HB[ qs->connectedHBAtoms[idx] ] )
                                    {
                                            Worse[i] = 1;
                                    }
                            }
                    }
            }
            for ( i = 0; i < ct->atomCount; i++ )
            {
                    if ( Worse[i] )
                            HB[i] = -1.0;
            }
            free((char *) Worse);
            return;
} static double MeasureClosest(Split *qs, Frag *q1, Split *str, Frag *f1, double *da, double *aa, int *r_fcnt )
{
        int *qmask;
        int *smask;
        int i,j,k;
        double best = 99999.0;
        int found = -1;
        double worst;
        int qid, sid;
        int *qMap, *strMap;
        FeatureType qfeature, strFeature;
        double x,y,z;
```

```
        double distsq;
        double otherDiff = 0.0;
        double *qryCords, *strCords;
        double attFact;
        double fieldDiff = 0.0;
        double extraDiff = 0.0;
        double featDiff;
        int centAtoms[6];
        int cidx;
        AromSet *qset, *strSet;
        int *covered;
        static int featureCnt[4];
        static int *extraFeatureCnt[4];
        int queryHB;
        int strHB;
        int origIdx;

*r_fcnt = 0;

featureCnt[0] = featureCnt[1] = featureCnt[2] = featureCnt[3] = 0;
        extraFeatureCnt[0] = extraFeatureCnt[1] = extraFeatureCnt[2] = extraFeatureCnt[3] = 0;
        qmask = qs->featureMask;
        smask = str->featureMask;
        qMap = q1->origMapping;
        strMap = f1->origMapping;
        if ( !q1->cords || !f1->cords )
        {
                return otherDiff;
        }
        covered = (int *) calloc(f1->atomCnt,sizeof(int) );

#ifdef DEBUG_DETAIL
        if ( q_debugfp )
        {
                fprintf(q_debugfp, "\n# Feature comparison  Query Id: %d  Structure Id: %d\n",
                        q1->id + 1, f1->id + 1 );
        }
endif /* do the single atom features first */
        for ( i = 0; i < q1->atomCnt ; i++ )
        {
                if ( qmask[ qMap[i] ] == FeatureNone )
                        continue;              /* no single atom feature at this atom */
                origIdx = qMap[i];

qfeature = qmask[qMap[i]];
```

```
                for ( k = 0; k < 4; k++ )
                {
                        if ( !( qfeature & fMasks[k] ) )
                                continue;
                        best = 999999.0;
                        found = -1;
                        worst = (double) featureWeights[k+1] * featureWeights[k+1];
                        for ( j = 0; j < f1->atomCnt; j++ )
                        {
                                if ( !( smask[ strMap[j] ] & fMasks[k] ) )
                                        continue;
                                strFeature = smask[ strMap[j] ];
#if 0
                                                                                        /* don't count attachment features in core mode */
                                if ( q_coremode && ( strMap[j] == f1->copyBaseAtom || strMap[j] == str2ndAttach ) )
                                        continue;
endif
                                qryCords = q1->cords + (i*3);
                                strCords = f1->cords + (j*3);
                                x = *qryCords - *strCords;
                                y = *(qryCords+1) - *(strCords+1);
                                z = *(qryCords+2) - *(strCords+2);
                                distsq = x*x + y*y + z*z;
                                if ( distsq < best )
                                {
                                        best = distsq;
                                        found = j;
                                }
#ifdef DEBUG_DETAIL
                                if ( q_debugfp )
                                        fprintf(q_debugfp, "# feature compare: %d %d  type:%d  distance:%7.4lf best:%7.4lf from:%d.%d\n",
                                                i+1, j+1, k+1, sqrt(distsq), best, q1->id+1, f1->id+1 );
#endif
                        }
                        if ( found != -1 )
                                covered[found] |= fMasks[k];

attFact = 1.0;
                        if ( best > 0.25 )              /* More than 0.5, this causes a penalty, best is a squared */
                        {
                                if ( q1->AtWts )
                                {
                                        if ( f1->AtWts && found != -1 )
```

```
                                attFact = ( q1->AtWts[i] + f1->AtWts[found] ) / 2.0;
                        else
                                attFact = q1->AtWts[i];
                }
                else if ( f1->AtWts && found != -1 )
                        attFact = f1->AtWts[found];

if ( best > 3.0625 )  /* worst case distance is greater than 1.75 perfect
mismatch (see GOLD/GASP papers) */
                {
                        featDiff = worst * attFact;
                        fieldDiff += featDiff;

}
                else
                {
                        featDiff = worst * attFact * (( best - 0.25 ) / 2.8125 );
                        fieldDiff += featDiff;
                }
        }
        else
        {
                featDiff = 0.0;
        }
        if ( qfeature & FeatureHBA )
        {
#if 0
                fprintf(stderr,"HBA %d %d, origIdx: %8.2lf   featDiff:%8.2lf\n",
                                i, origIdx, aa[origIdx], featDiff );
#endif
                if ( aa[origIdx] == -1.0 || aa[origIdx] > featDiff )
                {
                        aa[origIdx] = featDiff;
                        *r_fcnt += 1;
                }
        }
        if ( qfeature & FeatureHBD )
        {
#if 0
                fprintf(stderr,"HBD %d %d, origIdx: %8.2lf   featDiff:%8.2lf\n",
                                i, origIdx, da[origIdx], featDiff );
#endif
                if ( da[origIdx] == -1.0 || da[origIdx] > featDiff )
                {
                        da[origIdx] = featDiff;
                        *r_fcnt += 1;
                }
        }
```

```
                if ( qfeature & FeaturePos || qfeature & FeatureNeg )
                    otherDiff += featDiff;

#ifdef DEBUG_DETAIL
                if ( q_debugfp )
                {
                    fprintf(q_debugfp,
                        "# feature  q:%d  s:%d   ftype:%d  best: %7.4lf   a:%5.3lf  worst:%11.2lf  FieldDiff:%9.3lf\n",
                        i+1, found,  qmask[ qMap[i] ], best,  attFact, sqrt(worst), fieldDiff );
                }
endif
            }
        }

/* Now for the extra feature penalty, count all non-covered features */
        for ( j = 0; j < f1->atomCnt; j++ )
        {
            if ( smask[ strMap[j] ] != FeatureNone )
            {
#if 0
                if ( q_coremode && ( strMap[j] == str->copyBaseAtom || strMap[j] == str2ndAttach ) )
                    continue;
endif
                strFeature = smask[ strMap[j] ];
                for ( k = 0; k < 4; k++ )
                {
                    if ( !( strFeature & fMasks[k] ) )
                        continue;
                    if ( !( covered[j] & fMasks[k] ) )
                    {
                        worst = featureWeights[k+1] * ( (f1->AtWts) ? f1->AtWts[j] : 1.0);
                        featDiff = (worst * worst * q_extraFeatureFactor );
                        otherDiff += featDiff;
                        extraFeatureCnt[k] += 1;
#ifdef DEBUG_DETAIL
                        if ( q_debugfp )
                            fprintf(q_debugfp, "# missing feature %d,%d %d  worst:%11.2lf  FieldDiff: %9.3lf\n",
                                f1->id+1, j+1,
                                smask[ strMap[j] ], worst, fieldDiff );
#endif
                    }
                }
            }
        }
```

```
}
free((char *) covered );

/* end of single atom, now do the aromatic rings */

/* Find the 5 and 6 membered aromatic rings in the fragments, setup centroids for quick
comparisons */ if ( q1->aromCnt == -1 )
        {
                attFact = 1.0;
                q1->aromCnt = 0;
                for ( i = 0, qset = qs->aromSets; i < qs->numArom; i++, qset++ )
                {
                        for ( k = cidx = 0; cidx < 6 && k < q1->atomCnt; k++ )
                        {
                                if ( qset->atoms[ qMap[k] ] )
                                {
                                        if ( q1->AtWts )
                                                attFact = q1->AtWts[k];
                                        else
                                                attFact = 1.0;
                                        centAtoms[cidx] = k;
                                        cidx++;
                                }
                        }
                        if ( qset->numAtoms && qset->numAtoms == cidx )
                        {
                                if ( !computeCentroid(q1->cords, centAtoms, cidx, &x, &y, &z ) )
                                        addCentroid(q1, cidx, attFact, x, y, z );
                        }
                }
        }
        if ( f1->aromCnt == -1 )
        {
                f1->aromCnt = 0;
                attFact = 1.0;
                for ( i = 0, strSet = str->aromSets; i < str->numArom; i++, strSet++ )
                {
                        for ( k = cidx = 0; cidx < 6 && k < f1->atomCnt; k++ )
                        {
                                if ( strSet->atoms[ strMap[k] ] )
                                {
                                        if ( f1->AtWts )
                                                attFact = f1->AtWts[k];
                                        centAtoms[cidx] = k;
                                        cidx++;
```

```
                }
            }
            if ( strSet->numAtoms == cidx )
            {
                if ( !computeCentroid(f1->cords, centAtoms, cidx, &x, &y, &z ) )
                    addCentroid(f1, cidx, attFact, x, y, z );
            }
        }
    }

/* compare the query aromatic rings verses the structure's aromatic rings */
    for ( i = 0; i < q1->aromCnt; i++ )
    {
        best = 99999.0;
        found = 0;
        qryCords = q1->cent + (i*4);
        attFact = 1.0;
        worst = 20.0 * 20.0;
        for ( j = 0; j < f1->aromCnt; j++ )
        {
            strCords = f1->cent + (j*4);
            x = *qryCords - *strCords;
            y = *(qryCords+1) - *(strCords+1);
            z = *(qryCords+2) - *(strCords+2);
            distsq = x*x + y*y + z*z;
            if ( distsq < best )
            {
                found = j+1;
                best = distsq;
                attFact = *(qryCords+3) * *(strCords+3);
            }
#ifdef DEBUG_DETAIL
            if ( q_debugfp )
                fprintf(q_debugfp, "# arom centroid  dist: %8.3lf   from: %d.%d \n",
                    sqrt(distsq), q1->id+1, f1->id+1 );
#endif
        }
        if ( best > 0.25 )
        {
            if ( best > 3.0625 ) /* worst case distance is greater than 1.75 perfect mismatch
(see GOLD/GASP papers) */
                featDiff = worst * attFact;
            else
                featDiff = worst * attFact * (( best - 0.25 ) / 2.8125 );
            otherDiff += featDiff;
        }
#ifdef DEBUG_DETAIL
        if ( q_debugfp )
```

```
                            fprintf(q_debugfp ,"# arom centroid  q:%d,%d s:%d best:%8.3lf fieldDiff:
%8.4lf \n",
                                q1->id+1, i, f1->id+1,
                                best, fieldDiff );
#endif
        } worst = featureWeights[0];
        worst *= worst;
        /* add in penalty for extra aromatic rings in the structure not in the query */
        if ( f1->aromCnt > q1->aromCnt )
                otherDiff += worst * 0.1 * (double) (f1->aromCnt - q1->aromCnt) ;

#ifdef DEBUG_DETAIL
        if ( q_debugfp )
        {
                fprintf(q_debugfp, "# arom Counts: query : %d   structure : %d  %s\n",
                        q1->aromCnt, f1->aromCnt,
                        (q1->aromCnt && q1->aromCnt == 0 ) ? "Missing some rings" : "" );
        }
endif return otherDiff * q_featureFactor;
} static double compareFeatures(Split *qs, Frag *qry, Split *ss, Frag *str, int qry2ndAttach, int str2ndAttach )
{
        int *qmask;
        int *smask;
        int i,j,k;
        double best = 99999.0;
        int found = -1;
        double worst;
        int qid, sid;
        int *qMap, *strMap;
        FeatureType qfeature, strFeature;
        double x,y,z;
        double distsq;
        double *qryCords, *strCords;
        double attFact;
        double fieldDiff = 0.0;
        double extraDiff = 0.0;
        int centAtoms[6];
        int cidx;
        AromSet *qset, *strSet;
        int *covered;
        static double featureContributions[4][MAX_FEATURES]; /* maximum of 200 features per type
``` should be more than enough, for the above 4 features */
```
        static int featureCnt[4];
        static int extraFeatureCnt[4];
        int fidx;

featureCnt[0] = featureCnt[1] = featureCnt[2] = featureCnt[3] = 0;
        extraFeatureCnt[0] = extraFeatureCnt[1] = extraFeatureCnt[2] = extraFeatureCnt[3] = 0;
        qmask = qs->featureMask;
        smask = ss->featureMask;
        qMap = qry->origMapping;
        strMap = str->origMapping;
        if ( !qry->cords || !str->cords )
        {
                fprintf(stderr,"no coords: %d %d\n", qry->cords, str->cords);
                return 9999.0 * 9999.0;
        }
        covered = (int *) calloc(str->atomCnt,sizeof(int) );

#ifdef DEBUG_DETAIL
        if ( q_debugfp )
        {
                fprintf(q_debugfp, "\n# Feature comparison  Query Id: %d  Structure Id: %d\n",
                        qry->id + 1, str->id + 1 );
        }
endif /* do the single atom features first */
        for ( i = 0; i < qry->atomCnt ; i++ )
        {
                if ( qmask[ qMap[i] ] == FeatureNone )
                        continue;            /* no single atom feature at this atom */ qfeature = qmask[qMap[i]];
                for ( k = 0; k < 4; k++ )
                {
                        if ( !( qfeature & fMasks[k] ) )
                                continue;
                        fidx = featureCnt[k];
                        best = 999999.0;
                        found = -1;
                        worst = (double) featureWeights[k+1] * featureWeights[k+1];
                        for ( j = 0; j < str->atomCnt; j++          )
                        {
                                if ( !( smask[ strMap[j] ] & fMasks[k] ) )
                                        continue;
```

```
                                                                    /* don't
count attachment features in core mode */
                if ( q_coremode && ( strMap[j] == str->copyBaseAtom || strMap[j]
== str2ndAttach ) )
                        continue;
                qryCords = qry->cords + (i*3);
                strCords = str->cords + (j*3);
                x = *qryCords - *strCords;
                y = *(qryCords+1) - *(strCords+1);
                z = *(qryCords+2) - *(strCords+2);
                distsq = x*x + y*y + z*z;
                if ( distsq < best )
                {
                        best = distsq;
                        found = j;
                }
#ifdef DEBUG_DETAIL
                if ( q_debugfp )
                        fprintf(q_debugfp, "# feature compare: %d %d   type:%d
distance:%7.4lf best:%7.4lf from:%d.%d\n",
                                        i+1, j+1, k+1, sqrt(distsq), best, qry->id+1,
str->id+1 );
#endif
        }
        if ( found != -1 )
                covered[found] |= fMasks[k];

attFact = 1.0;
        if ( best > 0.25 )              /* More than 0.5, this causes a penalty, best is
a squared */
        {
                if ( qry->AtWts )
                {
                        if ( str->AtWts && found != -1 )
                                attFact = ( qry->AtWts[i] + str->AtWts[found] ) / 2.0;
                        else
                                attFact = qry->AtWts[i];
                }
                else if ( str->AtWts && found != -1 )
                        attFact = str->AtWts[found];

if ( best > 3.0625 )  /* worst case distance is greater than 1.75 perfect
mismatch (see GOLD/GASP papers) */
                {
                        fieldDiff += worst * attFact;
                        featureContributions[k][fidx] = worst * attFact;
                }
                else
```

```
                    {
                            fieldDiff += worst * attFact * (( best - 0.25 ) / 2.8125 );
                            featureContributions[k][fidx] = worst * attFact * ((best - 0.25 )
/ 2.8125);
                    }
            }
            else
            {
                    featureContributions[k][fidx] = 0.0;
            }
            if ( featureCnt[k] < (MAX_FEATURES - 1) )
                    featureCnt[k] += 1; /* just to avoid core dumps, don't increment if full
*/
#ifdef DEBUG_DETAIL
            if ( q_debugfp )
            {
                    fprintf(q_debugfp,
                            "# feature q:%d s:%d    ftype:%d best: %7.4lf    a:%5.3lf
worst:%11.2lf  FieldDiff:%9.3lf\n",
                            i+1, found,  qmask[ qMap[i] ], best,    attFact, sqrt(worst),
fieldDiff );
            }
endif
        }
    }

/* Now for the extra feature penalty, count all non-covered features */
        for ( j = 0; j < str->atomCnt; j++ )
        {
                if ( smask[ strMap[j] ] != FeatureNone )
                {
                        if ( q_coremode && ( strMap[j] == str->copyBaseAtom || strMap[j] ==
str2ndAttach ) )
                                continue;
                        strFeature = smask[ strMap[j] ];
                        for ( k = 0; k < 4; k++ )
                        {
                                if ( !( strFeature & fMasks[k] ) )
                                        continue;
                                if ( !( covered[j] & fMasks[k] ) )
                                {
                                        worst = featureWeights[k+1] * ( (str-> AtWts) ? str->AtWts[j]
: 1.0);

fieldDiff += (worst * worst * q_extraFeatureFactor );
                                        extraDiff += (worst * worst * q_extraFeatureFactor );
                                        extraFeatureCnt[k] += 1;
#ifdef DEBUG_DETAIL
                                        if ( q_debugfp )
```

```
                                               fprintf(q_debugfp, "# missing feature %d,%d %d
worst:%11.2lf FieldDiff: %9.3lf\n",
                                                   str->id+1, j+1,
                                                   smask[ strMap[j] ], worst, fieldDiff );
#endif
                                    }
                                }
                            }
    }
    free((char *) covered );

/* Almost the end of the single atom features.  If autoscaling is on for features, let's ignore the
featureDiff calculated so far
            auto scaling for features is NOT based upon hev atom count.  It's based upon the number of
features by type.
    */
    if ( q_partialMatch )
    {
            fieldDiff = featureScaling(featureCnt, extraFeatureCnt, (double *) featureContributions,
q_partialMatch );
            fieldDiff += extraDiff;
    }

/* end of single atom, now do the aromatic rings */

/* Find the 5 and 6 membered aromatic rings in the fragments, setup centroids for quick
comparisons */ if ( qry->aromCnt == -1 )
    {
            attFact = 1.0;
            qry->aromCnt = 0;
            for ( i = 0, qset = qs->aromSets; i < qs->numArom; i++, qset++ )
            {
                    for ( k = cidx = 0; cidx < 6 && k < qry->atomCnt; k++ )
                    {
                            if ( qset->atoms[ qMap[k] ] )
                            {
                                    if ( qry->AtWts )
                                            attFact = qry->AtWts[k];
                                    else
                                            attFact = 1.0;
                                    centAtoms[cidx] = k;
                                    cidx++;
                            }
                    }
                    if ( qset->numAtoms && qset->numAtoms == cidx )
```

```
                {
                        if ( !computeCentroid(qry->cords, centAtoms, cidx, &x, &y, &z ) )
                                addCentroid(qry, cidx, attFact, x, y, z );
                }
        }
}
if ( str->aromCnt == -1 )
{
        str->aromCnt = 0;
        attFact = 1.0;
        for ( i = 0, strSet = ss->aromSets; i < ss->numArom; i++, strSet++ )
        {
                for ( k = cidx = 0; cidx < 6 && k < str->atomCnt; k++ )
                {
                        if ( strSet->atoms[ strMap[k] ] )
                        {
                                if ( str->AtWts )
                                        attFact = str->AtWts[k];
                                centAtoms[cidx] = k;
                                cidx++;
                        }
                }
                if ( strSet->numAtoms == cidx )
                {
                        if ( !computeCentroid(str->cords, centAtoms, cidx, &x, &y, &z ) )
                                addCentroid(str, cidx, attFact, x, y, z );
                }
        }
}

/* compare the query aromatic rings verses the structure's aromatic rings */
for ( i = 0; i < qry->aromCnt; i++ )
{
        best = 99999.0;
        found = 0;
        qryCords = qry->cent + (i*4);
        attFact = 1.0;
        worst = 20.0 * 20.0;
        for ( j = 0; j < str->aromCnt; j++ )
        {
                strCords = str->cent + (j*4);
                x = *qryCords - *strCords;
                y = *(qryCords+1) - *(strCords+1);
                z = *(qryCords+2) - *(strCords+2);
                distsq = x*x + y*y + z*z;
                if ( distsq < best )
                {
                        found = j+1;
```

```
                best = distsq;
                attFact = *(qryCords+3) * *(strCords+3);
            }
#ifdef DEBUG_DETAIL
            if ( q_debugfp )
                fprintf(q_debugfp, "# arom centroid dist: %8.3lf from: %d.%d \n",
                    sqrt(distsq), qry->id+1, str->id+1 );
#endif
        }
        if ( best > 0.25 )
        {
            if ( best > 3.0625 ) /* worst case distance is greater than 1.75 perfect mismatch
(see GOLD/GASP papers) */
                fieldDiff += worst * attFact;
            else
                fieldDiff += worst * attFact * (( best - 0.25 ) / 2.8125 );
        }
#ifdef DEBUG_DETAIL
            if ( q_debugfp )
                fprintf(q_debugfp ,"# arom centroid  q:%d,%d s:%d best:%8.3lf fieldDiff:
%8.4lf \n",
                    qry->id+1, i, str->id+1,
                    best, fieldDiff );
#endif
    } worst = 20.0 * 20.0;
    /* add in penalty for extra aromatic rings in the structure not in the query */
    if ( str->aromCnt > qry->aromCnt )
        fieldDiff += worst * 0.1 * (double) (str->aromCnt - qry->aromCnt) ;

#ifdef DEBUG_DETAIL
        if ( q_debugfp )
        {
            fprintf(q_debugfp, "# arom Counts: query : %d   structure : %d  %s\n",
                qry->aromCnt, str->aromCnt,
                (str->aromCnt && qry->aromCnt == 0 ) ? "Missing some rings" : "" );
        }
endif return fieldDiff * q_featureFactor;
}

/*
    The data is in FeaturePos, FeatureNeg, FeatureHBA and FeatureHBD order
*/
static double featureScaling(int *featureCnts, int *extraFeatureCnts, double *featureContributions, int nbest )
```

```c
{
    static double *thebest;
    static int maxBest;
    double lowest, clowest;
    int cnt, lowidx;
    double dval;
    double fieldDiff = 0.0;
    double featDiff;
    double fieldIgnored = 0.0;
    double fieldFact;
    int k, idx, j, fidx;

if ( !thebest || nbest > maxBest )
    {
        if ( thebest )
            free((char *) thebest );
        thebest = (double *) malloc(sizeof(double) * nbest );
        maxBest = nbest;
    } featDiff = 0.0;
    for ( k = 0; k < 4; k++ )
    {
        if ( featureCnts[k] == 0 )
            continue;
        /* Find the N lowest contributing features by type.
           Think of this as partial match feature matching, like Unity's flexible searching.
        */
        for ( featDiff = 0.0, lowidx = -1, lowest = 999999999.0, cnt = idx = 0; idx < featureCnts[k]; idx++ )
        {
            fidx = (k * MAX_FEATURES) + idx;
            dval = featureContributions[fidx];
            featDiff += dval;
            if ( dval < lowest || cnt < nbest)
            {
                if ( cnt < nbest )
                {
                    if ( dval < lowest )
                    {
                        lowest = dval;
                        lowidx = cnt;
                    }
                    thebest[cnt] = dval;
                    cnt++;
                }
                else
```

```
                    {
                            thebest[lowidx] = dval;
                            lowest = dval;
                            for ( j = 0; j < nbest; j++ )
                            {
                                    if ( thebest[j] < lowest )
                                    {
                                            lowest = thebest[j];
                                            lowidx = j;
                                    }
                            }
                    }
            }
    }
    if ( cnt > 0 )
    {
            if ( k > 1 )                    /* we are looking at donors and acceptors */
            {
                    fieldFact = 2.0 / (double) cnt;  /* Mainly to increase the importance
when only one donor or acceptor exists */
                    if ( fieldFact < 0.9 )
                            fieldFact = 0.9;
                    for ( j = 0; j < cnt; j++ )
                    {
                            fieldDiff += thebest[j] * fieldFact;
                            featDiff -= thebest[j];
                    }
if 0
                    fieldFact = (1.0 / ( (double) (cnt+2) * (double) (cnt+1) ) );
#else
                    fieldFact = 0.0;
#endif
                    if ( cnt > 2 )
                            fieldFact *= 0.5;
                    fieldDiff += fieldFact * featDiff;
#if 0
                    fprintf(stderr,"field: %8.2lf best: %8.2lf remain:%8.2lf \n", fieldDiff,
thebest[0], featDiff );
#endif
            }
            else
            {
                    fieldDiff += featDiff;
            }
if 0
            if ( featureCnts[k] > 2 )
            {
```

```
                    /* so now what do we do about the 5th - Nth fields.
                       Should they or shouldn't they contribute */
                    for ( fieldIgnored = 0.0, j = cnt; j < featureCnts[k]; j++ )
                    {
                            fidx = ( k * MAX_FEATURES ) + j;
                            fieldIgnored += featureContributions[fidx];
                    }
                    fprintf(stderr,"Field ignored total: %8.2lf  sqrt is: %8.2lf\n",
                            fieldIgnored, sqrt(fieldIgnored) );
                    fprintf(stderr,"type: %d cnt: %d ", k, featureCnts[k] );
                    for ( j = 0; j < featureCnts[k]; j++ )
                    {
                            fidx = ( k * MAX_FEATURES ) + j;
                            fprintf(stderr,"%7.2lf ", featureContributions[fidx] );
                    }
                    fprintf(stderr,"\nBest %d: ", cnt);
                    for ( j = 0; j < cnt; j++ )
                            fprintf(stderr,"%7.2lf ", thebest[j] );
                    fprintf(stderr,"\n");
            }
endif
        }
    }
    return fieldDiff;
} static int SearchForFeatures(Split *S)
{
        int aromHit, featureHit;
        int numFeatures;
        FeaturePattern *fptr;
        int oxygen, nitrogen, sulfur;
        int ring_oxygen, ring_nitrogen, ring_sulfur;
        int nonSingleRingBond;
        CtAtom *atom;
        CtBond *bond;
        int i,j, k;
        int bcnt;
        int strInit;
        CtBondTypeDef bondType;
        CtSimpleBondTypeDef simpleTypes;
        struct Srch2Hits *hits;
        int nhits, hitidx;
        int atomId;
        int *atoms;
        int nonSingleRingBonds;
        AromSet *aset;
        int alreadyFound;
```

```
char *regid;

if ( !S || !S->ct )
        return -1;

aromHit = featureHit = 0;
oxygen = nitrogen = sulfur = nonSingleRingBond = 0;
ring_oxygen = ring_nitrogen = ring_sulfur = 0;
regid = (char *) 0;
DB_CT_GET_CT_ATTR(S->ct, CtCtRegId, ®id );

fptr = InitFeaturePatterns(&numFeatures); /* it won't re-initialize */

DB_CT_UTL_FIND_RINGS(S->ct);

for ( i = 0, atom = S->ct->atoms; i < S->ct->atomCount; i++, atom++ )
{
        if ( atom->class != CtAtomElement )
                continue;
        if ( atom->id.atomicNumber == OXYGEN )
        {
                oxygen++;
                if ( AB_IN_RING(atom) )
                        ring_oxygen++;
        }
        else if ( atom->id.atomicNumber == NITROGEN )
        {
                nitrogen++;
                if ( AB_IN_RING(atom) )
                        ring_nitrogen++;
        }
        else if ( atom->id.atomicNumber == SULFUR )
        {
                sulfur++;
                if ( AB_IN_RING(atom) )
                        ring_sulfur++;
        }
}
for ( i = nonSingleRingBonds = 0, bond = S->ct->bonds;
        i < S->ct->bondCount && nonSingleRingBonds == 0;
        i++, bond++ )
{
        if ( AB_IN_RING(bond) )
        {
                if ( bond->simpleBondType == CtSimpleBondTypeNotSimple )
                {
                        bondType = DB_CT_GET_BOND_TYPE(S->ct, STD_ID(i), &bcnt,
```

&simpleTypes );

```
                      if ( bondType != CtBondTypeSingle )
                              nonSingleRingBonds++;
              }
              else if ( bond->simpleBondType != CtSimpleBondTypeSingle )
                      nonSingleRingBonds++;
       }
}

S->numArom = 0;
S->aromSets = (AromSet *) 0;
S->featureMask = (int *) calloc(sizeof(int), S->atomCount);
if ( nonSingleRingBonds )
       S->aromMask = (int *) calloc(sizeof(int), S->atomCount );

for ( i = strInit = 0; i < numFeatures; i++, fptr++ )
{
       if ( fptr->weight == 0 )
              continue;              /* think of it as commented out */
       if ( fptr->f_type == FeatureArom && nonSingleRingBonds == 0 )
              continue;   /* Can't hit the feature aromatic, no non-single ring bonds */ if ( q_useFeatureCharges == 0 && ( fptr->f_type == FeaturePos || fptr->f_type
== FeatureNeg ) )
              continue;
       if ( fptr->atomicId > 0 )
       {
              if ( fptr->atomicId == OXYGEN && ( oxygen == 0 || fptr->ringIndicator
== 1 && ring_oxygen == 0 ) )
                      continue;
              if ( fptr->atomicId == NITROGEN && ( nitrogen == 0 ||
fptr->ringIndicator == 1 && ring_nitrogen == 0 ) )
                      continue;
              if ( fptr->atomicId == SULFUR && ( sulfur == 0 || fptr->ringIndicator
== 1 && ring_sulfur == 0 ) )
                      continue;
       }
       hits = DB_SRCH2_SEARCH_PATTERN( fptr->pattern, S->ct, strInit );
       strInit = 1;
       nhits = 0;
       if (hits)
       {
              nhits = DB_SRCH2_GET_HIT_COUNT(hits);
              if ( !nhits )
                      DB_SRCH2_FREE_HITS(hits);
       }
       if ( !nhits )
              continue;
```

```
                    atoms = (int *) 0;
                    /* get the atoms which matched and store accordingly, depending upon the feature
type */
                    if ( fptr->f_type == FeatureArom )
                    {
                            for ( hitidx = 0; hitidx < nhits; hitidx++ )
                            {
                                    atoms = (int *) calloc(S->ct->atomCount, sizeof(int) );
                                            /* store the atoms which define the centroid */
                                    for ( j = 1; j <= fptr->ct->atomCount; j++ )
                                    {
                                            atomId = DB_SRCH2_GET_ATOM_MAPPING(j, hits, hitidx,
0 );
                                            if ( !atomId)
                                            {
                                                    UTL_ERROR_CLEAR();
                                                    continue;
                                            }
                                            atomId--;
#ifdef DEBUG_DETAIL
                                            if ( q_debugfp )
                                                    fprintf(q_debugfp, "# feature %s atom:%d  ftype:%d
rule:%d\n",
                                                            regid, atomId+1, (int) fptr->f_type, i+1 );
#endif
                                            S->aromMask[atomId] = fptr->weight;
                                            atoms[atomId] = fptr->weight;
                                    }
                                    S->aromSets = (AromSet *) DB_CT_UTL_RECALLOC((char *)
S->aromSets, S->numArom * sizeof(AromSet),
                                            (S->numArom+1) * sizeof(AromSet) );
                                    aset = S->aromSets + S->numArom;
                                    S->numArom++;

aset->atoms = atoms;
                                    aset->numAtoms = fptr->ct->atomCount;
                            }
                    }
                    else
                    {
                            for ( hitidx = 0; hitidx < nhits; hitidx++ )
                            {
                                    atomId = DB_SRCH2_GET_ATOM_MAPPING(1, hits, hitidx, 0 );
                                    if ( !atomId )
                                    {
                                            UTL_ERROR_CLEAR();
                                            DB_SRCH2_FREE_HITS(hits);
```

```
                            continue;
                    }
                    atomId--; /* make it base 0 */
#ifdef DEBUG_DETAIL
                    if ( q_debugfp )
                            fprintf(q_debugfp, "#feature %s atom:%d ftype:%d rule:%d\n",
                                    regid, atomId+1, (int) fptr->f_type, i+1 );
#endif
                    S->featureMask[atomId] |= fptr->f_type;
                }
            }
            DB_SRCH2_FREE_HITS(hits);
        }
        return 0;
} static FeaturePattern *InitFeaturePatterns(int *r_numPatterns)
{
        static Srch2Control sctrl[1];
        static int numPatterns;
        struct CtConnectionTable *ct;
        FeaturePattern *fptr;
        FeaturePattern *fpats;
        static FeatureSetName currentSet;

static FeaturePattern Unityfpats[] = {
                { FeatureArom, 20, 0, 0, "Hev[1]:Hev:Hev:Hev:Hev:Hev:@1" },
                { FeatureArom, 20, 0, 0, "Hev[1]=[r]Hev-[r]Hev=[r]Hev-[r]Hev=[r]Hev-[r]@1" },
                { FeatureArom, 20, 0, 0, "Hev[1]:Hev:Hev:Hev:Hev:@1" },
                { FeatureArom, 20, 0, 0, "Hev[1]=[r]Hev-[r]Hev=[r]Hev-[r]Hev-[r]@1" },
                { FeatureArom, 20, 0, 0, "Hev[1]:[r]Hev-[r]Hev=[r]Hev-[r]Hev-[r]@1" },
                { FeaturePos, 200, 0, 0, "Any[+;not=Any*~Any[-]]" },
                { FeaturePos, 200, NITROGEN, 0, "N[not=N*Hev:=#Any,N*O](Any)(Any)Any" },
                { FeaturePos, 200, NITROGEN, 0, "N[not=N*~Any[-]](Any)(Any)(Any)Any" },
                { FeaturePos, 200, NITROGEN, 1,
"N[1:NOT=N*~Any[-1]](:Hev:Hev:Hev:Hev:Hev:@1)Any[not=O[f]-N]" },
                { FeaturePos, 200, NITROGEN, 0,
"N[not=N*~Any[-],N(=O)~O[f]](=Any)(~Any)~Any" },
                { FeaturePos, 200, NITROGEN, 0, "N[f;not=N*Hev:=#Any](Any)Any" },
                { FeaturePos, 200, NITROGEN, 0,
"N[F](Hc)(Hc)C(=N[F]Hc)Any[IS=C*,N*[f](Any[is=H,C])(Any[is=H,C])(Any[is=H,C])]{Hc:H,C
[NOT=C*=#Any]}" },
                { FeaturePos, 200, NITROGEN, 0,
"C[1:F](:N[F]:C(:C(:N:@1Hc)Any)Any)Any{Hc:H|C[NOT=C*=:#Any]}" },
                { FeaturePos, 200, NITROGEN, 1, "N[1:f](C):C:N[f](C):C:C:@1" },
```

{ FeatureNeg, 200, OXYGEN, 0, "O[is=O*H,O*[f]Hev]-:Hev[is=C*=:O,S*(=:O)(=:O)]" },
{ FeatureNeg, 200, OXYGEN, 0, "O[is=O*H,O*[f]Hev]P(=O)(O[is=O*H,O*[f]Hev])OHev" },
{ FeatureNeg, 200, OXYGEN, 0, "O[is=O*H,O*[f]Hev]P(=O)(OHev)OHev" },
{ FeatureNeg, 200, OXYGEN, 0, "O[is=O*H,O*[f]Hev]P(=O)(O[is=O*H,O*[f]Hev])CHev" },
{ FeatureNeg, 200, OXYGEN, 0, "O[is=O*H,O*[f]Hev]P(=O)(OHev)CHev" },
{ FeatureNeg, 200, OXYGEN, 0, "O[is=O*H]P[f](=O)C" },
{ FeatureNeg, 200, NITROGEN, 1, "Any[is=C[1]:NH:N:N:N:@1,C[1]:N:NH:N:N:@1,C[1]:N:N:NH:N:@1,C[1]:N:N:N:NH:@1]" }, { FeatureHBA, 100, OXYGEN, 0, "O[f]=Any[not=S,P,N(=O[f])~O[f]](Any)Any" },
{ FeatureHBA, 100, OXYGEN, 0, "O[f]~Any[is=S,P](Any[not=O])Any[not=O]" },
{ FeatureHBA, 100, NITROGEN, 0, "N[f](:Any):Any" },
{ FeatureHBA, 100, NITROGEN, 1, "N[1]H:N[f]:Z:Z:Z:@1{Z:C,N}" },
{ FeatureHBA, 100, NITROGEN, 1, "N[1]H:C:N[f]:Any:Any:@1" },
{ FeatureHBA, 100, OXYGEN, 0, "O[f]C:Any" },
{ FeatureHBA, 100, OXYGEN, 0, "O[f]HC[not=C=Any]-:Any" },
{ FeatureHBA, 100, OXYGEN, 0, "O[f](Z)Z{Z:C[not=C=Any]}" },
{ FeatureHBA, 100, OXYGEN, 1, "O[1:f]-:Z=:Z-:Z=:Z-:@1{Z:Any[is=C,N]}" },
{ FeatureHBA, 100, OXYGEN, 1, "O[not=O[1]Any[is=C,N]=Any[is=C,N]Any[is=C,N]=Any[is=C,N]@1](Any)C=Any[is=C,N]"},
{ FeatureHBA, 100, NITROGEN, 0, "N[f]H(Z)C[not=C=Het;is=C:Any,CHevN[f](Zz)Zz]{Z:C[not=C=Het]|N[not=NC=Het]|O[not=OC=O]|S(=O)=O|H}{Zz:H|N|O|C[not=C:=Hev]}" },
{ FeatureHBA, 100, NITROGEN, 0, "N[f](Z)(Z)C[not=C=Het;is=C:Any,CHevN[f](Zz)Zz]{Z:C[not=C=Het]|N[not=NC=Het]|O[not=OC=O]|S(=O)=O}{Zz:H|N|O|C[not=C:=Hev]}" },
{ FeatureHBA, 100, OXYGEN, 0, "O[f](Any[is=H,C])C=O" },
{ FeatureHBA, 100, OXYGEN, 0, "O[f]-:C~O[f]" },
{ FeatureHBA, 100, NITROGEN, 0, "NH=C[not=CN]" },
{ FeatureHBA, 100, NITROGEN, 0, "N[f](~Hev)=C[not=CN]" },
{ FeatureHBA, 100, NITROGEN, 0, "N[f](=C[is=NC*N,NC*C,NC*H])Hev[is=Hev=O,Hev=S,C#N,CN(~O[f])~O[f]]" },
{ FeatureHBA, 100, OXYGEN, 0, "O[f]~N(Any)~O[f]" },
{ FeatureHBA, 100, OXYGEN, 0, "O~Any[is=S,P](~O)~O " }, { FeatureHBD, 100, NITROGEN, 0, "N[not=C[1]:N*:N:N:N:@1,C[1]:N:N*:N:N:@1]H~[!type=3]Any" },
{ FeatureHBD, 100, OXYGEN, 0, "OHAny[not=C=O]" },
{ FeatureHBD, 100, NITROGEN, 0, "N[f](Hev[not=Any=O,Any=S,C#N,N(~O[f])~O[f]])=C" },
{ FeatureHBD, 100, NITROGEN, 0, "N[f](:C[1:not=COH,CSH]):C[not=COH,CSH]:C:C[not=COH,CSH]:C:@1" },
{ FeatureHBD, 100, NITROGEN, 1, "N[1:f;not=C[1]:N*:N:N:N:@1,C[1]:N:N*:N:N:@1]:Any:Any:N(Any):Any:@1" },
{ FeatureHBD, 100, NITROGEN, 1,

```
"N[1:f;not=C[1]:N*:N:N:N:@1,C[1]:N:N*:N:N:@1]:Any[1:not=N]:Any[is=C,N]:Any[is=C,N]:NH:@1" },
    { FeatureHBD, 100, NITROGEN, 0, "N[f](:C(Any[is=O,S]H)):Any:Any:Any" },
    { FeatureHBD, 100, NITROGEN, 0, "N[f](:C:C:C(Any[is=O,S]H)):Any" },
    { FeatureHBD, 100, NITROGEN, 0,
"N[f](Ya)(Ya)Ya{Ya:Any[not=H,C=O,C=N,S(=O)(=O)Any]}" },
    { FeatureHBD, 100, OXYGEN, 0, "O[f]~Any[is=S,P](~OH)(~O)" },
    { FeatureHBD, 100, SULFUR, 0,
"S[f]HZ{Z:C[not=C=O]|S[not=S~O]|N[not=N~O] }" },
    { FeatureNone, -1, 0, 0, (char *) 0 }
};

static FeaturePattern Unityfpats_WeLike[] = {
        { FeatureArom, 20, 0, 0, "Hev[1]:Hev:Hev:Hev:Hev:Hev:@1" },
        { FeatureArom, 20, 0, 0, "Hev[1]=[r]Hev-[r]Hev=[r]Hev-[r]Hev=[r]Hev-[r]@1" },
        { FeatureArom, 20, 0, 0, "Hev[1]:Hev:Hev:Hev:Hev:@1" },
        { FeatureArom, 20, 0, 0, "Hev[1]=[r]Hev-[r]Hev=[r]Hev-[r]Hev-[r]@1" },
        { FeatureArom, 20, 0, 0, "Hev[1]:[r]Hev-[r]Hev=[r]Hev-[r]Hev-[r]@1" },
        { FeaturePos, 200, 0, 0, "Any[+;not=Any*~Any[-]]" },
        { FeaturePos, 200, NITROGEN, 0, "N[not=N*Hev:=#Any,N*O](Any)(Any)Any" },
        { FeaturePos, 200, NITROGEN, 0, "N[not=N*~Any[-]](Any)(Any)(Any)Any" },
        { FeaturePos, 200, NITROGEN, 1,
"N[1:NOT=N*~Any[-1]](:Hev:Hev:Hev:Hev:Hev:@1)Any[not=O[f]-N]" },
        { FeaturePos, 200, NITROGEN, 0,
"N[not=N*~Any[-],N(=O)~O[f]](=Any)(~Any)~Any" },
        { FeaturePos, 200, NITROGEN, 0, "N[f;not=N*Hev:=#Any](Any)Any" },
        { FeaturePos, 200, NITROGEN, 0,
"N[F](Hc)(Hc)C(=N[F]Hc)Any[IS=C*,N*[f](Any[is=H,C])(Any[is=H,C])(Any[is=H,C])]{Hc:H,C[NOT=C*=#Any]}" },
        { FeaturePos, 200, NITROGEN, 0,
"C[1:F](:N[F]:C(:C(:N:@1Hc)Any)Any)Any{Hc:H|C[NOT=C*=:#Any]}" },
        { FeaturePos, 200, NITROGEN, 1, "N[1:f](C):C:N[f](C):C:C:@1" },
        { FeatureNeg, 200, OXYGEN, 0,
"O[is=O*H,O*[f]Hev]-:Hev[is=C*=:O,S*(=:O)(=:O)]" },
        { FeatureNeg, 200, OXYGEN, 0,
"O[is=O*H,O*[f]Hev]P(=O)(O[is=O*H,O*[f]Hev])OHev" },
        { FeatureNeg, 200, OXYGEN, 0, "O[is=O*H,O*[f]Hev]P(=O)(OHev)OHev" },
        { FeatureNeg, 200, OXYGEN, 0,
"O[is=O*H,O*[f]Hev]P(=O)(O[is=O*H,O*[f]Hev])CHev" },
        { FeatureNeg, 200, OXYGEN, 0, "O[is=O*H,O*[f]Hev]P(=O)(OHev)CHev" },
        { FeatureNeg, 200, OXYGEN, 0, "O[is=O*H]P[f](=O)C" },
        { FeatureNeg, 200, NITROGEN, 1,
"Any[is=C[1]:NH:N:N:N:@1,C[1]:N:NH:N:N:@1,C[1]:N:N:NH:N:@1,C[1]:N:N:N:NH:@1]" }, { FeatureHBA, 100, OXYGEN, 0, "O[f]=Any[not=S,P,N(=O[f])~O[f]](Any)Any" },
        { FeatureHBA, 100, OXYGEN, 0, "O[f]~Any[is=S,P](Any[not=O])Any[not=O]" },
        { FeatureHBA, 100, NITROGEN, 0, "N[f](:Any):Any" },
```

```
{ FeatureHBA, 100, NITROGEN, 1, "N[1]H:N[f]:Z:Z:Z:@1{Z:C,N}" },
{ FeatureHBA, 100, NITROGEN, 1, "N[1]H:C:N[f]:Any:Any:@1" },
{ FeatureHBA, 100, OXYGEN, 0, "O[f]C:Any" },
{ FeatureHBA, 100, OXYGEN, 0, "O[f]HC[not=C=Any]-:Any" },
{ FeatureHBA, 100, OXYGEN, 0, "O[f](Z)Z{Z:C[not=C=Any]}" },
{ FeatureHBA, 100, OXYGEN, 1, "O[1:f]-:Z=:Z-:Z=:Z-:@1{Z:Any[is=C,N]}" },
{ FeatureHBA, 100, OXYGEN, 1,
"O[not=O[1]Any[is=C,N]=Any[is=C,N]Any[is=C,N]=Any[is=C,N]@1](Any)C=Any[is=C,N]"},
{ FeatureHBA, 0, NITROGEN, 0,
"N[f]H(Z)C[not=C=Het;is=C:Any,CHevN[f](Zz)Zz]{Z:C[not=C=Het]|N[not=NC=Het]|O[not=
OC=O]|S(=O)=O|H}{Zz:H|N|O|C[not=C:=Hev]}" },
{ FeatureHBA, 0, NITROGEN, 0,
"N[f](Z)(Z)C[not=C=Het;is=C:Any,CHevN[f](Zz)Zz]{Z:C[not=C=Het]|N[not=NC=Het]|O[not
=OC=O]|S(=O)=O}{Zz:H|N|O|C[not=C:=Hev]}" },
{ FeatureHBA, 0, OXYGEN, 0, "O[f](Any[is=H,C])C=O" },
{ FeatureHBA, 100, OXYGEN, 0, "O[f]-:C~O[f]" },
{ FeatureHBA, 100, NITROGEN, 0, "NH=C[not=CN]" },
{ FeatureHBA, 100, NITROGEN, 0, "N[f](~Hev)=C[not=CN]" },
{ FeatureHBA, 100, NITROGEN, 0,
"N[f](=C[is=NC*N,NC*C,NC*H])Hev[is=Hev=O,Hev=S,C#N,CN(~O[f])~O[f]]" },
{ FeatureHBA, 100, OXYGEN, 0, "O[f]~N(Any)~O[f]" },
{ FeatureHBA, 100, OXYGEN, 0, "O~Any[is=S,P](~O)~O " }, { FeatureHBD, 100, NITROGEN, 0,
"N[not=C[1]:N*:N:N:N:@1,C[1]:N:N*:N:N:@1]H~[!type=3]Any" },
{ FeatureHBD, 100, OXYGEN, 0, "OHAny[not=C=O]" },
{ FeatureHBD, 100, NITROGEN, 0,
"N[f](Hev[not=Any=O,Any=S,C#N,N(~O[f])~O[f]])=C" },
{ FeatureHBD, 0, NITROGEN, 0,
"N[f](:C[1:not=COH,CSH]):C[not=COH,CSH]:C:C[not=COH,CSH]:C:@1" },
{ FeatureHBD, 0, NITROGEN, 1,
"N[1:f;not=C[1]:N*:N:N:N:@1,C[1]:N:N*:N:N:@1]:Any:Any:N(Any):Any:@1" },
{ FeatureHBD, 0, NITROGEN, 1,
"N[1:f;not=C[1]:N*:N:N:N:@1,C[1]:N:N*:N:N:@1]:Any[1:not=N]:Any[is=C,N]:Any[is=C,N]:N
H:@1" },
{ FeatureHBD, 0, NITROGEN, 0, "N[f](:C(Any[is=O,S]H)):Any:Any:Any" },
{ FeatureHBD, 0, NITROGEN, 0, "N[f](:C:C:C(Any[is=O,S]H)):Any" },
{ FeatureHBD, 0, NITROGEN, 0,
"N[f](Ya)(Ya)Ya{Ya:Any[not=H,C=O,C=N,S(=O)(=O)Any]}" },
{ FeatureHBD, 100, OXYGEN, 0, "O[f]~Any[is=S,P](~OH)(~O)" },
{ FeatureHBD, 100, SULFUR, 0,
"S[f]HZ{Z:C[not=C=O]|S[not=S~O]|N[not=N~O]}" },
{ FeatureNone, -1, 0, 0, (char *) 0 }
};
```

/*
From Sybyl 6.71/Unity 4.21 $TA_3DB/sln3d_macros.def
The structure above assumes first atom is the important atom, so right the sln the correct way the first time.

define:: Donor_Atom[name; target; rules; connection]
    sln=N[not=C[1]:N*:N:N:N:@1,C[1]:N:N*:N:N:@1]H~[!type=3]Any;
    features=1;
    sln=OHAny[not=C=O];
    features=1;
    sln=N[f](Hev[not=Any=O,Any=S,C#N,N(~O[f])~O[f]])=C;
    features=1;
    sln=C[1:not=COH,CSH]:N[f]:C[not=COH,CSH]:C:C[not=COH,CSH]:C:@1;
    features=2;
    sln=Any[1]:N(Any):Any:N[f;not=C[1]:N*:N:N:N:@1,C[1]:N:N*:N:N:@1]:Any:@1;
    features=5;

sln=Any[1:not=N]:Any[is=C,N]:Any[is=C,N]:NH:N[f;not=C[1]:N*:N:N:N:@1,C[1]:N:N*:N:N:@1]:@1;
    features=6;
    sln=Any:Any:Any:N[f]:C(Any[is=O,S]H);
    features=4;
    sln=Any:N[f]:C:C:C(Any[is=O,S]H);
    features=2;
    sln=N[f](Ya)(Ya)Ya{Ya:Any[not=H,C=O,C=N,S(=O)(=O)Any]};
    features=1;
    sln=O[f]~Any[is=S,P](~OH)(~O);
    features=1;
    sln=S[f]HZ{Z:C[not=C=O]|S[not=S~O]|N[not=N~O]};
    features=1;
  features=::name::_DL_1,
end_define define:: Acceptor_Atom[name; target; rules; connection]

sln=O[f]=Any[not=S,P,N(=O[f])~O[f]](Any)Any;
    features=1;
    sln=O[f]~Any[is=S,P](Any[not=O])Any[not=O];
    features=1;
    sln=Any:N[f]:Any;
    features=2;
    sln=Z[1]:Z:Z:NH:N[f]:@1{Z:C|N};
    features=4;
    sln=Any[1]:NH:C:N[f]:Any:@1;
    features=2;
    sln=O[f]C:Any;
    features=1;
    sln=O[f]HC[not=C=Any]-:Any;
    features=1;

```
    sln=ZO[f]Z{Z:C[not=C=Any]};
    features=2;
    sln=Z[1]-:O[f]-:Z=:Z-:Z=:@1{Z:Any[is=C,N]};
    features=2;

sln=O[not=O[1]Any[is=C,N]=Any[is=C,N]Any[is=C,N]=Any[is=C,N]@1](Any)C=Any[is=C,N];
    features=1;

sln=N[f]H(Z)C[not=C=Het;is=C:Any,CHevN[f](Zz)Zz]{Z:C[not=C=Het]|N[not=NC=Het]|O[n
ot=OC=O]|S(=O)=O|H}{Zz:H|N|O|C[not=C:=Hev]};
    features=1;

sln=N[f](Z)(Z)C[not=C=Het;is=C:Any,CHevN[f](Zz)Zz]{Z:C[not=C=Het]|N[not=NC=Het]|O[
not=OC=O]|S(=O)=O}{Zz:H|N|O|C[not=C:=Hev]};
    features=1;
    sln=O[f](Any[is=H,C])C=O;
    features=1;
    sln=O[f]-:C~O[f];
    features=1;
    sln=NH=C[not=CN];
    features=1;
    sln=Hev~N[f]=C[not=CN];
    features=2;
    sln=Hev[is=Hev=O,Hev=S,C#N,CN(~O[f])~O[f]]N[f]=C[is=NC*N,NC*C,NC*H];
    features=2;
    sln=AnyN(~O[f])~O[f];
    features=3;
    sln=O~Any[is=S,P](~O)~O;
    features=1;
  features=::name::_AL_1,
end_define

*/ static FeaturePattern orig_top_fpats[] = {
            { FeatureArom, 20, 0, 0, "Hev[1]:Hev:Hev:Hev:Hev:Hev:@1" },
            { FeatureArom, 20, 0, 0, "Hev[1]=[r]Hev-[r]Hev=[r]Hev-[r]Hev=[r]Hev-[r]@1" },
            { FeatureArom, 20, 0, 0, "Hev[1]:Hev:Hev:Hev:Hev:@1" },
            { FeatureArom, 20, 0, 0, "Hev[1]=[r]Hev-[r]Hev=[r]Hev-[r]Hev-[r]@1" },
            { FeatureArom, 20, 0, 0, "Hev[1]:[r]Hev-[r]Hev=[r]Hev-[r]Hev-[r]@1" },
            { FeaturePos, 200, 0, 0, "Any[+;not=Any*~Any[-]]" },
            { FeaturePos, 200, NITROGEN, 0, "N[not=N*Hev:=#Any,N*O](Any)(Any)Any" },
            { FeaturePos, 200, NITROGEN, 0, "N[not=N*~Any[-]](Any)(Any)(Any)Any" },
            {    F e a t u r e P o s ,    2 0 0 ,    N I T R O G E N ,    0 ,
"N[1:NOT=N*~Any[-1]](:Hev:Hev:Hev:Hev:Hev:@1)Any[not=O[f]-N]" },
            {    F e a t u r e P o s ,    2 0 0 ,    N I T R O G E N ,    0 ,
"N[not=N*~Any[-],N(=O)~O[f]](=Any)(~Any)~Any" },
            { FeaturePos, 200, NITROGEN, 0, "N[f;not=N*Hev:=#Any](Any)Any" },
```

{ FeaturePos, 200, NITROGEN, 0,
"N[F](Hc)(Hc)C(=N[F]Hc)Any[IS=C*,N*[f](Any[is=H,C])(Any[is=H,C])(Any[is=H,C])]{Hc:H,C[NOT=C*=#Any]}" },
{ FeaturePos, 200, NITROGEN, 1,
"C[1:F](:N[F]:C(:C(:N:@1Hc)Any)Any)Any{Hc:H | C[NOT=C*=:#Any]}" },
{ FeaturePos, 200, NITROGEN, 1, "N[1:f](C):C:N[f](C):C:C:@1" },
{ FeatureNeg, 200, OXYGEN, 0,
"O[is=O*H,O*[f]Hev]-:Hev[is=C*=:O,S*(=:O)(=:O)]" },
{ FeatureNeg, 200, OXYGEN, 0,
"O[is=O*H,O*[f]Hev]P(=O)(O[is=O*H,O*[f]Hev])OHev" },
{ FeatureNeg, 200, OXYGEN, 0, "O[is=O*H,O*[f]Hev]P(=O)(OHev)OHev" },
{ FeatureNeg, 200, OXYGEN, 0,
"O[is=O*H,O*[f]Hev]P(=O)(O[is=O*H,O*[f]Hev])CHev" },
{ FeatureNeg, 200, OXYGEN, 0, "O[is=O*H,O*[f]Hev]P(=O)(OHev)CHev" },
{ FeatureNeg, 200, OXYGEN, 0, "O[is=O*H]P[f](=O)C" },
{ FeatureNeg, 200, NITROGEN, 1,
"Any[is=C[1]:NH:N:N:N:@1,C[1]:N:NH:N:N:@1,C[1]:N:N:NH:N:@1,C[1]:N:N:N:NH:@1]" },
{ FeatureHBA, 100, OXYGEN, 0,
"O[is=O*=Any,O(Any)Any,O[f]Any,O[f](H)C=O,O[f]C=O;not=O*=:-N,O*[!r](Hev)Any=Het]"},
{ FeatureHBA, 100, OXYGEN, 0, "O[is=O*=NO,O*N=O,O*=N=O,O:N:O]" },
{ FeatureHBA, 100, NITROGEN, 0,
"N[is=N*(Any)(Any)Any,N*(Any)Any,N*[f](:Any):Any,N*#C,N*[1:f]:C:NH:C:C:@1,N*[1:f]H:C:N[f]:C:C:@1,N*[1:f]H:N[f]:C:C:C:@1,N*[1:f]H:N[f]:N[f]:C:C:@1,N*[1:f]H:N[f]:C:N:C:@1,N*[1:f]H:N[f]:N[f]:N[f]:C:@1,N*H=C,N*[f](Any)=C;not=N*(Any)(Any)Any[not=S]:=#O,N*C(=S)N,N*(Any)(Any)C(=S)C,N*(Any)(Any)(Any)Any,N*(Any)(Any)C:Hev,N*[f]HC:Hev,N*(Any[is=H,C])=C(N(Any[is=H,C])(C))(N(Any[is=H,C])(Any[is=H,C])),N(Any[is=H,C])=C(N*(Any[is=H,C])(C))(N(Any[is=H,C])(Any[is=H,C])),N(Any[is=H,C])=C(N(Any[is=H,C])(C))(N*(Any[is=H,C])(Any[is=H,C])),N*(:Hev)(:Hev):-Hev,N*(=O)O]" },
{ FeatureHBA, 100, NITROGEN, 1, "N[1]C[2]:N:C:N:C(:@2)C(=O)NHC=@1" },
{ FeatureHBA, 100, NITROGEN, 0, "N[is=N*=N=N,N*(=N)=N]" },
{ FeatureHBA, 100, NITROGEN, 0, "N[is=N*(C)=NC]" },
{ FeatureHBA, 100, NITROGEN, 0,
"N[is=N*(=C)N,N*[not=N*C=Het,N*C:Hev]N=C]" },
{ FeatureHBA, 100, SULFUR, 0,
"S[is=S*[f]HAny,S*[f](Hev)Hev,S*=C(N)(N);not=S*Any~O]" },
{ FeatureHBD, 100, OXYGEN, 0, "OHAny[not=C=O,P,S]" },
{ FeatureHBD, 100, NITROGEN, 0, "NH" },
{ FeatureHBD, 100, SULFUR, 0, "SH" },
{ FeatureHBD, 100, NITROGEN, 1,
"N[is=N*[1]=CNHC=C@1,N[1]:C:NH:C:C:@1,N*[1:f]:N[f]H:C:C:C:@1,N*[1:f]:N[f]H:C:C:N[f]:@1,N*[1:f]:N[f]:N[f]H:C:C:@1,N*[1:f]:C:C:N[f]:N[f]H:@1,N*[1:f]:N[f]H:C:N[f]:C:@1,N*[1:f]:C:N[f]:N[f]H:C:@1,N*[1:f]:N[f]H:C:N[f]:C:@1,N*[1:f]:C:N[f]H:N:C:@1,N*[1:f]:C:N[f]H:C:N[f]:@1]"
},
{ FeatureHBD, 100, NITROGEN, 0,
"N[not=N*Hev=#:Het,N*O,N*Hev:Hev](Hev)(Hev)Hev" },
{ FeatureNone, -1, 0, 0, (char *) 0 }
};

```
if ( numPatterns && currentSet == q_featureSet )
{
        *r_numPatterns = numPatterns;
        if ( q_featureSet == UseUnityFeatures )
                return Unityfpats;
        else if ( q_featureSet == UseTopomerFeatures )
                return orig_top_fpats;
        else
                return Unityfpats_WeLike;
} if ( q_featureSet == UseUnityFeatures )
        fpats = Unityfpats;
else if ( q_featureSet == UseTopomerFeatures )
        fpats = orig_top_fpats;
else
        fpats = Unityfpats_WeLike;

currentSet = q_featureSet;

memset((char *) sctrl, '\0', sizeof(Srch2Control) );
sctrl->maxHits = 0;
sctrl->searchControl = Srch2NoDuplicates;
sctrl->charge = 1;
sctrl->isotope = 1;
sctrl->stereoSearch = 1;

for ( numPatterns = 0, fptr = fpats; fptr->sln != (char *) 0; fptr++, numPatterns++ )
{
        if ( !fptr->ct )
                fptr->ct = DB_IMPORT_SLN(fptr->sln);
        if ( !fptr->ct )
        {
                UTL_ERROR_CLEAR();
                fprintf(stderr,"Problems importing the feature pattern\n%s\n", fptr->sln );
                continue;
        }
        if(!fptr->pattern&&!DB_SRCH2_OPEN_PATTERN(fptr->ct,sctrl,&(fptr->pattern)
))
        {
                UTL_ERROR_CLEAR();
                DB_CT_DELETE_CT(fptr->ct);
                fptr->pattern = (void *) 0;
                fprintf(stderr,"Problems building search pattern for the feature pattern\n%s\n", fptr->sln );
                continue;
        }
}
```

```
        *r_numPatterns = numPatterns;
        if ( q_featureSet == UseUnityFeatures )
                return Unityfpats;
        else if ( q_featureSet == UseTopomerFeatures )
                return orig_top_fpats;
        else
                return Unityfpats_WeLike;
} static int computeCentroid( double *cords, int *atoms, int numAtoms, double *r_x, double *r_y, double *r_z )
{
        double x, y, z;
        double *cptr;
        int i;
        double divfact;

if ( !cords || !atoms || numAtoms <= 0 || !r_x || !r_y || !r_z )
                return -1;

divfact = (double) numAtoms;
        x = y = z = 0.0;
        for ( i = 0; i < numAtoms; i++ )
        {
                cptr = cords + (atoms[i] * 3);
                x += *cptr;
                y += *(cptr+1);
                z += *(cptr+2);
        }
        *r_x = x / divfact;
        *r_y = y / divfact;
        *r_z = z / divfact;
        return 0;
} static void addCentroid(Frag *fptr, int natoms, double attFact, double x, double y, double z )
{
        double *cptr;
        double cdiff, xd, yd, zd;
        int i;
        int duplicate;

for ( i = duplicate = 0; !duplicate && i < fptr->aromCnt; i++ )
        {
                cptr = fptr->cent + (i*4);
                xd = x - *cptr;
                yd = y - *(cptr+1);
                zd = z - *(cptr+2);
```

```
            cdiff = xd*xd + yd*yd + zd*zd;
            if ( cdiff < 0.1 )
                    duplicate = 1;
    }
    if ( duplicate )
    {
            return;
    }
    fptr->cent = (double *) DB_CT_UTL_RECALLOC((char *) fptr->cent,
            fptr->aromCnt * sizeof(double) * 4,
            (fptr->aromCnt+1) * sizeof(double) * 4 );
    cptr = fptr->cent + (fptr->aromCnt * 4);
    fptr->aromCnt++;

*cptr = x;
    *(cptr+1) = y;
    *(cptr+2) = z;
    *(cptr+3) = attFact;
    return;
} static int compareFields(double *orig, double *atombased, int npoints )
{
    int i;

for ( i = 0; i < npoints; i++, orig++, atombased++ )
    {
            if ( ( fabs( *orig - *atombased) ) > 0.1 )
            {
                    fprintf(stderr,"field difference: %d of %6.3lf  %6.2lf %6.2lf\n",
                            i, *orig - *atombased, *orig, *atombased );
            }
    }
    return i;
}

/* functions from here to "end of core funcs" are for core searching */ int TOP_CORE_QUERY( struct CtConnectionTable *ct, FILE *fp)
{
    static Split core_split[1];
    CtAtom *atom;
    int i;
    int k_atomicid = 19;
    int na_atomicid = 11;
    int Kid, Naid;
```

```
int err = 0;
int *atomMask;
int *b1, *b2;
int hevCnt;
struct CtConnectionTable *dupct;
Frag *f1, *f2;

Kid = Naid = -1;

for ( atom = ct->atoms, i = 0; i < ct->atomCount; i++ , atom++ )
{
        if ( atom->class != CtAtomElement )
                continue;
        if ( atom->id.atomicNumber == k_atomicid )
        {
                if ( Kid >= 0 )
                        fprintf(stderr,"More than one K atom present in core query.\n"), err = 1;
                Kid = i;
                atom->id.atomicNumber = CARBON;
        }
        else if ( atom->id.atomicNumber == na_atomicid )
        {
                if ( Naid >= 0 )
                        fprintf(stderr,"More than one Na atom present in core query.\n"), err = 2;
                Naid = i;
                atom->id.atomicNumber = CARBON;
        }
}
if ( Kid == -1 )
{
        fprintf(stderr, "No K atom present in the core query.\n" );
        err = 3;
}
if ( Naid == -1 )
{
        fprintf(stderr,"No Na atom present in the core query.\n" );
        err = 4;
}
if ( err )
        return err;

atom = ct->atoms + Naid;
stripCharge(ct, atom, Naid);

atom = ct->atoms + Kid;
stripCharge(ct,atom, Kid);
```

```
b1 = (int *) malloc(ct->atomCount * sizeof(int) );
b2 = (int *) malloc(ct->atomCount * sizeof(int) );

for ( i = 0; i < ct->atomCount; i++ )
{
        b1[i] = b2[i] = 1;
}
b1[Kid]  = -1;   /* mark base atom */
b2[Naid] = -1;           /* mark base atom */ memset((char *) core_split, '\0', sizeof(Split) );

g_split2 = (split2 *) 0;
g_split3 = (split3 *) 0;
g_splitcnt = g_splitalloc = g_split3Cnt = g_split3Alloc = 0;

atomMask = createAtomMask(ct, q_termFlag, &hevCnt);
addSplit2(1, b1, b2 );
core_split->frags = createUniqFrags(ct->atomCount, g_split2, g_splitcnt, g_split3, g_split3Cnt, atomMask,
                &(core_split->numFrags) );

core_split->s2 = g_split2;
core_split->s2cnt = g_splitcnt;
core_split->bondCount = ct->bondCount;
core_split->atomCount = ct->atomCount;
core_split->atomMask = atomMask;

g_split2 = (split2 *) 0;
g_splitcnt = g_splitalloc = 0;

core_split->ct = ct;
SearchForFeatures(core_split);
qmode = 1;
BuildFrags(core_split);
BuildTopomers(ct, core_split, (Split *) 0);
qmode = 0;

if ( core_split->frags && fp )
{
        f1 = core_split->frags;
        f2 = core_split->frags + 1;

dupct = DB_CT_UTL_DUP_CT(f1->ct, CtCopyKeepAllAttrs );
```

```
        atom = dupct->atoms + Kid;
        atom->id.atomicNumber = k_atomicid;
        atom = dupct->atoms + Naid;
        atom->id.atomicNumber = na_atomicid;
        setAttr(dupct, "CORESIM", "0");
        setAttr(dupct, "TS_QID", "0");
        DB_CT_WRITE(fp, dupct);
        DB_CT_DELETE_CT(dupct);

dupct = DB_CT_UTL_DUP_CT(f2->ct, CtCopyKeepAllAttrs );
        atom = dupct->atoms + Kid;
        atom->id.atomicNumber = k_atomicid;
        atom = dupct->atoms + Naid;
        atom->id.atomicNumber = na_atomicid;
        setAttr(dupct, "CORESIM", "0");
        setAttr(dupct, "TS_QID", "0");
        DB_CT_WRITE(fp, dupct);
        DB_CT_DELETE_CT(dupct);

UTL_ERROR_CLEAR();
    } qs = core_split;

return 0;
} top_result *TOP_CORE_SEARCH(struct CtConnectionTable *ct, double radius, double max_attachpen, int *r_hascore )
{
    Split *S;
    double f1, f2, f3, f4;
    double s1, s2, s3, s4;
    double a1, a2, a3, a4;
    Frag *q1, *q2;
    Frag *fs1, *fs2;
    split3 *ss3;
    double sval, sval2, sval3, sval4;
    int i,j;
    double best;
    double bestAttach;
    static top_result res[1];
    Frag *bestFrag, *altFrag;
    int idx = 0;
    CtAtom *atom, *atm2;
    char value[80];
    struct CtConnectionTable *dupct;
```

```
int uniqId, hitId;

memset((char *) res, '\0', sizeof(top_result) );
q_bailout = radius * radius;

max_attachpen *= max_attachpen;

best = 999.9 * 999.9;
bestAttach = max_attachpen;
q_coremode = 1;
S = FindBreakPoints(ct, q_minatoms, q_termFlag, TRUE );
*r_hascore = 0;
if ( !S || S->s3cnt == 0 )
{
        q_coremode = 0;
        if ( S )
                freeSplit(S);
        return (top_result *) 0;
}
*r_hascore = S->s3cnt;

S->ct = ct;
SearchForFeatures(S);
BuildFrags(S);

q1 = qs->frags;
q2 = qs->frags + 1;
bestFrag = (Frag *) 0;

for ( j = 0, ss3 = S->s3; ss3 && j < S->s3cnt; j++, ss3++ )
{
        fs1 = S->frags + ss3->frag1;
        fs2 = S->frags + ss3->frag2;

if ( fs1->cords == (double *) 0 || fs2->cords == (double *) 0)
        {
                continue;
        } atom = fs1->ct->atoms + fs1->copyBaseAtom;
        atm2 = fs1->ct->atoms + fs2->copyBaseAtom;
        if ( atom->bondCount > 1 || atm2->bondCount > 1 )
        {
                fs1->cords = fs2->cords = (double *) 0;
                continue;

}
        if ( q_debugfp )
```

```
{
        DB_CT_WRITE(q_debugfp,fs1->ct );
        DB_CT_WRITE(q_debugfp,fs2->ct );
        UTL_ERROR_CLEAR();
} a1 = computeAttachmentPenalty(q1, fs1, q2, fs2 );
a2 = computeAttachmentPenalty(q2, fs1, q1, fs2 );
a3 = computeAttachmentPenalty(q1, fs2, q2, fs1 );
a4 = computeAttachmentPenalty(q2, fs2, q1, fs1 );
if ( a1 > max_attachpen && a2 > max_attachpen && a3 > max_attachpen && a4 > max_attachpen )
{
        fs1->cords = fs2->cords = (double *) 0;
        continue;
}
f1 = compareFeatures(qs, q1, S, fs1, q2->copyBaseAtom, fs2->copyBaseAtom );
f2 = compareFeatures(qs, q2, S, fs1, q1->copyBaseAtom, fs2->copyBaseAtom );
f3 = compareFeatures(qs, q1, S, fs2, q2->copyBaseAtom, fs1->copyBaseAtom );
f4 = compareFeatures(qs, q2, S, fs2, q1->copyBaseAtom, fs1->copyBaseAtom );

sval = f1 + a1;
sval2 = f2 + a2;
sval3 = f3 + a3;
sval4 = f4 + a4;
if ( sval > q_bailout && sval2 > q_bailout && sval3 > q_bailout && sval4 > q_bailout )
{
        fs1->cords = fs2->cords = (double *) 0;
        continue;
}
}
BuildTopomers(ct, S, (Split *) 0 );

for ( j = 0, ss3 = S->s3; ss3 && j < S->s3cnt; j++, ss3++ )
{
        fs1 = S->frags + ss3->frag1;
        fs2 = S->frags + ss3->frag2;

if ( fs1->cords == (double *) 0 || fs2->cords == (double *) 0)
                continue;

a1 = computeAttachmentPenalty(q1, fs1, q2, fs2 );
        a2 = computeAttachmentPenalty(q2, fs1, q1, fs2 );
        a3 = computeAttachmentPenalty(q1, fs2, q2, fs1 );
        a4 = computeAttachmentPenalty(q2, fs2, q1, fs1 );
        f1 = compareFeatures(qs, q1, S, fs1, q2->copyBaseAtom, fs2->copyBaseAtom );
        f2 = compareFeatures(qs, q2, S, fs1, q1->copyBaseAtom, fs2->copyBaseAtom );
```

```
f3 = compareFeatures(qs, q1, S, fs2, q2->copyBaseAtom, fs1->copyBaseAtom );
f3 = compareFeatures(qs, q2, S, fs2, q1->copyBaseAtom, fs1->copyBaseAtom );

s1 = topFieldCompressedDiff(q1->qtf[fs1->regionIdx], fs1->topField, fs1->npoints,
0.0 );
s2 = topFieldCompressedDiff(q2->qtf[fs1->regionIdx], fs1->topField, fs1->npoints,
0.0 );

s3 = topFieldCompressedDiff(q1->qtf[fs2->regionIdx], fs2->topField, fs2->npoints,
0.0 );
s4 = topFieldCompressedDiff(q2->qtf[fs2->regionIdx], fs2->topField, fs2->npoints,
0.0 );

sval = f1 + a1 + s1;
if ( sval < best && a1 < max_attachpen )
{
        best = sval;
        res->hexDiffs[0] = s1;
        res->featureDiffs[0] = f1;
        res->attachmentPenalty = a1;
        bestFrag = fs1;
        altFrag = fs2;
        idx = 0;
} sval = f2 + a2 + s2;
if ( sval < best && a2 < max_attachpen )
{
        best = sval;
        res->hexDiffs[0] = s2;
        res->featureDiffs[0] = f2;
        res->attachmentPenalty = a2;
        bestFrag = fs1;
        altFrag = fs2;
        idx = 1;
} sval = f3 + a3 + s3;
if ( sval < best && a3 < max_attachpen )
{
        best = sval;
        res->hexDiffs[0] = s3;
        res->featureDiffs[0] = f3;
        res->attachmentPenalty = a3;
        bestFrag = fs2;
        altFrag = fs1;
        idx = 0;
}
```

```
                sval = f4 + a4 + s4;
                if ( sval < best && a4 < max_attachpen )
                {
                        best = sval;
                        res->hexDiffs[0] = s4;
                        res->featureDiffs[0] = f4;
                        res->attachmentPenalty = a4;
                        bestFrag = fs2;
                        altFrag = fs1;
                        idx = 1;
                }
        }
}
if ( best < q_bailout )
{
        if ( best < 0.0 )
                best = 0.0;
        res->comfa_diff = sqrt(best);
        sprintf(value,"%d", (int) res->comfa_diff );
        setAttr(bestFrag->ct, "CORESIM", value );

sprintf(value,"%d", (int) sqrt(res->attachmentPenalty) );
        setAttr(bestFrag->ct, "TS_ATTACH_PEN", value );

sprintf(value,"%d", (int) sqrt(res->featureDiffs[0]) );
        setAttr(bestFrag->ct, "TS_FEATURE", value );

sprintf(value,"%d", (int) sqrt(res->hexDiffs[0]) );
        setAttr(bestFrag->ct, "TS_STERIC", value );

sprintf(value,"%d", idx+1 );
        setAttr(bestFrag->ct, "TS_QID", value );

res->strFrags[0] = DB_CT_UTL_DUP_CT(S->ct, CtCopyKeepAllAttrs );
        res->strFrags[1] = DB_CT_UTL_DUP_CT(bestFrag->ct, CtCopyKeepAllAttrs );
        dupct = res->strFrags[1];

if ( idx == 1 )
        {
                atom = dupct->atoms + bestFrag->copyBaseAtom;
                atom->id.atomicNumber = 11;
                stripCharge(dupct, atom, bestFrag->copyBaseAtom );
                atom = dupct->atoms + altFrag->copyBaseAtom;
                atom->id.atomicNumber = 19;
                stripCharge(dupct, atom, altFrag->copyBaseAtom);
        }
        else
        {
                atom = dupct->atoms + bestFrag->copyBaseAtom;
```

```
            atom->id.atomicNumber = 19;
            stripCharge(dupct, atom, bestFrag->copyBaseAtom);
            atom = dupct->atoms + altFrag->copyBaseAtom;
            atom->id.atomicNumber = 11;
            stripCharge(dupct, atom, altFrag->copyBaseAtom);
        }
        dupCheckCore(dupct, &uniqId, &hitId );

sprintf(value,"%d", uniqId);
        setAttr(dupct,"TS_UNIQ_ID", value );

sprintf(value,"%d", hitId);
        setAttr(dupct,"TS_HIT_ID", value );

freeSplit(S);

q_coremode = 0;
        return res;
    }
    q_coremode = 0;
    freeSplit(S);
    return (top_result *) 0;
} static void stripCharge(struct CtConnectionTable *ct, CtAtom *aptr, int atomidx)
{
    int relop, charge;

if ( aptr->attributeMask & CtAtomFormalCharge )
    {
        charge = 0;
        if(DB_CT_GET_ANY_ATOM_ATTR(ct,atomidx+1,CtAtomFormalCharge,&charge, &relop ) )
        {
            if ( charge > 0 )
                DB_CT_UTL_SUB_ANY_ATOM_ATTR(ct,   atomidx+1,
CtAtomFormalCharge );
        }
        UTL_ERROR_CLEAR();
    }
} static int dupCheckCore(struct CtConnectionTable *ct, int *r_uniqid, int *r_hitid )
{
    static UniqSln *uniqSlns;
    static int uniqAlloc;
    static int uniqCnt;
    UniqSln *uptr;
```

```
int i;
struct CtConnectionTable *dupct;
char *sln;
unsigned int crc;

dupct = DB_CT_UTL_DUP_CT(ct, CtCopyKeepAttrs );
DB_CT_UNIQ(dupct);
sln = DB_CT_SLN_GENERATE_NOATTR(dupct, (int **) 0);
crc = DB_CT_HOLO_GEN_CRC(sln);

DB_CT_DELETE_CT(dupct);

for ( i = 0, uptr = uniqSlns; i < uniqCnt; i++, uptr++ )
{
        if ( uptr->crc == crc && !strcmp(uptr->sln, sln ) )
        {
                uptr->hitcnt++;
                *r_uniqid = i+1;
                *r_hitid = uptr->hitcnt;
                UTL_MEM_FREE(sln);
                return uptr->hitcnt;
        }
}
if ( uniqCnt >= uniqAlloc )
{
        if ( uniqSlns )
        {
                uniqAlloc *= 2;
                uniqSlns = (UniqSln *) realloc((char *) uniqSlns, uniqAlloc * sizeof(UniqSln)
);
        }
        else
        {
                uniqAlloc = 100;
                uniqSlns = (UniqSln *) malloc(uniqAlloc * sizeof(UniqSln) );
        }
}
uptr = uniqSlns + uniqCnt;
uptr->sln = sln;
uptr->crc = crc;
uptr->hitcnt = 1;
uniqCnt++;

*r_uniqid = uniqCnt;
*r_hitid = uptr->hitcnt;
return 0;
}
```

```
int *TOP_MATRIX_SEARCH(char **slns, int numSlns )
{
        int i,j;
        int *matrix;
        int offset;
        struct CtConnectionTable *ct;
        struct CtConnectionTable *largest;
        Split **splits;
        Split *S;
        Split *QS;
        double *cord;
        int natoms;
        Frag *fptr;
        double comfa_diff;
        double radius;
        int nParts;
        int idx;
        int modified;
        int junk;
        double junk2;

int qidx, sidx, splitidx, splitInThree;
double best2;
double best3;
double attachPen;
int bailedout = 0;
        int tfrags = 0;

matrix = (int *) malloc( numSlns * numSlns * sizeof(int) );
        splits = (Split **) calloc(numSlns, sizeof(Split *) );

radius = 2000.0;
        q_bailout = radius * radius;    /* just force it very high */
#if 0
        q_minatoms = 3;
        q_termFlag = 1;
#endif
        q_matrixMode = 1;
        TOP_STER_REGION_MODE(2);

for ( i = 0; i < numSlns; i++ )
        {
                fprintf(stderr,"initializing %d for matrix total Frags:%d\n", i+1, tfrags);
                ct = DB_IMPORT_SLN(slns[i]);
                if ( !ct )
                {
                        UTL_ERROR_CLEAR();
```

```
            splits[i] = (Split *) 0;
            continue;
    }
    cord = (double *) 0;
    DB_CT_GET_CT_ATTR(ct, CtCt3DCoordSet, &cord, &natoms );
    if ( !cord )
    {
            DB_CT_DELETE_CT(ct);
            splits[i] = (Split *) 0;
            continue;
    }
    DB_CT_UTL_COUNT_FRAGS(ct, 0, (int *) 0, 0, (int *) 0, &nParts );
    if ( nParts > 1 )
    {
            largest = getLargestFrag(ct);
            DB_CT_DELETE_CT(ct);
            ct = largest;
    }
    DB_CT_NORM_AROM(ct);
    DB_CT_STANDARD(ct, &modified);
    DB_CT_UTL_FIND_RINGS(ct);
    UTL_ERROR_CLEAR();
    S = FindBreakPoints(ct, q_minatoms, q_termFlag, TRUE );
    if ( q_termFlag )
            j = q_minatoms - 1;
    else
            j = q_minatoms;

while ( ( (!S || S->s2cnt == 0 ) && j >= 3 )
    {
            if ( S )
                    freeSplit(S);
            S = FindBreakPoints(ct, j, 0, TRUE );
            q_minatoms = j;
            j--;
    }
    if ( S && S->s2cnt == 0 )
    {
            freeSplit(S);
            S = (Split *) 0;
    }
    splits[i] = S;
    if ( !S )
            continue;
    tfrags += S->numFrags;
    S->ct = ct;
    SearchForFeatures(S);
    BuildFrags(S);
```

```c
        BuildTopomers(ct, S, (Split *) 0);
        for ( j = 0, fptr = S->frags; j < S->numFrags; j++, fptr++ )
        {
                fptr->qtf[0] = fptr->topField;
        }
        freeFragCts(S);
    }
    fprintf(stderr,"Finished initializing for matrix\n");

for ( i = 0; i < numSlns; i++ )
    {
        QS = splits[i];
        qs = QS;
        for ( j = 0; j < numSlns; j++ )
        {
            idx = i*numSlns + j;
            if ( i == j )
            {
                matrix[idx] = 0;
                continue;
            }
            S = splits[j];
            if ( !QS || !S )
            {
                if ( !QS && !S )
                    matrix[idx] = 0;  /* both don't have coordinates */
                else
                    matrix[idx] = 5000;  /* one of them doesn't */
                continue;
            }
            if ( q_featureFactor > 0.0 )
                comfa_diff = CompareAllFeatures(QS,S,radius);
            comfa_diff = CompareTwoCompounds(QS, S, radius, &qidx, &sidx, &splitidx, &splitInThree, &junk,
                         &best2, &best3, &junk2, &attachPen, bailedout );
            matrix[idx] = (int) comfa_diff;
        }
        freeStrMap(QS);
        fprintf(stderr,"pass %d complete\n", i+1 );
    }
    q_matrixMode = 0;
    return matrix;
} struct CtConnectionTable *getLargestFrag(struct CtConnectionTable *ct )
{
        struct CtConnectionTable **cts;
```

```
struct CtConnectionTable *largest;
int maxAtoms;
int currAtoms;
int *whichPiece;
int nParts;
int idx;
int *atoms;
int natoms;
int i;
int *ordering;

DB_CT_UTL_SPLIT_CT(ct, &nParts, &cts, &whichPiece,(int **) 0);
largest = cts[0];
DB_CT_GET_CT_ATTR(largest, CtCtAtomCount, &maxAtoms );
idx = 1;
for ( i = 1; i < nParts; i++ )
{
        DB_CT_GET_CT_ATTR(cts[i], CtCtAtomCount, &currAtoms );
        if ( currAtoms > maxAtoms )
        {
                largest = cts[i];
                maxAtoms = currAtoms;
                idx = i+1;
        }
}
atoms = (int *) calloc(ct->atomCount, sizeof(int) );
for ( natoms = 0, i = 1; i <= ct->atomCount; i++ )
{
        if ( whichPiece[i] == idx )
        {
                atoms[natoms] = i;
                natoms++;
        }
}
largest = DB_CT_UTL_COPY_CT(ct, natoms, atoms, &ordering, CtCopyKeepAllAttrs );
for ( i = 0; i < nParts; i++ )
        DB_CT_DELETE_CT(cts[i]);
free((char *) atoms );

return largest;

}
```

We claim:
1. A computer implemented method to search a heterogeneous compound database composed of molecules from different sources and syntheses, some known and some unknown, for molecules which are likely to have the same biological activity as a known query molecule comprising the following steps:
  a) fragmenting a query molecule and database molecules according to a defined set of rules;
  b) generating shape descriptors for the query molecule fragments and for the database molecules fragments; and
  c) using the shape descriptors, comparing all combinations of query molecule fragments with database molecule fragments for each database molecule to identify the database molecule which has a shape similar to the query molecule; and
  d) outputting the identity of the database molecule.

2. The method of claim 1 in which the output displays the fragment of the best hits and the query fragment that it matches.

3. A computer implemented method to search a heterogeneous compound database composed of molecules from different sources and syntheses, some known and some unknown, for molecules which are likely to have the same biological activity as a known query molecule comprising the following steps:
  a) fragmenting a query molecule according to a defined set of rules;
  b) topomerically aligning the query molecule fragments to generate a topomeric conformation;
  c) generating the interaction energies between a probe and the atoms in the topomerically aligned query fragments at all intersection points in a three dimensional grid surrounding the aligned query fragments;
  d) fragmenting a database molecule according to a defined set of rules;
  e) topomerically aligning the database molecule fragments to generate a topomeric conformation;
  f) generating the interaction energies between a probe and the atoms in the topomerically aligned database molecule fragments at all intersection points in a three dimensional grid surrounding the aligned database molecule fragments;
  g) determining the similarity between query fragments and database molecule fragments by the root sum square differences in the field values; and
  h) identify the molecule in the database most similar to the query molecule as that molecule having the smallest field value difference in its fragments; and
  i) outputting the identity of the database molecule.

4. The method of claim 3 in which the output displays the fragment of the best hits and the query fragment that it matches.

5. A computer implemented method to search a heterogeneous compound database composed of molecules from different sources and syntheses, some known and some unknown, for molecules which are likely to have the same biological activity as a known query molecule comprising the following steps:
  a) fragmenting a query molecule according to a defined set of rules;
  b) topomerically aligning the query molecule fragments to generate a topomeric conformation;
  c) generating the interaction energies between a probe and the atoms in the topomerically aligned query fragments at all intersection points in a three dimensional grid surrounding the aligned query fragments;
  d) assigning features locations in the topomerically aligned query fragments;
  e) fragmenting a database molecule according to a defined set of rules;
  f) topomerically aligning the database molecule fragments to generate a topomeric conformation;
  g) generating the interaction energies between a probe and the atoms in the topomerically aligned database molecule fragments at all intersection points in a three dimensional grid surrounding the aligned database molecule fragments;
  h) assigning features locations in the topomerically aligned database molecule fragments;
  i) determining the similarity between query fragments and database molecule fragments by the root sum square differences in the field values;
  j) identifying all database molecule fragments which have features, similarly located in topomer space and similar in feature property, that match each feature in the query fragments; and
  k) identifying the molecule in the database most similar to the query molecule as that molecule having the smallest field value difference in its fragments and smallest difference in feature; and
  d) outputting the identity of the database molecule.

6. The method of claim 5 in which the feature contributions are weighted.

7. The method of claim 6 in which the output displays the fragment of the best hits and the query fragment that it matches.

8. The method of claim 5 in which only hydrogen-bond-donating and hydrogen-bond-accepting features are used.

9. The method of claim 8 in which the output displays the fragment of the best hits and the query fragment that it matches.

10. The method of claim 5 in which the output displays the fragment of the best hits and the query fragment that it matches.

11. A computer implemented method to search a heterogeneous compound database composed of molecules from different sources and syntheses, some known and some unknown, for molecular cores which are likely to have the same biological activity as a known query molecule core comprising the following steps:
  a) specifying a known core and its two attachment bonds;
  b) topomerically aligning the query core to generate a topomeric conformation;
  c) generating the interaction energies between a probe and the atoms in the topomerically aligned query core at all intersection points in a three dimensional grid surrounding the aligned query core;
  d) fragmenting database molecules into three fragments according to a defined set of rules;
  e) topomerically aligning the central database molecule fragments generated by the fragmentation process of step (d) to generate a topomeric conformation;
  f) generating the interaction energies between a probe and the atoms in the topomerically aligned central database molecule fragments at all intersection points in a three dimensional grid surrounding the aligned central fragments;

g) determining the similarity between query core and central database molecule fragments by the root sum square differences in the field values; and h) identifying the core in the database most similar to the query molecule core as that core having the smallest field value difference molecule; and d) outputting the identity of the core.

12. The method of claim 11 in which an attachment penalty multiplier is employed.

13. The method of claim 12 in which the output displays the fragment of the best hits and the query fragment that it matches.

14. The method of claim 11 in which the output displays the fragment of the best hits and the query fragment that it matches.

* * * * *